US007939263B2

(12) United States Patent
Clarke et al.

(10) Patent No.: US 7,939,263 B2
(45) Date of Patent: May 10, 2011

(54) COMPOSITIONS AND METHODS FOR TREATING AND DIAGNOSING CANCER

(75) Inventors: Michael F. Clarke, Menlo Park, CA (US); Xinhao Wang, Fremont, CA (US); John A. Lewicki, Los Gatos, CA (US); Austin L. Gurney, San Francisco, CA (US)

(73) Assignees: The Regents of the University of Michigan, Ann Arbor, MI (US); OncoMed Pharmaceuticals, Inc., Mountain View, CA (US)

( * ) Notice: Subject to any disclaimer, the term of this patent is extended or adjusted under 35 U.S.C. 154(b) by 0 days.

(21) Appl. No.: 12/512,655

(22) Filed: Jul. 30, 2009

(65) Prior Publication Data
US 2010/0093556 A1  Apr. 15, 2010

Related U.S. Application Data

(63) Continuation of application No. 11/451,774, filed on Jun. 13, 2006, now abandoned.

(60) Provisional application No. 60/690,001, filed on Jun. 13, 2005.

(51) Int. Cl.
C12Q 1/68 (2006.01)
(52) U.S. Cl. .......................................................... 435/6
(58) Field of Classification Search .................. None
See application file for complete search history.

(56) References Cited

U.S. PATENT DOCUMENTS

| | | | |
|---|---|---|---|
| 3,687,808 | A | 8/1972 | Merigan |
| 4,109,496 | A | 8/1978 | Allemann |
| 4,323,546 | A | 4/1982 | Crockford |
| 4,873,191 | A | 10/1989 | Wagner |
| 4,968,103 | A | 11/1990 | McNab |
| 4,981,785 | A | 1/1991 | Nayak |
| 5,034,506 | A | 7/1991 | Summerton |
| 5,223,409 | A | 6/1993 | Ladner |
| 5,225,539 | A | 7/1993 | Winter |
| 5,283,317 | A | 2/1994 | Saifer |
| 5,358,691 | A | 10/1994 | Clark |
| 5,489,677 | A | 2/1996 | Sanghvi |
| 5,538,848 | A | 7/1996 | Livak |
| 5,539,082 | A | 7/1996 | Nielsen |
| 5,565,332 | A | 10/1996 | Hoogenboom |
| 5,585,089 | A | 12/1996 | Queen |
| 5,599,677 | A | 2/1997 | Dowell |
| 5,602,240 | A | 2/1997 | de Mesmaeker |
| 5,614,396 | A | 3/1997 | Bradley |
| 5,631,169 | A | 5/1997 | Lakowicz |
| 5,639,606 | A | 6/1997 | Willey |
| 5,643,765 | A | 7/1997 | Willey |
| 5,705,188 | A | 1/1998 | Yano |
| 5,714,331 | A | 2/1998 | Buchardt |
| 5,719,262 | A | 2/1998 | Buchardt |
| 5,824,544 | A | 10/1998 | Armentano |
| 5,830,730 | A | 11/1998 | German |
| 5,872,154 | A | 2/1999 | Wilson et al. |
| 5,876,978 | A | 3/1999 | Willey |
| 5,885,530 | A | 3/1999 | Babson |
| 5,885,808 | A | 3/1999 | Spooner |
| 5,981,225 | A | 11/1999 | Kochanek |
| 5,994,106 | A | 11/1999 | Kovesdi |
| 5,994,128 | A | 11/1999 | Fallaux |
| 5,994,132 | A | 11/1999 | Chamberlain |
| 6,001,557 | A | 12/1999 | Wilson et al. |
| 6,004,528 | A | 12/1999 | Bergstein |
| 6,019,978 | A | 2/2000 | Ertl |
| 6,033,908 | A | 3/2000 | Merigan |
| 6,054,297 | A | 4/2000 | Carter |
| 6,080,912 | A | 6/2000 | Bremel et al. |
| 6,159,750 | A | 12/2000 | Edmonds |
| 6,180,370 | B1 | 1/2001 | Queen |
| 6,198,107 | B1 | 3/2001 | Seville |
| 6,506,559 | B1 | 1/2003 | Fire |
| 6,984,522 | B2 | 1/2006 | Clarke |

FOREIGN PATENT DOCUMENTS

| | | |
|---|---|---|
| WO | WO/90/08832 | 8/1990 |
| WO | WO/94/10300 | 5/1994 |
| WO | WO/97/30731 | 8/1997 |
| WO | WO/99/02685 | 1/1999 |
| WO | WO/00/09675 | 2/2000 |
| WO | WO/00/12738 | 3/2000 |
| WO | WO/02/12447 | 2/2002 |
| WO | WO/03/050502 | 6/2003 |
| WO | 2005/005601 A | 1/2005 |
| WO | 2006/138275 A | 12/2006 |

OTHER PUBLICATIONS

Yoshida et al (Int J Oncology, Mar. 2001, 18(3): abstract).*
Gossler et al. "Transgenesis by means of blastocyst-derived embryonic stem cell lines" Proc. Acad. Sci. USA vol. 83, 1986, p. 9065-9.
Greene et al., 1998, Eur. J. Neurosci. Greene et al., 1998, Eur. J. Neurosci. vol. 10 pp. 1911-1925 Identification and characterization of a novel member of the fibroblast growth factor family.
Griffin et al., "Initial clinical study of indium-111-labeled clone 110 anticarcinoembryonic antigen antibody in patients with colorectal cancer" J Clin Oncol. Apr. 1991;9(4):631-40.
Hage, et al. "Recent advances in chromatographic and electrophoretic methods for the study of drug-protein interactions" J. Chromatogr. Biomed. Sci. Appl vol. 699, 1997, pp. 499-525.
Hamacher et al.,2004, Dtsch. Med vol. 129pp. 1976-1980.

(Continued)

Primary Examiner — Sean E Aeder
(74) Attorney, Agent, or Firm — Casimir Jones, S.C.

(57) ABSTRACT

The present invention relates to compositions and methods for treating, characterizing, and diagnosing cancer. In particular, the present invention provides gene expression profiles and signatures associated with solid tumor stem cells, as well as novel stem cell cancer markers useful for the diagnosis, characterization, prognosis and treatment of solid tumor stem cells. More particularly, the present invention identifies two profiles of cancer stem cells useful for the diagnosis, characterization, and treatment of cancer and cancer metastases. The invention also provides a variety of reagents such as stem cell gene signatures for use in the diagnosis and management of cancer.

7 Claims, 17 Drawing Sheets

OTHER PUBLICATIONS

Hamburger, et al. "Primary Bioassay of Human Tumor Stem Cells," Science (Jul. 229, 1977) 197 (4302): 461-3.

Hanahan, et al. 'The hallmarks of cancer' CELL vol. 100, 2000, pp. 57-70.

Harris et al., 1991, Breast Diseases, Lippencott.

Hartigan, 1975, Clustering Algorithms, vol. xiii pp. 351.

Haskell, et al. "Efficient production of transgenic cattle by retroviral infection of early embryos" Mol. Reprod. Dev. vol. 40, 1995, p. 386-90.

Hazan et al., "Cadherin Switch in Tumor Progression," Annals NY Acad Science bol 1014, pp. 155-163 (2004).

Hedegpeth et al, "Regulation of Glycogen Synthase Kinase 3 and Downstream Wnt Signaling by Axin," Molecular and Cellular Biol, vol. 19, pp. 7147-7157 (1997).

"Hedgepeth et al., 1999, Mol Cell Biol. vol. 19 pp. 7147-57Regulation of Glycogen Synthase Kinase 3b and DownstreamWnt Signaling by Axin ".

Heegaard "Capillary electrophoresis for the study of affinity interactions" J. Mol. Recognit vol. 11, 1998, pp. 141-148.

Heppner, "Tumor Heterogeneity," Cancer Research vol. 44, pp. 2259-65 (1984).

Herbert et al, "Molecular physiology of cation-coupled Cl-cotransport: the SLC12 family" Pglugers Arch. European J Physiology vol. 447, pp. 580-593 (2004).

"Hillier et al., 1996, GenResvol. 6pp. 807-828 Generation and Analysis of 280,000 HumanExpressed Sequence Tags".

Hnatowich et al., "The preparation and labeling of DTPA-coupled albumin" Int. J Appl. Radiat. lot. vol. 33, 1982, p. 327-32.

Hoffman, 1999, Invest New Drugs vol. 17pp. 343-359 Orthotopic metastatic mouse models for anticancer drug discovery and evaluation: a bridge to the clinic.

Hogan et al.: 'Manipulating the Mouse Embryo', 1986, Cold Spring Harbor Laboratory Press.

Holen et al. "Positional effects of short interfering RNAs targeting the human coagulation trigger Tissue Factor" Nucleic Acids Res. vol. 30, 2002, pp. 1757-1766.

Hong et al., 2001, genesis vol. 29 pp. 163-171 The winged helix/forkhead transcription factor Foxq1 regulates differentiation of hair in satin mice.

Houghten "The use of synthetic peptide combinatorial libraries for the identification of bioactive peptides" Biotechniques vol. 13, 1992, pp. 412-421.

Howes et al, "Cationic Trypsingen Mutations and Pancreatitis" Clin Lab Med, vol. 25, pp. 39-59 (2005).

"Hughes et al., 2002. Mol Ther. vol. 5 pp. 16-24 Viral-Mediated Gene Transfer to Mouse PrimaryNeural Progenitor Cells".

Ikeda et al., 1993, Exp. Hematol vol. 21 pp. 1686-1694 Changes in phenotype and proliferative potential of human acute myeloblastic leukemia cells in culture with stem cell factor.

Imatani, A. & Callahan, R. Identification of a novel NOTCH-4/INT-3 RNA species encoding an activated gene product in certain human tumor cell lines. Oncogene 19,223-231 (2000).

Iwabuchi et al. "Use of the two-hybrid system to identify the domain of p53 involved in oligomerization" Oncogene vol. 8, 1993, pp. 1693-1696.

Jaenisch "Transgenic animals" Science vol. 240, 1988, p. 1468-74.

"Jaenisch 1976, PNAS vol. 73pp. 1260 Germ line integration and Mendelian transmission of the exogenous Moloney leukemia virus(in vitro infection of 4-8 cell embryos with exogenous Moloney leukemia virus/leukemia/genetic transmission/DNA annea".

Jahner et al. "Insertion of the bacterial gpt gene into the germ line of mice by retroviral infection" Proc. Natl. Acad Sci. USA vol. 82, 1985, p. 6927-31.

Jahner et al. "De novo methylation and expression of retroviral genomes during mouse embryogenesis" Nature vol. 298, 1982, p. 623-8.

Jehn, et al. "Cutting edge: protective effects of notch-1 on TCR-induced apoptosis" J Immunol., 162(2):635-8 (1999).

Jette et al, "The Tumor Supressor Adenomatous Polyposis Coli and Caudal Related Homeodomain Protein Regulate Expression of Retinol Gehydrohenase L" J. Biol Chem vol. 279, pp. 34397-405 (2004).

Jonsson, M., Borg, A., Nilbert, M. & Andersson, T. Involvement of adenomatopolyposis coli (APC)/beta-catenin signalling in human br~ast cancer. Eur J Cancer 36, 242-8 (2000).

Kawano & Kypta, 2003, J Cell Sci. vol. 116 pp. 2527-34 Secreted antagonists of the Wnt signalling pathway.

"Keane et al., 2001, Am. J. respir. Crit. Care Med. vol. 164 pp. 2239 ENA-78 Is an Important Angiogenic Factor in IdiopathicPulmonary Fibrosis".

Khaw et al., "Myocardial infarct imaging of antibodies to canine cardiac myosin with indium-111-diethylenetriamine pentaacetic acid" Science vol. 209, 1980, p. 295.

Kim et al, "Methylation and expression of p16INK4 tumor supressor gene in primary colorectal Carcnimoas" Int J. Oncol. vol. 26, pp. 1217-1226 (2005).

Kirikoshi et al, "Expression of WNT10A in human cancer," Int J Oncology vol. 19, pp. 997-1001 (2001) 2001 Spec.

Kirkoshi et al., 2001, Int. J. Oncol. vol. 19 pp. 997-1001.

Kobuke et al, ESDN a Novel Neuropilin-like Membrane Protein Clonsed from Vascular Cells with the Longest Secretory Signal Sequence among Eukaryotes . . . J Biol Chem Bol. 276, pp. 34105-34114 (2001).

Koehler & Milstein, Nature vol. 256 pp. 495, 1975.

Korinek, V. et al. Depletion of epithelial stem-cell compartments in the small intestine of mice lacking Tcf-4. Nat Genet 19, 379-83 (1998).

Korinek, V. et al. Two members of the Tcf family implicated in WnUbeta-catenin signaling during embryogenesis in the mouse. Mol Cell Biol 18, 1248-56 (1998).

Koshikawa et al, "Significant up—regulation of novel gene, CLCP1, in a highly metastatic lung cancer subline as well as in lung cancers in vivo" Oncogene, vol. 21, pp. 2822-2828 (2002).

"Kramps et al., 2002, Cell 109:47-60 Wnt/Wingless Signaling RequiresBCL9/Legless-Mediated Recruitment ofPygopus to the Nuclear—Catenin-TCF Complex".

Krasna, L. et al. Large expansion of morphologically heterogeneomammary epithelial cells, including the luminal phenotype, from human breast tumours. Breast Cancer Res Treat 71.219-35 (2002).

Kufe et al., "Biological Behavior of Human Breast Carcinoma-associated Antigens Expresses during Cellular Proliferation," Cancer Research, vol. 43, pp. 851-857 (1983).

Chakraborty & Pawelek, 2003, Clin Exp Metastasis vol. 20pp. 365-373 GnT-V, macrophage and cancer metastasis: a common link.

Chamow (Charnow)et al. "A humanized, bispecific immunoadhesin-antibody that retargets CD3+ effectors to kill HIV-1-infected cells" J Immunol vol. 153, 1994, p. 4268-80.

Chan et al, "A common human skin tumour is caused by activating mutations in catenin," Nature Genetics, vol. 21, pp. 410-413 (1999).

Chen et al, "Development of the Th1-type immune responses requires the type I Cytokine receptor TCCR" Nature vol. 407, pp. 916-920 (2000).

Cheng et al., 2000, Science vol. 287 pp. 1804-1808 Hematopoietic stem cell quiescence maintained by p21cip1/waf1.

Cheung et al., 1999, Nat. Genet. Supplement voI. 21 pp. 15-19.

"Chin et al., 1999, Nature, vol. 400 pp. 468-472 Essential role foroncogenicRas in tumourmaintenance".

Cho et al., "An unnatural biopolymer" Science, vol. 261, 1993, p. 1303-5.

Choong et al., Cytokine. Mar. 21, 2004;25(6):239-45. LIX: a chemokine with a role in hematopoietic stem cells maintenance.

Christensen, et al. 'Flk-2 is a marker in hematopoietic stem cell differentiation: a simple method to isolate long-term stem cells' Proc Natl Acad Sci USA vol. 98, 2001, pp. 14541-14546.

Clarke et al., "A recombinant bcl-x's adenovirus selectively induces apoptosis in cancer cells but not in normal bone marrow cells," Proc Natl Acad Sci USA (Nov. 1995) 92: 10024-11028.

Closs et al, "Identification of a Low Affinity, High Capacity Transporter of Cathionic Amino Acids in Mouse Liver" J Biol. Chem. vol. 268, pp. 7538-7544 (1993).

Cohen et al, "Role of Cabeolae and Cabeolins in Health and Disease" Physiol., Rev vol. 84, pp. 1341-1379 (2004).

Cristillo et al. "Cyclosporin A Inhibits Early mRNA Expression of G0S2) in Cultured Human Blood Mononuclear Cells" DNA and Cell Biology, vol. 16, pp. 1449-1458 (1997).

"Cui et al., 2003, J. Immunol. vol. 171 pp. 6814 Shedding of the Type II IL-1 Decoy Receptor Requires aMultifunctional Aminopeptidase, Aminopeptidase Regulator of TNF Receptor Type 1 Shedding".

Cull et al., "Screening for receptor ligands using large libraries of peptides linked to the C terminus of the lac repressor" Proc Nad Acad Sci USA vol. 89, 1992, p. 1865-1869.

Cwirla et al. "Peptides on phage: a vast library of peptides for identifying ligands" Proc. Nati. Acad. Sci. vol. 87, 1990, pp. 6378-6382.

Danish et al., 1992, Oncogene vol. 7 pp. 901-907 c-myb effects on kinetic events during MEL cell differentiation.

Devlin "Random peptide libraries: a source of specific protein binding molecules" Science vol. 249, 1990, pp. 404-406.

Dewitt et al. ""Diversomers": an approach to nonpeptide, nonoligomeric chemical diversity" Proc Natl Acad Sci., vol. 90, pp. 6909-6913, 1993.

Diederichs, et al, "S100 Family Members and Trypsinogens Are Predictors of Distant metastiasis and Survival in Early-Stage Non-Small Cell Lung Cancer" Cancer Res. vol. 64, pp. 5564-5569 (2004).

"Domen et al., 1998, Blood vol. 91 pp. 2272-2282 Systemic Overexpression of BCL-2 in the Hematopoietic System ProtectsTransgenic Mice From the Consequences of Lethal Irradiation".

Domen, et al. 'The Role of Apoptosis in the Regulation of Hematopoietic Stem Cells: Overexpression of BCL-2 Increases Both Their Number and Repopulation Potential' 1. Exp. Med. vol. 191, 2000, pp. 253-264.

Domen, J.; Weissman, I. L.: 'Hematopoietic stem cells need two signals to prevent apoptosis; BCL-2 can provide one of these, Kitl/c-Kit signaling the other' J Exp Med vol. 192, 2000, pp. 1707-1718.

"Dorrell et al., 2000, Blood, vol. 95, pp. 102-110 Expansion of human cord blood CD341CD382 cells in ex vivo culture duringretroviral transduction without a corresponding increase in SCID repopulating cell(SRC) frequency: dissociation of SRC phenotype and function".

Eisen et al., 1998, PNAS, 95:14863-14868 Cluster analysis and display of genome-wide expression patterns.

Elbashir et al. "Duplexes of 21-nucleotide RNAs mediate RNA interference in cultured mammalian cells" Nature vol. 411, 2001, pp. 494-498.

Elbashir et al. "Functional anatomy of siRNAs for mediating efficient RNAi in Drosophila melanogaster embryo lysate" Embo J. vol. 20, 2001, pp. 6877-6888.

Elbashir et al. "RNA interference is mediated by 21- and 22-nucleotide RNAs" Genes Dev. vol. 15, 2001, pp. 188-200.

Ellisen, L.W., et al., "TAN-1, the Human Homolog of the Drosophila Notch Gene, Is Broken by Chromosomal Translocations in T Lymphoblastic Neoplasms," Cell 66:649-661, Elsevier Inc., Amsterdam, The Netherlands (1991).

Emberely et al., 2004, Biochem Cell Biot vol. 82pp. 508-515 S100 proteins and their influence on pro-survival pathways in cancer.

Erb et al., "Recursive deconvolution of combinatorial chemical libraries" Proc Nad Acad Sci vol. 91 1994, p. 11422-6.

Ethier, et al. "Differential Isolation of normal luminal mammary epithelial cells and breast cancer cells from primary and metastatic sites using selective media" Cancer Res 53. 627-35 (1993).

Evans et al. "Establishment in culture of pluripotential cells from mouse embryos" Nature vol. 292, 1981, p. 154-6.

Felici, et al. "Selection of antibody ligands from a large library of oligopeptides expressed on a multivalent exposition vector" J. Mol. Biol. vol. 222, 1991, p. 301-10.

Fialkow, "Human Tumors Studied with Genetic Markers," Birth Defects, vol. 12, pp. 123-32 (1976).

Fodor "Multiplexed biochemical assays with biological chips" Nature col. 364, 1993, pp. 555-556.

Frank "MAL a proteolipid in glycosphingolipid enriched domains: functional implications in myelin and beyond" Progress in Neuroliology, vol. 60, pp. 531-44 (2000) 2000 Spec.

"Furley et al, 1986, Blood, vol. 68 pp. 1101-1107 Divergent Molecular Phenotypes of KG1 and KG1a Myeloid Cell LinesBy A.J. Furley, B.R. Reeves, S. Mizutani, L.J. Altass, S.M. Watt, M.C. Jacob, P. van den Elsen,C. Terhorst, and M.F. Greaves".

Gallahan, et al. "The mouse mammary tumor associated gene INT3 is a unique member of the NOTCH gene family (NOTCH4)", Oncogene, 14(16) pp. 1883-1890 (1997).

Gallop et al. "Applications of combinatorial technologies to drug discovery. 1. Background and peptide combinatorial libraries" J Med Chem vol. 37, 1994, p. 1233.

Gat, et al, "De Novo Hair Foliicle Morphogenesis and Hair Tumors in Mice Esxpression a Truncated Catenin in Skin" Cell vol. 95, pp. 605-614 (1998).

"Gazit et al., 1999, Oncogene 18:5959-66Human frizzled 1 interacts with transforming Wnts to transduce a TCFdependent transcriptional response".

Ghose et al. "Preparation of antibody-linked cytotoxic agents" Methods Enzymol. vol. 93, 1983, p. 280-333.

Glinsky et al, "Classification of Human Breast Cancer Using Gene Expression Profiling as a Component of the Survival Predictor Algorithm," Clinical Cancer Research, vol. 10, pp. 2272-2283 (2004).

Prince et al., 2007; "Identification of a subpopulation of cells with cancer stem cell properties in head and neck squamous cell carcinoma", Proceedings of the National Academy of Sciences of the United States of America, 104(3):973-978.

Supplementary European Search Report and European Search Opinion, dated Apr. 27, 2009, for Application No. EP 06 83 6728.

Kurochkin et al, "ALEX1, a Novel Human Armadillo Repeat Protein That Is Expressed Differentially in Normal Tissues and Carcinomas" Biochem Biophys Res Commun, vol. 280, pp. 340-347 (2001).

Kuukasjarvi et al., "Genetic Heterogeneity and Clonal Evolution Underlying Development of AsynchronoMetastasis in Human Breast Cancer," Cancer Res. (Apr. 15, 1997) 57: 1597-1604.

Lagasse, et al. 'bc1-2 inhibits apoptosis ofneutrophils but not their engulfment by macrophages' J Exp Med vol. 179, 1994, pp. 1047-1052.

Lahn et al, "Protein Kinase C Alpha Expression in Breast and Ovarian Cancer" Oncology vol. 67, pp. 1-10 (2004).

Lam "A new type of synthetic peptide library for identifying ligand-binding activity" Nature vol. 354, 1991, pp. 82-84.

Lapidot et al, "A cell Initiating human acute myeloid leukaemia after transplantation into SCID mice," Nature (Feb. 17, 1994) 367 (6464): 645-8.

Larochelle et al. "Identification of primitive human hematopoietic cells capable of repopulating NOD/SCID mouse bone marrow: Implications for gene therapy," Nature Medicine vol. 2, pp. 1329-1337 (1996).

Lauffer "Targeted relaxation enhancement agents for MRI" Magnetic Resonance in Medicine vol. 22, 1991, pp. 339-342.

Leethanakul, et al., "Distinct pattern of expression of differentiation and growth-related genes in aquamocell carcinomas of the head and neck revealed by the used of laser capture microdissection and cDNA arrays," Oncogene vol. 19, pp. 3220-3224 (2000).

"Li et al., 2003, J. Biol. Chem, vol. 278 pp. 33445 Positive and Negative Regulation of the -Secretase Activity byNicastrin in a Murine Model*".

Lin, S. Y. et al. "Beta-eatenin, a novel prognostic marker for breast cancer: its roles in cyclin D1 expression and cancer progression" Proc Nail Acad Sci USA 97, 4262-6 (2000).

Loeppen et al,. "Overexpression of Glutamine Synthetase is Associated with Catenin Mutations in Mouse Liver Tumors Durng Promotion of Hepatocarcinogenesis by Phenobarbital" Cancer Research vol. 62, pp. 5685-5688 (2002).

Loftus et al., 2002, PNAS vol. 99 pp. 4471-4476 Mutation of melanosome protein RAB38 in chocolate mice.

Ma, et al. "Functional Expression and Mutations of c-Met and Its Therapeutic Inhibition with SU11274 and Small Interfering RNA in Non-Small Cell Lung Cancer" Cancer Research vol. 65, pp. 1479-1488 (2005).

Madura et al. "N-recognin/Ubc2 interactions in the N-end rule pathway" J. Biol. Chem. vol. 268, 1993, pp. 12046-12054.

Mahajan et al, "NRC-interacting Factor 1 is a Novel Cotransducer That Interacts with and Regulated the Activity of the Nuclear Hormone Receptor Coactivator NRC" Molecular and Cellular Biology vol. 22, pp. 6883-6894 (2002).

Marambaud et al, "A presenilin-1/secretase cleavage releases the E-cadherin intracellular domain and regulates disassemble of adhrens junctions" EMBO 21: 1948 (2002).

Markova et al., 2003, Mol. Genet. Metab.vol. 78pp. 119-135 Expression pattern and biochemical characteristics of a major epidermal retinol dehydrogenase.

Liu et al., 1996, Genomics vol. 31 pp. 58-64 Epithelial expression and chromosomal location of human TLE genes: implications for notch signaling and neoplasia.

Martin, et al. "Ein neuer Zugang zu 2'-O-Alkylribonucleosiden and Eigenschaften deren Oligonucleotide" HELV. Chim. ACTA vol. 78, 1995, p. 486.

Martinerie et al., 2001, J. Clin. Endocrinol. Metab vol. 86. pp. 3929-3940 Altered Expression of novH Is Associated with Human Adrenocortical Tumorigenesis.

Martinez et al, "Single-Stranded Antisense si-RNAs Guide Target RNA Cleavage un RNAi" Cell, vol. 110, pp. 563-574 (2002).

Matsuo et al., 2000, Nat. genet. vol. 24pp. 184-187 FosI1 is a transcriptional target of c-Fos during osteoclast differentiation.

McConnell et al. "The cytosensor microphysiometer: biological applications of silicon technology" Science vol. 257, 1992, pp. 1906-1912.

Medina et al, "Glutamine Metabolism: Nutritional and Clinical Significance," American Soc. For Nutritional Sciences, J. of Nutrition vol. 131, pp. 2539S-3542S (2001).

Methods Enzymol, 1999, vol. 303 pp. 179-205.

Methods Enzymol, 1999, vol. 306 pp. 3-18.

Michallet, M. et al.: 'Transplantation with selected autologoperipheral blood CD34+ Thyl+ hematopoietic stem cells (HSCs) in multiple myeloma: impact of HSC dose on engraftment, safety, and immune reconstitution' EXP Hematol vol. 28, 2000, pp. 858-870.

Miller, C. L.; Eaves, C. J.: 'Expansion in vitro of adult murine hematopoietic stem cells with transplantable lympho-myeloid reconstituting ability' Proc Nail Acad Sci USA vol. 94, 1997, pp. 13648-13653.

Mills et al., "The emerging role of lysophosphatidic acid in cancer" Nat Rev Cancer, vol. 3, pp. 582-91 (2003).

Mitchell et al, "A Novel Melanoma Gene (MG50) Encoding the Interleukin 1 Receptor Antagonist and Six Epitopes Recognized by Human Cytolytic T Lymphocytes," Cancer Reearch vol. 60, pp. 6448-6456 (2000).

Miyashita et al., 2002, Cancer, vol. 94 pp. 2959-2966 Uridine phosphorylase is a potential prognostic factor in patients with oral squamous cell carcinoma.

Morrison et al., "Regulatory Mechanisms in Stem Cell Biology," Cell (Feb. 7, 1997) 88(3): 287-98.

Morrison, et al. "Hematopoietic stem cells: challenges to expectations" Curr Opinion Immunol (1997) 9(2): 216-21.

Morrison, et al. "The Biology of Hematopoietic Stem Cells," Annu Rev. Cell Dev Biol (1995) 11:35-71.

Morrison, et al. "The long-Term Repopulating Subset of Hematopoietic Stem Cells Is Detenninistic and Isolatable by Phenotype," Immunity (Nov. 1994) 1(8): 661-73.

Morrison, et al. "Transient Notch Activation Initiates an Irreversible Switch from Neurogenesis to Gliogenesis by Neural Crest Stem Cells," Cell (May 26, 2000) 101(5): 499-510.

Morrison, et al. 'A Genetic Determinant That Specifically Regulates the Frequency of Hematopoietic Stem Cells' J. Immunol. vol. 168, 2002, pp. 635-642.

Morrison, et al. 'Identification of a lineage of multipotent hematopoietic progenitors' Development vol. 124, 1997, pp. 1929-1939.

Mott et al, "Regulation of matrix biology by matrix metalloproteinases" Current Opinion Cell Biology vol. 16, pp. 558-564 (2004).

Mucenski et al., 1991, Cell vol. 65 pp. 677-689 A functional c-myb gene is required for normal murine fetal hepatic hematopoiesis.

"Mukai et al., 2000, J. Biol. Chem. vol. 66 pp. 17566-17570 NADE, a p75NTR-associated Cell Death Executor,ls Involved in Signal Transduction Mediated by theCommon Neurotrophin Receptor p75NTR*".

Mukai et al., 2003, Vitam. Horm, vol. 66 pp. 385-402 Nerve growth factor-dependent regulation of NADE-induced apoptosis.

Muller-Sieburg, C. E. et al.: 'Genetic control of hematopoietic stem cell frequency in mice is mostly cell autonomous' Blood vol. 95, 2000, pp. 2446-2448.

Natarajan et al, "Sturcture and Function of Natural Killer Cell Receptors" Annu Rev. Immunol. vol. 20, pp. 853-885 (2002).

Negrin, et al: 'Transplantation of highly purified CD34+Thy-1+ hematopoietic stem cells in patients with metastatic breast cancer' Biol Blood Marrow Transplant vol. 6, 2000, pp. 262-271.

Ahrens et al., "Soluble CD44 inhibits melanoma tumor growth by blocking cell surface CD44 binding to hyaluronic acid," Oncogene vol. 20, pp. 3399-3408 (Jun. 2001).

AJCC Cancer Staging manual, 5th Edition, 1997, pp. 171-180.

Akashi, et al. 'Developmental Biology of Hematopoiesis', 2001, Oxford Univ. Press.

Al-Hajj, "Prospective identification of tumorigenic breast cancer cells," PNAS (2003) 100: 3983-3988.

Ali et al., 2003, Norm. Metab. Res. vol. 35pp. 726-733 Epidemiology and biology of insulin-like growth factor binding protein-3 (IGFBP-3) as an anti-cancer molecule.

Andersen, 1998, Nucleic Acid Hybridization.

"Antonchuk & Humphries, 2002, Cell vol. 109pp. 39-45 HOXB4-Induced Expansion ofAdult Hematopoietic Stem Cells Ex Vivo".

Artavanis-Tsakonas et al, al. "Notch signaling: cell fate control and signal integration in development" Science 284: 770-6 (Apr. 30, 1999).

Aubele, et al. "Heterogeneity in breast cancer and the problem of relevance of findings," Analyt. Cell Path. (1999) 19: 53-8.

Austin, et al. "A role for the Wnt genie family in hematopoiesis: expansion of multilineage progenitor cells" Blood 89, 3624-35 (1997).

Ausubel et al., eds. Current Protocols in Molecular Biology, 1999, J. Wiley:New York.

"Baki et al., 2001, PNAS vol. 98 pp. 2381 Presenilin-1 binds cytoplasmic epithelial cadherin,inhibits cadherinyp120 association, and regulatesstability and function of the cadherinycateninadhesion complex".

Barbui, A. et al.: 'Negative selection of peripheral blood stem cells to support a tandem autologotransplantation programme in multiple myeloma' British Journal of Haematology. vol. 116, 2002, pp. 202-210.

Bartel et al. "Elimination of false positives that arise in using the two-hybrid system" Biotechniques vol. 14, 1993, pp. 920-924.

Baum, C. et al.: 'Bone Marrow Transplantation', 1994, Blackwell Scientific Publications.

Baum, C. M. et al.: 'Isolation of a candidate human hematopoietic stem-cell population' Proc Nail Acad Sci USA vol. 89, 1992, pp. 2804-2808.

Beerman, et al. "Flow Cytometric Analysis of DNA Stemline Heterogeneity in Primary and Metastatic Breast Cancer," Cytometry (1991) 12(2): 147-54.

Berg et al., "Bispecific antibodies that mediate killing of cells infected with human immunodeficiency virus of any strain" PNAS, vol. 88, 1991, pp. 4723-4727.

Bergsagel, et al. "Growth Characteristics of a Mouse Plasma Cell Tumor," Cancer Research vol. 28, pp. 2187-2196 (1968).

Berruyer et al, "Vanin-1-/- Mice Exhibit a Glutathione-Mediated Tissue Resistance to Oxidative Stress" Mol Cell Biol vol. 24, pp. 7214-7224 (2004).

Berry, et al. "Germ-line tumor formation caused by activation of glp-1, a *Caenorhabditis elegans* member of the Notch family of receptors" Development, vol. 124. pp. 925-936 (1997).

Bhardwaj et al., 2001, Nat. Immunol vol. 2 pp. 172-180 Sonic hedgehog induces the proliferation of primitive human hematopoietic cells via BMP regulation.

Bieller et al., 2001, DNA Cell Biol. vol. 20 pp. 555-561 Isolation and characterization of the human forkhead gene FOXQ1.

Bienz "β-Catenin: A Pivot between Cell Adhesion and Wnt-signalling," Current Biology vol. 15, pp. R64-7 (2004).

Birchmeier et al., 2003, Nat. Mol. Cell. Biol vol. 4 pp. 915.

Boccaccio et al., 2005, Nature vol. 434pp. 396-340 The MET oncogene drives a genetic programme linking cancer to haemostasis.

Boggs et al, "A glycosynapse in myelin?" Glycoconjugate J. vol. 21, pp. 97-110 (2004).

Bonnet et al. "Human acute myeloid leukemia is organized as a hierarachy that originates from a primitive hematopotetic cell," Nat. Med. 3:730-7, Nature Publishing Group, New York, NY, U.S.A. (1997).

Bonsing et al. "Allelotype analysis of flow-sorted breast cancer cells demonstrates genetically related diploid and aneuploid subpopulations in primary tumors and lymph node metastases" Genes Chromosomes & Cancer (2000) 82: 173-183.

Bonsing et al., "High Levels of DNA Index Het rog neity in Advanced Breast Carcinomas," Cancer 71: 382-391 (1993).

Bottcher et al, "Fibroblast Growth Factor Signaling during Early Vertebrate Development," Endocrine Reviews, vol. 26, pp. 63-77 (2005).

"Bourke et al., 2003, J. Immunol. vol. 170 pp. 5999 IL-1 Scavenging by the Type II IL-1 Decoy Receptor inHuman Neutrophils1".

Bradley et al. "Formation of germ-line chimaeras from embryo-derived teratocarcinoma cell lines" Nature vol. 309, 1984, p. 255-6.

Brennan, K. and Brown, A.M.C., "Is there a role for Notch signalling in human breast cancer?" Breast Cancer Res. 5:69-75, BioMed Central Ltd, London, UK (2003).

Brinster et al. "Factors affecting the efficiency of introducing foreign DNA into mice by microinjecting eggs" Proc. Natl. Acad. Sci. USA vol. 82, 1985, pp. 4438-4442.

Brown, "NCI's Anticancer Drug Screening Program May Not Be Selecting for Clinically Active Comounds" Oncology Research, vol. 9, pp. 213-215 (1997).

Bruce, W. R.; Gaag, H.: 'A quantitative assay for the number of murine lymphoma cells capable of proliferation in vivo' Nature vol. 199, 1963, pp. 79-80.

Brummelkamp et al. "A system for stable expression of short interfering RNAs in mammalian cells" Science vol. 296, 2002, pp. 550-553.

"Buske et al., 2002, Blood vol. 100 pp. 862-881 Deregulated expression of HOXB4 enhances the primitive growth activityof human hematopoietic cells".

"Bustin, 2000,J. Mol.Endocrinol vol. 25: pp. 169-93Absolute quantification of mRNA using real-time reversetranscription polymerase chain reaction assays".

Cadigan, et al. "Wnt signaling: a common theme in animal development" Genes &Development 11. 3286-305 (1997).

Candidus, et al. "No evidence for mutations in the alpha- and beta-catenin genes in human gastric and breast carcinomas" Cancer Res 56, 49-52 (1996).

Cao et al, "Identification of Novel Highly Expressed Genes in Pancreatic Ductal Adenocarcinomas through a Bioinformatics Analy" (2004) Cancer Biology & Therapy, vol. 3, pp. 1081-1089.

Caplen et al. "Specific inhibition of gene expression by small double-stranded RNAs in invertebrate and vertebrate systems" Proc Nail Acad Sci U.S.A. vol. 98, 2001, pp. 9742-9747.

"Capobianco et al., 1997, Mol Cell Biol. vol. 17 pp. 6265-6273 Neoplastic Transformation by Truncated Alleles of HumanNOTCH/TAN1 and NOTCH2".

Carney, et al. "Demonstration of the stem cell nature of clonogenic tumor cells from lung cancer patients" Stem Cells. 1982;1(3):149-64.

Carrell et al. "A Novel Procedure for the Synthesis of Libraries Containing Small Organic Molecules" Angew Chem Int Ed Engl vol. 33, 1994, pp. 2059-2061.

Weisenthal & Lippman "Clonogenic and Nonclonogenic In Vitro Chemosensitivity Assays," Cancer Treatment Reports, vol. 69, pp. 615-648 (1985).

Weissman 'Translating stem and progenitor cell biology to the clinic: barriers and opportunities' Science vol. 287, 2000, pp. 1442-1446.

"Williams&Lisanti, 2005, Am J Physiol Cell Physiol. vol. 288 pp. C494-C506 Caveolin-1 in oncogenic transformation, cancer, and metastasis".

Wodinsky, et al. 'Spleen colony studies of leukemia L1210.I. Growth kinetics of lymphocytic L1210 cells in vivo as determined by spleen colony assay' Cancer Chemother. Rep. vol. 51, 1967, pp. 415-421.

Wong et al., 1994, Mol Cell Biol. vol. 14 pp. 6278-6286Differential transformation of mammary epithelial cells by Wnt genes.

"Wong et al., J. Nucl. Med. vol. 23 pp. 229 1982 Imaging Endocarditiswith Tc-99m-Labeled Antibodyâ ∈" AnExperimentalStudy:Concise Communication.

Wong, 2003, PNAS vol. 98 pp. 10869.

Wong, S. C. et al. "Expression of frizzled-related protein and Wnt-signalling molecules in invasive human breast tumours" J Pathol196, 145-53 (2002).

Wu, et al., "RGS proteins inhibit Xwnt-8 signaling in Xenopembryonic development" Development vol. 127, pp. 2773-2784 (2000).

Yamasaki et al, "Cell cycle, protelysis and cancer" Curr Opin Cell Biol., vol. 16, pp. 623-628 (2004).

Yan et al., 2004, J. Neurosci. 24: 2942 Binding Sites of -Secretase Inhibitors in Rodent Brain.

Yan, et al. "Chronic DLL4 Blockade Induces Vascular Neoplasms," Nature, vol. 463, pp. E6-E7, Feb. 11, 2010.

Yantiss et al, "KOC (K Homology Domain Containing Protein Overexpression in Cancer)" Am J Durg. Pathol vol. 29, pp. 188-195 (2005).

Yeh et al, "Antisense overexpression of BMAL2 enhances cell proliferation" Oncogene vol. 22, pp. 5306-5314 (2003).

Yu et al., 2001, Nature vol. 411 pp. 1017-1021 Specific protection against breast cancers by cyclin D1 ablation.

Yukimasa et al "Enhanced expression of p46 Shc in the nucleand p52 Shc in the cytoplasm of human gastric cancer" Intl J Oncology, vol. 26, pp. 905-911 (2005).

Zagouras, P., et al., "Alterations in Notch signaling in neoplastic lesions of the human cervix," PNAS 92:6414-6418, the National Academy of Sciences, Washington, DC, U.S.A. (1995).

Zerangue et al, "ASCT-1 Is a Neutral Amino Acid Exchanger with Chloride Channel Activity" J Biol. Chem vol. 271, pp. 27991-27994 (1996).

Zervos et al. "Mxi1, a protein that specifically interacts with Max to bind Myc-Max recognition sites" Cell vol. 72, 1993, pp. 223-232.

Zhou et al, "Expression Cloning of 2-5A-Dependent RNAaseL A uniquely Regulated Mediator of Interferon Action" Cell, vol. 72, pp. 753-765 (1993).

Zhu, et al., "Catenin signaling modulatesproliferative potential of human epidermal keratinocytes independently of intracellular adhesion," Development vol. 126, pp. 2285-2298 (1999).

"Zuckennann et al., J. Med Chem vol. 37pp. 2678-2685 (1994) Discovery of Nanomolar Ligands for 7-Transmembrane G-Protein-CoupledReceptors from a Diverse N-(Substituted)glycine Peptoid Library".

Zuckermann et al., "Discovery of nanomolar ligands for 7-transmembrane G-protein-coupled receptors from a diverse N-(substituted)glycine peptoid library" J Med Chem vol. 37, 1994, p. 2678-85.

Renehan et al., 2004, Lancet, vol. 363pp. 1346 Insulin-like growth factor (IGF)-I, IGF binding protein-3, and cancer risk: systematic review and meta-regression analysis.

"Neilsen et al., 1999, Mol. Cell. Biol. vol. 19 pp. 1262-1270 Christiansen, JensDevelopmentRepresses Translation in LateFactor II mRNA-Binding ProteinsA Family of Insulin-Like Growth".

Nie et al, "A Novel PTB-PDZ Domain Interaction Mediates Isoform-specific Ubiquitylation of Mammalian Numb" J Biol. Chem. vol. 279, pp. 20807-20815 (2004).

Nie, et al, "LNX functions as a RING type E3 ubiquitin ligase that targets the cell fate determinate Numb for ubiquitin-dependent degradation," Embo J. vol. 21, pp. 93-102 (2002).

Nielsen et al."Sequence-selective recognition of DNA by strand displacement with a thymine-substituted polyamid" Science vol. 254, 1991, p. 1497.

Nusse "The Wnt gene family in tumorigenesis and in normal development" Journal of Steroid Biochemistry & Molecular Biology 43,9-12 (1992).

"Nusse, 1999, Trends genet, vol. 15pp. 1-3 Wnt targetsrepression and activation".

Nusse, R. "Insertional mutagenesis in mouse mammary tumorigenesis" Current Topics in Microbiology & Immunology 171,43-65 (1991).

Nusse, R. & Varrnus, H. E. "Many tumors induced by the mouse mammary tumor vircontain a provirintegrated in the same region of the host genome" Cell 31, 99-109 (1982).

Okamoto et al., 1994, PNAS, vol. 91pp. 11045 Mutations and altered expression of p16INK4 in human cancer.

Osanai et al, "Expression and characterization of Rab38, a new member of the Rab small G protein family," Biol Chem vol. 386, pp. 143-153 (2005).

Osawa, M. et al.: 'Long-term lymphohematopoietic reconstitution by a single CD34-low/negative hematopoietic stem cell' Science vol. 273, 1996, pp. 242-245.

Packeisen et al, "Detection of Surface Antigen 17-1A in breast and Colorectal Cancer" Hybridoma, vol. 18, pp. 37-40 (1999).

Pandis et al., Cytogenetic Comparison of Primary Tumors and Lymph Node Metastase in Breast Cancer Patients, Genes, Chromosomes & Cancer (1998) 12: 122-129.

Pantschenko et al, "The interleukin-1 family of cytokines and receptors in human breast cancer: Implications for tumor progression" Int. J Oncology, vol. 23, pp. 269-284 (2003).

Park, C. H.; Bergsagel, D. E.; Mcculloch, E. A.: 'Mouse myeloma tumor stem cells: a primary cell culture assay' J Natl Cancer Inst vol. 46, 1971, pp. 411-422.

Park, I. K. et al., "Bmi-1 is required for maintenance of adult self-renewing haematopoietic stem cells," Nature 423, 302-5 (2003).

Paul et al, "Effective expression of small interfering RNA in human cells" nature Biotech, vol. 29, pp. 505-508 (2002).

Paull et al., 1989, J. Nat. Cancer. Inst. vol. 81 pp. 1088-1092 Display and analysis of patterns of differential activity of drugs against human tumor cell lines: development of mean graph and COMPARE algorithm.

Phillips, et al. 'Genetic control of murine hematopoietic stem cell pool sizes and cycling kinetics' Proc Natl Acad Sci U SA vol. 89, 1992, pp. 11607-11611.

Pold et al, "Cyclooxygenase 2-Dependent Expression of Angionenic CXC Chemokins ENA-781CXC Ligand (CXCL) 5 and Interleukin-8/CXCL8 in Human Non-Small Lung Cancer" Cancer Res vol. 64, pp. 1853-1860 (2004).

Porter et al, "The Efficient Design of Transplantable Tumor Assays" Br. J Cancer vol. 17, pp. 583-595 (1964).

Prochowinki & Kukowska, 1986, Nature vol. 322 pp. 848-850.

Rafi et al, "A large deletion together with a point mutation in the GALC gene is a common mutant allele in patients with infantile Krabbe disease" Hum Mol Genet, vol. 4, pp. 1285-1289 (1995).

Ramalho-Santos, et al. "Sternness': Transcriptional Profiling of Embyonic and Adult Stem Cells," Science vol. 298, pp. 597-600 (2002).

Renehan et al., 2004, Lancet,vol. 363pp. 1346 Insulin-like growth factor (IGF)-I, IGF binding protein-3, and cancer risk: systematic review and meta-regression analysis.

Reya et al, "Wnt Signaling Regulates B Lymphocyte Proliferation through a LEF-1 Dependent Mechanism," Immunity vol. 13, pp. 15-24 (2000).

Reya, et al., "Stem cells, cancer, and cancer stem cells," Nature 2001, 414, 105-111.

Reyes et al., 1992, Science vol. 256 pp. 1193-1195 Identification of the Ah receptor nuclear translocator protein (Arnt) as a component of the DNA binding form of the Ah receptor.

Rivas, et al. "New developments in the study of biomolecular associations via sedimentation equilibrium" Trends Biochem Sci vol. 18, 1993, pp. 284-287.

Robertson et al. "Germ-line transmission of genes introduced into cultured pluripotential cells by retroviral vector" Nature vol. 322, 1986, p. 445-8.

Robinson et al, "Further Check points in Th1 Development" Immunity vol. 16, pp. 755-758 (2002).

Roda Navarro et al., 2001, Biochem. Biophys. Acta. vol. 1520pp. 141-146 Molecular characterization of two novel alternative spliced variants of the KLRF1 gene and subcellular distribution of KLRF1 isoforms.

Rosenkilde et al, "The chemikine system—a major regulator of angiogenesis in health and disease" APMIS, vol. 112, pp. 481-495 (2004).

Ross, 1997, Nucleic Acid Hybridization, Table of Contents, only.

Sahin et al, "RPL38, FOSL1 and UPP1 Are Predominantly Expressed in the Pancreatic Ductal Epithelium" Pancreas, vol. 30, pp. 158-167 (2005).

Saitoh et al. "Frequent up-regulation of WNT5A mRNA in primary gastric cancer" Intl J Mol Med vol. 9, pp. 515-519 (2002).

Saitoh et al., "Up-regulation of WNT8B mRNA in human gastric cancer," Int J Oncology vol. 20, pp. 343-348 (2002).

Sakakibara et al.,"Growth and Metastasis of Surgical Specimens of Human Breast Carcinomas in SCID Mice," Cancer Journal from Scientific American (Sep./Oct. 1996) 2: 291-300.

Sambrook et al, "Molecular Cloning: A laboratory Manual," 1989, Cold Spring Harbor Press pp. 9.31-9.58.

Santamaria et al, "Cathepsin L2 a Novel Human Cysteine Proteinase Produced by Breast and Colorectal Carcinomas" Cancer Res. vol. 58, pp. 1624-1630 (1998).

Saulnier-Blache et al., 2000 A simple and highly sensitive radioenzymatic assay for lysophosphatidic acid quantification. J. Lipid Res. vol. 41(12) pp. 1947-1951.

Sazani, et al, "Nuclear antisense effects of neutral, anionic and cationic oligonucleotide analogs" Nucleic Acids Research, vol. 29, pp. 3965-3974 (2001).

Schedlich & Graham, Microsc Res Tech. Oct. 1, 2002;59(1):12-22. Role of insulin-like growth factor binding protein-3 in breast cancer cell growth.

Scheinberg et al., 1982, Science, vol. 215pp. 1151 Tumor imaging with radioactive metal chelates conjugated to monoclonal antibodies.

Schenck et al, "A highly conserved protein family interacting with the fragile X mental retardation protein (FMRO) and displaying selective interactions . . ." PNAS, vol. 98, pp. 8844-8849 (2001).

Schlosshauer, P. W. et al. APC truncation and increased beta-catenin levels in a human breast cancer cell line. Carcinogenesis 21, 1453-6 (2000).

"Schoenhard et al., 2002, Am. J. Physiol. Cell. Physiol. vol. 283 pp. C103-C114 Alternative splicing yields novel BMAL2 variants:tissue distribution and functional characterization".

Schteingart et al., 2001, J. Clin. Endocrinol. Metab vol. 86 pp. 3968 Overexpression of CXC Chemokines by an Adrenocortical Carcinoma: A Novel Clinical Syndrome.

Scott, et al. "Searching for peptide ligands with an epitope library" Science vol. 249, 1990, pp. 386-390.

Shelly et al., 1999, J. Cell Biochem vol. 73pp. 164-175 Notch-1 inhibits apoptosis in murine erythroleukemia cells and is necessary for differentiation induced by hybrid polar compounds.

Shen L et al., "Genome-wide Search for Loss of Heterozygosity Using Laser Capture Microdissected Tissue of Breast Carcinoma: An implication for Mutator Phenotype and Breast Cancer Pathogenesis," Cancer Res.(Jul. 15, 2000) 60: 3884.

Shimizu et al., 1997, Cell Growth Diff. vol. 8. pp. 1349-58Transformation by Wnt family proteins correlates with regulation of beta-catenin.

Shivdasani et al., 1995, Nature vol. 373 pp. 432-434 Absence of blood formation in mice lacking the T-cell leukaemia oncoprotein tal-1/SCL.

Shridhar et al, "Loss of Expression of a New Member of the DNAJ Protein Family Confers Resistance to Chemotherapeutic Agents Used in the Treatment of Ovarian Cancer" Cancer Research vol. 61, pp. 4258-4265 (2001).

Silverman "Implications for Tnase L in Prostate Cancer Biology" Biochemistry, vol. 42, pp. 1805-18012 (2003).

"Sjolander & Urbaniczky, Anal Chem. vol. 63pp. 2338-2345 Integrated Fluid Handling System for Biomolecular InteractionAna I y s i s".

"Smith et al, 2004, Br. J. Cancer vol. 91 pp. 1515-1524 S100A2 is strongly expressed in airway basal cells, preneoplasticbronchial lesions and primary non-small cell lung carcinomas".

Sokal & Sneath, 1963, Principles in Numerical Taxonomy, vol. xvi pp. 359.

"Sorlie et al.,Gene expression patterns of breast carcinomasdistinguish tumor subclasses withclinical implications 2001, PNAS, 98:10869".

Sorlie, et al. "Truncating somatic mutation In exon 15 oltheAPC gene Is a rare event in human breast carcinomas" Mutations in brief No. 179. Online. Hum Mutatl2, 215 (1998).

Southam, C.; Brunschwig, A.: 'Quantitative studies of autotranspianation of human cancer' Cancer vol. 14, 1961, pp. 971-978.

Spangrude, G. J.; Heimfeld, S.; Weissman, I. L.: 'Purification and characterization of mouse hematopoietic stem cells' Science vol. 241, 1988, pp. 58-62.

Spink, et al. "Structural basis of the Axinadenomatopolyposis coli interaction" Embo J 19, 2270-9 (2000).

Stewart et al. "Expression of retroviral vectors in transgenic mice obtained by embryo infection" Embo J. vol. 6, 1987, p. 383-8.

Sumerdon et al., 1990, Nucl. Med. Biol. vol. 17 pp. 247-254.

Szabo et al. "Surface plasmon resonance and its use in biomolecular interaction analysis (BIA)" Curr. Opin. Struct. Biol. vol. 5, 1995, pp. 699-705.

"Szmola et al., 2003, J. Biol. Chem vol. 278 pp. 48580-48509 Human Mesotrypsin Is a Unique Digestive ProteaseSpecialized for the Degradation of Trypsin Inhibitors".

Taipale, et al. "The Hedgehog and Wnt Signalling Pathways in Cancer" Nature, 411, 349-54 (2001).

Thorpe et al. "Improved antitumor effects of immunotoxins prepared with deglycosylated ricin A-chain and hindered disulfide linkages" Cancer Res. vol. 48, 1988, p. 6396-403.

Tijssen, 1993, Techniques in Biochemistry & Molecular Biology.

Togayachi et al, "Molecular Cloning and Characterization of UDO-GlcNac: Lactosylceramide 1, 3 N-Acetylglucosaminyltransferase . . ." J Biol Chem vol. 26, pp. 22032-22040 (2001).

"Tokunou et al., 2001, Am. J. pathol. vol. 158 pp. 1451 c-MET Expression in MyofibroblastsRole in Autocrine Activation and Prognostic Significance inLung Adenocarcinoma".

Townsend et al "The transporters associates with antigen presentation" Seminars in Cell Biology, vol. 4, pp. 53-61 (1993).

"Traver et al., 1998, Immunity, vol. 9pp. 47-57 Mice Defective in Two Apoptosis Pathwaysin the Myeloid Lineage DevelopAcute Myeloblastic Leukemia".

Tricot, G. et al.: 'Collection, tumor contamination, and engraftment kinetics of highly purified hematopoietic progenitor cells to support high dose therapy in multiple myeloma' Blood vol. 91, 1998, pp. 4489-4495.

Tsukamoto, et al. "Expression of the int-1 gene in transgenic mice Is associated with mammary gland hyperplasia and adenocarcinomas In male and female mice" Cell, vol. 55, p. 619-25 (1988).

Tuschl, et al. "Small Interfering RNAs: A Revolutionary Tool for the Analysis of Gene Function and Gene Therapy" Molecular Intervent. vol. 2, No. 3, 2002, pp. 158-167.

Uchida, N. et al.: 'Direct isolation of human central nervosystem stem cells' Proceedings of the National Academy of Sciences vol. 97, 2000, pp. 14720-14725.

Uren et al., 2000, J. Biol. Chem vol. 275 pp. 4374-4382.

Van De Vijver et al, "A gene-expression signature as a predictor of survival in breast cancer" N Eng. J Med vol. 347, pp. 1999-2009 (2002).

van de Wetering, et al. "The beta-cateninfTCF-4 complex imposes a crypt progenitor phenotype on colorectal cancer cells" Cell 111, 241-50 (2002).

Van Den Berg, "The Hedgehog and Wnt signaling pathways in cancer," Nature, vol. 411, pp. 3189-202 (1998).

Van Der Lugt, N. M. et al, "Posterior transformation, neurological abnormalities, and severe hematopoietic defects in mice with a targeted deletion of the bmi-1 proto-oncogene" Genes and Development 8, 757-769 (1994).

Van Lohuizen, M. et al., "Sequence Similarity Between the Mammalian bmi-1 Ptoto-Oncogene and the Drosophila regulatory Genes Psc and Su (z)2." Nature 353-355 (1991).

van Noort et al., 2002, Exp. Cell res. vol. 274 pp. 264-272 Identification of two novel regulated serines in the N terminus of beta-catenin.

van Noort et al., 2002, J. Biol. Chem. vol. 277 pp. 17901-17908 Wnt Signaling Controls the Phosphorylation Status of—Catenin*.

Van Osdol et al., 1994, J. Natl Cancer Institiute. vol. 86: pp. 1853-1859.

Varnum-Finney, B. et al. Pluripotent, cytokine-dependent, hematopoietic stem cells are immortalized by constitutive Notch1 signaling. Nat Med 6, 1278-81 (2000).

Vestey et al, "Immunohistochemical expression of insulin-like growth factor binding protein 3 in invasive breast cancers and ductal carcinoma in situ: implications for clincopathology and patient outcome" Breast Cancer Res., vol. 7, pp. R119-R129 (2005).

Voena, C. et al.: 'Qualitative and quantitative polymerase chain reaction detection of the residual myeloma cell contamination after positive selection of CD34+ cells with small- and large-scale Miltenyi cell sorting system' Br J Haematol vol. 117, 2002, pp. 642-645.

Wagner, et al. "The insulin-like growth factor-1 pathway mediator genes: SHC1 Met300Val shows a protective effect in breast cancer" Carcinogenesis, vol. 25, pp. 2473-2478 (2004).

Wang, et al., "Gene-expression profiles to predict distant metastasis of lymphnode negative primary breast cancer," Lancet vol. 365, pp. 671-679 (2005).

Wantanabe & Uchida, 1995, Biochem.Biophys.Res. Commun.. vol. 2 pp. 265-272.

Webster et al., 2000, Genes Chromosomes Cancer vol. 28 pp. 443-453.

Weerararna, et al. "Wnt5a signaling directly affects cells motility and invasion of metastatic melanoma," Cancer Cell, Cell Press, vol. 1, No. 3, Apr. 1, 2002, pp. 279-288.

Weidmann et al., 1997, Leukemia,vol. 11 pp. 79-713 Establishment and characterization of a new, factor-independent acute myeloid leukemia line designated Ei501.

Weijzen S., et al., "Activation of Notch-1 signaling maintains the neoplastic phenotype in human Ras-transformed cells,"Nat. Med. 8:979-986, Nature Publishing Group New York, NY, U.S.A (2002).

Weinstein et al., 1992, Science, vol. 258 pp. 447-451 Neural computing in cancer drug development: predicting mechanism of action.

Weinstein et al., 1997, Science vol. 275 pp. 343-390 An information-intensive approach to the molecular pharmacology of cancer.

Bergsagel et al., 1969 Cancer Research vol. 29 pp. 2334-2338, "THe Improvement of the Animal Tumor Model.".

Dontu, et al. "Survival of mammary stem cells in suspension culture: implications for stem cell biology and neoplasia" J Mammary Gland Biol Neoplasia. Jan. 2005;10(1):75-86.

US 5,962,233, 10/1999, Livak (withdrawn)

* cited by examiner

A. B. C.

A.

B.

C.

B

A

Real-time PCR showed differential expression of α-catenin and E-cadherin in passaged breast tumors Real-time PCR showed differential expression of α-catenin and E-cadherin in a colon tumor

SEQUENCE LISTING

```
<160> NUMBER OF SEQ ID NOS: 1

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
gggcaagttt cccgtgcagt t                                              21
```

COMPOSITIONS AND METHODS FOR TREATING AND DIAGNOSING CANCER

This application is a Continuation of U.S. patent application Ser. No. 11/451,774, filed Jun. 13, 2006, which claims the benefit of the filing date of U.S. Provisional Appl. No. 60/690,001, filed Jun. 13, 2005, both of which are incorporated herein by reference in their entireties.

U.S. application Ser. No. 11/050,282, filed Feb. 3, 2005, U.S. Appl No. 60/541,527, filed Feb. 3, 2004, and U.S. application Ser. No. 10/864,207, filed Jun. 9, 2004, are herein incorporated by reference in their entirety.

This invention was made with government support under Grant No. 5P01CA07513606 awarded by the National Institutes of Health. The Government has certain rights in the invention.

FIELD OF THE INVENTION

The present invention relates to compositions and methods for treating, characterizing, and diagnosing cancer. In particular, the present invention provides gene expression profiles and signatures associated with solid tumor stem cells, as well as novel stem cell cancer markers useful for the diagnosis, characterization, prognosis, and treatment of solid tumor stem cells and cancer.

BACKGROUND OF THE INVENTION

Breast cancer is the most common female malignancy in most industrialized countries, as it is estimated to affect about 10% of the female population during their lifespan. Although its mortality has not increased along with its incidence, due to earlier diagnosis and improved treatment, it is still one of the predominant causes of death in middle-aged women. Despite earlier diagnosis of breast cancer, about 1-5% of women with newly diagnosed breast cancer have a distant metastasis at the time of the diagnosis. In addition, approximately 50% of the patients with local disease who are primarily diagnosed eventually relapse with the metastasis. Eighty-five percent of these recurrences take place within the first five years after the primary manifestation of the disease.

On presentation, most patients with metastatic breast cancer have only one or two organ systems involved. As the disease progresses over time, multiple sites usually become involved. Indeed, metastases can be found in nearly every organ of the body at autopsy. The most common sites of metastatic involvement observed are locoregional recurrences in the skin and soft tissues of the chest wall, as well as in axilla, and supraclavicular area. The most common site for distant metastasis is the bone (30-40% of distant metastasis), followed by lung and liver. Metastatic breast cancer is generally considered to be an incurable disease. However, the currently available treatment options often prolong the disease-free state and overall survival rate, as well as increase the quality of the life. The median survival from the manifestation of distant metastases is about three years.

Current methods of diagnosing and staging breast cancer include the tumor-node-metastasis (TNM) system that relies on tumor size, tumor presence in lymph nodes, and the presence of distant metastases as described in the American Joint Committee on Cancer: AJCC Cancer Staging Manual. Philadelphia, Pa.: Lippincott-Raven Publishers, 5th ed., 1997, pp 171-180, and in Harris, J R: "Staging of breast carcinoma" in Harris, J. R., Hellman, S., Henderson, I. C., Kinne D. W. (eds.): Breast Diseases. Philadelphia, Lippincott, 1991. These parameters are used to provide a prognosis and select an appropriate therapy. The morphologic appearance of the tumor can also be assessed but because tumors with similar histopathologic appearance can exhibit significant clinical variability, this approach has serious limitations. Finally assays for cell surface markers can be used to divide certain tumors types into subclasses. For example, one factor considered in the prognosis and treatment of breast cancer is the presence of the estrogen receptor (ER) as ER-positive breast cancers typically respond more readily to hormonal therapies such as tamoxifen than ER-negative tumors. Yet these analyses, though useful, are only partially predictive of the clinical behavior of breast tumors, and there is much phenotypic diversity present in breast cancers that current diagnostic tools fail to detect.

Traditional modes of cancer therapy include radiation therapy, chemotherapy, and hormonal therapy. Yet because of the difficulty in predicting the clinical course of early stage breast cancer from standard clinical and pathologic features, current practice is to offer systemic chemotherapy to most women even though the majority of these women can have a good outcome in the absence of chemotherapy. Chemotherapy has severe side effects and itself carries a 1% mortality rate, and thus unnecessary suffering and deaths could be avoided if patients could be divided into high and low risk subgroups. Thus, there exists a need for improved methods of classifying tumors for better prognosis and treatment selection.

Furthermore, although current therapies can often prolong the disease-free state and overall survival when used on high-risk patients, they are limited by their lack of specificity and the emergence of treatment-resistant cancer cells. Approximately two thirds of people diagnosed with cancer will die of their cancer within five years. Thus there is a great need for the identification of additional genes that can serve as selective therapies for the treatment of cancer.

Colorectal cancer is the third most common cancer and the fourth most frequent cause of cancer deaths worldwide. Approximately 5-10% of all colorectal cancers are hereditary with one of the main forms being familial adenomatous polyposis (FAP), an autosomal dominant disease in which about 80% of affected individuals contain a germline mutation in the adenomatous polyposis coli (APC) gene. Colorectal carcinoma has a tendency to invade locally by circumferential growth and for lymphatic, hematogenous, transperitoneal, and perineural spread. The most common site of extralymphatic involvement is the liver, with the lungs the most frequently affected extra-abdominal organ. Other sites of hematogenous spread include the bones, kidneys, adrenal glands, and brain.

The current staging system for colorectal cancer is based on the degree of tumor penetration through the bowel wall and the presence or absence of nodal involvement. This staging system is defined by three major Duke's classifications: Duke's A disease is confined to submucosa layers of colon or rectum; Duke's B disease has tumors that invade through muscularis propria and can penetrate the wall of the colon or rectum; and Duke's C disease includes any degree of bowel wall invasion with regional lymph node metastasis.

Surgical resection is highly effective for early stage colorectal cancers, providing cure rates of 95% in Duke's A and 75% in Duke's B patients. The presence of positive lymph node in Duke's C disease predicts a 60% likelihood of recurrence within five years. Treatment of Duke's C patients with a post surgical course of chemotherapy reduces the recurrence rate to 40%-50%, and is now the standard of care for these patients. Because of the relatively low rate of reoccurrence, the benefit of post surgical chemotherapy in Duke' B has been harder to detect and remains controversial. However, the Duke's B classification is imperfect as approximately 20-30% of these patients behave more like Duke's C and relapse within five years. Thus there is a clear need to identify better prognostic factors for selecting Duke's B patients that are likely to relapse and would benefit from therapy.

During normal animal development, cells of most or all tissues are derived from normal precursors, called stem cells (Morrison et al., Cell 88(3): 287-98 (1997); Morrison et al., Curr. Opin. Immunol. 9(2): 216-21 (1997); Morrison et al., Annu. Rev. Cell. Dev. Biol. 11: 35-71 (1995)). Stem cells are cells that: (1) have extensive proliferative capacity; 2) are capable of asymmetric cell division to generate one or more kinds of progeny with reduced proliferative or developmental potential; and (3) are capable of symmetric cell divisions for self-renewal or self-maintenance. In adult animals, some cells (including cells of the blood, gut, breast ductal system, and skin) are constantly replenished from a small population of stem cells in each tissue. The best-known example of adult cell renewal by the differentiation of stem cells is the hematopoietic system where developmentally immature precursors (hematopoietic stem and progenitor cells) respond to molecular signals to form the varied blood and lymphoid cell types.

Solid tumors are composed of heterogeneous cell populations. For example, breast cancers are a mixture of cancer cells and normal cells, including mesenchymal (stromal) cells, inflammatory cells, and endothelial cells. Classic models of cancer hold that phenotypically distinct cancer cell populations all have the capacity to proliferate and give rise to a new tumor. In the classical model, tumor cell heterogeneity results from environmental factors as well as ongoing mutations within cancer cells resulting in a diverse population of tumorigenic cells. This model rests on the idea that all populations of tumor cells would have some degree of tumorigenic potential. (Pandis et al., Genes, Chromosomes & Cancer 12:122-129 (1998); Kuukasjrvi et al., Cancer Res. 57: 1597-1604 (1997); Bonsing et al., Cancer 71: 382-391 (1993); Bonsing et al., Genes Chromosomes & Cancer 82: 173-183 (2000); Beerman H et al., Cytometry. 12(2): 147-54 (1991); Aubele M & Werner M, Analyt. Cell. Path. 19: 53 (1999); Shen L et al., Cancer Res. 60: 3884 (2000).).

An alternative model for the observed solid tumor cell heterogeneity is that solid tumors result from a "solid tumor stem cell" (or "cancer stem cell" from a solid tumor) that subsequently undergoes chaotic development through both symmetric and asymmetric rounds of cell divisions. In this stem cell model, solid tumors contain a distinct and limited (possibly even rare) subset of cells that share the properties of normal "stem cells", in that they extensively proliferate and efficiently give rise both to additional solid tumor stem cells (self-renewal) and to the majority of tumor cells of a solid tumor that lack tumorigenic potential. Indeed, mutations within a long-lived stem cell population can initiate the formation of cancer stem cells that underlie the growth and maintenance of tumors and whose presence contributes to the failure of current therapeutic approaches.

Although great strides have been made understanding the genetic changes that lead to cancer (e.g. breast cancer and colorectal cancer), the lack of reliable tumor assay for de novo human cancer cells has hindered the ability to understand the effects of these mutations at the cellular level. Also, the lack of identified cancer markers for solid tumor stem cells has hindered the development of diagnostics and therapeutics for cancer patients (e.g. breast cancer patients). As such, what is needed is a reliable tumor assay as well as the identification of cancer markers for solid tumor stem cells.

SUMMARY OF THE INVENTION

The present invention relates to compositions and methods for treating, characterizing, and diagnosing cancer. In particular, the present invention provides gene expression profiles and signatures associated with solid tumor stem cells, as well as novel stem cell cancer markers useful for the diagnosis, characterization, prognosis, and treatment of solid tumor stem cells. The present invention further provides cancer stem cell gene signatures derived from solid tumor stem cell markers that when detected in a tumor sample act as significant predictors of poor clinical outcome, including high risk of metastasis and death.

In some embodiments, the present invention provides methods of detecting solid tumor stem cells, comprising; a) providing a tissue sample from a subject, and b) detecting at least one stem cell cancer marker (e.g., 1, 2, 3, 5, 10, . . . etc.) from Tables 4-9 in the tissue sample under conditions such that the presence or absence of solid tumor stem cells in the tissue sample is determined. In a further embodiment, the present invention provides methods of detecting solid tumor stem cells, comprising: a) obtaining a mixture of solid tumor stem cells and solid tumor cells from, for example, a tissue sample from a subject; and, b) detecting those cancer cells that express low levels or undetectable levels of e-cadherin or alpha catenin as compared to normal breast epithelial cells. In some embodiments, the mark is e-cadherin or alpha catenin. Those cancer cells expressing low levels or undetectable levels of e-cadherin or alpha catenin are confirmed to be solid tumor stem cells by demonstrating their tumorigenicity. In a further embodiment of the present invention a method of detecting solid tumor stem cells is provided comprising: a) obtaining a mixture of solid tumor stem cells and solid tumor cells from, for example, a tissue sample from a subject; and b) detecting those cancer cells that express low levels or undetectable levels of e-cadherin and also express low or undetectable levels of one or more of MMP7, Nov, FOSL1 or IL1R2 (e.g., e.g., the levels being compared to normal breast epithelia). Those cancer cells expressing low or undetectable levels of e-cadherin and one or more of MMP7, Nov, FOSL1 or IL1R2 are confirmed to be solid tumor stem cells by demonstrating their tumorigenicity. In a further embodiment of this invention a method of detecting solid tumor stem cells is provided comprising: a) obtaining a mixture of solid tumor stem cells and solid tumor cells from, for example, a tissue sample from a subject; and, b) detecting those cancer cells that express low levels or undetectable levels of e-cadherin and express elevated levels of one or both of SHC1 or FLJ20152 (e.g., e.g., the levels being compared to normal breast epithelia). Those cancer cells expressing low or undetectable levels of e-cadherin and elevated levels of one or both of SHC1 or FLJ20152 are confirmed to be solid tumor stem cells by their tumorigenicity. In a further embodiment of the present invention a method of detecting solid tumor stem cells is provided comprising: a) obtaining a mixture of solid tumor stem cells and solid tumor cells from, for example, a tissue sample from a subject; and b) detecting those cancer cells that express low levels or undetectable levels of alpha-catenin and also express low or undetectable levels of one or more of NCSTN, LNX, ARMCX3, D2S448, GLUL or RB1 (e.g., e.g., the levels being compared to normal breast epithelia). Those cancer cells expressing low or undetectable levels of alpha-catenin and low or undetectable levels of one or more of NCSTN, LNX, ARMCX3, D2S448, GLUL or RB1 are confirmed to be solid tumor stem cells by demonstrating their tumorigenicity. In yet another embodiment, the present invention provides methods of detecting solid tumor stem cells, comprising a) obtaining a mixture of solid tumor stem cells and solid tumor cells from, for example, a tissue sample from a subject; and b) detecting those cancer cells that express low levels or undetectable levels of alpha-catenin and also express elevated levels of one or more of EDG2, CAV1, CAV2, DCBLD2, IGFBP3, S100A2, CXCL5, MET, FOXQ1, CDKN2A or MFHAS1 (e.g., e.g., the levels being compared to normal breast epithelia). Those cancer cells expressing low or undetectable levels of alpha-catenin and elevated levels of one or more of EDG2, CAV1, CAV2, DCBLD2, IGFBP3, S100A2, CXCL5, MET, FOXQ1, CDKN2A or MFHAS1 are confirmed to be solid tumor stem cells by demonstrating their tumorigenicity. In another embodiment of the present invention, a method of detecting solid tumor stem cells is provided comprising: a) obtaining a mixture of solid tumor stem cells and solid tumor cells from, for example, a tissue sample from a subject; and b) detecting those cancer cells that express low levels or undetectable levels of alpha-catenin and express elevated levels of MET (e.g., e.g., the levels being compared to normal breast epithelia). Those cancer cells expressing low or undetectable levels of alpha-catenin and elevated levels of MET are confirmed to be solid tumor stem cells by demonstrating their tumorigenicity. In still a further embodiment of the present invention, a method of detecting solid tumor stem cells and then separating those solid tumor stem cells into one or more populations of solid tumor stem cells is provided comprising: a) obtaining a mixture of solid tumor stem cells and solid tumor cells from, for example, a tissue sample from a subject; and, b) separating those cells that express low levels or undetectable levels of e-cadherin from those cells expressing low levels or undetectable levels of alpha-catenin (e.g., e.g., the levels being compared to normal breast epithelia). In each case, those cancers cells expressing low levels or undetectable levels of either e-cadherin or alpha-catenin are confirmed to be solid tumor stem cells by demonstrating their tumorigenicity.

In a further embodiment of the present invention a method of detecting solid tumor stem cells is provided comprising: a) obtaining a mixture of solid tumor stem cells and solid tumor cells from, for example, a tissue sample from a subject; and b) detecting those cancer cells that express low levels or undetectable levels of two or more of e-cadherin MMP7, Nov, FOSL1 or IL1R2 (e.g., e.g., the levels being compared to normal breast epithelia). Those cancer cells expressing low or undetectable levels of two or more of e-cadherin, MMP7, Nov, FOSL1 or IL1R2 are confirmed to be solid tumor stem cells by demonstrating their tumorigenicity. In a further embodiment of the present invention a method of detecting solid tumor stem cells is provided comprising: a) obtaining a mixture of solid tumor stem cells and solid tumor cells from, for example, a tissue sample from a subject; and b) detecting those cancer cells that express low levels or undetectable levels of two or more of alpha-catenin, NCSTN, LNX, ARMCX3, D2S448, GLUL or RB1 (e.g., e.g., the levels being compared to normal breast epithelia). Those cancer cells expressing low or undetectable levels of two or more of alpha-catenin, NCSTN, LNX, ARMCX3, D2S448, GLUL or RB1 are confirmed to be solid tumor stem cells by demonstrating their tumorigenicity. In yet another embodiment, the present invention provides methods of detecting solid tumor stem cells, comprising a) obtaining a mixture of solid tumor stem cells and solid tumor cells from, for example, a tissue sample from a subject; and b) detecting those cancer cells that express elevated levels of two or more of EDG2, CAV1, CAV2, DCBLD2, IGFBP3, S100A2, CXCL5, MET, FOXQ1, CDKN2A or MFHAS1 (e.g., e.g., the levels being compared to normal breast epithelia). Those cancer cells expressing elevated levels of two or more of EDG2, CAV1, CAV2, DCBLD2, IGFBP3, S100A2, CXCL5, MET, FOXQ1, CDKN2A or MFHAS1 are confirmed to be solid tumor stem cells by demonstrating their tumorigenicity. In another embodiment, the present invention provides methods of detecting solid tumor stem cells, comprising a) obtaining a mixture of solid tumor stem cells and solid tumor cells from, for example, a tissue sample from a subject; and b) detecting those cancer cells that express elevated levels of SHC1 and FLJ20152 (e.g., the levels being compared to normal breast epithelia). Those cancer cells expressing elevated levels of SHC1 and FLJ20152 are confirmed to be solid tumor stem cells by demonstrating their tumorigenicity. In another embodiment, the present invention provides methods of detecting solid tumor stem cells, comprising a) obtaining a mixture of solid tumor stem cells and solid tumor cells from, for example, a tissue sample from a subject; and b) detecting those cancer cells that express elevated levels of SHC1 and FLJ20152 (the levels being compared to normal breast epithelia). Those cancer cells expressing elevated levels of SHC1 and FLJ20152 are confirmed to be solid tumor stem cells by demonstrating their tumorigenicity.

In particular embodiments, detecting the solid tumor stem cells comprises determining the presence of (or absence of), or an expression level for at least one stem cell cancer marker. In other embodiments, the detecting comprises detecting mRNA expression of the at least one stem cell cancer marker. In particular embodiments, the detecting comprises exposing the stem cell cancer marker mRNA to a nucleic acid probe complementary to the stem cell cancer marker mRNA.

In certain embodiments, the detecting comprises detecting polypeptide expression of the at least one stem cell cancer marker. In other embodiments, the detecting comprises exposing the stem cell cancer marker polypeptide to an antibody specific to the stem cell cancer marker polypeptide and detecting the binding of the antibody to the stem cell cancer polypeptide. In further embodiments, the subject comprises a human subject. In additional embodiments, the tissue sample comprises tumor tissue. In some embodiments, the tumor tissue sample is a post-surgical tumor tissue sample (e.g. tumor biopsy).

In certain embodiments, the present invention provides an isolated population of solid tumor stem cells obtained from a solid tumor of epithelial origin, wherein the population comprises at least 75% solid tumor stem cells and less than 25% solid tumor cells (alternatively at least about 90% solid tumor stem cells and less than 10% solid tumor cells), wherein the solid tumor stem cells: are tumorigenic; and, express low levels or undetectable levels of e-cadherin or alpha-catenin as compared to normal epithelium. In another embodiment, the present invention provides an isolated population of solid tumor stem cells obtained from a solid tumor of epithelial origin, wherein the population comprises at least about 75% solid tumor stem cells and less than 25% solid tumor cells (alternatively at least about 90% solid tumor stem cells and less than 10% solid tumor cells), wherein the solid tumor stem cells: are tumorigenic; express low levels or undetectable levels of e-cadherin; and, express low levels or undetectable levels of one or more of MMP7, Nov, FOSL1, or IL1R2 (e.g., the levels being compared to normal breast epithelia). In still another embodiment, the present invention provides an isolated population of solid tumor stem cells obtained from a solid tumor of epithelial origin, wherein the population comprises at least about 75% solid tumor stem cells and less than 25% solid tumor cells (alternatively at least about 90% solid tumor stem cells and less than 10% solid tumor cells), wherein the solid tumor stem cells: are tumorigenic; express low levels or undetectable levels of e-cadherin; and, express elevated levels of SHC1 or FLJ20152 (e.g., the levels being compared to normal breast epithelia). In yet another embodiment, the present invention provides an isolated population of solid tumor stem cells obtained from a solid tumor of epithelial origin, wherein the population comprises at least about 75% solid tumor stem cells and less than 25% solid tumor cells (alternatively at least about 90% solid tumor stem cells and less than 10% solid tumor cells), wherein the solid tumor stem cells: are tumorigenic; express low levels or undetectable levels of e-cadherin; express low levels or undetectable levels of one or more of MMP7, Nov, FOSL1, or IL1R2; and, express elevated levels of SHC1 or FLJ20152 (e.g., the levels being compared to normal breast epithelia).

In another embodiment, the present invention provides an isolated population of solid tumor stem cells obtained from a solid tumor of epithelial origin, wherein the population comprises at least about 75% solid tumor stem cells and less than 25% solid tumor cells (alternatively at least about 90% solid tumor stem cells and less than 10% solid tumor cells), wherein the solid tumor stem cells: are tumorigenic; and express low levels or undetectable levels of two or more of e-cadherin, MMP7, Nov, FOSL1, or IL1R2 (e.g., the levels being compared to normal breast epithelia). In another embodiment, the present invention provides an isolated population of solid tumor stem cells obtained from a solid tumor of epithelial origin, wherein the population comprises at least about 75% solid tumor stem cells and less than 25% solid tumor cells (alternatively at least about 90% solid tumor stem cells and less than 10% solid tumor cells), wherein the solid tumor stem cells: are tumorigenic; and, express elevated levels of SHC1 and FLJ20152 (e.g., the levels being compared to normal breast epithelia). In still another embodiment the present invention provides an isolated population of solid tumor stem cells obtained from a solid tumor of epithelial origin, wherein the population comprises at least about 75% solid tumor stem cells and less than 25% solid tumor cells (alternatively at least about 90% solid tumor stem cells and less than 10% solid tumor cells), wherein the solid tumor stem cells: are tumorigenic; express low levels or undetectable levels of one or more of e-cadherin, MMP7, Nov, FOSL1, or IL1R2 (e.g., the levels being compared to normal breast epithelia); and, express elevated levels of SHC1 or FLJ20152 (e.g., the levels being compared to normal breast epithelia).

In certain embodiments, the present invention provides an isolated population of solid tumor stem cells obtained from a solid tumor of epithelial origin, wherein the population comprises at least 75% solid tumor stem cells and less than 25% solid tumor cells (alternatively at least about 90% solid tumor stem cells and less than 10% solid tumor cells), wherein the solid tumor stem cells: are tumorigenic; and, express low levels or undetectable levels of alpha-catenin; and, express low levels or undetectable levels of one or more of NCSTN, LNX, ARMCX3, D2S448, GLUL or RB1 (e.g., the levels being compared to normal breast epithelia). In still another embodiment, the present invention provides an isolated population of solid tumor stem cells obtained from a solid tumor of epithelial origin, wherein the population comprises at least about 75% solid tumor stem cells and less than 25% solid tumor cells (alternatively at least about 90% solid tumor stem cells and less than 10% solid tumor cells), wherein the solid tumor stem cells: are tumorigenic; express low levels or undetectable levels of alpha-catenin; and, express elevated levels of one or more of EDG2, CAV1, CAV2, DCBLD2, IGFBP3, S100A2, CXCL5, MET, FOXQ1, CDKN2A, CTSL2, or MFHAS1 (e.g., the levels being compared to normal breast epithelia). In yet another embodiment, the present invention provides an isolated population of solid tumor stem cells obtained from a solid tumor of epithelial origin, wherein the population comprises at least about 75% solid tumor stem cells and less than 25% solid tumor cells (alternatively at least about 90% solid tumor stem cells and less than 10% solid tumor cells), wherein the solid tumor stem cells: are tumorigenic; express low levels or undetectable levels of alpha-catenin; express low levels or undetectable levels of one or more of NCSTN, LNX, ARMCX3, D2S448, GLUL or RB1; and, express elevated levels of one or more of EDG2, CAV1, CAV2, DCBLD2, IGFBP3, S100A2, CXCL5, MET, FOXQ1, CDKN2A, CTSL2, or MFHAS1 (e.g., the levels being compared to normal breast epithelia). In another embodiment, the present invention provides an isolated population of solid tumor stem cells obtained from a solid tumor of epithelial origin, wherein the population comprises at least about 75% solid tumor stem cells and less than 25% solid tumor cells (alternatively at least about 90% solid tumor stem cells and less than 10% solid tumor cells), wherein the solid tumor stem cells: are tumorigenic; express low levels or undetectable levels of alpha-catenin; and, elevated levels of MET (e.g., the levels being compared to normal breast epithelia).

In certain embodiments, the present invention provides an isolated population of solid tumor stem cells obtained from a solid tumor of epithelial origin, wherein the population comprises at least 75% solid tumor stem cells and less than 25% solid tumor cells (alternatively at least about 90% solid tumor stem cells and less than 10% solid tumor cells), wherein the solid tumor stem cells: are tumorigenic; and, express low levels or undetectable levels of two or more of alpha-catenin, NCSTN, LNX, ARMCX3, D2S448, GLUL or RB1 (e.g., the levels being compared to normal breast epithelia). In another embodiment, the present invention provides an isolated population of solid tumor stem cells obtained from a solid tumor of epithelial origin, wherein the population comprises at least about 75% solid tumor stem cells and less than 25% solid tumor cells (alternatively at least about 90% solid tumor stem cells and less than 10% solid tumor cells), wherein the solid tumor stem cells: are tumorigenic; and, express elevated levels of two or more of EDG2, CAV1, CAV2, DCBLD2, IGFBP3, S100A2, CXCL5, MET, FOXQ1, CDKN2A, CTSL2, or MFHAS1 (e.g., the levels being compared to normal breast epithelia). In still another embodiment, the present invention provides an isolated population of solid tumor stem cells obtained from a solid tumor of epithelial origin, wherein the population comprises at least 75% solid tumor stem cells and less than 25% solid tumor cells (alternatively at least about 90% solid tumor stem cells and less than 10% solid tumor cells), wherein the solid tumor stem cells: are tumorigenic; express low levels or undetectable levels of one or more of alpha-catenin, NCSTN, LNX, ARMCX3, D2S448, GLUL or RB1 (e.g., the levels being compared to normal breast epithelia); and express elevated levels of one or more of EDG2, CAV1, CAV2, DCBLD2, IGFBP3, S100A2, CXCL5, MET, FOXQ1, CDKN2A, CTSL2, or MFHAS1 (e.g., the levels being compared to normal breast epithelia).

In certain embodiments, the present invention provides an isolated population of solid tumor stem cells obtained from a solid tumor of epithelial origin, wherein the population comprises at least 75% solid tumor stem cells and less than 25% solid tumor cells (alternatively at least about 90% solid tumor stem cells and less than 10% solid tumor cells), wherein the solid tumor stem cells: are tumorigenic; and, express low levels or undetectable levels of e-cadherin or alpha-catenin as compared to normal epithelium. In another embodiment, the present invention provides an isolated population of solid tumor stem cells obtained from a solid tumor of epithelial origin, wherein the population comprises at least about 75% solid tumor stem cells and less than 25% solid tumor cells (alternatively at least about 90% solid tumor stem cells and less than 10% solid tumor cells), wherein the solid tumor stem cells: are tumorigenic; express low levels or undetectable levels of e-cadherin; and, express low levels or undetectable levels of one or more of MMP7, Nov, FOSL1, IL1R2, SFRP1, KRT6B, G0S2, IL8, B3GNT5, or FGFBP1. (e.g., the levels being compared to normal breast epithelia). In still another embodiment, the present invention provides an isolated population of solid tumor stem cells obtained from a solid tumor of epithelial origin, wherein the population comprises at least about 75% solid tumor stem cells and less than 25% solid tumor cells (alternatively at least about 90% solid tumor stem cells and less than 10% solid tumor cells), wherein the solid tumor stem cells: are tumorigenic; express low levels or undetectable levels of e-cadherin; and, express elevated levels of one or more of SHC1, FLJ20152, ARNT, CYFIP2, C17orf27, TAP1, RNASEL, or LOC57168 (e.g., the levels being compared to normal breast epithelia). In yet another embodiment, the present invention provides an isolated population of solid tumor stem cells obtained from a solid tumor of epithelial origin, wherein the population comprises at least about 75% solid tumor stem cells and less than 25% solid tumor cells (alternatively at least about 90% solid tumor stem cells and less than 10% solid tumor cells), wherein the solid tumor stem cells: are tumorigenic; express low levels or undetectable levels of e-cadherin; express low levels or undetectable levels of one or more of MMP7, Nov, FOSL1, IL1R2, SFRP1, KRT6B, G0S2, IL8, B3GNT5, or FGFBP1; and, express elevated levels of one or more of SHC1, FLJ20152, ARNT, CYFIP2, C17orf27, TAP1, RNASEL, or LOC57168 (e.g., the levels being compared to normal breast epithelia).

In another embodiment, the present invention provides an isolated population of solid tumor stem cells obtained from a solid tumor of epithelial origin, wherein the population comprises at least about 75% solid tumor stem cells and less than 25% solid tumor cells (alternatively at least about 90% solid tumor stem cells and less than 10% solid tumor cells), wherein the solid tumor stem cells: are tumorigenic; and express low levels or undetectable levels of two or more of e-cadherin, MMP7, Nov, FOSL1, IL1R2, SFRP1, KRT6B, G0S2, IL8, B3GNT5, or FGFBP1 (e.g., the levels being compared to normal breast epithelia). In another embodiment, the present invention provides an isolated population of solid tumor stem cells obtained from a solid tumor of epithelial origin, wherein the population comprises at least about 75% solid tumor stem cells and less than 25% solid tumor cells (alternatively at least about 90% solid tumor stem cells and less than 10% solid tumor cells), wherein the solid tumor stem cells: are tumorigenic; and, express elevated levels of two or more of SHC1, FLJ20152, ARNT, CYFIP2, C17orf27, TAP1, RNASEL, or LOC57168 (e.g., the levels being compared to normal breast epithelia). In still another embodiment, the present invention provides an isolated population of solid tumor stem cells obtained from a solid tumor of epithelial origin, wherein the population comprises at least about 75% solid tumor stem cells and less than 25% solid tumor cells (alternatively at least about 90% solid tumor stem cells and less than 10% solid tumor cells), wherein the solid tumor stem cells: are tumorigenic; express low levels or undetectable levels of one or more of e-cadherin, MMP7, Nov, FOSL1, IL1R2, SFRP1, KRT6B, G0S2, IL8, B3GNT5, or FGFBP1 (e.g., the levels being compared to normal breast epithelia); and express elevated levels of one or more of SHC1, FLJ20152, ARNT, CYFIP2, C17orf27, TAP1, RNASEL, or LOC57168 (e.g., the levels being compared to normal breast epithelia).

In certain embodiments, the present invention provides an isolated population of solid tumor stem cells obtained from a solid tumor of epithelial origin, wherein the population comprises at least 75% solid tumor stem cells and less than 25% solid tumor cells (alternatively at least about 90% solid tumor stem cells and less than 10% solid tumor cells), wherein the solid tumor stem cells: are tumorigenic; and, express low levels or undetectable levels of alpha-catenin; and, express low levels or undetectable levels of one or more of NCSTN, LNX, ARMCX3, D2S448, TUSC1, GLUL, RB1, BEX2, SLC12A2, GALC, NGFRAP1, FGF13, KIAA1102, SLC1A4, and DNAJD1 (e.g., the levels being compared to normal breast epithelia). In still another embodiment, the present invention provides an isolated population of solid tumor stem cells obtained from a solid tumor of epithelial origin, wherein the population comprises at least about 75% solid tumor stem cells and less than 25% solid tumor cells (alternatively at least about 90% solid tumor stem cells and less than 10% solid tumor cells), wherein the solid tumor stem cells: are tumorigenic; express low levels or undetectable levels of alpha-catenin; and, express elevated levels of one or more of EDG2, CAV1, CAV2, DCBLD2, IGFBP3, S100A2, CXCL5, MET, FOXQ1, CDKN2A, MFHAS1, IL27RA, KLRF1, PKCA, UPP1, CTSL2, SLC7A5, ARNTL2, PRSS1, PRSS2, PRSS3, VNN1, RAB38, ZBED2, MYEOV, MAL, IMP-3, and DHRS9 (e.g., the levels being compared to normal breast epithelia). In yet another embodiment, the present invention provides an isolated population of solid tumor stem cells obtained from a solid tumor of epithelial origin, wherein the population comprises at least about 75% solid tumor stem cells and less than 25% solid tumor cells (alternatively at least about 90% solid tumor stem cells and less than 10% solid tumor cells), wherein the solid tumor stem cells: are tumorigenic; express low levels or undetectable levels of alpha-catenin; express low levels or undetectable levels of one or more of NCSTN, LNX, ARMCX3, D2S448, TUSC1, GLUL, RB1, BEX2, SLC12A2, GALC, NGFRAP1, FGF13, KIAA1102, SLC1A4, and DNAJD1; and, express elevated levels of one or more of EDG2, CAV1, CAV2, DCBLD2, IGFBP3, S100A2, CXCL5, MET, FOXQ1, CDKN2A, MFHAS1, IL27RA, KLRF1, PKCA, UPP1, CTSL2, SLC7A5, ARNTL2, PRSS1, PRSS2, PRSS3, VNN1, RAB38, ZBED2, MYEOV, MAL, IMP-3, and DHRS9 (e.g., the levels being compared to normal breast epithelia). In another embodiment, the present invention provides an isolated population of solid tumor stem cells obtained from a solid tumor of epithelial origin, wherein the population comprises at least about 75% solid tumor stem cells and less than 25% solid tumor cells (alternatively at least about 90% solid tumor stem cells and less than 10% solid tumor cells), wherein the solid tumor stem cells: are tumorigenic; express low levels or undetectable levels of alpha-catenin; and, elevated levels of MET (e.g., the levels being compared to normal breast epithelia).

In certain embodiments, the present invention provides an isolated population of solid tumor stem cells obtained from a solid tumor of epithelial origin, wherein the population comprises at least 75% solid tumor stem cells and less than 25% solid tumor cells (alternatively at least about 90% solid tumor stem cells and less than 10% solid tumor cells), wherein the solid tumor stem cells: are tumorigenic; and, express low levels or undetectable levels of two or more of alpha-catenin, NCSTN, LNX, ARMCX3, D2S448, TUSC1, GLUL, RB1, BEX2, SLC12A2, GALC, NGFRAP1, FGF13, KIAA1102, SLC1A4, and DNAJD1 (e.g., the levels being compared to normal breast epithelia). In another embodiment, the present invention provides an isolated population of solid tumor stem cells obtained from a solid tumor of epithelial origin, wherein the population comprises at least about 75% solid tumor stem cells and less than 25% solid tumor cells (alternatively at least about 90% solid tumor stem cells and less than 10% solid tumor cells), wherein the solid tumor stem cells: are tumorigenic; and, express elevated levels of two or more of EDG2, CAV1, CAV2, DCBLD2, IGFBP3, S100A2, CXCL5, MET, FOXQ1, CDKN2A, MFHAS1, IL27RA, KLRF1, PKCA, UPP1, CTSL2, SLC7A5, ARNTL2, PRSS1, PRSS2, PRSS3, VNN1, RAB38, ZBED2, MYEOV, MAL, IMP-3, and DHRS9 (e.g., the levels being compared to normal breast epithelia). In still another embodiment, the present invention provides an isolated population of solid tumor stem cells obtained from a solid tumor of epithelial origin, wherein the population comprises at least 75% solid tumor stem cells and less than 25% solid tumor cells (alternatively at least about 90% solid tumor stem cells and less than 10% solid tumor cells), wherein the solid tumor stem cells: are tumorigenic; express low levels or undetectable levels of one or more of alpha-catenin, NCSTN, LNX, ARMCX3, D2S448, TUSC1, GLUL, RB1, BEX2, SLC12A2, GALC, NGFRAP1, FGF13, KIAA1102, SLC1A4, and DNAJD1 (e.g., the levels being compared to normal breast epithelia); and express elevated levels of one or more of EDG2, CAV1, CAV2, DCBLD2, IGFBP3, S100A2, CXCL5, MET, FOXQ1, CDKN2A, MFHAS1, IL27RA, KLRF1, PKCA, UPP1, CTSL2, SLC7A5, ARNTL2, PRSS1, PRSS2, PRSS3, VNN1, RAB38, ZBED2, MYEOV, MAL, IMP-3, and DHRS9 (e.g., the levels being compared to normal breast epithelia).

In certain embodiments, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; and, express low levels or undetectable levels of e-cadherin or alpha-catenin as compared to normal epithelium. In another embodiment, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; express low levels or undetectable levels of e-cadherin; and, express low levels or undetectable levels of one or more of MMP7, Nov, FOSL1, or IL1R2 (e.g., the levels being compared to normal breast epithelia). In still another embodiment, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; express low levels or undetectable levels of e-cadherin; and, express elevated levels of SHC1 or FLJ20152 (e.g., the levels being compared to normal breast epithelia). In yet another embodiment, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; express low levels or undetectable levels of e-cadherin; express low levels or undetectable levels of one or more of MMP7, Nov, FOSL1, or IL1R2; and, express elevated levels of SHC1 or FLJ20152 (e.g., the levels being compared to normal breast epithelia).

In yet other embodiments, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; express low levels or undetectable levels of two or more of e-cadherin, MMP7, Nov, FOSL1, or IL1R2 (e.g., the levels being compared to normal breast epithelia). In still another embodiment, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; express elevated levels of SHC1 and FLJ20152 (e.g., the levels being compared to normal breast epithelia). In another embodiment, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; express low levels or undetectable levels of one or more of e-cadherin, MMP7, Nov, FOSL1, or IL1R2; and, express elevated levels of SHC1 or FLJ20152 (e.g., the levels being compared to normal breast epithelia).

In certain embodiments, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; and, express low levels or undetectable levels of e-cadherin or alpha-catenin as compared to normal epithelium. In another embodiment, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; express low levels or undetectable levels of e-cadherin; and, express low levels or undetectable levels of one or more of MMP7, Nov, FOSL1, IL1R2, SFRP1, KRT6B, G0S2, IL8, B3GNT5, or FGFBP1 (e.g., the levels being compared to normal breast epithelia). In still another embodiment, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; express low levels or undetectable levels of e-cadherin; and, express elevated levels of one or more of SHC1, FLJ20152, ARNT, CYFIP2, C17orf27, TAP1, RNASEL, or LOC57168 (e.g., the levels being compared to normal breast epithelia). In yet another embodiment, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; express low levels or undetectable levels of e-cadherin; express low levels or undetectable levels of one or more of MMP7, Nov, FOSL1, IL1R2, SFRP1, KRT6B, G0S2, IL8, B3GNT5, or FGFBP1; and, express elevated levels of one or more of SHC1, FLJ20152, ARNT, CYFIP2, C17orf27, TAP1, RNASEL, or LOC57168 (e.g., the levels being compared to normal breast epithelia).

In yet other embodiments, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; express low levels or undetectable levels of two or more of e-cadherin, MMP7, Nov, FOSL1, IL1R2, SFRP1, KRT6B, G0S2, IL8, B3GNT5, or FGFBP1 (e.g., the levels being compared to normal breast epithelia). In still another embodiment, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; express elevated levels of two or more of SHC1, FLJ20152, ARNT, CYFIP2, C17orf27, TAP1, RNASEL, or LOC57168 (e.g., the levels being compared to normal breast epithelia). In another embodiment, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; express low levels or undetectable levels of one or more of e-cadherin, MMP7, Nov, FOSL1, IL1R2, SFRP1, KRT6B, G0S2, IL8, B3GNT5, or FGFBP1; and, express elevated levels of one or more of SHC1, FLJ20152, ARNT, CYFIP2, C17orf27, TAP1, RNASEL, or LOC57168 (e.g., the levels being compared to normal breast epithelia).

In certain embodiments, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; and, express low levels or undetectable levels of alpha-catenin; and, express low levels or undetectable levels of one or more of NCSTN, LNX, ARMCX3, D2S448, GLUL or RB1 (e.g., the levels being compared to normal breast epithelia). In still another embodiment, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; express low levels or undetectable levels of alpha-catenin; and, express elevated levels of one or more of EDG2, CAV1, CAV2, DCBLD2, IGFBP3, S100A2, CXCL5, MET, FOXQ1, CDKN2A, CTSL2, or MFHAS1 (e.g., the levels being compared to normal breast epithelia). In yet another embodiment, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; express low levels or undetectable levels of alpha-catenin; express low levels or undetectable levels of one or more of NCSTN, LNX, ARMCX3, D2S448, GLUL or RB1; and, express elevated levels of one or more of EDG2, CAV1, CAV2, DCBLD2, IGFBP3, S100A2, CXCL5, MET, FOXQ1, CDKN2A or MFHAS1 (e.g., the levels being compared to normal breast epithelia). In another embodiment, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; express low levels or undetectable levels of alpha-catenin; and, elevated levels of MET (e.g., the levels being compared to normal breast epithelia).

In certain embodiments, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; and, express low levels or undetectable levels of two or more of alpha-catenin, NCSTN, LNX, ARMCX3, D2S448, GLUL or RB1 (e.g., the levels being compared to normal breast epithelia). In still another embodiment, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; express elevated levels of two or more of EDG2, CAV1, CAV2, DCBLD2, IGFBP3, S100A2, CXCL5, MET, FOXQ1, CDKN2A, CTSL2, or MFHAS1 (e.g., the levels being compared to normal breast epithelia). In yet another embodiment, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; express low levels or undetectable levels of one or more of alpha-catenin, NCSTN, LNX, ARMCX3, D2S448, GLUL or RB1; and, express elevated levels of one or more of EDG2, CAV1, CAV2, DCBLD2, IGFBP3, S100A2, CXCL5, MET, FOXQ1, CDKN2A, CTSL2, or MFHAS1 (e.g., the levels being compared to normal breast epithelia).

In further embodiments, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; and, express low levels or undetectable levels of alpha-catenin; and, express low levels or undetectable levels of one or more of NCSTN, LNX, ARMCX3, D2S448, TUSC1, GLUL, RB1, BEX2, SLC12A2, GALC, NGFRAP1, FGF13, KIAA1102, SLC1A4, and DNAJD1 (e.g., the levels being compared to normal breast epithelia). In still another embodiment, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; express low levels or undetectable levels of alpha-catenin; and, express elevated levels of one or more of EDG2, CAV1, CAV2, DCBLD2, IGFBP3, S100A2, CXCL5, MET, FOXQ1, CDKN2A, MFHAS1, IL27RA, KLRF1, PKCA, UPP1, CTSL2, SLC7A5, ARNTL2, PRSS1, PRSS2, PRSS3, VNN1, RAB38, ZBED2, MYEOV, MAL, IMP-3, and DHRS9 (e.g., the levels being compared to normal breast epithelia). In yet another embodiment, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; express low levels or undetectable levels of alpha-catenin; express low levels or undetectable levels of one or more of NCSTN, LNX, ARMCX3, D2S448, TUSC1, GLUL, RB1, BEX2, SLC12A2, GALC, NGFRAP1, FGF13, KIAA1102, SLC1A4, and DNAJD1; and, express elevated levels of one or more of EDG2, CAV1, CAV2, DCBLD2, IGFBP3, S100A2, CXCL5, MET, FOXQ1, CDKN2A, MFHAS1, IL27RA, KLRF1, PKCA, UPP1, CTSL2, SLC7A5, ARNTL2, PRSS1, PRSS2, PRSS3, VNN1, RAB38, ZBED2, MYEOV, MAL, IMP-3, and DHRS9 (e.g., the levels being compared to normal breast epithelia). In another embodiment, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; express low levels or undetectable levels of alpha-catenin; and, elevated levels of MET (e.g., the levels being compared to normal breast epithelia).

In certain embodiments, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; and, express low levels or undetectable levels of two or more of alpha-catenin, NCSTN, LNX, ARMCX3, D2S448, TUSC1, GLUL, RB1, BEX2, SLC12A2, GALC, NGFRAP1, FGF13, KIAA1102, SLC1A4, and DNAJD1 (e.g., the levels being compared to normal breast epithelia). In still another embodiment, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; express elevated levels of two or more of EDG2, CAV1, CAV2, DCBLD2, IGFBP3, S100A2, CXCL5, MET, FOXQ1, CDKN2A, MFHAS1, IL27RA, KLRF1, PKCA, UPP1, CTSL2, SLC7A5, ARNTL2, PRSS1, PRSS2, PRSS3, VNN1, RAB38, ZBED2, MYEOV, MAL, IMP-3, and DHRS9 (e.g., the levels being compared to normal breast epithelia). In yet another embodiment, the present invention provides an enriched population of solid tumor stem cells obtained from a solid tumor of epithelial origin, wherein the population comprises solid tumor stem cells and solid tumor cells, wherein the solid tumor stem cells: are enriched at least two-fold (alternatively 5-6 fold or 10-fold) compared to unfractionated tumor cells; are tumorigenic; express low levels or undetectable levels of one or more of alpha-catenin, NCSTN, LNX, ARMCX3, D2S448, TUSC1, GLUL, RB1, BEX2, SLC12A2, GALC, NGFRAP1, FGF13, KIAA1102, SLC1A4, and DNAJD1; and, express elevated levels of one or more of EDG2, CAV1, CAV2, DCBLD2, IGFBP3, S100A2, CXCL5, MET, FOXQ1, CDKN2A, MFHAS1, IL27RA, KLRF1, PKCA, UPP1, CTSL2, SLC7A5, ARNTL2, PRSS1, PRSS2, PRSS3, VNN1, RAB38, ZBED2, MYEOV, MAL, IMP-3, and DHRS9 (e.g., the levels being compared to normal breast epithelia).

In other embodiments, the methods further comprise c) providing a prognosis to the subject. In some embodiments, the at least one stem cell cancer marker is from Table 8. In some embodiments, the at least one stem cell cancer marker comprises: Bmi-1, eed, easyh1, easyh2, rnf2, yy1, smarcA3, smarcA5, smarcD3, smarcE1, mllt3, FZD1, FZD2, FZD3, FZD4, FZD6, FZD7, FZD8, FZD9, FZD10, WNT2, WNT2B, WNT3, WNT5A, WNT10B, WNT16, AXIN1, BCL9, MYC, and (TCF4). In some embodiments, the at least one stem cell marker comprises: e-cadherin, alpha-catenin; e-cadherin and MMP7, Nov, FOSL1, IL1R2, SHC1, or FLJ20152; alpha-catenin and NCSTN, LNX, ARMCX3, D2S448, GLUL, RB1, EDG2, CAV1, CAV2, DCBLD2, IGFBP3, S100A2, CXCL5, MET, FOXQ1, CDKN2A or MFHAS1.

In other embodiments reagents and methods for predicting the clinical outcome including metastasis and death are provided using the cancer stem cell markers of the present invention. The invention provides various diagnostic methods using the reagents, identified herein, related to solid tumor stem cells. The diagnostic methods of this invention include a method of classifying a cancer comprising: a) obtaining a tumor biopsy from a patient; b) determining expression or activity of one or more of genes encoding a protein or polypeptide selected from a solid tumor stem cell gene signature; and c) classifying the tumor as belonging to a high or low risk tumor class based on the results of (b). In another embodiment of the invention, the method further comprises further providing a diagnosis, prognosis, selection of a therapy, or a means for monitoring a therapy based on the classification of the tumor. According to certain of the inventive methods the presence or amount of a gene product, e.g. a polypeptide or a nucleic acid, encoded by a solid tumor stem cell gene is detected in a sample derived from a subject (e.g. a sample of tissue or cells obtained from a tumor or a blood sample obtained from a subject). In general the subject is a human, however the subject can also be an animal of another kind. The subject can be an individual who has or can have a tumor. The sample can be subject to a number of processing steps prior to or in the course of detection. In certain embodiments of the invention the gene product is a polypeptide that is detected using an antibody capable of binding to the polypeptide. In certain embodiments of the invention the antibody is used to perform immunohistochemical staining on a sample obtained from a subject. In certain embodiments of the invention solid tumor stem cell gene mRNA expression is measured using a microarray. In other embodiments of the invention solid tumor stem cell gene mRNA is measured by quantitative PCR using a set of primers designed to amplify a portion of the gene. Other detection means are know to one of ordinary skill in the art e.g. see U.S. Pat. No. 6,057,105.

In certain embodiments, the present invention provides a method of classifying a cancer comprising: (a) providing a cancer sample; (b) determining expression levels of one or more genes comprising alpha-catenin signature 2 in cancer sample; (c) comparing the expression levels of the genes comprising the alpha-catenin profile in the cancer sample to a alpha-catenin signature 2; and (d) classifying the cancer sample to either a high risk or low risk group based on the comparison in (c). The method of classifying a cancer can further comprise providing diagnostic, prognostic, or predictive information based on the classifying in (d). In certain embodiments the method of determining the expression levels of one or more genes comprising alpha catenin signature 2 is by measuring the expression of the corresponding protein or polypeptide. In some embodiments the protein or polypeptide is detected by immunohistochemical analysis of the cancer sample using an antibody that binds to the protein or polypeptide. In other embodiments the protein or polypeptide is detected by ELISA assay using an antibody that specifically binds to the protein or polypeptide. In still other embodiments the protein or polypeptide is detected using a protein array comprising an antibody that specifically binds to the protein or polypeptide. In some embodiments the antibody that binds to the protein or polypeptide is an anti-CD44 antibody. In other embodiments the antibody that binds to the protein or polypeptide is an anti-beta-catenin antibody. In other certain embodiments the method of determining the expression levels of one or more genes comprising alpha catenin signature 2 is by measuring the expression of the corresponding mRNA. In some embodiments the mRNA is detected using a polynucleotide array comprising a polynucleotide that specifically hybridizes to the mRNA. In other embodiments the mRNA is detected using polymerase chain reaction comprising polynucleotide primers that specifically amplify the mRNA.

In certain embodiments, the present invention provides a method of classifying a cancer comprising: (a) providing a cancer sample; (b) determining expression levels of one or more genes comprising alpha-catenin signature 3 in the cancer sample; (c) comparing the expression levels of the genes comprising the alpha-catenin profile in the cancer sample to the alpha-catenin signature 3; and (d) classifying the cancer sample to either a high risk or low risk group based on the comparison in (c). The method of classifying a cancer can further comprise providing diagnostic, prognostic, or predictive information based on the classifying in (d). In certain embodiments the method of determining the expression levels of one or more genes comprising alpha catenin signature 3 is by measuring the expression of the corresponding protein or polypeptide. In some embodiments the protein or polypeptide is detected by immunohistochemical analysis of the cancer sample using an antibody that binds to the protein or polypeptide. In other embodiments the protein or polypeptide is detected by ELISA assay using an antibody that specifically binds to the protein or polypeptide. In still other embodiments the protein or polypeptide is detected using a protein array comprising an antibody that specifically binds to the protein or polypeptide. In some embodiments the antibody that binds to the protein or polypeptide is an anti-CD44 antibody. In other embodiments the antibody that binds to the protein or polypeptide is an anti-beta-catenin antibody. In other certain embodiments the method of determining the expression levels of one or more genes comprising alpha catenin signature 3 is by measuring the expression of the corresponding mRNA. In some embodiments the mRNA is detected using a polynucleotide array comprising a polynucleotide that specifically hybridizes to the mRNA. In some embodiments the mRNA is detected using polymerase chain reaction comprising polynucleotide primers that specifically amplify the mRNA.

In particular embodiments, the present invention provides methods for reducing the size of a solid tumor (e.g. in research drug screening, or therapeutic applications) comprising contacting cells of a solid tumor with a biologically (e.g. therapeutically) effective amount of a composition comprising at least one agent directed against at least one stem cell cancer marker shown in Tables 4-9. In some embodiments, the biologically effective amount is an amount sufficient to cause cell death of or inhibit proliferation of solid tumor stem cells in the solid tumor. In other embodiments, the biologically effective amount is an amount that interference with the survival pathways (e.g. notch related genes) or self-renewal pathways (e.g. WNT pathways) of the solid tumor stem cell.

Examples of solid tumors from which solid tumor stem cells can be isolated or enriched for according to the invention include, but are not limited to, sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. The invention is applicable to sarcomas and epithelial cancers, such as ovarian cancers and breast cancers.

In additional embodiments, the at least one agent is an antibody, peptide or small molecule. In further embodiments, the antibody, peptide, anti-sense, siRNA, or small molecule is directed against an extracellular domain of the at least one stem cell cancer marker. In some embodiments, the at least one stem cell cancer marker is selected from the group consisting of: Bmi-1, eed, easyh1, easyh2, rnf2, yy1, smarcA3, smarcA5, smarcD3, smarcE1, mllt3, FZD1, FZD2, FZD3, FZD4, FZD6, FZD7, FZD8, FZD9, FZD10, WNT2, WNT2B, WNT3, WNT5A, WNT10B, WNT16, AXIN1, BCL9, MYC, and (TCF4). In a further embodiment, the at least one stem cell marker is selected from the group consisting of: e-cadherin, alpha-catenin, MMP7, Nov, FOSL1, IL1R2, SHC1, FLJ20152, NCSTN, LNX, ARMCX3, D2S448, GLUL, RB1, EDG2, CAV1, CAV2, DCBLD2, IGFBP3, S100A2, CXCL5, MET, FOXQ1, CDKN2A or MFHAS1.

In other embodiments, the present invention provides methods for reducing the size of a solid tumor, comprising contacting cells of a solid tumor with a biologically (e.g. therapeutically) effective amount of a composition comprising at least one agent that modulates the activity of at least one stem cell cancer marker shown in Tables 4-9. In some embodiments, the present invention provides methods for killing or inhibiting the proliferation of solid tumor stem cells comprising contacting the solid tumor stem cells with a biologically effective amount of a composition comprising at least one agent targeted to at least one stem cell cancer marker shown in Tables 4-9. In certain embodiments, the methods further comprise identifying the death of or the prevention of the growth of the solid tumor stem cells following the contacting. In additional embodiments, the cell death is caused by apoptosis. In other embodiments, the biologically effective amount is an amount that interferes with the survival pathways (e.g. notch related genes) or self-renewal pathways (e.g. WNT pathways) of the solid tumor stem cell. In other embodiments, the at least one stem cell cancer marker is selected from the group consisting of: Bmi-1, eed, easyh1, easyh2, rnf2, yyl, smarcA3, smarcA5, smarcD3, smarcE1, mllt3, FZD1, FZD2, FZD3, FZD4, FZD6, FZD7, FZD8, FZD9, FZD10, WNT2, WNT2B, WNT3, WNT5A, WNT10B, WNT16, AXIN1, BCL9, MYC, and (TCF4). In further embodiments, the at least one stem cell marker is selected from the group consisting of: e-cadherin, alpha-catenin, MMP7, Nov, FOSL1, IL1R2, SHC1, FLJ20152, NCSTN, LNX, ARMCX3, D2S448, GLUL, RB1, EDG2, CAV1, CAV2, DCBLD2, IGFBP3, S100A2, CXCL5, MET, FOXQ1, CDKN2A and MFHAS1.

In particular embodiments, the solid tumor stem cells express cell surface marker CD44, ESA, or B38.1. In other embodiments, the solid tumor stem cells fail to express at least one LINEAGE marker selected from the group consisting of CD2, CD3, CD10, CD14, CD16, CD31, CD45, CD64, and CD140b (see, e.g., U.S. App. Pub. Nos. US20040037815A1, and US20020119565, both of which are herein incorporated by reference).

In other embodiments, the present invention provides methods for selectively targeting a solid tumor stem cell comprising, (a) identifying at least one stem cell cancer marker from Tables 4-9 present on a solid tumor stem cell; and (b) obtaining an agent or set of agents that selectively binds to or regulates the at least one stem cell cancer marker. In some embodiments, the agent genetically modifies the solid tumor stem cell. In particular embodiments, the agent comprises a bi-specific conjugate. In further embodiments, the agent comprises an adenoviral vector.

In some embodiments, the present invention provides methods for forming a tumor in an animal, comprising: introducing purified solid tumor stem cells (e.g. a cell dose of) into an animal, wherein: (a) the solid tumor stem cells are derived from a solid tumor; and (b) the solid tumor stem cells are enriched at least 2-fold relative to unfractionated tumor cells based on the presence of at least one stem cell cancer marker in Tables 4-9. In other embodiments, the animal is an immunocompromised animal. In certain embodiments, the animal is an immunocompromised mammal, such as a mouse (e.g., a nude mouse, SCID mouse, NOD/SCID mouse, Beige/SCID mouse; and microglobin deficient NOD/SCID mouse). In particular embodiments, the number of cells in the cell dose is about 100 cells and about $5 \times 10^5$ cells.

In certain embodiments, the present invention provides kits for detecting solid tumor stem cells in a subject, comprising: a) a reagent capable of specifically detecting at least one stem cell cancer marker from Tables 4-9 in a tissue or cell sample from a subject, and, optionally, b) instructions for using the reagent for detecting the presence or absence of solid tumor stem cells in the tissue sample. In further embodiments, the reagent comprises a nucleic acid probe complementary to mRNA from the at least one stem cell cancer marker. In other embodiments, the reagent comprises an antibody or antibody fragment.

In some embodiments, the present invention provides methods of screening compounds, comprising: a) providing i) a solid tumor stem cell and ii) one or more test compounds; and b) contacting the solid tumor stem cell with the test compound; and c) detecting a change in expression of at least one stem cell cancer marker shown in Tables 4-9 in the presence of the test compound relative to the absence of the test compound. In particular embodiments, the detecting comprises determining an expression level for the at least one stem cell cancer marker. In particular embodiments, the detecting comprises detecting mRNA expression of the at least one stem cell cancer marker. In some embodiments, the detecting comprises detecting polypeptide expression of the at least one stem cell cancer marker. In additional embodiments, the solid tumor stem cell is in vitro. In other embodiments, the solid tumor stem cell is in vivo. In further embodiments, the test compound comprises a drug (e.g. small molecule, antibody, antibody-toxin conjugate, siRNA, etc.).

In some embodiments, the present invention provides compositions comprising at least two agents (e.g. small molecule, antibody, antibody-toxin conjugate, siRNA, etc.), wherein each of the agents modulates the activity of at least one stem cell cancer marker shown in Tables 4-9. In additional embodiments, the composition comprises at least three agents.

In particular embodiments, the present invention provides methods of distinguishing tumorigenic from non-tumorigenic cancer cells, comprising: detecting the presence of β-catenin in a cancer cell such that the localization of β-catenin in the cancer cell is determined to be primarily nuclear or primarily cytoplasmic. In some embodiments, the method further comprises identifying the cancer cell as tumorigenic if the β-catenin localization is primarily nuclear, or identifying the cancer cell as non-tumorigenic if the β-catenin localization is primarily cytoplasmic.

In certain embodiments, the present invention provides methods of distinguishing a tumorigenic from a non-tumorigenic cancer cell, comprising: a) providing; i) a cancer cell, and ii) a composition comprising an agent configured to bind β-catenin; and b) contacting the cancer cell with the composition under conditions such that the localization of β-catenin in the cancer cell is determined to be primarily nuclear and cytoplasmic or primarily cytoplasmic and membrane associated, and c) identifying the cancer cell as tumorigenic if the β-catenin localization is primarily nuclear and cytoplasmic, or identifying the cancer cell as non-tumorigenic if the β-catenin localization is primarily cytoplasmic and membrane associated.

DESCRIPTION OF THE FIGURES

FIG. 17 shows the correlation of the E-cadherin tumor stem cell signature with five gene expression patterns that distinguish different tumor subclasses. Luminal A, Luminal B, ERBB2, Basal, and Normal-like.

GENERAL DESCRIPTION

Figure 1:
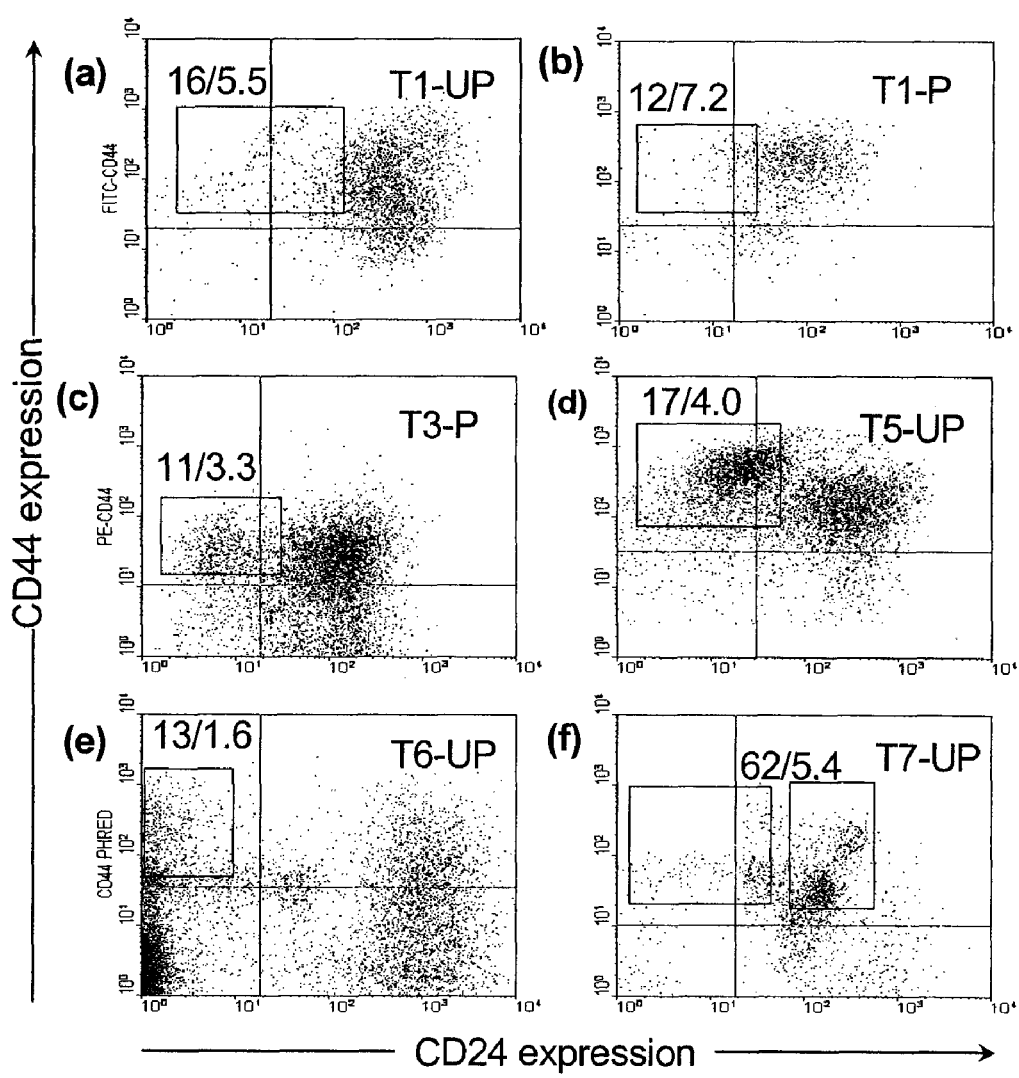
FIG. 1 shows isolation of tumorigenic cells.

This invention is based on the discovery of solid tumor stem cells (also referred to as cancer stem cells from a solid tumor) as a distinct and limited subset of cells within the heterogenous cell population of established solid tumors. These cancer stem cells share the properties of normal stem cells in that they extensively proliferate and efficiently give rise both to additional solid tumor stem cells (self-renewal) and to the majority of tumor cells of a solid tumor that lack tumorigenic potential. Identification of cancer stem cells from solid tumors relied on their expression of a unique pattern of cell-surface receptors that could be used to isolate them from the bulk of non-tumorigenic tumor cells and on the assessment of their properties of self-renewal and proliferation in culture and in xenograft animal models. An ESA+; CD44+; CD24−/low; Lineage—population greater than 50-fold enriched for the ability to form tumors relative to unfractionated tumor cells was discovered (Al-Hajj et al., 2003).

The present invention relates to compositions and methods for treating, characterizing and diagnosing cancer. In particular, the present invention provides gene expression profiles associated with solid tumor stem cells, as well as novel markers useful for the diagnosis, characterization, and treatment of solid tumor stem cells. Suitable markers that can be targeted (e.g. for diagnostic or therapeutic purposes) are the genes and peptides encoded by the genes that are differentially expressed in solid tumor stem cells as shown in Tables 4-9. The differentially expressed genes, and the peptides encoded thereby, can be detected (e.g. quantitatively) in order to identify the presence of solid tumor stem cells, and to determine and screen molecules suitable for reducing the proliferation (or killing), interfering with self-renewal pathways, or interfering with survival pathways of any solid tumor stem cells that are present. The differentially expressed genes, and peptides encoded thereby, shown in these tables are also useful for generating therapeutic agents targeted to one or more of these markers (e.g. to inhibit or promote the activity of the marker).

In order to identify solid tumor stem cell markers, cells from 5 patients, AML stem cells and non-tumorigenic cancer cells from 6 patients, normal hematopoietic stem cells (HSC5), normal hematopoietic cells, normal colon epithelial cells, and normal breast epithelial cells were analyzed for differential expression.

The present invention also provides solid tumor stem cells that differentially express from other cells one or more of the markers provided in Tables 4-9. The solid tumor stem cells can be isolated from humans or other animals. The expression can be either to a greater extent or to a lesser extent. The other cells can be selected from normal cells, hematopoietic stem cells, acute myelogenous leukemia (AML) stem cells, or any other class of cells.

The invention provides a method of selecting cells of a population, which results in a purified population of solid tumor stem cells (e.g. from a patient to select or test therapeutic agents are some for the patient). The present invention also provides a method of selecting a purified population of tumor cells other than solid tumor stem cells, such as a population of non-tumorigenic (NTG) tumor cells. The present invention provides methods of raising antibodies to the selected cells. The invention provides diagnostic methods using the selected cells. The invention also provides therapeutic methods, where the therapeutic is directed to a solid tumor stem cell (e.g. directed to one of the stem cells cancer markers identified herein directly or indirectly).

Accordingly, the invention provides methods of selecting cells, diagnosing disease, conducting research studies, and treating solid tumors using selection methods, diagnostic methods and therapeutics directed to specific genes on a given pathway. Included are one or more of the following genes and gene products: Bmi-1, eed, easyhi, easyh2, mf2, yyl, smarcA3, smarcA5, smarcD3, smarcE 1 and mllt3, as well as those shown in Tables 4-9. Many of these genes are differentially expressed in solid tumor stem cells as compared with normal cells and non-tumorigenic cancer cells, as shown herein.

The invention provides in vivo and in vitro assays of solid tumor stem cell function and cell function by the various populations of cells isolated from a solid tumor. The invention provides methods for using the various populations of cells isolated from a solid tumor (such as a population of cells enriched for solid tumor stem cells) to identify factors influencing solid tumor stem cell proliferation. By the methods of the present invention, one can characterize the phenotypically heterogeneous populations of cells within a solid tumor. In particular, one can identify, isolate, and characterize a phenotypically distinct cell population within a tumor having the stem cell properties of extensive proliferation and the ability to give rise to all other tumor cell types. Solid tumor stem cells are the tumorigenic cells that are capable of re-establishing a tumor following treatment.

Figure 10:
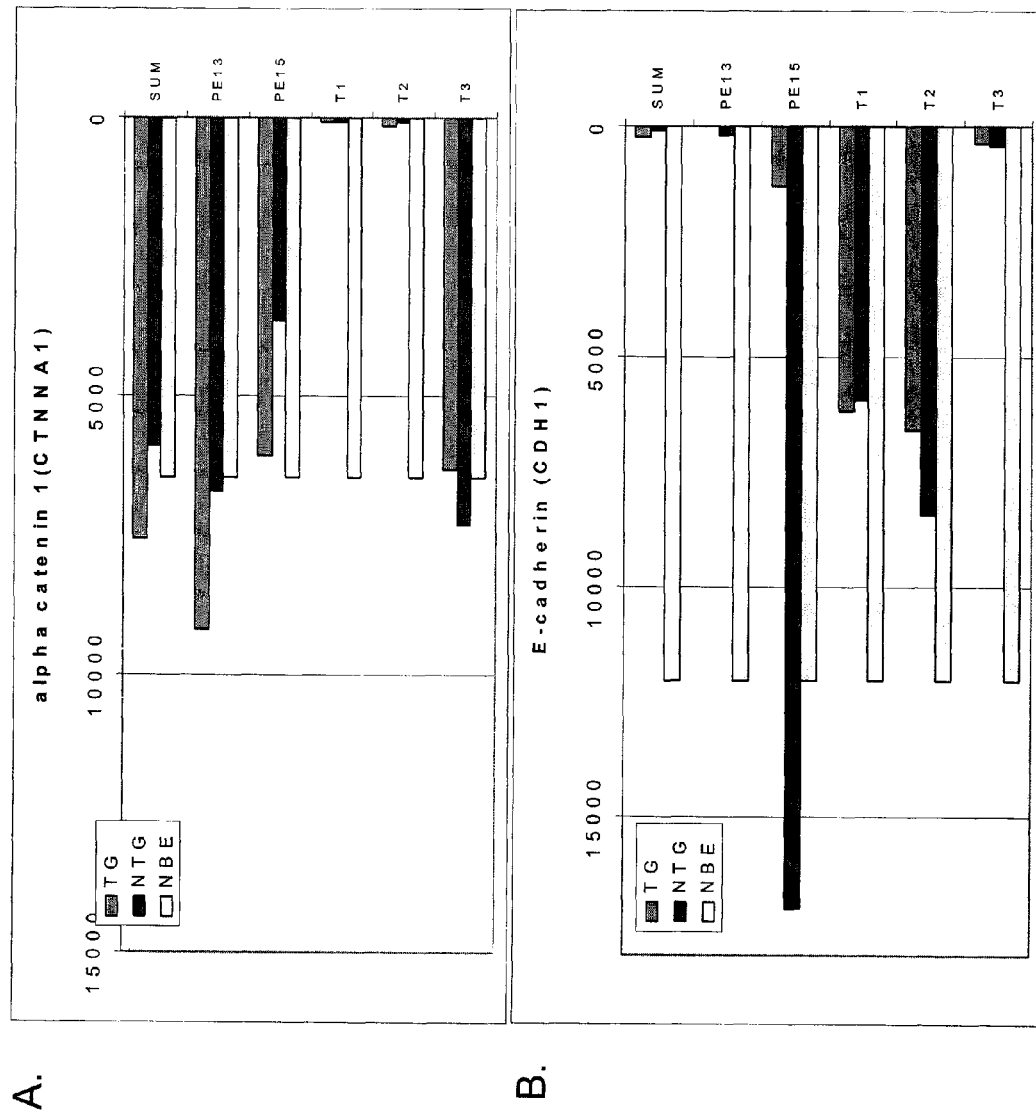
FIG. 10 shows expression of alpha-catenin and E-cadherin from microarray analysis in tumorigenic (TG), non-tumorigenic (NTG), and normal breast epithelium (NBE) in three primary tumors: T1, T2, T3 and three passaged tumors: SUM, PE13, PE15.
Figure 11:
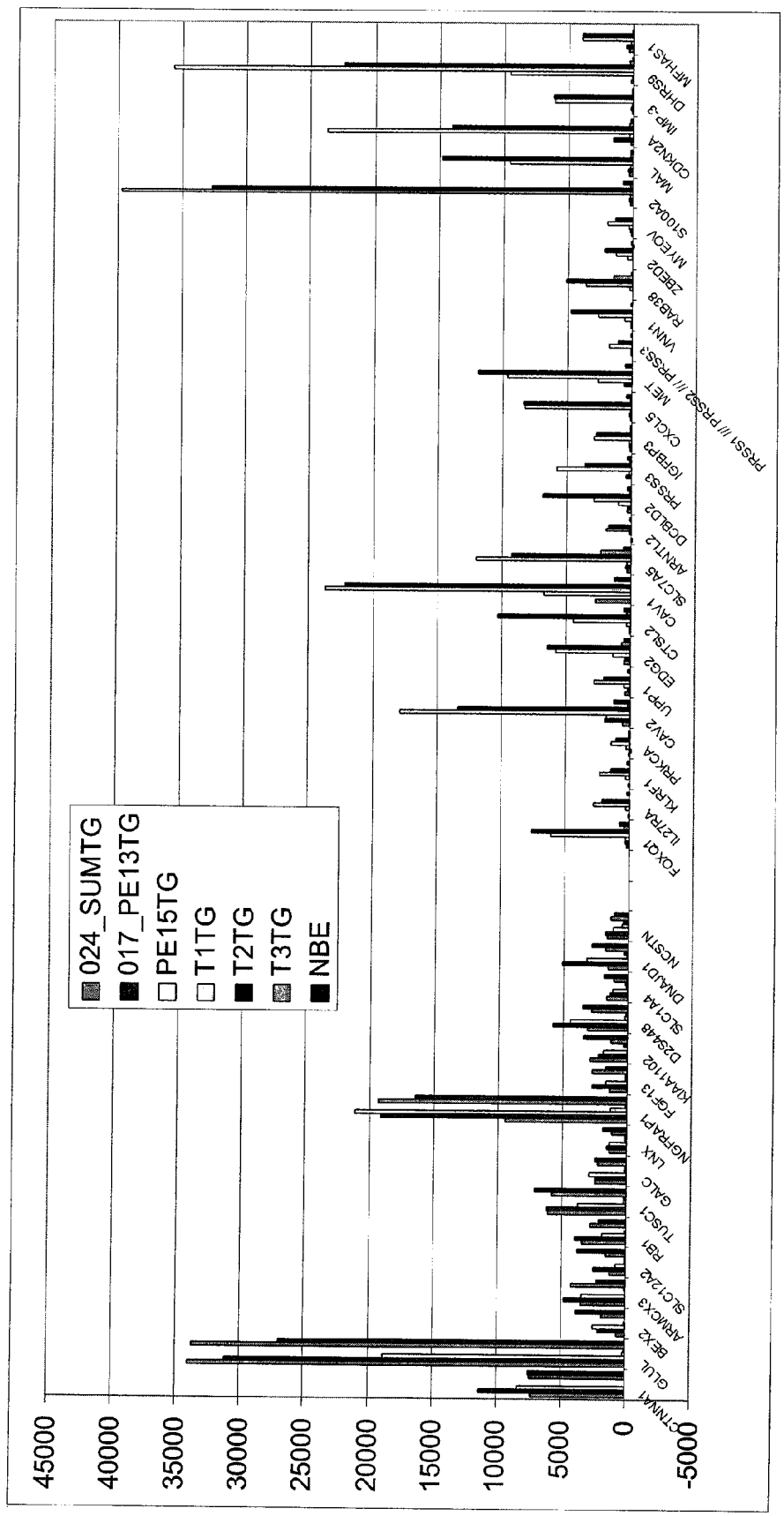
FIG. 11 shows gene expression levels as determined by microarray analysis for A) the alpha-catenin gene signature.

This invention using the microarray data of this invention identifies two clearly defined molecular signatures of cancer stem cell gene expression referred to as signature 1 (alpha-catenin signature) and signature 2 (e-cadherin signature) (See Table 9 and FIGS. 10, 11). These signatures can detect the presence of cancer stem cells, enabling the characterization, isolation, targeting, and treatment of cancer. Using the knowledge of the alpha-catenin and E-cadherin cancer stem cell gene signatures one can: develop diagnostic assays for the presence or absence of cancer stem cells; isolate enriched populations of cancer stem cells; conduct research studies; develop assays that enable identification of agents that impact the behavior of cancer stem cells; develop drugs that impact cancer stem cells; treat solid tumors using selection methods, diagnostic methods, and therapeutics; and identify additional markers of cancer stem cells for the further isolation and targeting of specific populations of cancer stem cells. Also, the discovery that the signature 1 and signature 2 gene expression of the present invention include alterations in the expression of alpha-catenin and E-cadherin respectively indicates that signature 1 and signature 2 cancer stem cells are associated with changes in the capability to metastasize. Thus the gene expression signatures of the present invention further enable the monitoring and treatment of metastases.

The invention thus provides a method for selectively targeting diagnostic or therapeutic agents to solid tumor stem cells. The invention also provides an agent, such as a biomolecule, that is selectively targeted to solid tumor stem cells (e.g. directed to one of the solid tumor stem cell cancer markers disclosed herein). In some embodiments, the stem cell cancer marker this targeted is part of a self-renewal or cell survival pathway. One example of such a marker is Bmi-1, which was shown to be required for maintenance of adult self-renewing hematopoietic stem cells (see, e.g., Park et al., Nature, 2003, 15; 423(6937): 302-5, herein incorporated by reference). In other some embodiments, the cancer diagnosed or targeted expresses an alpha-catenin or an E-cadherin gene expression pattern that is high correlated with an alpha-catenin signature. More specifically the cancer stem cell displays either: 1) low or undetectable levels of alpha-catenin expression in combination with an increase or decrease in one or more signature 1 gene markers including, for example, low or undetectable levels of Nicastrin expression or an increase in EDG2, DCBLD2, or c-Met expression or 2) low or undetectable levels of e-cadherin expression in combination with an increase or decrease in one or more signature 2 gene markers including, for example, low or undetectable levels of MMP7, Nov, or IL1R2 expression or an increase in SHC1 expression.

In certain embodiments, the present invention provides methods for screening for anti-cancer agents; for the testing of anti-cancer therapies; for the development of drugs targeting novel pathways; for the identification of new anti-cancer therapeutic targets; the identification and diagnosis of malignant cells in pathology specimens; for the testing and assaying of solid tumor stem cell drug sensitivity; for the measurement of specific factors that predict drug sensitivity; and for the screening of patients (e.g., as an adjunct for mammography).

The present invention further identifies for the first time a cancer stem cell gene signature, the alpha-catenin signature, comprising stem cell markers that are predictive of clinical outcome including metastasis and overall survival. The alpha-catenin signature as well as one or more of the individual predictor genes that comprise the alpha-catenin signature are established as predictive of a poor prognosis. In some embodiments of the present invention the alpha-catenin signature or individual predictor genes are used clinically to classify tumors as low or high risk and to assign a tumor to a low or high-risk category. The alpha-catenin signature can further be used to provide a diagnosis, prognosis, and select a therapy based on the classification of a tumor as low or high risk as well as to monitor the diagnosis, prognosis, and/or therapy over time. In another embodiment, the alpha-catenin signature can be used experimentally to test and assess lead compounds including, for example, small molecules, siRNAs, and antibodies for the treatment of cancer.

In certain embodiments a cancer stem cell profile, including an alpha-catenin gene profile, can be detected in a tumor sample by quantifying expression levels of polynucleotides by, for example, RT-PCR. The polynucleotides selected for quantification by RT-PCR are those polynucleotides comprising the cancer stem cell gene signature. Alternatively the cancer stem cell profiles, including the alpha-catenin gene profiles, can be detected in a tumor sample by quantifying expression levels of proteins by, for example, quantitative immunofluorescence or ELISA. The proteins selected for quantification are those proteins encoded by genes comprising the cancer stem cell gene signature. In some embodiments the alpha-catenin gene profile is detected in a tumor sample by microarray analysis using microarrays that comprise an alpha-catenin gene signature. These microarrays can detect the presence of an alpha-catenin profile by expression levels of polynucleotides, for example mRNA, in a patient sample or, alternatively, by expression levels of proteins in a patient sample using, for example, antibodies. In another some embodiment, an alpha-catenin profile is detected in a sample by real-time PCR using primer sets that specifically amplify the genes comprising the cancer stem cell signature. In other embodiments of the invention, microarrays are provided that contain polynucleotides or proteins (e.g., antibodies) that detect the expression of the genes comprising an alpha-catenin signature for use in prognosis.

Other features, objects, and advantages of the invention will be apparent from the detailed description below. Additional guidance is provided in WO 02/12447 and WO 03/50502 by the Regents of the University of Michigan, both of which are incorporated herein by reference.

Definitions

To facilitate an understanding of the present invention, a number of terms and phrases are defined below.

As used here, the term "antibody" includes monoclonal antibodies (including full length monoclonal antibodies), polyclonal antibodies, multispecific antibodies (e.g., bispecific antibodies), and antibody fragments so long as they exhibit the desired biological activity (e.g. able to bind a stem cell cancer marker as described herein). Antibodies can be conjugated to other molecules (e.g., toxins).

As used herein, the term "antibody fragments" refers to a portion of an intact antibody. Examples of antibody fragments include, but are not limited to, linear antibodies; single-chain antibody molecules; Fc or Fc' peptides, Fab and Fab fragments, and multispecific antibodies formed from antibody fragments.

As used herein, "humanized" forms of non-human (e.g., murine) antibodies are chimeric antibodies that contain minimal sequence, or no sequence, derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies can comprise residues that are not found in the recipient antibody or in the donor antibody. These modifications are generally made to further refine antibody performance. In general, the humanized antibody will comprise substantially all of at least one, and typically two, variable domains, in which all or substantially all of the hypervariable loops correspond to those of a nonhuman immunoglobulin and all or substantially all of the FR residues are those of a human immunoglobulin sequence. The humanized antibody can also comprise at least a portion of an immunoglobulin constant region (Fc), typically that of a human immunoglobulin. Examples of methods used to generate humanized antibodies are described in U.S. Pat. No. 5,225,539 to Winter et al. (herein incorporated by reference).

"Enriched", as in an enriched population of cells, can be defined phenotypically based upon the increased number of cells having a particular marker (e.g. as shown in Tables 4-9) in a fractionated set of cells as compared with the number of cells having the marker in the unfractionated set of cells. However, the term "enriched can be defined functionally by tumorigenic function as the minimum number of cells that form tumors at limit dilution frequency in test mice. For example, if 500 tumor stem cells form tumors in 63% of test animals, but 5000 unfractionated tumor cells are required to form tumors in 63% of test animals, then the solid tumor stem cell population is 10-fold enriched for tumorigenic activity. The stem cell cancer markers of the present invention can be used to generate enriched populations of cancer stem cells. In some embodiments, the stem cell population is enriched at least 1.4 fold relative to unfractioned tumor cells (e.g. 1.4 fold, 1.5 fold, 2 fold, 5 fold, 10 fold, . . . , 20 fold, . . . ).

"Isolated" in regard to cells, refers to a cell that is removed from its natural environment (such as in a solid tumor) and that is isolated or separated, and is at least about 30%, 50%, 75% free, or about 90% free, from other cells with which it is naturally present, but which lack the marker based on which the cells were isolated. The stem cell cancer markers of the present invention can be used to generate isolated populations of cancer stem cells.

As used herein, the terms "low levels", "decreased levels", "low expression", "reduced expression" or "decreased expression" in regards to gene expression are used herein interchangeably to refer to expression of a gene in a cell or population of cells, particularly a cancer stem cell or population of cancer stem cells, at levels less than the expression of that gene in a second cell or population of cells, for example normal breast epithelial cells. "Low levels" of gene expression can refer to expression of a gene in a cancer stem cell or population of cancer stem cells at levels: 1) half that or below expression levels of the same gene in normal breast epithelial cells and 2) at the lower limit of detection using conventional techniques. "Low levels" of gene expression can be determined by detecting decreased to nearly undetectable amounts of a polynucleotide (mRNA, cDNA, etc.) in cancer stem cells compared to normal breast epithelium by, for example, quantitative RT-PCR or microarray analysis. Alternatively "low levels" of gene expression can be determined by detecting decreased to nearly undetectable amounts of a protein in cancer stem cells compared to normal breast epithelium by, for example, ELISA, Western blot, or quantitative immunofluorescence.

The terms "high levels", "increased levels", "high expression", "increased expression" or "elevated levels" in regards to gene expression are used herein interchangeably to refer to expression of a gene in a cell or population of cells, particularly a cancer stem cell or population of cancer stem cells, at levels higher than the expression of that gene in a second cell or population of cells, for example normal breast epithelial cells. "Elevated levels" of gene expression can refer to expression of a gene in a cancer stem cell or population of cancer stem cells at levels twice that or more of expression levels of the same gene in normal breast epithelial cells. "Elevated levels" of gene expression can be determined by detecting increased amounts of a polynucleotide (mRNA, cDNA, etc.) in cancer stem cells compared to normal breast epithelium by, for example, quantitative RT-PCR or microarray analysis. Alternatively "elevated levels" of gene expression can be determined by detecting increased amounts of a protein in cancer stem cells compared to normal breast epithelium by, for example, ELISA, Western blot, quantitative immunofluorescence, etc.

The term "undetectable levels" or "loss of expression" in regards to gene expression as used herein refers to expression of a gene in a cell or population of cells, particularly a cancer stem cell or population of cancer stem cells, at levels that cannot be distinguished from background using conventional techniques such that no expression is identified. "Undetectable levels" of gene expression can be determined by the inability to detect levels of a polynucleotide (mRNA, cDNA, etc.) in cancer stem cells above background by, for example, quantitative RT-PCR or microarray analysis. Alternatively "undetectable levels" of gene expression can be determined by the inability to detect levels of a protein in cancer stem cells above background by, for example, ELISA, Western blot, or immunofluorescence.

As used herein, the term "receptor binding domain" refers to any native ligand for a receptor, including cell adhesion molecules, or any region or derivative of such native ligand retaining at least a qualitative receptor binding ability of a corresponding native ligand.

As used herein, the term "antibody-immunoadhesin chimera" comprises a molecule that combines at least one binding domain of an antibody with at least one immunoadhesin. Examples include, but are not limited to, the bispecific CD4-IgG chimeras described in Berg et al., PNAS (USA) 88:4723-4727 (1991) and Charnow et al., J. Immunol., 153:4268 (1994), both of which are hereby incorporated by reference.

As used herein, the terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

"Metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

The term "epitope" as used herein refers to that portion of an antigen that makes contact with a particular antibody.

When a protein or fragment of a protein is used to immunize a host animal, numerous regions of the protein can induce the production of antibodies which bind specifically to a given region or three-dimensional structure on the protein; these regions or structures are referred to as "antigenic determinants". An antigenic determinant can compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer can also have one or more risk factors. A subject suspected of having cancer has generally not been tested for cancer. However, a "subject suspected of having cancer" encompasses an individual who has received an initial diagnosis but for whom the stage of cancer is not known. The term further includes people who once had cancer (e.g., an individual in remission).

As used herein, the term "subject at risk for cancer" refers to a subject with one or more risk factors for developing a specific cancer. Risk factors include, but are not limited to, gender, age, genetic predisposition, environmental exposure, previous incidents of cancer, preexisting non-cancer diseases, and lifestyle.

As used herein, the term "characterizing cancer in subject" refers to the identification of one or more properties of a cancer sample in a subject, including but not limited to, the presence of benign, pre-cancerous or cancerous tissue, the stage of the cancer, and the subject's prognosis. Cancers can be characterized by the identification of the expression of one or more cancer marker genes, including but not limited to, the cancer markers disclosed herein.

The terms "cancer stem cell", "tumor stem cell", or "solid tumor stem cell" are used interchangeably herein and refer to a population of cells from a solid tumor that: (1) have extensive proliferative capacity; (2) are capable of asymmetric cell division to generate one or more kinds of differentiated progeny with reduced proliferative or developmental potential; and (3) are capable of symmetric cell divisions for self-renewal or self-maintenance. These properties of "cancer stem cells", "tumor stem cells" or "solid tumor stem cells" confer on those cancer stem cells the ability to form palpable tumors upon serial transplantation into an immunocompromised mouse compared to the majority of tumor cells that fail to form tumors. Cancer stem cells undergo self-renewal versus differentiation in a chaotic manner to form tumors with abnormal cell types that can change over time as mutations occur. The solid tumor stem cells of the present invention differ from the "cancer stem line" provided by U.S. Pat. No. 6,004,528. In that patent, the "cancer stem line" is defined as a slow growing progenitor cell type that itself has few mutations but which undergoes symmetric rather than asymmetric cell divisions as a result of tumorigenic changes that occur in the cell's environment. This "cancer stem line" hypothesis thus proposes that highly mutated, rapidly proliferating tumor cells arise largely as a result of an abnormal environment, which causes relatively normal stem cells to accumulate and then undergo mutations that cause them to become tumor cells. U.S. Pat. No. 6,004,528 proposes that such a model can be used to enhance the diagnosis of cancer. The solid tumor stem cell model is fundamentally different than the "cancer stem line" model and as a result exhibits utilities not offered by the "cancer stem line" model. First, solid tumor stem cells are not "mutationally spared". The "mutationally spared cancer stem line" described by U.S. Pat. No. 6,004,528 can be considered a pre-cancerous lesion, while the solid tumor stem cells described by this invention are cancer cells that themselves contain the mutations that are responsible for tumorigenesis. That is, the solid tumor stem cells ("cancer stem cells") of the invention would be included among the highly mutated cells that are distinguished from the "cancer stem line" in U.S. Pat. No. 6,004,528. Second, the genetic mutations that lead to cancer can be largely intrinsic within the solid tumor stem cells as well as being environmental. The solid tumor stem cell model predicts that isolated solid tumor stem cells can give rise to additional tumors upon transplantation (thus explaining metastasis) while the "cancer stem line" model would predict that transplanted "cancer stem line" cells would not be able to give rise to a new tumor, since it was their abnormal environment that was tumorigenic. Indeed, the ability to transplant dissociated, and phenotypically isolated human solid tumor stem cells to mice (into an environment that is very different from the normal tumor environment), where they still form new tumors, distinguishes the present invention from the "cancer stem line" model. Third, solid tumor stem cells likely divide both symmetrically and asymmetrically, such that symmetric cell division is not an obligate property. Fourth, solid tumor stem cells can divide rapidly or slowly, depending on many variables, such that a slow proliferation rate is not a defining characteristic.

As used herein "tumorigenic" refers to the functional features of a solid tumor stem cell including the properties of self-renewal (giving rise to additional tumorigenic cancer stem cells) and proliferation to generate all other tumor cells (giving rise to differentiated and thus non-tumorigenic tumor cells) that allow solid tumor stem cells to form a tumor.

As used herein, the terms "stem cell cancer marker(s)", "cancer stem cell marker(s)", "tumor stem cell marker(s)", or "solid tumor stem cell marker(s)" refer to a gene or genes or a protein, polypeptide, or peptide expressed by the gene or genes whose expression level, alone or in combination with other genes, is correlated with the presence of tumorigenic cancer cells compared to non-tumorigenic cells. The correlation can relate to either an increased or decreased expression of the gene (e.g. increased or decreased levels of mRNA or the peptide encoded by the gene).

"Gene expression profile" refers to identified expression levels of at least one polynucleotide or protein expressed in a biological sample.

A "gene profile," "gene pattern," "expression pattern" or "expression profile" refers to a specific pattern of gene expression that provides a unique identifier of a biological sample, for example, a breast or colon cancer pattern of gene expression, obtained by analyzing a breast or colon cancer sample and in those cases can be referred to as a "breast cancer gene profile" or a "colon cancer expression pattern". "Gene patterns" can be used to diagnose a disease, make a prognosis, select a therapy, and/or monitor a disease or therapy after comparing the gene pattern to a cancer stem cell gene signature.

The terms "cancer stem cell gene signature", "tumor stem cell gene signature", "cancer stem cell signature", "tumor stem cell signature", "tumorigenic gene signature", and "TG gene signature" are used interchangeably herein to refer to gene signatures comprising genes differentially expressed in cancer stem cells compared to other cells or population of cells, for example normal breast epithelial tissue. In one some embodiment the cancer stem cell gene signature comprises genes differentially expressed in cancer stem cells versus normal breast epithelium by a fold change, for example by 2 fold reduced and/or elevated expression, and further limited by using a statistical analysis such as, for example, by the P value of a t-test across multiple samples. In some embodiments, the genes differentially expressed in cancer stem cells are divided into cancer stem cell gene signatures based on the correlation of their expression with a chosen gene in combination with their fold or percentage expression change.

The terms "alpha-catenin signature", "alpha-catenin gene signature", "alpha catenin gene expression signature", "signature 1", or "cancer stem cell signature 1" as used herein refer to a distinct subset of cancer stem cell signatures. Cancer stem cells expressing an alpha-catenin gene signature are referred to as displaying a "signature 1 gene expression" or as "signature 1", "signature 1 type", or "alpha-catenin signature" cancer stem cells. The alpha-catenin signature comprises: 1) undetectable or low level expression as compared to normal human breast epithelium of one or more of a distinct set of genes comprising: alpha-catenin (CTNNA1); nicastrin (NCSTN); ligand of numb-protein X (LNX); armadillo repeat containing, X-linked 3 (ARMCX3); melanoma associated gene (D2S448); tumor suppressor candidate 1 (TUSC1); glutamine synthase (GLUL); retinoblastoma 1 (RB1); brain expressed X-linked 2 (BEX2); solute carrier family 12, member 2 (SLC12A2); galactosylceramidase (GALC); nerve growth factor receptor associated protein 1 (NGFRAP1); fibroblast growth factor 13 (FGF13); KIAA1102; solute carrier family 1, member 4 (SLC1A4); and DnaJ homolog, subfamily D, member 1 (DNAJD1) and/or 2) elevated expression compared to normal human breast epithelium of one or more of a distinct set of genes comprising: endothelial differentiation, lysophosphatidic acid G-protein coupled receptor 2 (EDG2); caveolin 1 (CAV1); caveolin 2 (CAV2); discoidin, CUB and LCCL domain containing 2 (DCBLD2); insulin-like growth factor binding protein 3 (IGFBP3); S100A2; CXCL5; c-Met (MET); forkhead box Q1 (FOXQ1); cyclin-dependent kinase inhibitor 2A (CDKN2A); malignant fibrous histiocytoma amplified sequence 1 (MFHAS1); interleukin 27 receptor, alpha (IL27RA); killer cell lectin-like receptor subfamily F, member 1 (KLRF1); protein kinase C, alpha (PKCA); uridine phosphorylase 1 (UPP1); cathepsin L2 (CTSL2); solute carrier family 7, member 5 (SLC7A5); aryl hydrocarbon receptor nuclear translocator-like 2 (ARNTL2); protease, serine, 1, 2, and 3 (PRSS1, PRSS2, PRSS3); vanin 1 (VNN1); RAB38; zinc finger, BED domain containing 2 (ZBED2); myeloma overexpressed gene (MYEOV); MAL; IGF-II mRNA-binding protein 3 (IMP-3); and dehydrogenase/reductase SDR family, member 9 (DHRS9). In some embodiments of the present invention a undetectable or low level of alpha-catenin expression is accompanied by 1) undetectable or low level expression of one or more of the genes including: nicastrin (NCSTN); ligand of numb-protein X (LNX); armadillo repeat containing, X-linked 3 (ARMCX3); melanoma associated gene (D2S448); glutamine synthase (GLUL); and retinoblastoma 1 (RB1) and/or 2) elevated expression of one or more of a distinct set of genes that includes: endothelial differentiation, lysophosphatidic acid G-protein coupled receptor 2 (EDG2); caveolin 1 (CAV1); caveolin 2 (CAV2); discoidin, CUB and LCCL domain containing 2 (DCBLD2); insulin-like growth factor binding protein 3 (IGFBP3); S100A2; CXCL5; c-Met (MET); forkhead box Q1 (FOXQ1); cyclin-dependent kinase inhibitor 2A (CDKN2A); cathepsin L2 (CTSL2); and malignant fibrous histiocytoma amplified sequence 1 (MFHAS1). In another embodiment, the alpha-catenin signature comprises undetectable or low level expression of two or more of the genes: alpha-catenin; NCSTN; LNX; ARMCX3; D2S448; GLUL; and RB1. In another embodiment, the alpha-catenin signature comprises elevated expression of two or more of the genes EDG2; CAV1; CAV2; DCBLD2; IGFBP3; S100A2; CXCL5; MET; FOXQ1; CDKN2A; CTSL2; and MFHAS1. Alternatively the alpha-catenin signature comprises: 1) undetectable or low level expression of one or more of the genes: alpha-catenin; NCSTN; LNX; ARMCX3; D2S448; GLUL; and RB1 and 2) elevated expression of one or more of the genes: EDG2; CAV1; CAV2; DCBLD2; IGFBP3; S100A2; CXCL5; MET; FOXQ1; CDKN2A; CTSL2; and MFHAS1.

The terms "E-cadherin signature", "E-cadherin gene signature", "E-cadherin gene expression signature", "signature 2", or "cancer stem cell signature 2" as used herein refer to a distinct subset of cancer stem cell signatures. Cancer stem cells expressing an E-cadherin gene signature are referred to as displaying a "signature 2 gene expression" or as "signature 2", "signature 2 type", or "E-cadherin signature" cancer stem cells. The E-cadherin signature comprises: 1) undetectable or low level expression compared to normal breast epithelium of one or more of the genes comprising: e-cadherin (CDH1); matrix metalloproteinase 7 (MMP7); nephroblastoma overexpressed gene (Nov); FOS-like antigen 1 (FOSL1); interleukin 1 receptor, type II (IL1R2); secreted frizzled-related protein 1 (SFRP1); keratin 6B (KRT6B); putative lymphocyte G0/G1 switch gene (G0S2); interleukin 8 (IL8); UDP-GlcNAc:betaGal beta-1,3-N-acetylglucosaminyltransferase 5 (B3GNT5); and fibroblast growth factor binding protein 1 (FGFBP1) and/or 2) the increased expression compared to normal breast epithelium of one or more of the genes comprising Src homology 2 domain containing transforming protein 1 (SHC1); FLJ20152; aryl hydrocarbon receptor nuclear translocator (ARNT); cytoplasmic FMR1 interacting protein 2 (CYFIP2); chromosome 17 open reading frame 27 (C17orf27); transporter 1, ATP-binding cassette, sub-family B (TAP1); RNASEL; and similar to aspartate beta hydroxylase (LOC57168). In some embodiments of the present invention undetectable or low level expression of E-cadherin is accompanied by undetectable or low level expression of one or more of the genes that includes: matrix metalloproteinase 7 (MMP7); nephroblastoma overexpressed gene (Nov); FOS-like antigen 1 (FOSL1); and interleukin 1 receptor, type II (IL1R2) and/or 2) elevated expression of one or more of the genes that includes: SHC (Src homology 2 domain containing) transforming protein 1 (SHC1) and FLJ20152. In another embodiment, the E-cadherin signature comprises undetectable or low level expression of two or more of the genes: E-cadherin; MMP7; Nov; FOSL1; and IL1R2. In another embodiment, the E-cadherin signature comprises elevated expression of the genes SHC1 and FLJ20152. Alternatively the E-cadherin signature comprises: 1) undetectable or low level expression of one or more of the genes: E-cadherin;

MMP7; Nov; FOSL1; and IL1R2 or 2) elevated expression of one or more the genes: SHC1 and FLJ20152.

As used herein, the term "a reagent that specifically detects expression levels" refers to reagents used to detect the expression of one or more genes (e.g., including but not limited to, the cancer markers of the present invention). Examples of suitable reagents include but are not limited to, nucleic acid probes capable of specifically hybridizing to the gene of interest, aptamers, PCR primers capable of specifically amplifying the gene of interest, and antibodies capable of specifically binding to proteins expressed by the gene of interest. Other non-limiting examples can be found in the description and examples below.

As used herein, the term "detecting a decreased or increased expression relative to non-cancerous control" refers to measuring the level of expression of a gene (e.g., the level of mRNA or protein) relative to the level in a non-cancerous control sample. Gene expression can be measured using any suitable method, including but not limited to, those described herein.

As used herein, the term "detecting a change in gene expression in a cell sample in the presence of said test compound relative to the absence of said test compound" refers to measuring an altered level of expression (e.g., increased or decreased) in the presence of a test compound relative to the absence of the test compound. Gene expression can be measured using any suitable method.

As used herein, the term "instructions for using said kit for detecting cancer in said subject" includes instructions for using the reagents contained in the kit for the detection and characterization of cancer in a sample from a subject.

As used herein, "providing a diagnosis" or "diagnostic information" refers to any information that is useful in determining whether a patient has a disease or condition and/or in classifying the disease or condition into a phenotypic category or any category having significance with regards to the prognosis of or likely response to treatment (either treatment in general or any particular treatment) of the disease or condition. Similarly, diagnosis refers to providing any type of diagnostic information, including, but not limited to, whether a subject is likely to have a condition (such as a tumor), information related to the nature or classification of a tumor as for example a high risk tumor or a low risk tumor, information related to prognosis and/or information useful in selecting an appropriate treatment. Selection of treatment can include the choice of a particular chemotherapeutic agent or other treatment modality such as surgery or radiation or a choice about whether to withhold or deliver therapy.

As used herein, the terms "providing a prognosis", "prognostic information", or "predictive information" refer to providing information regarding the impact of the presence of cancer (e.g., as determined by the diagnostic methods of the present invention) on a subject's future health (e.g., expected morbidity or mortality, the likelihood of getting cancer, and the risk of metastasis).

The term "low risk" in regards to tumors or to patients diagnosed with cancer refers to a tumor or patient with a lower probability of metastasis and/or lower probability of causing death or dying within about five years of first diagnosis than all the tumors or patients within a given population.

The term "high risk" in regards to tumors or to patients diagnosed with cancer refers to a tumor or patient with a higher probability of metastasis and/or higher probability of causing death or dying within about five years of first diagnosis than all the tumors or patients within a given population.

As used herein, the term "post surgical tumor tissue" refers to cancerous tissue (e.g., biopsy tissue) that has been removed from a subject (e.g., during surgery).

As used herein, the term "subject diagnosed with a cancer" refers to a subject who has been tested and found to have cancerous cells. The cancer can be diagnosed using any suitable method, including but not limited to, biopsy, x-ray, blood test, and the diagnostic methods of the present invention.

As used herein, the terms "biopsy tissue", "patient sample", "tumor sample", and "cancer sample" refer to a sample of cells, tissue or fluid that is removed from a subject for the purpose of determining if the sample contains cancerous tissue, including cancer stem cells or for determining gene expression profile of that cancerous tissue. In some embodiment, biopsy tissue or fluid is obtained because a subject is suspected of having cancer. The biopsy tissue or fluid is then examined for the presence or absence of cancer, cancer stem cells, and/or cancer stem cell gene signature expression.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns can contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g., mRNA, rRNA, tRNA, or snRNA) through "transcription" of the gene (e.g., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (e.g., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene can also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region can contain regulatory sequences such as promoters and enhancers that control or influence the transcription of the gene. The 3' flanking region can contain sequences that direct the termination of transcription, post-transcriptional cleavage and polyadenylation.

The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs can also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene can be endogenous or exogenous to the organism, present integrated into a chromosome or present in a transfection vector that is not integrated into the genome. The expression of the gene is either completely or partially inhibited. RNAi can also be considered to inhibit the function of a target RNA; the function of the target RNA can be complete or partial.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region can be present in a cDNA, genomic DNA or RNA form. When present in a DNA form, the oligonucleotide or polynucleotide can be single-stranded (i.e., the sense strand) or double-stranded. Suitable control elements such as enhancers/promoters, splice junctions, polyadenylation signals, etc. can be placed in close proximity to the coding region of the gene if needed to permit proper initiation of transcription and/or correct processing of the primary RNA transcript. Alternatively, the coding region utilized in the expression vectors of the present invention can contain endogenous enhancers/promoters, splice junctions, intervening sequences, polyadenylation signals, etc. or a combination of both endogenous and exogenous control elements.

As used herein the term "portion" when in reference to a nucleotide sequence (as in "a portion of a given nucleotide sequence") refers to fragments of that sequence. The fragments can range in size from four nucleotides to the entire nucleotide sequence minus one nucleotide (10 nucleotides, 20, 30, 40, 50, 100, 200, etc.).

The phrases "hybridizes", "selectively hybridizes", or "specifically hybridizes" refer to the binding or duplexing of a molecule only to a particular nucleotide sequence under stringent hybridization conditions when that sequence is present in a complex mixture (e.g., a library of DNAs or RNAs). See, e.g., Andersen (1998) Nucleic Acid Hybridization Springer-Verlag; Ross (ed. 1997) Nucleic Acid Hybridization Wiley.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances.

Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide. For high stringency hybridization, a positive signal is at least two times background, or 10 times background hybridization. Exemplary high stringency or stringent hybridization conditions include: 50% formamide, 5×SSC, and 1% SDS incubated at 42° C. or 5×SSC and 1% SDS incubated at 65° C., with a wash in 0.2×SSC and 0.1% SDS at 65° C. For PCR, a temperature of about 36° C. is typical for low stringency amplification, although annealing temperatures can vary from about 32° C. and 48° C. depending on primer length. For high stringency PCR amplification, a temperature of about 62° C. is typical, although high stringency annealing temperatures can range from about 50-65° C., depending on the primer length and specificity. Typical cycle conditions for both high and low stringency amplifications include a denaturation phase of 90-95° C. for 30-120 sec, an annealing phase lasting 30-120 sec., and an extension phase of about 72° C. for 1-2 min.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide can be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide can be single-stranded), but can contain both the sense and anti-sense strands (i.e., the oligonucleotide or polynucleotide can be double-stranded).

"Amino acid sequence" and terms such as "polypeptide", "protein", or "peptide" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein can be produced by recombinant means or can be isolated from a naturally occurring source.

As used herein the term "portion" when in reference to a protein (as in "a portion of a given protein") refers to fragments of that protein. The fragments can range in size from four amino acid residues to the entire amino acid sequence minus one amino acid.

The term "Southern blot" refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA can be cleaved with restriction enzymes prior to electrophoresis. Following electrophoresis, the DNA can be partially depurinated and denatured prior to or during transfer to the solid support. Southern blots are a standard tool of molecular biologists (J. Sambrook et al., Molecular Cloning: A Laboratory Manual, Cold Spring Harbor Press, NY, pp 9.31-9.58 [1989]).

The term "Northern blot" as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies can be detected by various methods, including the use of radiolabeled antibodies.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and can include gene sequences found in that animal so long as the introduced gene does not reside in the same location as does the naturally occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 1.5-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention. In some embodiments of the present invention, test compounds include antisense compounds.

As used herein, the term "sample" includes a specimen or culture obtained from any source, as well as biological and environmental samples. Biological samples can be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

DETAILED DESCRIPTION OF THE INVENTION

The present invention provides compositions and methods for treating, characterizing, and diagnosing cancer. In particular, the present invention provides gene expression profiles associated with solid tumor stem cells, as well as novel markers useful for the diagnosis, characterization, and treatment of solid tumor stem cells.

I. Stem Cells and Solid Tumor Stem Cells

Common cancers arise in tissues that contain a large subpopulation of proliferating cells that are responsible for replenishing the short-lived mature cells. In such organs, cell maturation is arranged in a hierarchy in which a rare population of stem cells give rise to the mature cells and perpetuate themselves through a process called self renewal (Akashi & Weissman, Developmental Biology of Hematopoiesis, Oxford Univ. Press, NY, 2001; Spangrude et al., 1988, Science 241:58-61; Baum et al., 1992, PNAS 89:2804-8; Morrison et al., 1995, PNAS 92:10302-6; Morrison et al., 1996, Immunity 5:207-16; Morrison et al., 1995, Annu. Rev. Cell Dev. Biol. 11:35-71; Morrison et al., 1997, Dev. 124:1929-39; Morrison & Weissman, 1994, Immunity 1:661; Morrison et al., 1997, Cell 88:287-98; Uchida et al., 2000, PNAS 97:14720-5; Morrison et al., 2000, Cell 101:499-510). Due to their rarity, stem cells should be isolated in order to study their biological, molecular, and biochemical properties. Although it is likely that they give rise to most tissues, stem cells have been rigorously identified and purified in only a few tissues. The stem cells that give rise to the lympho-hematopoietic system, called hematopoietic stem cells (HSCs), have been isolated from mice and humans and are the best characterized stem cells. The utility of tissue containing HSCs has been demonstrated in cancer therapy with their extensive use for bone marrow transplantation to regenerate the hematolymphoid system following myeloablative protocols (Baum et al., Bone Marrow Transplantation, Blackwell Scientific Publications, Boston, 1994). The prospective isolation of HSCs from patients can result in a population that is cancer free for autologous transplantation (Tricot et al., 1998, Blood 91:4489-95; Negrin et al., 2000, Biol Blood Marrow Transplantation 6:262-5; Michallet et al., 2000, Exp. Hematol. 28:858-70; Veona et al., 2002, Br. J. Haematol. 117:642-5; Barbui et al., 2002, Br. J. Haemat. 116:202-10).

Understanding the cellular biology of the tissues in which cancers arise, and specifically of the stem cells residing in those tissues, provides new insights into cancer biology. Several aspects of stem cell biology are relevant to cancer. First, both normal stem cells and cancer stem cells undergo self-renewal, and emerging evidence suggests that similar molecular mechanisms regulate self-renewal in normal stem cells and their malignant counterparts. Next, it is quite likely that mutations that lead to cancer accumulate in normal stem cells. Finally, it is likely that tumors contain a "cancer stem cell" population with indefinite proliferative potential that drives the growth and metastasis of tumors (Southam & Brunschwig, 1961, Cancer 14:971-78; Bruce & Gaag, 1963, Nature 199:79-80; Wodinsky et al., 1967, Cancer Chemother. Rep. 51:415-21; Bergsagel & Valeriote, 1968, Cancer Res. 28:2187-96; Park et al., 1971, J. Natl. Cancer Inst. 46:411-22; Hamburger & Salmon, 1977, Science 197:461-3; Lagasse & Weissman, 1994, J. Exp. Med. 179:1047-52; Reya et al., 2001, Nature 414:105-11; Al-Hajj et al., 2002, PNAS 100:3983).

HSCs are the most studied and best understood somatic stem cell population (Akashi & Weissman, Developmental Biology of Hematopoiesis, Oxford Univ. Press, NY, 2001). Hematopoiesis is a tightly regulated process in which a pool of hematopoietic stem cells eventually gives rise to the lymphohematopoietic system consisting of the formed blood elements, e.g., red blood cells, platelets, granulocytes, macrophages, and B- and T-lymphocytes. These cells are important for oxygenation, prevention of bleeding, immunity, and infections, respectively. In the adult, HSCs have two fundamental properties. First, HSCs need to self-renew in order to maintain the stem cell pool; the total number of HSCs is under strict genetic regulation (Morrison et al., 2002, J. Immunol. 168:635-42). Second, they must undergo differentiation to maintain a constant pool of mature cells in normal conditions, and to produce increased numbers of a particular lineage in response to stresses such as bleeding or infection.

In the hematopoietic system, multipotent cells constitute 0.05% of mouse bone marrow cells and are heterogeneous with respect to their ability to self-renew. There are three different populations of multipotent cells: long-term self-renewing HSCs, short-term self-renewing HSCs, and multipotent progenitors without detectable self-renewal potential (Morrison & Weissman, 1994, Immunity 1:661; Christensen & Weissman, 2001, PNAS 98:14541-6). These populations form a hierarchy in which the long-term HSCs give rise to short-term HSCs, which in turn give rise to multipotent progenitors (FIG. 1 in Morrison & Weissman, 1994, Immunity 1:661). As HSCs mature from the long-term self-renewing pool to multipotent progenitors they become more mitotically active but lose the ability to self-renew. Only long-term HSCs can give rise to mature hematopoietic cells for the lifetime of the animal, while short-term HSCs and multipotent progenitors reconstitute lethally irradiated mice for less than eight weeks (Morrison & Weissman, 1994, Immunity 1:661).

Despite the fact that the phenotypic and functional properties of mouse and human HSCs have been extensively characterized (Baum et al., 1992, PNAS 89:2804-8), our understanding of the fundamental stem cell property, self-renewal, is minimal (Weissman, 2000, Science 287:1442; Osawa et al., 1996, Science 273:242-5; Reya et al., 2001, Nature 414:105-11). In most cases, HSCs differentiate when exposed to combinations of growth factors that can induce extensive proliferation in long-term cultures (Domen et al., 2000, J. Exp. Med. 192:1707-18). Although recent progress has been made in identifying culture conditions that maintain HSC activity in culture for a limited period of time (for example see Miller & Eaves, 1997, PNAS 94:13648-53), it has proven to be exceedingly difficult to identify tissue culture conditions that promote a significant and prolonged expansion of progenitors with transplantable HSC activity.

Maintenance of a tissue or a tumor is determined by a balance of proliferation and cell death (Hanahan & Weinberg, 2000, Cell 100:57-70). In a normal tissue, stem cell numbers are under tight genetic regulation resulting in maintenance a constant number of stem cells in the organ (Phillips et al., 1992, PNAS 89:11607-11; Muller-Sieburg et al., 2000, Blood 95:2446-8; Morrison et al., 2002, J. Immunol. 168:635-42). By contrast, cancer cells have escaped this homeostatic regulation and the number of cells within a tumor that have the ability to self renew is constantly expanding, resulting in the inevitable growth of the tumor. As would be expected, many of the mutations that drive tumor expansion regulate either cell proliferation or survival. For example, the prevention of apoptosis by enforced expression of the oncogene Bcl-2 promotes the development of lymphoma and also results in increased numbers of HSCs in vivo, suggesting that cell death plays a role in regulating the homeostasis of HSCs (Domen et al., 1998, Blood 91:2272-82; Domen et al., 2000, J. Exp. Med. 191:253-64). In fact, the progression to experimental acute myelogenous leukemia in mice requires at least 3, and likely 4 independent events to block the several intrinsically triggered and extrinsically induce programmed cell death pathways of myeloid cells (Traver et al., 1998, Immunity 9:47-57). Proto-oncogenes such as c-myb and c-myc that drive proliferation of tumor cells are also essential for HSCs development (Prochowinki & Kukowska, 1986, Nature 322: 848-50; Clarke et al., 1988, Mol. Cellular Biol. 8:884-92; Mucenski et al., 1991, Cell 65:677-89; Danish et al., 1992, Oncogene 7:901-7).

Since cancer cells and normal stem cells share the ability to self-renew, it is not surprising that a number of genes classically associated with cancer can also regulate normal stem cell development (reviewed in Reya et al., 2001, Nature 414: 105-11 and Taipale & Beachy, 2001, Nature 411:349-54). In combination with other growth factors, Shh signaling has also been implicated in the regulation of self-renewal by the finding that cells highly enriched for human hematopoietic stem cells (CD34$^+$Lin$^-$CD38$^-$) exhibited increased self-renewal in response to Shh stimulation in vitro (Bhardwaj et al., 2001, Nat. Immunol. 2:172-80). Several other genes related to oncogenesis have been shown to be important for stem cell function. For example, mice deficient for tal-1/SCL, which is involved in some cases of human acute leukemia, lack embryonic hematopoiesis (Shivdasani et al., 1995, Nature 373:432-4) suggesting that it is required for intrinsic or extrinsic events necessary to initiate hematopoiesis, for maintenance of the earliest definitive blood cells, or for the decision to form blood cells downstream of embryonic HSCs (Shivdasani et al., 1995, Nature 373:432-4; Porcher et al., 1996, Cell 86:47-57). Members of the Hox family have also been implicated in human leukemia. Enforced expression of HoxB4 can affect stem cell functions (Buske et al., 2002, Blood 100:862-681; Antonchuk & Humphries, 2002, Cell 109:39-45). One of the major targets of the p53 tumor suppressor gene is $p21^{cip1}$. Bone marrow from $p21^{cip1}$ deficient mice has a reduced ability to serially reconstitute lethally irradiated recipients. Failure at serial transfer could result from exhaustion of the stem cell pool, loss of telomeres, or loss of transplantability (Cheng et al., 2000, Science 287:1804-8). In mice, bmi-1, a gene that cooperates with c-myc to induce lymphoma (van Lohuizen et al., 1991, Nature 353:353-55; van der Lugt et al., 1994, Genes & Dev. 8:757-69), is required for the maintenance of adult HSCs and leukemia cells. Thus, many genes involved in stem cell fate decisions are also involved in malignant transformation.

Two other signaling pathways implicated in oncogenesis in both mice and humans, the Wnt/β-catenin and Notch pathways, can play central roles in the self-renewal of both normal and cancer stem cells. The Notch family of receptors was first identified in *Drosophila* and has been implicated in development and differentiation (Artavanis-Tsakonas et al., 1999, Science 284:770-6). In *C. elegans*, Notch plays a role in germ cell self-renewal (Berry et al., 1997, Dev 124:925-36). In neural development transient Notch activation initiates an irreversible switch from neurogenesis to gliogenesis by embryonic neural crest stem cells (Morrison et al., 2000, Cell 101:499-510). Notch activation of HSCs in culture using either of the Notch ligands Jagged-1 or Delta transiently increased primitive progenitor activity that could be observed in vitro and in vivo, suggesting that Notch activation promotes either the maintenance of progenitor cell multipotentiality or HSC self-renewal (Shelly et al., 1999, J. Cell Biochem. 73:164-75; Varnum-Finney et al., Nat. Med. 6:1278-81). While the Notch pathway plays a central role in development and the mouse int-3 oncogene is a truncated Notch4 (Gallahan & Callahan, 1997, Oncogene 14:1883-90), the role for Notch in de novo human cancer is complex and less well understood. Various members of the Notch signaling pathway are expressed in cancers of epithelial origin and activation by Notch by chromosomal translocation is involved in some cases of leukemia (Ellisen et al., 1991, Cell 66:649-61; Zagouras et al., 1995, PNAS 92:6414; Liu et al., 1996, Genomics 31:58-64; Capobianco et al., 1997, Mol. Cell Biol. 17:6265-73; Leethanakul et al., 2000, Oncogene 19:3220-4). Microarray analysis has shown that members of the Notch pathway are often over-expressed by tumor cells (Liu et al., 1996, Genomics 31:58-64; Leethanakul et al., 2000, Oncogene 19:3220-4). A truncated Notch4 mRNA is expressed by some breast cancer cell lines (Imatani & Callahan, 2000, Oncogene 19:223-31). Overexpression of Notch1 leads to growth arrest of a small cell lung cancer cell line, while inhibition of Notch1 signals can induce leukemia cell lines to undergo apoptosis (Shelly et al., 1999, J. Cell Biol. 73:164-75; Artavanis-Tsakonas, 1999, Science 284:770-6; Jehn et al., 1999, J. Immunol. 162:635-8). Work by Miele and colleagues showed that activation of Notch-1 signaling maintains the neoplastic phenotype in Ras-transformed human cells (Weizen et al., 2002, Nat. Med. 8:979-86). They also found that in de novo cancers, cells with an activating Ras mutation also demonstrated increased expression of Notch-1 and Notch-4.

Wnt/β-catenin signaling also plays a pivotal role in the self-renewal of normal stem cells and malignant transformation (Cadigan et al., 1997, Genes & Dev. 11:3286-305; Austin et al., 1997, Blood 89:3624-35; Spink et al., 2000, EMBO 19:2270-9). The Wnt pathway was first implicated in MMTV-induced breast cancer where in deregulated expression of Wnt-1 due to proviral insertion resulted in mammary tumors (Tsukamoto et al., 1988, Cell 55:619-25; Nusse et al., 1991, Cell 64:231). Subsequently, it has been shown that Wnt proteins play a central role in pattern formation. Wnt-1 belongs to large family of highly hydrophobic secreted proteins that function by binding to their cognate receptors, members of the Frizzled and low-density lipoprotein receptor-related protein families, resulting in activation of β-catenin (Cadigan & Nusse, 1997, Dev 11:3286-305; Leethanakul et al., 2000, Oncogene 19:3220-4; Reya et al., 2000, Immunity 13:15-24; Wu et al., 2000, Dev. 127:2773-84; Taiple & Beachy, 2001, Nature 411:349-54). In the absence of receptor activation, β-catenin is marked for degradation by a complex consisting of the Adenomatous Polyposis Coli (APC), Axin and glycogen synthase kinase-3β proteins (Austin et al., 1997, Blood 89:3624-35; van den Berg et al., 1998, Blood 92:3189-202; Gat et al., 1998, Cell 95:605-14; Chan et al., 1999, Nat. Genet. 21:410-3; Hedgepeth et al., 1999, Mol Cell Biol. 19:7147-57; Spink et al., 2000, EMBO 19:2270-9; Leethanakul et al., 2000, Oncogene 19:3220-4). Wnt proteins are expressed in the bone marrow, and activation of Wnt/β-catenin signaling by Wnt proteins in vitro or by expression of a constitutively active β-catenin expands the pool of early progenitor cells and enriched normal transplantable hematopoietic stem cells in tissue culture and in vivo (Austin et al., 1997, Blood 89:3624-35; van den Berg et al., 1998, Blood 92:3189-202; Reya et al., 2001, Nature 414:105-11) Inhibition of Wnt/β-catenin by ectopic expression of Axin, an inhibitor of β-catenin signaling, leads to inhibition of stem cell proliferation both in vitro and in vivo. Other studies suggest that the Wnt/β-catenin pathway mediates stem or progenitor cell self-renewal in other tissues (Gat et al., 1998, Cell 95:605-14; Korinek et al., 1998, Nat. Genet. 19:379-83; Zhu & Watt, 1999, Dev. 126:2285-98; Chan et al., 1999, Nat. Genet. 21:410-3). Higher levels of β-catenin are seen in keratinocytes with higher proliferative potential than those seen in keratinocytes with lower proliferative capacity (Gat et al., 1998, Cell 95:605-14; Chan et al., 1999, Nat. Genet. 21:410-3; Zhu & Watt, 1999, Dev. 126:2285-98). Like their normal hematopoietic stem cell counterparts, enforced expression of an activated β-catenin increased the ability of epidermal stem cells to self renew and decreased their ability to differentiate. Mice that fail to express TCF-4, one of the transcription factors that is activated when bound to β-catenin, soon exhaust their undifferentiated crypt epithelial progenitor cells, further suggesting that Wnt signaling is involved in the self renewal of epithelial stem cells (Korinek et al., 1998, Nat. Genet. 19:379-83; Taipale & Beachy, 2001, Nature 411:349-54).

Activation of β-catenin in colon cancer by inactivation of the protein degradation pathway, most frequently by mutation of APC, is common (Hedgepeth et al., 1999, Mol. Cell. Biol. 19:7147-57; Leethanakul et al., 2000, Oncogene 19:3220-4; Spink et al., 2000, EMBO 19:2270-9; Taipale & Beachy, 2001, Nature 411:349-54). Expression of certain Wnt genes is elevated in some other epithelial cancers suggesting that activation of β-catenin is secondary to ligand activation in such cancers (Nusse, 1992, J. Steroid Biochem. Mol. Biol. 43:9-12; Cadigan & Nusse, 1997, Genes & Dev. 11:3286-305; Kirkoshi et al., 2001, Int. J. Oncol. 19:997-1001; van de Wetering et al., 2002, Cell 111:241-50; Weeraratna et al., 2002, Cancer Cell 1:279-88; Saitoh et al., 2002, Int. J. Oncology 20:343-8; Saitoh et al., 2002, Int. J. Mol. Med. 9:515-9). There is evidence that constitutive activation of the Wnt/β-catenin pathway can confer a stem/progenitor cell phenotype to cancer cells. Inhibition of β-catenin/TCF-4 in a colon cancer cell line induced the expression of the cell cycle inhibitor $p21^{cip-1}$ and induced the cells to stop proliferating and to acquire a more differentiated phenotype (van de Wetering et al., 2002, Cell 111:241-50). Enforced expression of the proto-oncogene c-myc, which is transcriptionally activated by β-catenin/TCF-4, inhibited the expression of $p21^{cip-1}$ and allowed the colon cancer cells to proliferate when β-catenin/TCF-4 signaling was blocked, linking Wnt signaling to c-myc in the regulation of cell proliferation and differentiation. Although many studies have implicated the Wnt/β-catenin pathway in breast cancer, activating mutations of β-catenin are rare in this disease and no studies have definitively linked this pathway to human breast cancer (Candidus et al., 1996, Cancer Res. 56:49-52; Sorlie et al., 1998, Hum. Mutat. 12:215; Jonsson et al., 2000, Eur. J. Cancer 36:242-8; Schlosshauer et al., 2000, Cancinogenesis 21:1453-6; Lin et al., 2000, PNAS 97:4262-6; Wong et al., 2002, J. Pathol. 196: 145-53).

The implication of roles for genes like Notch, Wnt, c-myc and Shh in the regulation of self-renewal of HSCs and perhaps of stem cells from multiple tissues suggests that there can be common self-renewal pathways in many types of normal somatic stem cells and cancer stem cells. It is important to identify the molecular mechanisms by which these pathways work and to determine whether the pathways interact to regulate the self-renewal of normal stem cells and cancer cells.

The Wnt pathway is involved in the self-renewal of normal stem cells and activating mutations of Wnt induce breast cancer in mice. This pathway plays a role in tumor formation by human breast cancer stem cells isolated from some patients. Furthermore, evidence suggests that the ability of different populations of breast cancer cells to form tumors differs. Interestingly, the expression of members of the Wnt/Frizzled/β-catenin pathway are heterogeneously expressed by different populations of cancer cells and expression of particular members of the pathway can correlate with the capacity to form tumors.

The different populations of cancer cells and tumor cells drive the proliferation of breast cancer cells. Activated β-catenin is seen in the cancer cells in a significant number of patients. The tumors that contain cancer cells with this pathway constitutively active behave differently than those without constitutively activated β-catenin.

II. Xenograft Model of Human Breast Cancer

Although cell lines have led to remarkable advances in our understanding of the molecular and biochemical changes in cancer cells, their use in the identification of effective cancer therapies is somewhat limited. Cell lines are imperfect predictors of drug efficacy in de novo tumors (Brown, 1997, Oncol. Res. 9:213-5; Hoffman, 1999, Invest. New Drugs 17:343-359). Several factors likely account for this deficiency. Cancer cell lines are selected from a sub-population of cancer cells that are specifically adapted to growth in tissue culture and the biological and functional properties of these cell lines can change dramatically (Leglise et al., 1988, Blood Cells 13:319-37; Ikeda et al., 1993, Exp. Hematol. 21:1686-94; Weidmann et al., 1997, Leukemia 11:709-13; Dorrell et al., 2000, Blood 95:102-10). Furthermore, cancer cells from only a minority of breast cancer tumors establish cell lines or xenograft tumors (Ethier et al., 1993, Cancer Res. 53:627-35; Krasna et al., 2002, Breast Cancer Res Treat. 71:219-35). The phenotypic and functional characteristics of these cell lines can change drastically relative to their properties in vivo (Leglise et al., 1988, Blood Cells 13:319-37). For example, the marker expression of both normal hematopoietic and leukemic tissue culture cells can change rapidly in tissue culture and often does not reflect that of the original stem cells from which they were derived (Furley et al., 1986, Blood 68:1101-7; Leglise et al., 1988, Blood Cells 13:319-37; Ikeda et al., 1993, Exp. Hematol. 21:1686-94; Dorrell et al., 2000, Blood 95:102-10). Even when conditions are devised to permit the proliferation of normal stem cells in culture, the conditions often promote self-renewal or differentiation in a way that prevents the stem cells in culture from recapitulating the hierarchy of cell populations that exist in vivo. Taken together, these observations suggest that the biological properties of cancer cell lines can differ markedly from the cancer cells from which they were derived. This likely explains at least in part why the cell lines often are poor predictors of a drug's efficacy in the clinic.

Thus, the lack of an effective method to consistently grow primary human breast cancer cells in vitro or in vivo for long periods of time has severely limited our ability to understand the biology of this disease. The most efficient xenograft models report the engraftment of pieces of breast cancer tumors in the ovarian, but not mammary, fat pad of SCID mice approximately 60-75% of the time (Sakakibara et al., 1996, Cancer J. Si Am. 2:291-300). Engraftment of dissociated cells is not possible in this model, and cancer cells isolated from pleural effusions only form tumors in immunodeficient mice approximately 10% of the time (Hoffman, 1999, Invest. New Drugs 17:343-59). The present invention (see Example 1 below) provides a xenograft model in which one is able to establish tumors from primary breast tumors via injection of tumors in the mammary gland of severely immunodeficient mice. The xenograft of the present invention allows one to do biological and molecular tests to characterize the clonogenic breast cancer cell as well as other cell types. Importantly, the xenograft tumors developed in accordance with the present invention contain the phenotypically diverse cancer cell types found in the human tumors from which they were derived and the different populations of cancer cells differ markedly in their ability to form tumors (Al-Hajj et al., 2003, PNAS 100:3983).

The development of an efficient xenograft model in accordance with the present invention (see e.g., Example 1), has for the first time reliably allows dissociated solid tumor cells obtained from a patient to form tumors. Importantly, this enables one to routinely analyze biochemical pathways in an individual patient's cancer cells and to do molecular manipulations that allow one to understand the cellular consequences of specific genetic pathways on tumor formation by de novo human solid tumor cancer cells.

III. Solid Tumor Stem Cells Cancer Markers

The present invention provides markers whose expression is specifically altered in solid tumor stem cells (e.g. up regulated or down regulated). Such markers find use in the diagnosis and characterization and alteration (e.g., therapeutic targeting) of various cancers (e.g. breast cancer).

Example 4, provided below, describes methods used to identify solid tumor cancer markers. Some cancer markers are provided below in Tables 4-9, as well as Notch 4. While these tables provide gene names, it is noted that the present invention contemplates the use of both the nucleic acid sequences as well as the peptides encoded thereby, as well as fragments of the nucleic acid and peptides, in the therapeutic and diagnostic methods and compositions of the present invention.

TABLE 4

Up Regulated in UPTG versus UPNTG

S100A8, KRT18, CEACAM6, IFITM2, HLA-C, S100P, S100A9, H2BFT, HLA-C, FXYD3, S100A10, KRT19, TUBB, HLA-DPA1, CEACAM5, LCN2, FTH1, RPS26, IFITM2, S100A7, CAP, HUMMHCW1A, HLA-DRB3, CD63, S100A6, HSPB1, HLA-B, MGLL, PTS, HLA-A, RAI3, DAF, UBC, HLA-A, KDELR3, SERF2, CTSB, CEACAM6, PDLIM1, SHC1, GOLPH2, GABARAP, AQP3, COL3A1, AHCYL1, FXYD3, ITM2B, BF, RBMS1, DUSP1, PSAP, AHRGDIB, ENO1, ATP6V0E, MUC1, RARRES1, CD81, TRIM44, ASS, CD59, PRG1, HLA-E, TXNIP, INHBA, CSTB, H2AFO, HLA-DRB4, RAB31, P4HB, LOC22689, B2M, CSNK2B, MGST3, DKFZp564I1922, C4B, UCP2, FN1, COL1A2, LOC51186, LTF, TIMP1, NPC2, TSPAN-1, COL1A2, SLPI, CIB1, IQGAP1, SPARC, FN1, CCNI, SPTBN1, H2AFO, BTN3A3, FN1, SEPX1, GFPT1, ANXA11, CD74, RAB25, APP, PSEN1, IFI27, FHL2, CPB1, BACE2, PSMD8, LGALS1, PLAT, EIF3S4, ANXA2P2, PILB, IFI30, ATP6V0E, LOH11CR2A, LBP, HLA-DRB1, MIC2, OPN3, SVIL, FDFT1, PTGIS, ORMDL2, PIG7, ERBB3, GSN, FN1, GOT2, BCL6, WBSCR21, ANXA1, CLU, PIK3R3, TNFSF10, NBL1, PEX11B, CDKN1A, SAS, RIC-8, RABAC1, ADD3, ARPC5, GUK1, NQO1, FER1L3, PPAP2A, TSPAN-3, PLOD2, TGM2, LOC51760, TST, TM9SF1, LGALS3BP, C14orf1, D2S448, OPTN, GPX1, MBC2, PTGES, DPYSL2, PEN-2, DAG1, GM2A, DKFZP564G2022, FAT, SLC21A11, ACADVL, ABLIM1, HLA-DPB1, COPA, PPP1R7, DAF, SSBP2, TES, MUC16, PPL, MGC10765, SECTM1, C3, NNMT, ARF3, SEPW1, H1F2, SERPINB1, KIAA0746, RDGBB, ELF3, TUBB4, VCAM1, FOXO1A, EGFL6, ATP1A1, PLS3, LMNA, TGFBI, DD96, GLRX, PROSC, IL1R1, SERPINB2, KRT7, RGS16, TNFAIP1, SYNGR2, PAFAH1B3, GPI, C6orf37, ATF3, HLA-DMA, FLJ22418, DCN, FOXO3A, HLA-DQB1, CPD, DF, HTATIP2, MUC5B, CTSB, PBEF, H11, CAPNS1, Z39IG, MAGED2, TNFSF13, HLA-DRB3, H2BFQ, SGK, P4HA2, VPS28, NDUFB8, PON3, ENSA, EDF1, SERPINB6, FDPS, RGS3, CREB3, PRNP, YWHAB, A2M, HLA-DQB1, PDGFRA, CLMN, INHBB, SURF1, NFIL3, S100A11, HPGD, CLDN7, DAB2, NT5C2, PLXNB2, SGTP1, AP2B1, COL3A1, HRMT1L1, SRPR, RNASE6PL, ANXA8, PROML1, C1S, GALNT6, BAT3, BC-2, GLS, CD14, FYCO1, SQSTM1, CSPG2, DEFB1, BAT3, GALNT2, SPARC, WT1, DUSP6, MONDOA, MACF1, ATP2C1, THBS2, CD53, PGM3, HLA-DRB6, COL1A1, SCAP2, KIAA0436, CYR61, TNFSF13, SLC6A14, CUGBP2, LAMP1, CCL22, CLU, CD163, ANXA3, MBLL39, IL4R, SERPINB1, CNP, TUBB4, FLJ20265, MAFB, EFEMP1, DPP7, SYNE-2, PLSCR1, PDE4DIP, P2Y5, RAGA, SIAT1, N4WBP5, SPUVE, BPAG1, DEPP, BASP1, CTSB, HLA-E, KIAA0308, GAS1, ABR, ABCA1, GRN, WDR1, PM5, CYFIP2, SGP28, FLRT2, ACACA, LUM, FLJ21432, FEM1C, RIN2, PCDH7, SLC7A7, FLJ21347, SOX9, MB, S100A8, DAP, MVP, SPP1, TM9SF1, DOC1, COL5A2, RNF24, GLB1, GRN, HLA-DRB5, ENPP2, CSGlcA-T, KIAA0937, H2BFT, JUP, KYNU, APOL6, GM2A, C1orf24, SYNGR3, COL6A1, CRYM, LXN, FARP1, p100, ANK1, NPC1, RBPMS, VLDLR, ARHC, UBE1, HDLBP, LYZ, DCN, PLAB, SERPINE2, EGLN3, FSTL1, LAPTM5, TRIM29, ACTN4, MUC1, SH3GLB1, BIK, ZNF91, CLIC4, NARF, LIM, SLC1A1, KIAA0746, APOC1, TYROBP, FLNB, EMP1, UBE2L6, KRT6B, MAN2A1, GCN5L1, APEH, F-LAN-1, PRKCZ, CD163, HLA-DQA1, KIAA1668, MUC5B, LAIR1, BCL2L13, CXX1, MPZL1, NR3C1, AHR, TABLE 4-continued Up Regulated in UPTG versus UPNTG FLJ12389, ATP6V0C, MD-1, H2BFA, HSPC023, OSBPL8, ZNF36, TRIM14, UGTREL1, CTSL, COL5A1, PDGFC, UBE2N, SF1,
ARHGEF10, SH3GLB1, HLA-G, KIAA0084, HT012, SULF1, TTC1, UBAP1, PGLS, M6PR, TEM7, NPR2L, GRN, EXT2, DCN, HLA-
DMB, HLA-DQB1, NAGK, MMP19, LBP, ATP10B, CLN3, SP100, CSPG2, VIM, IGFBP3, ANK1, DUSP3, STAT3, CED-6, KIAA0196,
SOX9, NKX3-1, TGFBR2, CAV1, TREM1, PTD009, GPX2, LAPTM5, HSPC022, SSA1, ABS, CPD, DXS9928E, DUSP6, PGBD5,
CNN3, PIP5K1B, FLJ13840, CLDN4, ABCA3, BPAG1, CAPZB, PPIB, ACTA2, CDH11, FLJ10815, HLA-DPA1, FLJ20539, MUC4,
CAV2, ACAA2, CEACAM1, GALNT10, MYO10, C9orf9, PAM, C6orf29, MGC: 5244, RetSDR2, ATP2B4, DHCR7, GP, LOXL2, MIR,
DCTD, BCKDK, RTP801, KIF1B, ENTPD3, PAFAH1B1, LGMN, UBE2L3, PTPRH, RPS6KA2, ALDH1A2, FHL1, GALT, AP1M2,
MAF, C4BPA, POLR2J, KIAA0790, TM4SF3, HPGD, THY1, NCALD, PADI2, KIAA0557, SMARCA1, CD83, AZGP1, SMARCA1,
MRPS11, RAGD, PIGB, FYN, TM7SF1, HLA-E, BRE, PLA2G4C, NOS1, ID3, HLA-DQB1, SSSCA1, PPP1R14B, HLA-DPA1, ANK1,
PRKCH, CALU, PEF, DOK5, COL9A2, ATP2C1, DPH2L1, MUC5B, LOC113146, NDN, PIG3, HLA-DRA, GPS2, CX3CL1, C1QB,
TGFBR3, APOC1, BIN1, CBR3, TGIF, EFEMP2, SCDGF-B, TUBB-5, MAP4K4, CCL3, CCR1, RNF10, RGL, CD1C, FBLN1, GW112,
ALTE, ALP, PLAC1, ISG20, PTE1, NPD009, LOC55893, AP3B1, PRKAR2B, KRT9, COPZ2, LYN, FLJ21478, DKFZP566C243,
NUMA1, ANAPC5, FLJ10134, ADPRTL1, ITGAM, PIP, FLJ22559, IFI16, TMPRSS4, HAIK1, PCSK7, ANK1, FCER1G, IMPA2, HLA-
DQA1, IFNAR2, NEO1, PRKCQ, SMARCD3, CECR1, FLJ11286, TBC1D1, MS4A6A, C1orf16, LRRN1, MRPL23, PUM1, SMA3,
PDE4B, SLC22A4, MMP2, ICA1, SLC22A1L, RRP22, GBA, TMEM8, DUSP2, TREX1, SLC6A8, C3AR1, BSCL2, ARFGAP3, TRIM2,
SERPINB8, TNFRSF6, LDB1, CCND2, RGS2, MEIS1, HRIHFB2122, IF, P1P373C6, UPK1B, WDR10, CGI-49, PSMB8, RARRES1,
SLC16A1, DPYD, DNPEP, FLJ20254, COL5A1, FLJ11017, CCR5, MX2, PIAS1, CAPG, CDC42EP3, IL1RL1LG, SCGB2A1, RNH,
INPP4B, B3GALT4, PLAU, DFNA5, KIAA0852, CRIP2, TIP-1, ZNF142, HSD17B2, MYO1B, PCOLCE, FLJ22169, APOE, DAB2,
CXCR4, NAG, SNCAIP, GBP1, ASRGL1, SLC6A8, REC8, SLC7A11, CPE, MPZL1, TDO2, GALNT12, CDKN2A, KIAA1395,
LGALS8, FLNC, NPR2L, GRB10, MGC15523, PTPRC, CAPN9, IFI16, NBL1, CRYL1, PSMC2, IGF1, BIN1, HNOEL-iso,
DKFZp566O084, FGB, GPNMB, TLR5, FLJ20686, UROS, CX3CR1, HCA112, PRKCB1, BDKRB2, CLTB, KIAA0652, KIAA1668,
DCN, HLA-DQB1, C6orf9, CPR8, TIMP2, PSMB10, LTBP2, FLJ20452, HTATIP, LAMA4, GLUL, SH3BP2, HES2, KIAA1115, KDR,
PROCR, TNFSF10, FGFR1, ELF4, F8A, BAG1, COL5A1, THY1, H2BFG, TOSO, KRT15, AIF1, LY75, KRT17, CEACAM1, GAK,
AGTR1, ASB8, KIAA0792, CDKN1C, C1R, PTGS1, TM4SF6, XT3, HLA-B, DKFZP434B044, ALDH1A3, NID2, U2AF1RS2, H2BFL,
FUT3, PVALB, ITPR3, PODXL, QPRT, PTRF, PSMC4, ACATE2, MAP2K3, ATP2B4, CEACAM1, CALB2, TTR, TRIM38, JM5,
FLJ21135, FLJ23221, FLJ20452, GATA6, RABL4, KIAA1199, IGFBP7, MGC14376, CITED2, CASP4, MEIS2, PHLDA1, OXA1L,
IL1RL1, FLII, EFEMP1, PYGL, LMO4, GPR3, G1P3, APOE, ZNF193, AP1S2, PTGDS, TEM7, LOC51279, SLA, BTG1, INE2, WIT-1,
LBH, CXCL1, RAB31, POMZP3, COL6A3, EXTL3, MGC4309, LOC114990, KYNU, NAB1, CYP2J2, SMURF1, BRAF, HLA-DQA1,
CAV1, KIAA0779, CHKL, SEC6, CG1I, FLJ20920, CGI-49, EIF3S10, P4HB, GYG, DYRK2, DKK1, MAF, TRIM22, CENTA2,
FLJ20113, NR3C1, CYP1B1, HSD11B2, RRP46, FOLR1, HHLA1, THY28, H3FB, FOS, GAA, FLJ13171, RHOBTB3, ZNF32, HOXA5,
CFLAR, PAX6, KIAA0076, CTSS, ALOX15B, MGP, FLJ20084, AKR1B1, LOXL1, H1F3, BNI1, GMDS, FLJ10631, SIAT4A, PIM1,
LRMP, SLI, TFPT, RAGD, DSCR1L1, SETMAR, KIAA0657, GPRC5B, TIMM22, ARHGEF6, H2BFA, PPFIBP2, SALL2, FLJ21820,
ABCD1, CPA3, SNX7, CUTL1, PALMD, ERCC1, MSTP9, PTPN3, GAL3ST-4, C6orf9, PTPRT, RGC32, AD-017, CRELD1, FLJ10097,
RNASE1, S100A4, RORC, CMAR, USF2, FLJ13544, CASP3, SMUG1, RAF1, MYL9, GFR, PDGFRA, DPP4, ARL7, SLC3A2, RHD,
FGL2, RBMS1, EGFR, PRO1580, FCGR3A, PTENP1, H4FH, MSCP, CSGlcA-T, ADAMTS5, TNFAIP6, PRKCDBP, PRKG1, CAPN1,
OAS1, H2BFH, SCHIP1, FLJ21736, BMP1, IQGAP2, KRT5, LMO2, HIC, PLAGL1, AQP6, ZNF42, PHLDA1, YBX2, INPP1, CHST6,
MGC4171, PL6, SPPL2B, EPHA2, CRYAB, MST1, ZNF211, MD-2, CRI1, KIAA0057, PACE4, LOC93349, RALGPS1A, LAMB3,
HLX1, RIN3, SERPINB5, PLD1, DLC1, PIPOX, PTHR2, UBE2G2, CHI3L2, KIAA1111, TGFB2, PLAUR, ID1, ALOX5, IGF1, REPS2,
CDH2, BCHE, SNFT, FLJ11286, MAPRE2, MAOA, SERPING1, PTGER3, KIAA0602, PGM3, MATN2, DNASE1L1, PGD, FZD2,
PPAP2C, GOLGA1, ADAT1, TEX13B, MGP, FLJ20084, ART1, EVI2A, SART2, RFXANK, FBLN5, DPYSL3, ZNF187, RBMS1, MLN,
NRXN3, WASF3, DSC3, PPAP2A, EEF1A2, UBE2H, GABRQ, TFEB, MGC3123, GFPT2, WIG1, FBLN1, PTPRF, MEPE, SLC6A8,
IL1B, GAC1, EPHX1, C11orf9, OSF-2, FLJ10111, SRPX, DAPK1, RBM10, MBD4, MECP2, ILVBL, KIAA0375, JAM3, PRSS25,
KIAA0913, TNFRSF6, CSRP2, CCL4, C20orf19, CA2, SLC7A8, BNC, PHEMX, ADAMTS1, XRCC1, PEMT, H2AFA, NEU1, OPTN,
NRP1, TPM1, WISP3, GPX6, MRPL2, HP, BIKE, PLXN3, FACL5, FLJ11506, GLS, MAPK7, KIAA1053, CDH3, CST3,
KIAA0752, ROR1, TAP2, SBLF, AKAP13, USP21, PP35, ELOVL1, CYBA, KHSRP, MRC1, FLJ12057, H2AFN, MSN, TPM1,
SLC16A3, ADD1, IL1RAPL1, SPTAN1, FLJ10847, SNAI2, FLJ12986, GSPT2, FLJ10450, MAN1C1, MEF2A, VEGFC, RANBP3,
MGC17330, SCD, F5, PIK3CD, SELPLG, LOX, VAX2, MSF, RANGAP1, BIKE, ARHGEF7, FLJ20300, MYLK, GMPR2, CENTD2,
PPP1R9A, ANG, DNAJB2, IDH3G, ODAG, ADPRTL3, COG7, KIAA0429, NEDD4L, ALEX2, ATP6IP2, PTGES, MAN1B1, CYP3A43,
AP3S2, DEFA6, PTGER3, FCGBP, CPSF1, NNMT, HAMP, CGI-38, BAZ2A, HLA-DRA, SP110, CA5B, UBE1L, BTN3A2, KIAA0842,
T1A-2, PTGER4, PTGDS, MARCO, EPB41L1, IL13RA2, CXCL6, APOA1, NPAS2, ETV5, HFL3, EPB41L3, CHI3L1, SSB1, EVI2B,
KIAA1608, MEIS3, FLJ13385, NQO1, BGN, MOX2, dJ222E13.1, GMFG, TBC1D2, SKIP, RABGGTA, MRPL28, FLJ21034, CRY2,
SLC4A2, MGC20727, HAP1, CYBB, GRIT, PTN, FUT2, CDSN, STAF65(gamma), BENE, ENPP2, PAK4, CULN, ICSBP1, NPAS2,
FLJ23516, FLJ23537, AADAC, MFAP2, ERCC4, STK13, MCAM, GPR65, CYP17, FLJ20373, TNS, TRA1, NPY, PTPLA, PNLIPRP1,
RBMS1, TM7SF2, MKL1, NCF2, AP4M1, ITGB4, SLC11A1, PSCDBP, NFE2L3, ELAC2, CBFA2T1, S100A12, PACE4, KIAA1395,
HLA-G, EDN1, FLJ20730, IGLJ3, UNC93B1, RPL29, RIL, TCF8, RYR3, TCFL4, MCRS1, HML2, FLJ10357, FLJ22405, FLJ20627,
HFE, DKFZp564K142, ATP10D, SLC12A4, P311, FLJ13055, ADCY9, EYA1, ACO2, CIAS1, INHD3, ZFPM2, MGC11279, MALT1,
NDUFS8, IL10RB, TCF3, HLALS, DKFZp761K1423, DDX8, G0S2, SLC16A3, CCL18, ZDHHC4, FKBP1A, HRH1, GSA7, PTPRM,
HBP17, APPBP2, TNRC15, JM1, PSME3, HFL2, BCL11B, SCARA3, APEG1, LHFP, IGF1, PDGFRL, MUC13, IGF1, NXF2,
HRMT1L3, ARHD, KIAA0582, KIAA0977, FCN1, LAMP3, DNAJC6, ALDH3B1, TNXB, MAPK3, FLJ13491, APOA1, RBP4, OAS3,
CLTB, GP2, MID1, FGR, DISC1, PP1044, PSAP, CHODL, FLJ22173, TPD52L2, DD5, PSIP1, HSPB7, EMP3, KRT6A, C5R1, ENO2,
PF4, SYN1, PLSCR3, HMGCS2, BCAR3, LOC51693, ANGPTL2, TAHCCP1, LOC51063, KIAA0561, GJB3, CPVL, PCBD, CGI-96,
PKIA, NR3C1, GAS7, FBN1, MPV17, SLC21A3, ARHGAP6, FMO1, CSPG2, FLJ22531, STX7, SCN1B, TETRAN, FGF23, CLECSF12,
CDKN1C, HF1, GSTT1, VILL, BLAME, ROD1, TAPBP-R, HLA-G, HT017, CHP, SLC25A10, LST1, FLJ11196, VAMP2, NR0B2,
CSNK2A1, SLIT3, MAPK7, CXCL2, GYG2, PGS1, CDYL, VNN2, CLN5, NPAS2, MLL, TRPM4, LYPLA3, MYO7A, PSMB1,
PAFAH2, PITX1, GRB10, TIMELESS, APOBEC3G, KIAA0819, GALNT10, PTPRO, NMB, FLJ12298, RAMP1, OR2F1, HPGD,
CALB1, CCR7, KIAA1614, SLC2A3, OLFM1, DKFZP564G202, FEZ1, AKR1C3, ACADS, CALB1, PIK4CB, FOXA2, FLJ20581,
RRAS, BHLHB3, HUNK, MLLT3, RBMS2, KIAA0620, SLC29A2, SIRT5, SLC27A2, FLJ21458, DTR, ACTN1, KIAA0429, SLC21A9,
FLJ10211, LOC63920, FLJ12377, ARPC4, TSSC4, MEF2D, RPL10, NOV, CGI-72, FAIM2, TBX2, GABRD, C1orf24, MGC2615,
NR1H3, FLJ14675, AQP5, ZNFN1A3, SSPN, SIGLEC7, COL5A2, HLA-DOB, SLC12A3, Apg4B, HERC3, HEM1, EBI2, ZNF323,
FLJ20950, FASTK, C6orf32, LILRB2, SPP2, DHPS, UBE2B, MET, ST14, EGR3, SIGLEC5, SAMHD1, PGCP, PTPNS1, SPARCL1,
FLJ22160, RANBP2, IL15RA, OXT, FLJ21168, PTPN14, BAIAP3, TPM4, NCR3, TEK, H2BFE, SLC34A2, SLC26A2, KIAA0870, MET,
SENP3, PTGER4, CGI-48, PDGFB, CD86, GTF2H4, KIAA0053, PTX3, BIMLEC, CAMK4, PROS1, AOX1, KIAA0931, COL4A1,
USF2, PLINP-1, TM6SF1, PTPRG, SNX17, SLC5A4, MSTP032, PCTP, PQBP1, CDV-1, AD037, RNASE6, SNAI1, KIAA0872, MEF2C,
ZNF3, LOC157542, FCER1A, PRB1, SIRT3, DKFZP434K046, ABCC6, NPC1L1, BCL2A1, LOC64167, GS3955, UP, CLECSF6,
MGC20727, CHN2, CD3D, BAD, KIAA0435, PECAM1, IGSF4, BCAS3, C8A, ZNF131, MGC10771, SEC14L1, SERPINH1, IL1F6,
KLK11, THBD, FKSG28, KIAA0173, HKE2, PFTK1, FLJ11560, APOL1, CHRM4, ALLC, MS4A4A, SLC1A1, BBP, ILT11, SAMSN1,
IGF2R, FLJ20421, PBX2, MAP1LC3B, 37872.00, NCK1, FGFR2, CD86, FLJ23506, SCD, FCGR2B, CYP4A11, S100A2, AP2S1,
PLAGL1, PTGIS, PCOLCE2, SLC2A3, DKFZP761N09121, GPR105, OSBPL3, RPLP2, DKFZP586I2223, CD36, BBOX1, VNN3,

TABLE 4-continued

Up Regulated in UPTG versus UPNTG

AKR1B10, ZFHX1B, DKFZp434H2215, RoXaN, RSN, GALNS, PROSC, PCDHA3, PLXNA2, CCR8, BACH1, NPAT, SPAG6, DGCR13, CAPN5, OSBPL3, CYP-M, FLJ13902, FLJ13659, ADAMTS3, IL1RAP, ELF1, HYAL1, WNT2, CCS, TREM2, KIAA1036, FLJ20574, FLJ13215, CUGBP2, FLJ20010, GABRE, RCE1, SCIN, HLALS, MGC10940, ADARB1, PLA2G7, KIAA1237, KIAA0889, FLJ22593, CD244, NEK9, TAT, RAP1GDS1, SMA5, MYH11, APAA, MERTK, GJA4, TNFRSF1B, MRPS12, HSF1, COL11A2, DAB2, PCQAP, WDR4, ABCA8, CLPS, ARHN, PHF3, AKAP12, LST1, MGC12904, FLJ11539, ZFP36L2, SERPINF1, MGAM, PRG4, RAB5EP, CASP2, DIPA, AQP3, VAMP5, DXS1283E, COL4A2, MMP10, CD97, MGAT3, FCN2, KIAA0475, FGF9, CTSZ, SQV7L, H326, PLD3, TRPC1, OR7E24P, GRIA2, KIP2, BARX2, MHC2TA, RECQL, NUP214, DHRS2, P2RY1, KIAA1155, HLA-DRB4, CAPN6, TLR7, AHCYL1, TRGC2, NEB, POU2F1, CPSF1, APOB48R, CLDN9, FLJ21276, AEBP1, MN1, PKD2, PACRG, CALM1, TSPAN-3, KIAA0233, ATP6V0E, TRIM34, DKFZP564J102, CNOT8, STC1, NFE2, FCN3, CKIP-1, PLA2G4A, TRGC2, DES, CDC42EP2, HSD3B1, CSN10, PRKACB, RDH5, CDW52, XYLT2, HPN, WIZ, GOLGA2, CSHL1, GLRX, PCDHB11, TNFSF18, KLRD1, 384D8-2, WHSC1, TNFRSF10C, EVPL, TNFRSF5, SIAH2, GYPB, PMM1, DPYSL3, FLJ14297, ZNF42, BSN, OMG, AXL, ACK1, PKD2, KIAA0711, FLJ00060, GUCA1A, PAPPA, CBLN1, FRCP1, BTD, FLJ20591, FGG, CXCL14, NPR1, CAMK2G, HLCS, SECP43, BCAT1, MSR1, IGFBP4, C13orf1, PRO2577, KIR2DL4, BAALC, FLJ21919, CNTF, LOC51295, ENTPD1, TAPBP-R, CAP350, PKD2L1, EVX1, NR1H2, FLJ13868, ERCC3, DKFZp434L0850, NR3C1, DMD, BST1, CARD15, SKD3, CASP1, PCDHA6, NR4A1, HAS2, COPEB, R29124_1, THPO, AQP6, MGC10848, RAB6B, ABP1, APOB, UTRN, MICA, SSTR4, FLJ23056, C6orf32, ROM1, FLJ90005, KCNN4, MGA, HSPC219, CGEF2, CDC42BPB, CCR4, GLS, MAGE-E1, PILR(ALPHA), PGK2, KIAA0657, SF3A2, NOTCH4, CLECSF2, FBLN2, B4GALT1, WNT2B, NRBP, LTB, FLJ22021, CDH6, TUBGCP2, GCN1L1, ZIC4, HR44, AGA, SIAT9, EMP1, EPOR, IGKC, TAHCCP1, PECR, FLJ21477, EDG1, MS4A2, BCAS4, FLJ22404, DPYS, PRCC, POLD4, BIKE, GAS7, KIAA1000, ZFP, WNT7B, MUC4, FLJ10477, CD1D, MGC4614, CCR1, NEU3, SIX3, FLJ10640, GPR51, STOM, SERPINE1, HLA-DQB1, PTN, DNCLI2, EN2, FLJ20378, IFP38, LOC90326, IGLJ3, NCYM, KIAA1107, GP2, PLAUR, CD47, BIN1, MGC14799, IGFBP1, SSX1, IDUA, RECK, CD6, IGHM, ADD2, AKAP2, HSF4, MDS032, FLJ20086, TNXB, IGFBP3, KLKB1, PRB4, KCNF1, PDE9A, SIPA1, SMARCB1, COL4A6, PDE10A, NFATC1, CDH16, COL6A1, ZNF272, LDB2, HCRTR2, B1, ATP12A, FLJ11710, LOC116150, KIAA1049, HSPC157, FLJ20701, IGSF6, TOMM22, TGFB1, CHML, FAAH, COL6A1, DGUOK, LRRN3, B7, KIAA0876, C1orf22, CYP2A13, CXCL5, CD5L, FBXL6, GALNT2, GJA10, COL15A1, TEX13A, 7h3, TRD@, RIL, OTC, SAST, KLF8, TUBA8, MGC45806, FLJ13479, GRP, LRP4, CD84, WBSCR14, EPOR, BRAP, zizimin1, DNAJC4, FLJ20356, SERPINA2, FLJ10432, CD209L, NRP1, PGDS, PLA2G2A, TNFRSF4, PRO2214, DNAJB6, RDHL, FOSL2, DEPP, FLJ20241, MMP11, HLA-DQB1, RBM10, 8D6A, MAX, CUGBP2, CKTSF1B1, ISL1, CREBBP, ACTA1, NUDT2, OR1A2, GPR86, SH3BP2, APAF1, PRO1386, IGL@, EVI5, KIAA0443, MFNG, XCL1, ITM2A, IGLJ3, SIN3B, CCL18, NRXN3, AQP7, HLF, SEC14L1, DNM1, KIAA0551, STK17B, GNS, IL10, MGC20727, COL5A1, SEMA3B, C11ORF30, CASP10, ORM2, NPEPPS, CALCRL, ALK, SH3BGRL3, FOXD1, MNDA, LCP2, ANK1, GSTA1, FLJ20856, ALOX15, L1CAM, DRF1, TM4SF9, SLC24A1, NR4A1, ATP7A, PCLO, TSHR, CAMK1G, MSR1, GLIPR1, KIAA1069, LYN, FLJ00001, MIG2, DLGAP2, TF, SOD2, ELMO1, BMP2, SLC12A5, PSG11, EPB41L3, CAMK2B, TGM4, SCN11A, CALU, F11, GPR75, KIAA1053, SIX1, WBSCR5, RIN3, CCNT2, CABIN1, NR2C2, TRPM1, ABCD2, VDU1, FLJ20811, GJB3, ASAHL, RAB1A, HAND1, BAI2, EDG8, TNFSF13, HPIP, PTPRN2, PRO0618, PRKCI, PSTPIP1, FACL4, ETV4, CACNA1D, WISP1, PRLR, FEZ2, CCL25, PCNX, SNX10, LILRA2, KIAA1086, MKRN3, PRG1, HGC6.1.1, GUCA1B, RIG, FLT1, HLA-C, KIAA0427, LILRB2, MAP2K5, FLJ11125, EFNA5, DUOX1, LIG4, MRE11A, DEFB126, DNAJC9, RQCD1, ABCB8, HPR, MRS3/4, KPI2, NR1I3, FBXW7, HS3ST3B1, LAD1, SHMT1, CITED2, DNALI1, POLYDOM, PFKFB4, KIAA1019, UTY, SCAND2, ZNF215, FOSL1, CDH17, PCSK5, ACE2, ERG, FLJ11619, KIAA1466, KIAA0675, IL18, FLJ21562, BTN3A3, FACL6, FANCA, ANKRD6, CALCR, CSF1, FLJ13262, CALR, TFEC, SSTR2, HBD, MGC10986, GTF3C2, HRC, RHOK, KIAA1117, KIAA0924, ITGB1, DEFCAP, FLJ12525, TBXA2R, GLIPR1, AVPR2, CCNE2, TBXAS1, RGS5, HAGE, FOXO3A, SYK, 384D8-2, ABO, 24432.00, MASS1, PF4V1, CASP5, CNGA1, FLJ14251, SLC9A3, UPK3B, DLG1, COL17A1, PCDHB12, UACA, CUL7, LGALS2, ELK1, TRPM8, MGC2655, NR3C2, PPARG, MXD3, FLJ13055, UBE2I, PRO2176, CACNB4, FOXH1, RASA2, PML, BCAT1, EDG2, OCRL, ATPAF2, PMS2, POU2F3, PTPN21, SUPT6H, HAN11, ROR1, COPEB, KIAA1654, DKFZP434B204, TNIP3, EPAG, CACNB2, NEK2, XRCC4, IL6ST, TNRC11, CAPN11, 37870.00, PLA2G4B, NPEPL1, RASGRP1, HABP4, CYLD, C15orf5, ITGB3, FLJ23093, NPPC, MCOLN1, GAD2, TRO, LOC51063, OGN, NR1H4, MTRR, SS-56, NT5E, C22orf4, SLC4A5, SGCG, C8orf1, LGALS2, ELK1, TRPM8, MGC2655, NR3C2, PPARG, MXD3, SERPINB3, PRO0461, GNAI1, AVPR2, PEG10, SPINK1, CLDN1, STC1, KIAA1045, F2, GNG11, FY, H4F2, D21S2056E, CAPZB, KIAA0599, C1orf29, RGS12, GCG, NCOA2, FOXL2, UGT1A8, PKLR, NRG1, ITGA7, CNOT3, SPRY2, PIK3R1, ZF, PTPRR, KSR, TCEB3L, IREB2, PRO0899, PAWR, SOX18, Gene Symbol, RPL28, FLJ13352, C20orf114, PIGR, ERAP140, MYO5B, EGR1, LOC124220, TCEB2, BACE2, NMES1, KIAA1324, MGC45416, WASF2, APOA1BP, FLJ32115, ATP6V0E, TIMP2, H2AFJ, C9orf5, RASD1, KIAA1437, H2AFJ, RDH-E2, DKFZp434G171, GUK1, FLJ20671, CAPNS1, KIAA1671, H19, FLJ23153, NDUFB10, FLJ13593, GLTP, TLP19, ENPP5, MGC39329, MRPL41, ARF3, LOC51255, HSPCA, BRI3, FLJ14525, LOC113246, RAP2B, FLJ14117, GLCCI1, PPP3CA, PHP14, MIR, ADCY4, FLJ11320, MSTP028, Cab45, TNFSF13B, ZNFN2A1, MGC14327, KIAA1404, RAB34, RBMS1, ARHU, SPUVE, LOC54516, SAMHD1, LOC170394, SAMHD1, PIGR, CYP4X1, NFIA, KIAA1715, CTHRC1, DKFZp547A023, KIAA1434, MYBBP1A, MGC4248, H4F2, H4FH, NPD007, MGC14839, FLJ21791, HDLBP, C8orf13, FLJ23393, FLJ11046, DKFZp434C0328, BCAT1, BAT5, FLJ31235, LOXL4, RNF7, MGC2803, CLDN1, KIAA2002, STMN3, MYO5B, CTSS, ATP1B1, MGC4309, UBE2H, DKFZp762H185, LOC115265, MGC13045, SH3KBP1, MGC4604, TRIM47, C9orf5, SDCBP2, AP1S2, C20orf110, LOC51234, SAT, dJ55C23.6, CKLFSF7, PCDHA10, MGC11115, MGC15397, LOC116238, TRIM8, FLJ25157, NAV1, KIAA1870, ALS2CR9, GCNT1, GALNT4, HSCARG, PPP1R1B, PHP14, TGFBR3, ARIH2, MGC1842, SELM, AKAP2, MAFB, FLJ23091, MBNL, TEM8, CFL2, KIAA1554, SEMA4B, FLJ10961, SCAP2, KIAA1244, RIG-I, TRABID, TRIM56, MK-STYX, TMEM9, FAD104, GLTSCR2, MGC: 13379, MGC40555, FLJ14251, NOL6, FLJ23499, DHRSX, DKFZP564D166, CED-6, LOC57168, KIAA1337, CRB3, EMILIN-2, GJB2, ECGF1, CHDH, LOC120224, ZNF75A, EPSTI1, NESHBP, FLJ10210, FBXO25, MS4A6A, NOTCH2, FLJ39885, FOXP1, ORMDL2, MGC11134, MS4A6A, HSPC195, KIAA1913, UACA, C1orf13, USP28, LCMR1, GBA2, DKFZp547D065, TH1L, RORC, PAK1, MGC2555, KIAA0146, FLJ20186, SCAMP2, NGEF, C14orf58, CED-6, LOC55893, GTAR, MGC24103, MS4A6A, DAG1, KIAA1394, FLJ20073, MGC13114, FBXO32, CD44, CTL2, ARNT, C21orf63, CLIC6, C20orf64, FLJ90586, RBPMS, LOC51242, MGC45441, CLMN, FLJ35564, MGC4604, DRCTNNB1A, CGI-125, DKFZp547A023, MGC39325, CD109, FLJ23499, EHD3, MGC4840, USP21, DKFZP761E1824, FLJ22215, IL17D, MGC16028, MS4A7, GALNT2, CDKN2B, LOC90550, CKLFSF3, FS, KIAA1949, MRPL10, MGC45714, MAP4K1, SLC4A11, HPS3, DNAJC5, LOC120224, FLJ11036, KIAA1337, FLJ10697, SENP2, SART1, MGC2474, SCD, FLJ14486, KIAA1214, CARD6, KIAA1691, MLL5, C20orf102, FBXW5, RARA, SLC13A3, FLJ33817, NRP2, BACE, LOC55971, FLJ14855, LOC133957, GPR108, MRPL41, MGC10485, CMG2, C8orf2, PIAS3, DKFZp434G118, KIAA1500, APXL2, MGC16028, COGI, UBE2H, CMG2, CTSB, LOC143903, CANX, PIG, CP, FLJ40432, LOC137392, DKFZP586F1524, SAMHD1, DKFZP761A052, HSPC002, C20orf23, DKFZp434N061, SLB, PSMB7, MGC4342, DKFZP434P106, FLJ22678, SYTL4, DKFZP566J2046, LOC51249, PARVA, FLJ23091, YR-29, LOC55893, OGN, CPNE2, KIAA1784, Spir-2, DNAJA4, TMOD4, FLJ30726, C9orf19, SNX8, DUSP16, FLJ34633, FLJ25785, OSAP, B2M, DERMO1, ZNFN1A4, SCYL1, C16orf44, MAF1, MGC12435, MSCP, JAK3, PPP1R16A, MGC4607, G6PT1, MGC16212, FLJ22283, SRA1, HBP1, CTL2, HCC-4, SPTB, C6orf37, KIAA1337, SNCAIP, SMOC2, PYGO2, FLJ12770, FLJ40432, BMF, SLC27A4, C1orf19, SLC5A1, CHRM1, FLJ14457, DKFZp434F054, SES2, MGC45474, BTC, APOA5, DKFZP434P106, KIAA1522, ZNF317, a1/3GTP, PCDHB3, MGC26963, HSPC182, SNX9, NFAT5, C4orf7, NCAG1, KIAA1363, TAF6L, NAV1, KIAA1361, ZDHHC9, MGC2615, PHLDA1, AD-003, LOC90268, FLJ10101, PCDHB16, SLC2A12, CKLFSF2, FLJ23518, SEMA6D, PS1D, SLC31A1, MGC10485, SLC5A2, ARHGAP9, NKD2, ETS1, FLJ90586, REN, FLJ14981, DKFZp761H0421, DKFZp434F2322, MUM2, SPP2, MGC4734, FLJ13687, BANK, CNTN3, TLR8, HM13, FLJ36525, SLC12A6, TABLE 4-continued Up Regulated in UPTG versus UPNTG DAPP1, VANGL1, MSH5, P5CR2, HAVCR2, CXCL14, GALNT5, ANKH, MGC29463, FLJ00028, TMPRSS6, AMOTL1, ODF3, MGC4604, ARG2, FLJ10052, FLJ13881, PP2135, SLC12A4, MGC10500, MAP1B, DKFZp547I094, FLJ30473, FLJ12886, ST6GALNAC6, ESDN, SEC15B, FLJ33903, LATS2, ZNFN1A1, SLC16A10, DSCR1L2, PSMB5, GPR34, FLJ20557, CGI-85, HCA127, DKFZp434I1930, FLJ90811, LOC113026, FBXO18, MGC8721, BLVRA, MGC10974, PRO1635, MAP4K1, HKE2, FLJ32122, FLJ35867, FLJ10392, WFDC3, C21orf6, FLJ23654, DKFZP586D0824, C21orf91, ENTPD2, RGNEF, GPRC5C, RALBP1, FLJ31052, C11ORF30, FLJ30803, ITGA11, KIAA1053, AGTRAP, NDUFS2, FLJ32069, ACTR1A, SLC2A4RG, PPARBP, FLJ10055, C20orf167, FLJ12649, KIAA1909, IFIT2, EMR2, CD5, HT036, SERPINB9, MAP1LC3A, IGKC, ZD52F10, FLJ32028, BTEB1, FLJ20539, CCL28, MGC21621, KIAA1130, KIAA1554, FLJ31937, RPL29, GSA7, FLJ25067, FLJ20989, LOC92689, FLJ12604, MS4A6A, ELA1, SMOC1, C1QG, MGC14421, KIAA1576, FLJ20245, LOC155066, PRDM6, DAP10, PCDHB14, FLJ25124, SNRK, ADAMTS16, SES2, SECP43, EPSTI1, KIAA1948, NOL6, PALMD, PAG, MGC39807, TTY7, NUDE1, KIAA1210, HRB2, USP21, C9orf19, LOC93589, DKFZp434E1822, MGC10561, RNO2, GLCCI1, MGC3234, AMOTL1, FLJ33868, B3GNT5, FAM11A, SBBI31, FLJ23654, SLT, CPM, DKFZp762K222, NSE1, KIAA1817, NYD-SP21, LUC7L, FLJ13063, SIAT6, CASP14, FLJ11896, GPR92, FLJ25027, EVC, HOXA3, HTGN29, MGC4281, MGC15548, GSN, AD023, FLJ14311, TAGAP, KIAA1276, CGN, ZDHHC12, FLJ21736, FGFR2, LOC91461, GNG2, BACH1, KIAA1921, KIAA1957, FLJ10111, KIAA1145, ARHGEF7, STARD4, retSDR3, HBXAP, ARFGAP1, NY-REN-60, RIG-I, X102, AF1Q, SYTL4, ICAP-1A, KIAA0872, LOC148932, SCML1, NOL6, Hes4, LOC57038, TRPM6, ABCC13, CGI-85, DRLM, BCAR1, NR0B1, MCOLN2, KIAA1836, MGC35048, VIL1, LOC124245, MRP63, TTYH5, FLJ14735, PRIC285, KIAA1999, GALNT7, EGR4, DKFZp434F2322, PHACS, LOC51219, LOC132158, PRO0971, SUI1, SKD3, RNF26, TTTY6, TNRC18, CTXL, FLJ12666, FLJ39957, FACL5, POLK, SLC25A13, FLJ31318, ZFP91, MGC19825, TPM2, PPP1R14C, LOC142820, ALDOA, EGFR-RS, FBXO27, PRO0038, MGC10992, NPCR, HCMOGT-1, RSP3, PPP1R9A, KCNMB3, GPR55, ZFP28, PRO1635, PRO0038, MS4A6A, KIAA1647, KIAA1607, BAZ2B, FLJ32752, ZNF216, PP2135, KIAA1357, MGC16207, KIAA1694, GBP1, FLJ10474, FLJ10826, ELAVL3, LOC90668, CPXM, MGC2452, FLJ20273, MIC2L1, FAD104, GPR107, MGC15419, SORCS2, ST6GalNAcI, RP4-622L5, DKFZP434F011, TNKS2, DKFZp761K2222, Ells1, SLC4A11, KIAA1163, CALN1, KIAA1828, MEGF10, GRIN3A, REV1L, BHLHB5, ADMP, DKFZp667I133, MGC13275, KIAA1889, DKFZP434A236, GPS2, FLJ20309, NAV1, MGC2603, ARHU, FLJ33071, NUMBL, CDGAP, FLJ35713, DKFZp761A132, FLJ10300, FLJ12634, GTF3A, NEO1, RRAD, MGC10966, PTPN2, FLJ10292, ACPP, CISH, DOT1L, POLRMT, CGI-149, KIAA1202, DKFZp761J139, MGC40178, GATA4, EVIN2, MS4A8B, FLJ10057, NDUFV3, SF3b10, RP2, FLJ21032, CLG, MGC3040, ODZ2, AQP1, DKFZp566F0947, CCL27, TARD9, MGC40222, DKFZp564C236, SDS-RS1, SNCAIP, ENDOGLYX1, CGI-30, FLJ10314, MGC20470, KLHL6, KIAA0212, PRO0899, KIAA1894, FLN29, FLJ20373, GTF2I, GJC1, BHLHB3, CPNE5, GPC6, IL6R, RRN3, DKFZP564J047, C20orf99, CED-6, DKFZP434P1735, TGIF2LY, LOC83690, GPR110, FLJ34922, FLJ20211, FREQ, USP26, MGC15634, ZSIG11, ZFHX2, C7, UNKL, LOC151835, MGC21854, FLJ25410, EGLN2, KIF9, KIAA1550, CIP1, DNAJC9, FLJ14768, MGC2599, LOC57018, DDX12, MGC33993, SLC22A3, KIAA1399, DKFZP434F091, EG1, SE70-2, DKFZP564I1171, CDH26, TRPC7, DKFZP566K1924, C20orf60, ROR2, KLHL5, SCARA3, PRO1580, MGC15523, DKFZp434C0328, FLJ31528, CR1L, FLJ32734, NXF3, MGC41906, CLECSF9, SSBP4, ZNFN1A4, FBXO22, NCAG1, MAP2, KIAA1529, TIGD5, SNX9, FLJ32001, RPC5, AK2, KIAA1887, ACK1, FLJ37312, ARSD, FLJ31564, LOC51134, MYEOV, GNAI1, MGC12335, FLJ20356, KIAA1617, HNT, C21orf59, LOC221468, ENAM, PB1, TBXAS1, NMNAT, MGC10204, TNKS1BP1, LOC57401, FLJ32194, ENTH, APOA1, ITGA6, MGC12458, FLJ23403, BCL10, H19, C7orf2, DNER, PDE11A, MAF, FLJ10378, MGC14276, TLE1, SH3GLB2, TTTY8, KCNH3, LOC90693, ENDOGLYX1, LOC144402, CGI-105, LOC153222, ASAH2, MGC4415, KIAA1495, SFRS12, and AGPAT3.

TABLE 5

Up Regulated in UPTG versus HSC

CFL1, S100A8, SERPINA3, UBC, MUC1, SFN, ANXA2, ANXA2, COX7A2, HSPA1A, KRT18, ANXA2, OAZ1, TMSB10, CA12, DNCL1, CEACAM6, ASAH1, RAC1, ARF4, TACSTD2, MYL6, MSF, JTB, CKAP4, TFF1, IER3, GATA3, IFITM2, SFN, MTCH1, TPM1, CD24, NET-6, MLC-B, MLPH, QP-C, SCGB2A2, S100P, S100A9, COX6A1, CAPN2, COX5B, CD24, H2BFT, XBP1, FXYD3, RNP24, PTS, GSPT1, COX6C, TIP-1, HIG1, RPS16, SAT, HSPCA, TPD52L1, TMSB4X, S100A10, JTB, RBPMS, KRT19, FLJ10830, TUBB, JTB, ITGB1, CEACAM5, MT2A, LIV-1, HN1L, LCN2, LOC51142, LGALS3, RAB13, FTH1, TCTEL1, IFITM2, S100A7, PSMB4, MAGED1, FLJ20151, DBI, COX6B, C20orf24, ARHA, NFIB, PTP4A2, NDUFB2, CALM1, ATP1B1, GNG5, CD63, NAT1, S100A6, EIF4B, ESR1, HSPB1, TAGLN2, ALCAM, NDUFS5, AGR2, C8FW, TXN, HDLBP, NDUFA4, PPIC, GLO1, RAB11A, LPP, HDGF, CALM1, MGLL, PTS, ARF1, DC12, SNRPD2, C4A, RAI3, NDUFA6, ATP6V1D, MLCB, TEGT, DSP, PNN, ACTN1, NIFIE14, NDUFB4, DAF, VAV3, UBC, SSR2, MKNK2, HSPC014, KDELR3, TACSTD1, DKFZP564A2416, ASAH1, DDR1, ENAH, KDELR2, DNCI2, PPP1R11, PP, SERF2, CTSB, SSR4, GNAS, PGM1, CEACAM6, PDLIM1, GATA3, MGC3178, SHC1, GOLPH2, GNAS, VAMP3, S100A14, GABARAP, ALDOA, TAX1BP1, LASP1, NFIB, CCT3, AQP3, DBI, VCL, GNAS, ALDOA, COL3A1, ATP5J2, MGC16723, USP9X, TMEM4, MTX1, HSPC134, ZMPSTE24, UQCR, AHCYL1, GOCAP1, HT011, EDF1, CRIP1, FXYD3, MRPL9, RIP60, TIMM17A, BF, RER1, DC50, CTBP2, HEBP2, YIF1P, LOC54499, APMCF1, UGDH, PSAP, SPEC1, FLJ12619, TUFT1, COX5B, LRP10, ATP6V0E, CYP27A1, PON2, NQO1, PTPRK, EIF4EL3, GNAS, CLTA, MDH2, TCEB2UBE3A, TM9SF2, MUC1, RARRES1, PRDX4, MIF, TPD52, CD81, DSTN, HRY, HSPC051, SMBP, HDGF, C14orf2, BRD3, NHP2L1, PPP2CB, DLG5, ASS, ENSA, MAGED1, CD59, SHAPY, CAST, JDP1, HK1FBXO9, RPL38, INHBA, EMS1, HRI, APP, HAX1, FKBP11, GOLGB1, SPINT2, GORASP2, CD24, HSPA1B, FLJ13593, MGC5466, E2F4, PRO1855, UBE2V1, KIAA0882, RPL36AL, CSTB, ATP5I, OASIS, DKFZP564K0822, RCP, MAGED1, PSMB5, NDUFS2, YWHAZ, KIAA0310, RPL38, FLJ20273, RAB3-GAP150, PSMA5, ATP2A2, C20orf97, TUBB2, RAB31, C9orf7, HIG1, INSR, TPM1, GSPT1, PSME2, CSNK1A1, P4HB, EIF2S1, LOC92689, NDUFA3, KIF5B, PAM, MT1H, SHAPY, FLJ10898, GUSB, BNIP3, KIAA0992, FLOT1, C20orf28, PSMB7, TAF10, CSNK2B, EPRS, PIG7, DAP3, ECHS1, AP3D1, COX8, PMP22, LOC54499, ALDH3B2, MGST3, PRDX2, PTD011, COX5B, CAST, LASS2, PSMB2, MT1X, MYD88, DKFZp564I1922, FLJ20719, C4B, H2AFL, FLOT1, PIN4, TCEB1, WFDC2, SQRDL, CSTA, PTD009, PTPRF, DAD1, PDEF, FN1, GPX4, DDR1, ARHD, COL1A2, PDEF, HSPC009, MEA, ABCD3, CYB5, MLCB, PRO1489, PDEF, RPS11, IDH1, SLC12A7, H2BFB, SH3BP4, CD24, SLC38A1, RAB31, LTF, TIMP1, SH3YL1, SEMA3F, TSPAN-1, KIAA0852, NDUFA8, COL1A2, SLPI, PSMD4, RPL27A, GNAS, KIAA0876, DP1, CEBPD, CIB1, IQGAP1, TSG101, MGC3077, CYB5, FN1, LOC51128, EMP2, CETN2, PACSIN2, PBEF, MRPL24, CTSB, SDFR1, MLP, TM4SF1, C20orf3, PRKAR2A, MGC5178, FN1, FLJ20054, MMP24, SEPX1, GFPT1, ANXA11, ADFP, GMFB, AP3S2, PTBP1, BAG1, FLJ10496, CYB5, CXADR, RAB25, FH, APP, CDR2, PSEN1, RFP, SEC22L1, GGPS1, ARMET, USP7, FLJ20847, EFA6R, HSPA4, RDBP, TNFSF10, DDR1, KIAA0429, PLP2, RABGGTB, BAG3, IFI27, GATA3, LAMP2, CD24, MRPS14, FHL2, CGI-130, CPB1, SCAMP3, NESCA, BACE2, PSMD8, LGALS1, MPHOSPH6, FLJ14154, COPZ1, CALR, HK2, WIRE, PTP4A1, TRA1, DKFZP564G2022, CTSH, CRAT, PLAT, ANXA2P2, YME1L1, PILB, ITGB5, KIAA1026, FKBP4, TBL2, PIGT, WSB2, IFI30, TUBB2, E2IG5, YME1L1, ATP6V0E, RAB4A, LOH11CR2A, PLU-1, KIAA0483, SLC2A1, LBP, MGC11256, FMOD, TLE1, POLR2H, TOB1, NSF, TACC2, OPN3, USP3, PSMB1, TMP21, DUSP4, RAB2, SVIL, FDFT1, NFE2L1, PTGIS, RPP20, PGLS, ORMDL2, NR2F6, PIG7, ERBB3, TRAP1, DDR1, SDC4, HSA243666, PLU-1, ATP6V1E1, DAAM1, GSN, MCP, KIAA0143, P17.3, PIN4, WARS, FN1, TABLE 5-continued Up Regulated in UPTG versus HSC TFG, COPB2, ERP70, MRPS18A, C22orf5, LYSAL1, POLR2I, SAR1, ATP6V0B, TUFM, NDUFB2, BCL6, PDCD6IP, TRIM33, UBE2N, WBSCR21, NEDD5, LOC51123, GMFB, PFN2, KRTHB1, NANS, CLU, TOMM20-PENDING, NDUFS8, MT1G, ANK3, PIK3R3, IL13RA1, TNFSF10, DNPEP, TNRC9, NIPSNAP1, BRP44L, PEX11B, FLJ13612, FLJ22028, POLB, ANXA4, SEC61G, PREI3, CDKN1A, MT1L, SAS, PSMD5, COBL, CARD10, UBE2D3, RABAC1, CPD, C21orf97, PAM, MRPS10, CGI-109, GBP2, TC10, NMA, FASTK, P4HA1, GTF2I, COG2, MYO6, LMNA, TCF3, C14orf3, PEA15, PRKCBP1, GALNT3, IRS1, ACP1, GUK1, MBD2, PTD008, RBM4, TNFRSF10B, KIAA0266, NQO1, DNAJA1, FACL3, FER1L3, CD59, PPAP2A, FACL3, IGSF1, KIAA1598, TGM2, MTMR9, LOC51760, TST, TM9SF1, LGALS3BP, P24B, D2S448, RPL27, KDELR2, TJP1, OPTN, NME2, HRI, F12, RABIF, TJP2, ATP1B1, GGPS1, FLJ10116, PTGES, SCO2, PEN-2, PSMB3, CDS2, RAD23B, PPM1A, ARL3, TXNDC4, GOLGA5DDX32, DAG1, VIL2, TPBG, GM2A, EIF2S2, NEUGRIN, DKFZP564G2022, KIAA0934, ADM, CSRP1, GRIM19, FAT, SLC21A11, ACADVL, NDUFA2, GALNAC4S-6ST, EIF5, RAB1B, NME1, ASPH, MUT, ARF4, FBXL11, COPA, UBL5, CSNK1E, ATP5I, CCND1, HT021, PPP1R7, LOC56851, SRP54, DAF, CTBP2, TLE2, HSD17B1, SRD5A1, SLC9A3R1, MUC16, PPL, MGC10765, EPB41L4B, SECTM1, CHPPR, SORD, VTI1B, CRABP2, EFNA1, HERPUD1, CDYL, MRPS17, SGPL1, DUSP14, SSBP1, C20orf35, C3, HSPC163, ATP6V1G1, YF13H12, FLJ13052, ABCC10, STUB1, NNMT, RAB20, CALU, PLCB1, NR2F2, HSPE1, TM4SF1, RSN, FLJ20813, TPARL, SEPW1, H1F2, GRHPR, HSPA1A, RAB2L, SARS, FIBP, PSMB6, RER1, BCL10, ATP9A, IDS, PPIB, RAB2, Cab45, PYCR1, GSTM3, SEC24A, MAPT, FLJ10579, ADAM9, FLJ21603, DNAJB1, C20orf116, DKFZP564G0222, RDGBB, RRAS2, AKAP9, KIAA1243, DCI, ELF3, PDE4A, CRIM1, CORO1B, PXMP4, S100A13, DPP3, GTF2H2, PSMB8, TUBB4, MRPL33, STK39, VCAM1, MAOB, DKFZP566C134, CSNK1A1, FLJ20761, EGFL6, ATP1A1, APH-1A, FLJ22055, TOP1, RCL, SMT3H2, POLR2K, LMNA, ID4, JTV1, CLN5, AKIP, TGFBI, LLGL2, ITGAVPPP2R5A, IFNGR1, JAG1, DD96, PGRMC2, SNRPE, MGC19606, DJ971N18.2, CKAP1, MGC3180, HYOU1, PACE-1, FLJ22662, KIAA0674, ALS2CR3, EPLIN, MYO1C, CD164, PCMT1, IL1R1, SERPINB2, HSD17B4, FOLR1, HRIHFB2122, FLJ22457, MXI1, TCFL1, POR1, FLJ20375, H4FD, KRT7, TFAP2B, MRPL15, SLC5A6, RGS16, TNFAIP1, FLJ14146, HOXB7, PIK4CB, RPS20, C11orf24, SYNGR2, NCKAP1, APG3, RHBDL2, ASC, C1orf9, KIAA0247, HRB, PAFAH1B3, SNK, ASB13, LSM1, GPI, MCJ, CASK, HOXB7, RBBP6, PKIG, SMARCA4, BLVRB, HYPK, SUCLG2, KIAA0494, SLC2A10, HIG2, TSTA3, TNRC9, SEC23B, SELENBP1, RAB6C, VAPB, ZNF144, PCNP, SULT1A3, NQO2, SNMP1, FLJ30656, NUBP2, FLJ20152, ATP5H, FLJ22418, DCN, SOD2, FLJ20958, YWHAZ, TRPS1, CYP51, SUCLG2, CGI-45, ZFP103, MID2, CPD, TFAP2C, C1orf37, dJ222E13.1, ICMT, UNC84A, CALM1, DF, SUPT16H, BZRP, SLC9A1, FLJ13110, ATIP1, MUC5B, CTSB, GJA1, SDHC, SUCLG2, MGC3067, PBEF, IL27w, HSD17B7, GRSF1, CD9, H11, FLJ10099, NIT1, LAMC1, HBXIP, NDUFV2, STX12, SDHA, D123, Z39IG, RPL5, PA200, SC4MOL, HSPC171, STXBP1, CACNG4, MAGED2, MGC4368, MPZL1, ZDHHC7, RPA40, IGSF3, FLJ22638, SPTLC2, MTVR1, FLJ21016, SGK, NCOA1, MAP4, GLRX2, P4HA2, JAG1, MTVR1, FLJ22940, NDUFB8, ISGF3G, B4GALT5, EMS1, C22orf2, LRPAP1, PON3, EIF5A, ENSADKFZP564F0522, FLJ11273, EPS8R1, EDF1, ISG20, EPS8R1, FLJ10525, PSMD4, NINJ1, TSSC3, FDPS, RGS3, CREB3, UBE2D1, ProSAPiP1, CAST, WBSCR20A, MAPKAPK2, RPP38, YWHAB, A2M, RBX1, PDGFRA, EFS2, RAB9A, RAD23B, BAZ1A, BCL3, SNX4, CLMN, HRY, INHBB, NPD009, AHNAK, TNRC9, S100A11, MYO1C, LDLR, KIAA0102SCYE1, LARP, GNA11, NDUFA7, CKAP1, KPNA1, NDUFS7, RDH11, RAP140, MTCH2, HPGD, ITGB4BP, CLDN7, CGI-147, GTF2IRD1, LRRFIP1, DAB2, DKFZp667G2110, LGALS8, MARS, MGC14480, MGC3038, PLXNB2, ZFP36L1, DBI, AP2B1, PLS1, CYC1, PPIF, COL3A1, PDHB, NSAP1, PFDN2, GAS2L1, DMBT1, FZD1, GBA, DNCL2A, VCP, MYO1B, ANXA8, C11orf13, DSS1, KIF13B, CECR5, GARS, COPB, NFE2L1, DLG3, FLJ12443, NALP2, APM2, KIAA0790, C1S, HN1, GALNT6, CLPP, STK24, PP3111, MTA1, CAMTA2, BAT3, FADD, BC-2, CLOCK, UAP1, AAK1, MGC3121, CD14, CDC2L5, FYCO1, SQSTM1, UBE3B, CSPG2, EIF5, DEFB1, MTMR6, KIAA0643, 101F6, SLC35A2, TNKS2, TPMT, WWP1, LHFPL2, NEDD8, PC326, PTK2, FLJ20748, FOXA1, IDE, FLJ20275, CACNB3, CDC42, TEX27, KIF3B, PP3501, CDCP1, HNRPU, TULIP1, SPARC, DVL1, GMDS, EZF-2, AP2S1, GNA11, SEMA4C, WT1, KIAA0010, LAMA5, PTDSR, ETFB, KIAA0284, TFF3, GRHPR, RPL37A, G1P2, MGC11242, FLJ23189, FKBP9, MGC35048, RTN1, ASL, PTK9, THBS2, SDHC, HIS1, DSTN, MGC3047, PAFAH1B1, AGPAT1, PGM3, AKR7A3, COL1A1, KIAA0436, GDI1, CYR61, RNPEP, SGPL1, APBA3, GNB2, SOCS5, FGFR3, RGS19IP1, ORC5L, SLC6A14, KIAA0229, FLJ22028, LAMP1, SNRPD3, MAPK13, DNAJA3, FLJ22471, CKMT1, PSMB4, CCL22, CLU, CD163, ANXA3, ATOX1, GTF2E2, ANXA6, FLJ21127, BMPR1A, WBSCR20C, MBLL39, IL4R, SEC24D, SLC19A2, RNASEH1ALAS1, ACAA1, DPM3, ABL1, TUBB4, EFNB2, CALR, ARPC1B, MCP, SH3GL1, ECT2, LOC51619, NEK11, MAFB, EFEMP1, G10, DPP7, FUT2, ATP6V0E, SLC22A5, SSH-3, SYNE-2, PH-4, CTBP2, BATF, PDE4DIP, TRIP6, P2Y5, RNASE4, CANX, CD2AP, HIP1R, FH, ADCY2, SPUVE, FLJ10462, QSCN6, CLTA, SLC31A1, DEPP, CLTB, KIAA0544, CTSB, MARS, PAK4, PHIP, HIP2, FLJ23375, ARHGAP8, TNFRSF12A, KRT8, UBE2V1, PDPK1, KIAA0251, PPGB, GAS1, RAD17, PIAS3, 37872.00, ABCA1, FLJ10375, KIAA0217, SPR, GRN, EIF2B4, ITGB5, RPN1, APLP2, WDR1, SDC1, MGC2963, PM5, MGC5178, TBCE, EEF1D, SGP28, FEM1B, FLJ10829, FLRT2, KIAA0934, PCDHGC3, COPS6, PART1, ACACA, AMPH, LUM, FLJ23338, EPHB4, FBP1, WSB2, HBP1, EVA1, MUS81, POLR2K, KIAA0103, HPS1, LOC55831, FEM1C, RIN2, DKFZP564O092, ENDOFIN, DHCR24, FLJ20604, LOC90141, PCDH7, SLC7A7, SLC12A2, FLJ21047, S100A11P, CGI-115, TOM1L1, C1orf34, SOX9, MB, EIF4EL3, S100A8, APLP2, TDP1, FGF13, URG4, RARRES3, FLJ12910, DAP, RFX5, MVP, FLJ21749, PAXIP1L, FLJ20152, ATF7IP, GPSN2, RIL, VEGF, TM4SF6, SPP1, NVL, CALR, CKAP1, AKAP1, HSPC166, TMPRSS3, TM9SF1, LOC56902, ENT3, GRB2, COG5, DOC1, COL5A2, RLN2, GRN, ADCY9, KIAA0690, ENPP2, ILF1, SLC35A3, SLC39A1, C20orf11, PCDHGA1, CGI-148, WBSCR20A, CSG1cA-T, KIAA0937, KIAA0674, LTBP1, H2BFT, SEMA3C, SULT1A1, ERP70, KIAA1078, KIAA0869, PLA2G12, PACE-1, KIAA0984, AUP1, RBSK, AMOTL2, SULT1A3, LANCL2, PAIP1, JUP, PPP3CB, KYNU, SH120, PRKCI, ARG2, OSBPL2, APOL6, GATM, LOC113251, GM2A, FLJ12436, CD24, SYNGR3, HSPA1A, CTNND1, SEC61A1, IFRD2, PCK2, PSMA3, COL6A1, ARHGEF5, RAI, VPS45A, BECN1, GNPI, PA200, PXF, BZW1, KIAA0876, KIAA0471, ATP6V1D, CRYM, KCNS3, FARP1, ANK1, FLJ20234, PLU-1, NPC1, ZNF339, RNF14, RBPMS, SEC13L1, KIAA1630, SIX2, SGSH, RPA3, VLDLR, ENPP1, ITSN1, AP2B1, ARHC, SWAP2, UBE1, MARK4, MK-STYX, HDLBP, ZNF185, KIAA0227, GOLGA3, KIAA0033, RAB26, SHANK2, ALDH3A2, DCN, HT008, PLAB, IMPDH1, GRIT, FARP1, MAPK13, ERBB2, TGOLN2, RALA, ARHE, ABCF2, PRSS11, PLCD1, HSPC111, TRIM29, ARL1, ACTN4, MUC1, DJ434O14.5, FLJ11619, SH3GLB1, TCN1, FLJ11149, BIK, ZNF91, PRSS8, CYB5R1, TRIM16, EPS15R, NARF, SLC11A2, AUTS2, LIM, SLC1A1, ALDH7A1, TC10, SC65, IRF7, HLXB9, RAB17, KIAA0746, PCDHGC3, APOC1, AKAP1, EPS8R1, TBCC, DDAH2, TYROBP, N33, FLNB, DKFZp564A176, PREI3, JAG2, UGCG, OSR2, KRT6B, CDC42EP4, TPD52, C20orf149, FLJ12975, MAN2A1, GCN5L1, MCF2L, FLJ22386, STHM, RAB26, AP1S1, GMPPB, CYP2B6, F-LAN-1, PRKCZ, DC-TM4F2, KIAA0556, FLJ12619, CD163, DAZAP1, TIMM13, MADH2, COL4A5, POGK, FXC1, POP4, NET1, ARHGEF5, NS, KMO, PTP4A2, LOC57228, MUC5B, AUH, BAIAP3, SFMBT, CD44, BYSL, FLJ20085, PARG1, C4.4A, PSMD4, GSK3B, PSMD12, EIF2AK3, SCARB1, DP1, STRN3, FLJ23263, CTSD, HSGP25L2G, TFIP11, MPZL1, SNAPC3, RBM3, PP591, TGFB1I1, GRHPR, AHR, FLJ12389, SORT1, KDELR3, ATP6V0C, MD-1, D8S2298E, XAP135, HSPC023, C9orf7, C21orf97, DNCH1, ZNF36, PPP1R7, VIL2, RAB2, MYH9, TRIM14, UGTREL1, CTSL, KIAA0977, RPC62, UBE2N, DCAMKL1, FUCA1, ATP7B, RBSK, ST5, CGI-90, NOH1, FLJ10925, RAB22A, RTN2, KIAA0089, SH3GLB1, CDS1, MGC5466, WFS1, AMMECR1, COX17, ACOX2, FLJ10101, HT012, LMNA, PRDX2, SULF1, KIAA0923, FLJ22637, SCA1, PAIP1, CAP2, CMT2, ZNF217, CYB561, PAPSS2, STX18, FZD4, DDXx, UBAP1, ITPKC, PTS, PGLS, LAD1, DSC2, STOML1, DDX16, PTP4A1, FLJ10901, SLC12A8, NME3, TEM7, NPR2L, ACY1, GNB1, GRN, PLEK2, KRAS2, ARHGAP8, FLJ11856, DCN, LOC55871, NAGK, FLJ14154, FLJ22709, TP53TG1, STK6, COX5B, MICA, EPPK1, EPS8R2, MMP19, WWP1, TUBG1, LBP, ATP10B, CLN3, UBE2G1, SULF1, FLJ30002, SYN47, CSPG2, CACNB3, IGFBP3ELOVL1, DTNA, ANK1, C12orf22, EPN3, IDE, mDKFZp761F2014, SEC22L1, ILF2, ACTR1A, FLJ10052, STAT3, CED-6, FLJ10359, SOX9, PIASY, KIAA1169, CAV1, HOXB2, FLJ22191, LOC57117, PMVK, BLNK, TREM1, HSRTSBETA, EIF4EBP1, SIGIRR, TSLRP, C20orf44, PTD009, PP1665, HMG20B, RTCD1, PDE8A, CNNM2, GNA11, GPX2, KIAA0599, FLJ13868, DBN1, GEMIN6, PMM2, SPTAN1, PFN1, DCTN1, UBE2A, GPR107, MRPS2, SNARK, SSA1, SH120, UBPH, CPD, HOXC6, DXS9928E, TEAD3, PGBD5, ST14, TABLE 5-continued Up Regulated in UPTG versus HSC CNN3, KIAA0256, MGC3262, FLJ13840, CLDN4, FLJ11939, ABCA3, OAZIN, MRPL17, PPP2R4, CGI-135, KIAA0802, AP1M2, SCN10A, PPIB, MRPL40, ZK1, FLJ12517, CDH11, CDC42EP2, CLN3, CGI-152, FLJ10815, C11orf13, MADH1, FLJ20539, HMGE, KIAA0923, LAP1B, PTGDS, FLJ20559, SFXN1, KRTHB6, UNC13, MUC4, FUT8, NET1, NEBL, BCS1L, RAI16, CAV2, FAAH, CEACAM1, LEF1, GALNT10, NAGA, ABHD3, STOML2, C1orf27, OSTF1, KIAA0227, PCLO, MYO10, THBS1, LANO, HMCS, H3FK, SPS, C9orf9, PITPN, SCRIB, PAM, NPDC1, ASNS, SLC33A1, HSPA6, HMBS, FLJ21918, FLJ11939, C6orf29, PRSS15, ENC1, HTR4, SSH-3, RECK, NAV2, TRN-SR, MRS2L, FLJ20366, LOC51754, LGALS8, KIAA1040, B4GALT1, FLJ21841, KIAA0237, IL8RA, MLF1, ANXA9, VRP, LOXL2, MIR, ATP5D, KIAA0632, FLJ20174, FRAT2, DDX26, BCKDK, ATP6V0A4, KIF1B, ENTPD3, RAB1A, EGLN1, KIAA0268, LGMN, PTPRH, KMO, UGCGL1, AKR7A3, RIG-I, CYB5R2, FLJ11773, RPS6KA2, CLCN3, PTPN18, GNG12, PKP3, ALDH1A2, NEK3, UQCRC1, ZNF236, RASAL1, RPL14, FLJ12287, AP1M2, C4BPA, MAF, FLJ10815, FLJ90798, TRAM, POLR2J, TLN2, DNASE2, PEX11A, KIAA0790, TM4SF3, HPGD, TRIP10, THY1, CGI-143, TPR, AQR, CTNND1, HOXC10, CDC42EP4, PLEC1, PSFL, PTP4A1, FLJ22353, NCALD, INPP5E, MKRN4, PADI2, SMARCA1, KIAA0317, EHD1, AZGP1, SMARCA1, NOVA1, MRPS11, FLJ23091, HOXC4, OCRL, CKAP4, CD44, CD2BP2, FLJ10055, TM7SF1, PVRL2, ID4, DJ434O14.5, SLC7A8, DKFZP564I122, MIPEP, PLA2G4C, KPNB2, DAXX, NOS1, ID3, MRC2, SSSCA1, PPP1R14B, MTHFS, HSPA5, ELF5, MARCKS, KIAA0514, RRAS2, ADRM1, ANK1, KIAA1324, PSEN2, UBXD2, CALU, DOK5, KCNMA1, COL9A2, ATP2C1, FGFR2, DPM2, KIAA0895, DPH2L1, MUC5B, SSR1, LOC113146, KIAA0644, LOC51042, DNAL4, PIG3, GPS2, CX3CL1, INHBC, C1QB, PDPK1, RLPL2, HRI, MGC4825, TGFBR3, LAMC2, PEX7, HFE, DJ434O14.5, FLJ20296, MGC5347, FLJ10521, RARA, KLC2, SLC21A2, SPTAN1, APOC1, LARGE, STK38, GCC1, SNX13, TNNT1, NTRK3, TGIF, H3FH, KIAA0485, KIAA1416, EFEMP2, SMARCE1, KREMEN2, UMPK, KIAA0268, DDEF2, VAMP3, CGTHBA, OSBPL10, CGI-96, MGC3248, TUBB-5, PXMP3, RBM9, LOC51257, LAMC1, SLC30A5, PPARD, KIAA0349, MAP4K4, GNG4, CCL3, GPRC5C, CCR1DKFZP586B0923, RNF10, SCGB1D2, VIPR1, RGL, TESK1, AK3, KIAA0649, SCARB2, MGC2494, FLJ20048, EPS8, DNAJC1, MOB, FLJ11200, CD1C, AGPAT1, FBLN1, GW112, ICT1, CGI-141, DSCR1, PIP5K1C, PRY, ALP, PRDM4, PLAC1, ISG20, FLJ20457, TCF-3, PTE1, TNK1, MAGED1, FLJ13782, NPD009, UCHL3, PRELP, LOC55893, KIAA0451, AK1, LMCD1, NET-7, AP3B1, OS4, ABI-2, NOTCH3, KRT9, COPZ2, CGI-58, RISC, DKFZP566C243, ATP6V1C1, TRIM38, PTOV1, PDGFB, PIP, IDN3, FLJ10199, BCAT2, HOXA11, PDXK, NEDD4L, MGC29816, TPD52, TMPRSS4, HAIK1, SUPT4H1, WNT5A, PCSK7, ANK1, FCER1G, FLJ13397, ERO1L, BPGM, HLA-DQA1, DCXR, KIAA1094, NEO1, FKBP4, SMARCD3, TPSG1, FLJ21940, APBA2BP, TMPRSS6, TBC1D1, MS4A6A, U2AF1RS2, MGC11308, MRPL23, PCDHA12, SMA3, CELSR3, SLC22A4, MGEA6, ICA1, STX4A, EFS2, RRP22, X123, GBA, DNAJB1, TGFB3, CRAT, FLJ11159, TMEM8, GALE, FLJ20555, DDX3, TULP3, TACC2, SLC6A8, C3AR1, BSCL2, TRIM2, ELF3, SPTBN5, SERPINB8, FLJ23259, TNFRSF6, MIPEP, CELSR2, LDB1, MOG1, PXF, HPIP, HMOX2, SURB7, HRIHFB2122, FLJ22056, CLASP2, IF, HSKM-B, UPK1B, WDR10, IQGAP1, PSPHL, DUSP4, FLJ10856, RARRES1, ALAD, PARVA, KIAA0608, DNPEP, GMPPA, FLJ20254, IDE, COL5A1, GFER, PSMA7, FLJ11017, ZNF144, MYC, PEX14, CCR5, ARL1, NME5, NDUFB7, PPAP2B, C21orf80, CAPG, MRPL52, MIG2, HSPC039, DPH2L2, SRD5A1, SDR1, RAB36, SCGB2A1, PRDM4, ASM3A, FRA, GLUD1, FLJ13187, CARM1, RPS6KB2, LOC55565, B3GALT4, ALOX5AP, PLAU, DMN, DFNA5, CGI-36, TC10, SLC38A6, KIAA0852, CRIP2, HSPC003, NSFL1C, FLJ20605, GPC1, FLJ10504, MKLN1, TIP-1, SCAM-1, IL13RA1, UPLC1, FLJ20171, LOC88523, HSD17B2, MYO1B, ZNF364, CDK7, MAP7, PCOLCE, IL13RA1, SSNA1, ESRRA, CPS1, APOE, MY014, CHK, THBS3, DAB2, PCMT1, MAP7, SLC7A4, APPD, ITCH, KIAA0255, BCMP1, AKAP9, SNCAIP, MRPS7, PIGPC1, HIVEP1, SLC6A8, DKFZP564O0823, CRK, BAIAP2, SLC7A11, CPE, MPZL1, TDO2, FUT1, STAB2, CDKN2A, CGI-12, TPM4, IL1RN, MGC4504, KIAA1395, COQ7, CARHSP1, PARVA, FLNC, C11orf24, NPR2L, GFPT1, ARVCF, CAPN9, SRRM2, NBL1, KIAA1078, SURF5, ARHGEF4, F23149_1, FKBP11, KIAA1102, IGF1, RBT1, HNOEL-iso, LAMB2, DKFZp566O084, FGB, GPNMB, TLR5, CX3CR1, THBS1, GORASP1, HCA112, AQP3, BDKRB2, SLC4A7, CLTB, MRPS18A, CTSK, CELSR2, KIAA0652, NKX3-1, MXD4, ALDH4A1, DYSF, ECGF1, DCN, PSME3, TIMP2, HOXB6, EGFR-RS, EPS8R1, ECM1, LTBP2, PRPS1, CDA08, HUMAUANTIG, MGC955, FLJ22678, LAMA4, GLUL, MAGED2, HES2, FASN, CYB561, IDH3A, MPPE1, PRKAR1A, KDR, DICER1, PROCR, TNFSF10, HAGH, FBXO3, TC10, PRKAR1A, ZNF20, AK1, ALDH3A2, FSTL3, ZNF408, PTP4A1, PMS2L9, BAG1, DKFZp667G2110, MUC2, KIAA0265, ZFP100, KCNK1, IFI35, THY1, FLJ23186, H2BFG, ARSA, KRT15, ICA1, FLNA, BPHL, PCTK1, TUBA2, KRT17, SHANK2, CEACAM1GAK, VARS2, AGTR1, ASB8, MPZL1, RFPL3, DNM1L, SUPF, KIAA0792, NUCKS, C1R, HRASLS3, TM4SF6, SPINT1, XT3, SLC16A5, FLJ21079, MST1, MMP9, DKFZP434B044, NY-REN-24, ALDH1A3, NID2, KIAA0409, ANKRD5, KIAA0513, U2AF1RS2, IGF2R, H2BFL, FUT3, LEC2, LY6E, CSH2, SRCAP, DKFZp434G2311, CHST4, PPP2R1B, PVALB, FLJ12960, ITPR3, PODXL, PARD3, PRSS22, FLJ10697, MGC2376, SLC39A4, MRPS16, QPRT, GFRA1, BRD2, CNGB3, LAK, C5orf8, PPP2R3A, HCGII-7, ANK1, OAZ3, PSMC4, ACATE2, DKFZP434L0117, EDAR, PPFIA3, GRB7, MCM3AP, CALB2, APXL, ABI-2, TTR, CSNK1D, DJ1042K10.2, TRIM38, PSCD2, HSPC134, SREBF1, HUS1, PSK, C12orf5, SPOCK, EDG4, FLJ10769, ANKRD3, FLJ21135, PPP2R4, CED-6, GATA6, MGC10963, ZNF14, CPR2, KIAA1199, HIP1R, NOL3, ZNF306, FLJ14298, RAGE, IDH3A, GPR107, KIAA0368, RPA40, MEIS2, PHLDA1, CELSR1, N33, BLZF1, FLJ22637, IL1RL1, GOLGA1, SAR1, FGFR2, FLII, ANK3, SIRT7, BAP29, EFEMP1, FLJ20277, DXS1283E, LAMB1, TLE2, TJP1, PDE8A, RCV1, HYAL2, ERdj5, KIAA0350, FLJ12571, FLJ10534, MDK, LOC51762, APOE, KIAA0964, SSH-3, TJP3, ZNF193, PRDX2, PTGDS, TEM7, DNAJB4, POLR2D, DKFZP586J1624, JAM1, LHX3, FLJ10252, KIAA0451, INE2, WIT-1, FLJ23209, CXCL1, RAI2, KIAA0857, FLJ21062, KIAA1096, ARF4L, THBS1, RAB31, SS18, NDRG3, TGOLN2, FLJ10665, COL6A3, TAZ, AGRN, PGC, SOX11, MCP, EXTL3, ACRV1, NELL2, MGC4309, LOC114990, KYNU, SNX11, ANGPTL2, CYP2J2, SMURF1, SDCCAG16, BRAF, NFYA, ADD1, LIG3, CAV1, BIRC1, TJP3, STEAP, NDUFA2, MYBPC3, CINP, KIAA1096, ACLY, TUBB, GREB1, MARK3, TEAD4, CG1I, UNG2, SLC30A5, FLJ20920, ACAA1, EIF3S10, SEC5, SLC31A2, MGC10993, VEGF, P4HB, TFPI2, DKK1, ARPC1A, CHST1, MAF, FLJ90798, KIAA0682, GRP58, CACNA2D2, MAPKAP1, GPR27, ICAM1, RPL39L, CYP1B1, PIGO, KIF5B, HSD11B2, CLDN3, FLJ20255, SNX16, FKBP10, STK23, DRD2, SPA17, FOLR1, WNT16, KIAA1010, FLJ11467, EFNA4, H3FB, RAB5C, EHD1, SLC7A11, RHOBTB3, COQ7, SLC21A11, FLJ14827, SPRR1A, PVR, MAST205, CFLAR, PAX6, N33, ADAM10, GNA11, ZFP26, GPR48, KRT4, C2, CRIM1, MGC3121, FLJ23071, GGCX, PPP4C, PAWR, PTHLH, KIAA1219, SRP72, ETV6, ALOX15B, SLC24A3, SLC25A4, RDS, DAXX, ICAM1, LOXL1, GMDS, TRAF4, NTHL1, LISCH7, GAS2L1, TRIM10, SIAT4A, FLJ22584, SLI, ITGB5, TFPT, CD8A, DSCR1L1, KIAA0779, GPRC5B, PP591, SEC31B-1, PPFIBP2, CYP27B1, DOC-1R, COP9, KIAA1193, MST1R, HBS1L, RARG-1, FZD7, KIAA0626, SMT3H1, RALGDS, SOX13, FLJ22612, NFE2L1, CST7, KCNJ5, PALMD, KIAA0644, MRPL9, ERCC1, MSTP9, PTPN3, SUPV3L1, GAL3ST-4, SUHW1, PRSS16, C6orf9, PTPRT, CGI-112, TBX3, ARD1, KDELR3, CGA, TSPY, SPAG1, CRELD1, FLJ20967, RNASE1, LRP3, LARP, SOX11, TULIP1, RORC, HARC, RPL5, FLJ13544, MAP3K12, KIAA1096, PLA2G10, RAB2, FLJ12681, FLJ23469, PP1057, MAPT, TMEM4, PSME3, FLJ21963, SGCB, GLI3, PRRG2, MYL9, GFR, HOMER-3, PDGFRA, DPP4, D15Wsu75e, KPNA1, SGCD, RABGGTB, MMP24, FGL2, ATF6, STX10, ARHGEF12, UPK1B, EGFR, MCAM, CYP3A43, FCGR3A, FLJ10534, FLJ12571, FLJ20422, CD80, KIAA1023, C21orf18, H4FH, TEL2, MSCP, PEX10, B4GALT2, ADAMTS5, CSG1cA-T, TNFAIP6, PRKCDBP, TRIP11, PTN, FGD1, NPEPPS, CAPN1, H2BFH, LOC51337, FLJ21736, VAV3, FLJ11198, KIAA0923, NONO, ALDOB, AQP6, FLJ20315, PHLDA1, VDR, KIR3DL7, YBX2, DUSP3, MGC11271, CHST6, MGC4171, PL6, SH3BGR, SPPL2B, EPHA2, CRYAB, MST1, RGS16, CLPTM1, MD-2, KIAA0152, PACE4, DKFZp564K142, RALGPS1A, DKFZP564A022, RTN1, LAMB3, PLD1, SERPINB5, ENSA, DKFZP586N0721, PLAA, FKBP14, LRIG1, RARA, BN51T, PTHR2, PPP1R3C, HSPC002, CNTNAP2, HNF4A, CHI3L2, TGFB2, CGI-58, PPFIA1, KIAA0440, PLAUR, SNTB2, ID1, ALOX5, IGF1, OPCML, TAGLN2, UBXD2, M11S1, REPS2, BCHE, SRD5A1, TED, EIF5, KIAA0595, BAIAP1, KIAA1718, TRA@, STS, C11orf17, ASNA1, MAOA, PTGER3, NPY1R, SMARCA4, PGM3, PCTK1, MATN2, FLJ23393, MGC2821, MGC2376, FZD2, SLC7A6, PPAP2C, PHKA1, GOLGA1, WARS, GADD45G, LIV-1, NEK1, C22orf3, VAMP4, C18B11, MGP, KIAA0040, IGLJ3, FLJ21125, BTD, G3BP, CLEC1, NUP98, MLN, NRXN3, FBXL7, DLG1, PLA2G5, CYP26A1, OR52A1, DSC3, PPAP2A, C20orf121, UBE2H, EEF1A2, TABLE 5-continued Up Regulated in UPTG versus HSC ATP10A, TFEB, GABRQ, GFPT2, WIG1, FBLN1, PTPRF, MEPE, RAMP3, COL13A1, SLC6A8, PPP1R10, COL18A1, GAC1, EPHX1, C11orf9, OSF-2, ETS1, INSIG1, FLJ10111, CEACAM7, DCX, C14orf58, MIRO-2, SRPX, EPHA1, CRK, CPE, TIMM17A, LCN7, CENTG2, FLJ10534, C6orf18, FLJ12671, VEGF, SPANXA1, MECP2, EPHB3, TSTA3, ILVBL, F7, BAZ1B, MGEA5, E4F1, PPP1R13B, PZP, KIAA0913, CSRP2, DKFZP564K2062, CA2, SLC7A8, BNC, ADAMTS1, PIASY, MGC11061, FER1L4, FKSG28, ZAP128, FLJ21610, ATRN, NEU1, H2AFA, IL10RA, BNIP3, NRP1, WISP3, C8orf4, TGFA, FLJ11526, MRPL2, HP, DHPS, SLC7A8, GPX5, PLXN3, CDC34, POLR3K, FLJ11506, KIAA0980, PDCD8, EVI5, CST3, KIAA0752, C1orf16, CYP4F3, ROR1, MAP3K9, HSPC121CDKN2A, CAPN9, DUSP8, APOD, CCRK, DDX26, USP21, PP35, ABCA1, IGHG3, IL1RL1, ELOVL1, HPIP, FLJ12650, KIAA1078, IL17R, H2AFN, FLJ13352, ELK1, TPM1, TLN2, PPIC, SLC16A3, FZD3, CARS, TNFSF8, zizimin1, GALGT, DSCR6, TP53TG1, SPTAN1, FBXL2, H2AFX, HMGE, TCEB3, PLN, FLJ10847, SNAI2, STC2, MACF1, ARF1, UGT1A9, PCDH7, MAN1C1, NESG1, EVIN1, FKBPL, KIAA0417, VDR, SPUF, SCGN, IGSF4, ARK5, F5, LIMK2, POP3, RGS5, LOX, ADORA2A, PEX14, VAX2, RANGAP1, MSF, TNFAIP1, C6.1A, ARHGEF7, LPIN1, KIAA0876, ZFX, FLJ22635, PLIN, TRIM2, EDG2, POF1B, IF2, PPP1R9A, ANG, STC1, DNAJB2, ODAG, KIAA0763, FLJ11274, FLJ20151, MARCKS, ECGP, MFNG, COG7, KIAA0429, NEDD4L, ATP6IP2, DONSON, MUC6, PTGES, SOAT1, MAN1B1, TNFRSF9, SEC61A2, KIAA0500, AP3S2, KIAA1089, B4GALT4, PTGER3, TLR2, FCGBP, ZDHHC3, KIAA0716, MMP12, CYP2A6, GRAF, LOC54499, NNMT, COL8A2, OXTR, NOL3, ZNF79, HRASLS, HAMP, AIF1, CGI-38, SPUF, BAZ2A, FLRT3, PDEF, PDK3, SLC4A7, HMOX1, IFNA21, HKE4, CA5B, KLK8, PLUNC, NCBP2, KIAA0703, T1A-2, MSX2, FLJ20374, ANXA2P3, DLG3, PON2, IL17BR, AGRN, PRDM11, TNFRSF6B, STXBP2, PTGDS, MARCO, UBE2G2, EPB41L1, PDGFA, IL13RA2, CXCL6, CGI-96, APOA1, MRF-1, NPAS2, MRPL41, LENG4, FGF1, TRAM, AMBP, GPLD1, CHI3L1, AQP1, SSB1, KIAA1608, MEIS3, FLJ13385, IL1RAPL2, NQO1, MINK, KIAA0843, DKFZp564A176, MOP3, BGN, BIG1, FLJ13110, dJ222E13.1, SWAP70, DKFZP586L151, TBC1D2, MAGEA3, ARF3, CSNK1A1, KRTHA6, FLJ21034, GPR58, KIAA1735, MGAT4A, GNA11, SLC4A2, H41, HAP1, CYBB, MARK1, GRIT, ETFDH, FUS1, PTN, FUT2, CDSN, MAP3K6, CHST8, BENE, ATF5, ENPP2, PEX13, PAK4, CUBN, SLC39A2, MYO6, DRIL1, SELT, SLC25A22, HFE, KIAA0237, PKD1, NPAS2, ZNF3, FLJ23516, SIX2, LIMR, STAM2, NEIL1, VIL2, MATN3, FLJ23537, AADAC, MCAM, GPR65, TP53TG1, CAP350, CYP17, EMS1, DKFZp547O146, TNS, MGC13523, ASTN2, TRA1, NPY, CEBPD, PNLIPRP1, PNMT, TM7SF2, NCF2, AP4M1, ITGB4, SLC11A1, LIM, CBFA2T1, FLJ20184, RAI14, WBSCR20B, BAIAP2, COPS7A, PNMA2, KIAA0923, PACE4, FLJ10261, KIAA1395, EDN1, ADAMDEC1, LTBR, KIAA0509, RIL, LPPCALD1, MCRS1, HML2, FLJ22965, FLJ21870, ME1, FLJ22405, RIT1, FLJ11565, KIAA0481, FLJ20627, XLKD1, RAB5C, AMPD1, PDCD4, BMPR1A, SLC26A6, KIAA0939, FLJ10874, KCNK15, ARHGEF9, HDLBP, MCF2L, AQP1, FLJ13055, PVRL3, RNPEPL1, GPC4, ADCY9, PTPN13, MGC2656, TSNAXIP1, ACO2, IRX5, IF2, CIC, KIAA0976, BDH, ZFPM2, PSEN2, C20orf46, NDUFS8, GGA2, FLJ10490, TPD52L1, HLALS, ALFY, FLJ20699, UEV3, AES, DKFZp761K1423, JAG2FLJ13195, DDX8, G0S2, ITPK1, SEMA6B, SLC16A3, CCL18, HUMPPA, EIF4G1, HRH1, GSA7, FASTK, HBP17, FLJ14117, LOC146542, APPBP2, TNRC15, CLDN11, SCARA3, H2BFJ, APEG1, PPP5C, TDRD1, IRS3L, IGF1, PDGFRL, MUC13, DUSP10, KPNA6, FLJ22795, OASL, HRMT1L3, MOS, SCGB1A1, PEX11A, ARHD, KIAA0977, MMP24, FCN1, ACP1, LAMP3, AKAP6, ALDH3B1, TNXB, NF1, APOA1, RBP4, CLTB, GP2, FBXO2, DRG2, DLG3, PCDHB3, FOLR2, NCBP1, SOX13, HOXD4, FGR, EFEMP2, KIAA0625, TULP2, GPRK5, EVIN1, CHODL, CDH8, FLJ22173, OR10J1, IFNGR1, PRO1787, ACADSB, LAMP1, HSPB7, PCSK2, KRT6A, C5R1, DUSP5, MGC1136, TPSD1, HMGCS2, BCAR3, MOCS2, KIAA1233, VSNL1, UBD, ANGPTL2, GENX-3414, FLJ12547, HMGCS1, KDELR1, CPT1A, VAMP2, GSTZ1, GJB3, MRPS12, PCBD, FLJ23322, PASK, ARGBP2, SEL1L, FST, FARP2, HSF2BP, CGI-96, MGC2601, PBX2, FZD1, ABAT, TSHB, KIAA0874, RHEB2, FMO1, NCDN, CSPG2, KIAA0844, FLJ22531, COL4A3BP, ACE2, NAV3, SULT2B1, TETRAN, RODH-4, MADHIP, HT009, ACR, CLECSF12, SULT1B1, ELMO3, NICE-1, HSA243396, NDRG2, GSTT1, BLAME, TAPBP-R, SERPINA1, CNNM4, TCF3, SSX5, MPDU1, CHP, FLJ11183, NOL6, FLJ23129, FLJ11196, DKFZP761I2123, KNSL3, DTNA, BDKRB1, CSNK2A1, ID4, OCLN, CLCN2, SLIT3, MAPK7, EZF-2, GYG2, K6HF, ALS2CR3, TMEM2, NPAS2, HOXB9, MAN1B1, APOBEC2, HFSE-1, DNAJC7, POU5F1, PSMB1, PAFAH2, FLJ13852, CCK, PITX1, NTE, ABL2, CLN8, KIAA0819, GALNT10, FLJ13841, NEFL, ARHGAP12, APOC2, PTPRO, HSPA6, NMB, OR2F1, MPP2, HPGD, CALB1, ADRBK2, AMBP, PPP1R1A, CCR7, C20orf28, TRA@, EFNA3, CX3CL1, F25965, CD2BP2, CDC42EP1, OLFM1, C20orf31, SNAPC3, MIRO-2CALB1, PIK4CB, FOXA2, C11ORF4, RRAS, HUNK, TGFB2, RBMS2, MASP1, ATP6V1C1, NMU, PCDHGA1, SLC29A2, PPIE, GGA2, FLJ20535, POU5F1, MGC5509, CITED1, ATP6V0E, LIPE, ACTN1, SLC26A10, SLC21A9, WNT4, RBMS2, MRPS15, P8, KIAA1609, FBXL11, TGM2, CHRNA1, TSSC4, SBBI31, KIAA0356, OLFM1, SEMACAP3, CD6, ITGA2, GTF2H1, FAIM2, FLJ21313, STAT5B, TBX2, GABRD, AVIL, MGC2615FJX1, FLJ14675, IL1RL2, AK3, ZNFN1A3, SSPN, RELN, SIGLEC7, COL5A2, HLA-DOB, SLC12A3, HFE, PLINP-1, Apg4B, MGC39851, HIPK2, HSPC159, PSK-1, ABCA12, MMP15, PKP3, HERC3, RECQL4, DKFZp434C0923, UNC84A, FTS, AZGP1, FASTK, ARFGEF2, DSCAM, MED8, SPP2, P2RY6, RPIP8, DHPS, ST14, SAMHD1, MGC32043, SPARCL1, FLJ22160, GHR, YAP1, MTMR3, SLC20A2, PART1, PTPN14, BAIAP3, EPPB9, ED1, TPM4, TEK, PRO1942, H2BFE, LEPR, NAPG, MGC29761, SLC34A2, ZNF358, GRB14, CMKLR1, KIR-023GB, MET, PBX1, CYP2D6, SLC7A8, IL13RA1, ARNT2, GTF2H4, CD86, BM88, CEACAM1, BIRC1, CAMTA1, PDZK1, MOCS1, GLYAT, ChGn, RQCD1, CRA, BAIAP2, PTX3, CYR61, VAMP4, HSPA4, HUG1, GBL, EPS8R3, PTPRU, DLGAP1, GEMIN7, MADH6, PTPRG, RFPL1, KIAA1028, RNASE6, AD037, PI15, SNAI1, LOC157542, ACTG2, SLC35A3, SIRT3, NPR2, NPC1L1, HCK, DDR2, SLC5A2, OASIS, FLJ21511, LRP2, RGS10, ALDH8A1, COL4A3, GS3955, CLECSF6, UP, MKL1, MADH6, PRDM5, WNT1, SPAG4, SORBS1, ASPH, PLK, IGSF1, ARHF, CAPN2, LIG3, SULF1, CCKBR, TEAD4, C8A, MGC10771, FCGR2A, SEC14L1, KLK11, SPIN2, C8orf17, THBD, FKSG28, NEURL, FLJ10647, LTB4R, CHRM4, C3orf4, ALLC, SLC3A1, SLC1A1, MS4A4A, EDNRA, ILT11, IGHMBP2, MACF4276, IGF2R, FLJ20421, PBX2, 37872.00, FLJ23604, FOXI1, LUC7L, CD86, PVR, SCD, GPR37, UNC119, NXPH4, FCGR2B, S100A2, MORF, BMPR2, AKT1, FLJ11715, IL13, TADA3L, NFATC4, PPP3CC, CARM1, PTGIS, PLOD, CD36, BBOX1, VNN3, AKR1B10, SEMA6A, E2IG4, HOXC13, RNASE4, DKFZp434H2215, EKI1, MGC5356, KIAA0752, RUNX2, ACCN2, GALNS, CABYR, PCDHA3, SSX2, GOT1NPAT, CORO2A, DGCR13, CAPN5, GPM6A, GLRB, NPEPPS, RIPK1, CYP-M, GLRA3, BIGM103, UTX, NY-REN-45, ATP1A3, ANXA2P1, IL1RAP, PRO1600, WNT2, HYAL1, SH2D1A, TREM2, TUB, KIAA1036, KCNB1, CNN1, BLAME, PLXN3, DXS542, ADORA1, TNXB, GABRE, FABP3, PGRMC1, FLJ20513, SCIN, FLJ13052, CP, LIMK1, MSF, EDN2, FLJ20623, ESRRG, KIAA1237, INADL, KIAA0889, HS3ST3A1, FLJ22593, ASIC4, FLJ21144, FLJ11827, TAT, FLJ20584, SMA5, NCOA3, GLP1R, PRODH, FABP3, FDXR, DEFA4, SORBS1, MRPS12, HSF1, EEF1E1, CTLA4, WDR4, ASB7, ABCA8, CLPS, PSMA7, ARHN, PEG10, AKAP12, MGC12904, FLJ10312, FLJ11539, RAD1, SERPINF1, MGAM, PVT1, PTHLH, STS, PRG4, SYNCOILIN, CASP2, FLJ12168, MARCKS, HTR3B, RECQL, COL4A2, CD97, TRIM36, MGAT3, GRIN1, SOX4, KIAA0475, DKFZP586M1120, SLC2A4RG, CTSZ, SQV7L, PLD3, OR7E24P, CDK5, GRIA2, PRLR, MHC2TA, CST6, LOC56920, NUP214, BET1L, FIGF, THBS4, HLA-DRB4, CAPN6, TLR7, MBTPS1, KIAA0992, BG1, FLJ12681, MAK, APOH, TNFAIP6, CRYAA, PKD2, IGFBP2, TSPAN-3, ATP6V0E, KIAA1579, MGC20727, KIAA1093, LOC55565, HS322B1A, LOC51285, STC1, KIAA0992, CGI-01, TRGC2, EPHB4, DES, CNOT4, MAP4, CDC42EP2, HSD3B1, RDH5, XYLT2, CHRD, SPBPBP, PDP, MYBL1, HPN, GOLGA2, LOC63929, EXO70, PCDHB11, KIAA1036, ANGPTL4, TNFRSF10C, EVPL, TEAD1, SIAH2, PMM1, DPYSL3, FLJ14297, TACSTD2, BSN, FAP, SEMA3A, RER1, AXL, PROL4, CASKIN2, RENT1, CLDN3, DRAP1, ADAMTS7, TCEB2, EPB41L1, GUCA1A, FLJ22659, PAPPA, CBLN1, FRCP1, IL1F9, ITCH, MMP26, STRN3, CEBPD, COL21A1, BTD, KIAA1034, MIG2, FLJ20591, FGG, ASCL1, CXCL14, PDE1A, OR7C1, HLCS, PTPN21, HUMMLC2B, SECP43, BCAT1, DRD2, TAT, MSR1, OMD, IGFBP4, C13orf1, FLJ21919, FLJ11807, AMELX, KIAA0346, FLJ21916, OLIG2, L1CAM, TAPBP-R, Cab45, NR1H2, TCP10, KRTHB5, PCDHA9, TNC, DKFZp434L0850, FLJ11011, SKD3, SPINK4, DZIP1, FLJ23548, FLJ23420, TFEB, PCDHA6, LOC160313, FLJ10496, R29124_1, THPO, AQP6, KIR3DL2, MGC10848, C21orf18, ACCN2, TBL1X, RAB6B, BHMT2, APOB, IGSF4, PAPSS2, RBP1, TCF2, R30953_1, CD3G, ZXDA, TNFRSF10C, FLJ21665, CYSLTR2, IL6ST, ZNF214, AICDA, PTAFR, FLJ12806, BA526D8.4,

TABLE 5-continued

Up Regulated in UPTG versus HSC

CYP2C9, TWIST, PPP2R5C, MASP2, DUSP9, CGEF2, GABRB1, CDC42BPB,
TNFRSF5, CCR4, PYY, PILR(ALPHA), BIRC7, LANGERIN, H2AFI, PLCE1, OGG1, TAZ, PDCD5, SE57-1, FKBP2, FBLN2, RBM9,
384D8-2, WNT2B, NRBP, CDH6, G6PD, C1orf22, LSM4, STX6, ZIC4, FPRL1, CALCB, AGPAT3, SHB, TOM1, AGA, ZIC1, SIAT9,
PTPRZ1, MSC, DKFZP566F0546, FLJ32069, CD28, PPP2R3A, ASTN2, ARHGEF11, JPH3, FLJ21477, GH1, HOXD3, MS4A2, SVIL,
DPYS, F2RL1, ECGF1, PRCC, POLD4, OAZIN, CHRNA3, KIAA1000, DKFZP586D2223, DAZ4, WNT7B, MUC4, GCNT3, OR1E1,
CLSP, CD1D, CCR1, ORCTL3, EEA1, SIX3, FLJ10140, FLJ10884, HNRNPG-TRTHSD3B2, SERPINE1, RHO, MUC4, PTN, DNCLI2,
TNFRSF10B, LOC90326, NR6A1, NCYM, SCGB1D1, EPHB1, NOX4, DJ122O8.2, PLAUR, PDE4C, PIP5K1A, MGC14799, IGFBP1,
IDUA, IGHM, NAPA, PARD3, LIM2, ADD2, HSF4, CABP5, TF, TNXB, NET-5, ITGA3, IGFBP3, GDF10, PRB4, KCNF1, ATP11A,
KIR2DL2, SMARCB1, MBP, IGL@, NFATC1, CDH16, RHO6, CCL20, FLJ20605, ASIP, LDB2, HCRTR2, HOXD3, GPR87, VCX-
8rLOC116150, TPM3, LRP1B, MAGEA6, FLJ20701, PAX3, IGSF6, TOMM22, GALNT3, CHML, COL6A1, FAAH, B7, RANBP1,
KIAA0876, CYP2A13, CD5L, C21orf2, RYBP, GJA10, COL15A1, TEX13A, SCNN1B, TRD@, RIL, ITGB8, PLEKHA1, GRIN2A,
FSHB, PDK2, SAST, PRPF18, FLJ13479, GRP, SLC4A8, SMURF1, GK2, INSL4, FLJ20311, GLRA3, KIAA0828, DLX2, EPOR,
RRBP1, SDC2, zizimin1, CCND1, P2RY2, CD28, B4GALT4, ARHGDIG, TBL3, IL17, FLJ20519, FAT2, UPK1A, SERPINA2, CD209L,
NRP1, ACINUS, RREB1, TNFRSF4, PRO2214, DKFZp76lO0113MAP3K7, SPRR2B, DNAI1, NOVA1, DEPP, LOC51725, SCAMP-4,
TLR4, MAX, PRDM16, KRTHA5, PCDHB1, GNAL, P37NB, ISL1, SH2D3A, TFPI2, CREBBP, ACTA1, ALP, OR1A2, CGI-58,
SH3BP2, APAF1, CD209, DKK4, IL18RAP, ESM1, PAX2, EVI5, MFNG, ATF5, CUGBP1, FLJ10376, CMKLR1, SLC23A1,
MGC34772, FLJ23033, IGLJ3, AMACR, SIN3B, CCL18, CSPG4, FLJ20241, DNM1, FHR-4, GNS, GDF11, PAL, PPFIA2, CASP10,
ORM2, SPTAN1, SPUF, CALCRL, USH1C, ALK, FLJ11850, FOXD1, SH3BGRL3, MNDA, EPB41L4A, MMP16, ANK1, WISP2,
GSTA1, FER1L3, MGC33190, DAZ2, CHST3, DRF1, TM4SF9, CDC25C, ACVR1B, LU, SGCE, POP2, PCLO, COL18A1, TSHR, Eu-
HMTase1, MSR1, GPD2, CLDN17, KIAA1069, CYLC1, ABCB11, MIG2, LY6H, ARFRP1, BMP2, ACOX1, FZR1, CAMK2B,
HUMCYT2A, LILRB5, ENPP3, IL4, SCN11A, CALU, IGKC, THEA, OPRL1, KIAA1053, SIX1CABIN1, SCN7A, THOP1, NR2C2,
FLJ23462TRPM1, RAB3D, CREBL1, ABCD2, VDU1, GAL, CPN2, FLJ10408, PHLDA1, RAB1A, HAND1, MGC5347, BAI2, EDG8,
GPR30, PCDHB8, TYRO3, PRO0618, PRKCI, UCP3, GSG1, PRO1048, HRH3, SARDH, FLJ10803, WISP1, PRLR, RIPX, NNAT, SFN,
APBB2, TLL1, PCNX, KYNU, MKRN3, HGC6.1.1, PLN, RIPX, CDC2L5, ATP11A, SPI1, RIGPDK3, AFAP, KIAA0427, CYP4F12,
EFNA5, FLJ11125, DUOX1, FLJ21240, DNAJC9, RQCD1, DLG5, PIGO, ABCB8KCNA5, KIAA0409, FLJ12891, SHMT1, DNALI1,
POLYDOM, PFKFB4, SHOX2, DGKE, ELF2, MUC5B, WHN, SCAND2, LOC160313, FLJ23510, AK5, FLJ11871, ITGB5, CPS1, DBT,
CDH17, FCGR2B, PCK1, PLXNA2, ACE2, CD7, FLJ11619, ZDHHC11, FLJ21562, FLJ20211, MGC2821, FLJ20624, ICK, PARK2,
PNAS-4, CLECSF6, PCDH11XFGFR3, PTGER3, PROX1, HRC, EPB41L2, KIAA1117, ATSV, LAMC2, ITGB1, TRA@, PAK2,
DKFZp762C186, OCM, HNF4A, AVPR2, FTCD, TNNI3, HR, SLC35A2, PP1665, GA, RGS5, OPLAH, GDF1, OR3A2, FOXO3A,
TNRC21ABO, ITSN1, PVR, CNGA1, UPK3B, PCDHB12, ALCAM, HFE, KCNJ15, KIAA0997, RGS11, NDUFB7, ADAM28,
FLJ13055, PRO2176, CACNB4, RIN3, SLC5A7, FOXH1, PKDREJ, FLJ10232, DGKA, retSDR4, EDG2, SEMA3E, SARCOSIN, THPO,
PTPN21, POU2F3, MAP1A, ZFP37, SUPT6H, ADAMTS6, ASMT, DKFZp434C0328, ROR1, FLJ22800, VAMP1, KIAA1654, RBM8A,
EPAG, TNIP3, INSM1, XRCC4, IL6ST, UNC84A, UBE4B, CAPN11, NPEPL1, TAS2R10, FLJ23093, NPPC, PTPN21, SLC22A8GAD2,
LOC51063, OGN, MAGEA8, GUCY2C, NT5E, SGCG, C8orf1, LGALS2, PRKAR1B, DEDD, PPARG, PDGFB, PRO0461, ALFY,
TNFRSF11A, DNAJC9, KCND2, PEG10, SPINK1, GCM1, VHL, CLDN1, PRSS7, H4F2, D21S2056E, CXCR6, LIFR, KIAA0599,
TNXB, EHD1, ARNTL2, CGR11, SOCS1, PKLR, ZFP318, ZF, CHRNA1, DKFZp434M0331, DES, TMOD3, SP140, KSR, BS69, IREB2,
PAWR, CACNA2D1, C21orf62, Gene Symbol, OAZ1, CFL1, RPL28, JAM1, CGI-119, NICE-3, RNP24, JTBFLJ12806, ARHA,
FLJ13352, SYNE-1, TRPS1CGI-119, NDUFB9C20orfl14, JAM1, RALA, FLJ30532, PIGR, MRPS24, MYO5B, LOC155465, STUB1,
MGC14353, ARF1, C20orf24, EGR1, ANAPC11, MRPS15, MIR, PIGPC1, MRPS21, CL25084, H41LOC124220, RAB10, B4GALT1,
PPP1CB, MGST1, TCEB2, MGC19825, HSPC163BACE2, BRI3BP, FLJ14511, MRPL47, NMES1, FLJ14735, DAD1, KIAA1324,
ENAH, PSMB2, RHPN2, HTPAP, DKFZp761P0423, C20orf108, MGC45416, TMEM9, UBQLN1STK35, APOA1BP, GRLF1,
SPEC1INSR, LOC150678, SMP1, FLJ32115STUB1, HLA-C, ORF1-FL49, TAF10, RAB40C, DPP3, AIBZIP, LOC55971, SSR3,
ATP6V0E, SNX6, SNAPAP, ALS2CR9, KPNB2, EPC1, NTN4, C20orf52, H2AFJ, UGCG, IMAGE3451454, EEF2K, MRPL14, E2IG5,
MRPL36, GPCR1, E2IG5, MGC14151, RASD1, CGI-141, AGR2, KIAA1437, HSPC210, BTBD6, H2AFJ, MGC14151, FLJ20048PSMB4,
MGST1, FLJ31364, EGLN1, MRPL53, LOC88745, IRX3NFKBIEUNC5H2, TAF13, RDH-E2, MGC12966, DKFZp434G171, GUK1,
FLJ20671, FLJ20623, CAPNS1, PFN1, KIAA1671, FGG, H19, C20orf149, CAPZA1, RAB18, FLJ23153, CGI-19ABCF1, TCEA3,
NDUFB10, NDUFB10, RNF7MAL2, NUCKS, RPL23A, LOC51290, TMEPAI, APH2, FLJ13593ATP6V0B, TLP19, SLC17A5, ENPP5,
C20orf24, AKIP, D1S155E, FLJ20171, MGC39329, MRPL41, NDUFV3, KIAA1096, LRG, BPNT1, LOC51255, CISHPGK1, PLEKHA1,
HSPCA, COPZ1, DKFZP434L1435, TMEPAI, BRI3, AKIP, KIAA1191, LOC92840, CLDN12, FLJ14525, C20orf149, CDC42,
TMPRSS3, LOC199692, FLJ22174, LOC113246PKIB, RAP2B, HIBADH, LOC57038, FLJ14117, EDG3, MBC3205MGC2550, RCP,
NUDT5, LOC51260, SIPL, KIAA1223, HINT2, HN1, ERdj5, PHP14, MRPS36MRPL32, C6orf49, CAPN13, MIR, RNF19, ATP11A,
LOC51128, FLVCR, ADCY4, KIF5B, ARV1, RAB5EP, PX19, RREB1, MIR16, LOC51248SMAP-5, SYTL2, FLJ11320, MSTP028,
OCLN, MGC14833, SMBPRDH13, MGC40107, KIAA1165, SPPL2A, Cab45, MGC20781, LOC51241, MGC11266, DKFZP566J2046,
FLJ14624, CKLFSF6, LOC147184, DKFZP566F084, FLJ20203, FLJ10856, MGC11034IMUP, CAMK2D, MK-STYX, RAB3D,
C20orf142, DNAJB11, MGC23908, FLJ10074SURF4MGC11102HSCARG, MGC14327, HYPK, HSPC121, TOB1SRA1, MGC14832,
JAM1, MGC27385, PX19, FNTB, MIR, LOC56932, POSH, MPP5, MRPL52, MIG-6, LTB4DH, ZAK, FLJ22649, SCGB3A1, MGC33974,
FLJ21016MGAT4B, KIAA1404RBMS1, DKFZp761H0421, ARHU, FLJ12697, CGI-149, SPUVE, TINF2, RPL17, LOC54516, WTAP,
MAGI-3SAMHD1, FLJ11011, FLJ10052FLJ23751UCK1, LOC170394, TP53INP1, HOXD8, XPR1, MGC10540, SORBS1,
BCCIPFLRT3, FLJ22558, FLJ11200, SAMHD1, PIGR, FAM3B, CYP4X1, NFIA, KIAA1715, FLJ20160, CTHRC1,
DKFZp547A023HSPC121, LOC84661, LOC113386SH120, GNPNAT1, FLJ32499, UBXD1, LOC90120, HBLD1, MGC13186, SPEC1,
MYBBP1A, MGC4248, DKFZP434I1735, LOC127018, FLJ37318, FLJ20421, PTGFRN, p25, PIGM, MGC43399, ERdj5, SYT13,
IHPK2TH1L, FLJ20727, POLE4ASH1, KIAA1130, LOC55829, MGC10084, ZPR9, KIAA1458, CNN3, WASLFLJ20097, SURF4,
HSPC163YAP1, H4FH, MGC40214KIAA1200, C20orf139, PKIB, CGI-36, CLMN, SET7, SEC10L1, MGC22825, FLJ10525,
LOC113386SELENBP1, SLMAP, VPS29, KIAA1972, MTCH2, NPD007, OLD35DNCLI1MGC14839, SH120 UBPH, APOA1BPLANPL,
UBQLN1, FLJ11101, C8orf13, DKFZp434A2417, C14orf31, C14orf100, MMP24, CRIM1, FLJ23393, MGC45714, INADL, SEI1, OPN3,
CGI-97, MGC21874, C14orf47, KIF3B, FLJ11046, C(27)-3BETA-HSD, RAB18, IR1899308, MGC17299KIAA1223, KIAA1322,
RAB23FLJ32205, DKFZP434K114, EHF, ShrmL, KIAA1434, KIF1B, ERO1L, MGC15397, BAT5, C20orf45, FLJ31235, LOXL4,
FLJ20707, Cab45RNF7, MGC2803, FLJ36445, CLDN1, DKFZp761N0624FLJ20308, MGC33338, MYO5BRBM8A, MGC10765,
C14orf9, FLJ32642, ATP1B1, MGC4309, KIAA1272, LOC154467KIAA1483, UBE2H, EHD4, UBE2J2, FLJ20085, DKFZp762H185,
MGC20486, MGC26847, MGC15854, LOC115265, NEK6, SPRR2AMGC13045, MGC4604, LOC51256, ANKRD9FLJ31208TRIM47,
AP1G1DNAJC1DKFZP434I116, LNX, SDCBP2MacGAP, FLJ14957, C20orf110, SURF4, RAB5EPC12orf4, GL004, DC-TM4F2, SAT,
DKFZP434A0225, GK003, dJ55C23.6, JUB, LOC89894, LOC115294, C20orf129, PCDHA10, HSPC242RAB18, COX15, MGC11115,
MRPL27, MGC15397, FLJ11752, LOC116238, C9orf25, LOC51760, MGC45408TBX3, HSZFP36, TRIM8MGC22793, BAL, FLJ25157,
C20orf155, RPL35A, ZNF265ILF2, MGC23166, FBXO6, KIAA1870, DKFZp761D0614, ZNF398, ALS2CR9, MGC26818, EMS1,
FLJ90119, GALNT4, LOC54516, BRI3, HSCARG, PPP1R1B, GPR54, FLJ14299, PPP2R2A, MGC5391, SDCCAG28, PHP14, TGFBR3,
MGC1842, MLLT4, DFFA, SELM, MAPKAP1, MGC10974, AD-003, FLJ10902, MEF-2, MURR1, MGC2541, GSR, MGC19825, MAFB,
LOC139231, FLJ23091TEM8, RERGKIAA1553, CFL2, CEBPG, KIAA1554, SEMA4BPDCD4, PNAS-131, MGC31963, HT002, HRD1,
MESDC2, PRO2605, PTGFRN, KIAA1244, MGC10999, MGC10715, CGI-85, KIAA0779, NUCKS, FLJ13881, LOC127829, HR, TABLE 5-continued Up Regulated in UPTG versus HSC KIAA1538, KIAA1255, STUB1, KIAA1841, CALM2, RIG-I, HOXB8N4WBP5, HTPAP, CXCL16NAC1, TRABID, LOC135154, TRIM56, MK-STYX, Eu-HMTase1FLJ30794, DIRC2PTPN23, GBP2, TRIM11, KIAA1976, MRPS26, TMEM9, FLJ23420, KIAA1337, MK-STYX, IDS, EPI64, KIAA1724, MGC2477, FAD104MGC32065, MRAS, DKFZP761L0424MGC4840, FLJ20739, GFRA1, FLJ23867, MGC40555, FLJ14251, FLJ38628, MGC2941, MGC22805, NOL6, MESDC1, FLJ22865, FLJ25357, DLG5 ARHGEF5, HYPK, DHRSX, PCDHB2, FLJ90165, C17orf26PVRL2, DKFZP564D166, NOR1, GLIS2, SPPL3, TTC8, FLJ14502CED-6, MGC14141, MLZE, LOC57168, KIAA1337, CRB3, KIAA1350, PPM1AFLJ20273CCL28, PDP, MGC14859, GJB2, GPR, ECGF1LOC92399, HOXB9, LOC90522, KIAA1951, MANBAL, MGC11386, RIPK1, NLNHCC8LOC115548NUP88, TMEM8, CHDH, FLJ20507FGFR1FLJ30803, KIAA1280, FLJ13089, LOC120224, ZNF75A, DNAJC5, SDOS, MRPS15, MGC2628, FLJ11236, TRIM39, NESHBPFLJ10839SULF2., FLJ10210, METL, FLJ12707, HUMAGCGB, FLJ13195, FLJ1016, BOK, FBXO25, OSBPL5, DKFZP434N1511, KIAA1813, VANGL2, LOC124446, HDCMA18P, C20orf7, MGC1314, MS4A6AANLN, MGC40499, KIAA1337, FLJ10116, NOTCH2, RRP40, PFKFB4FLJ14681, KIAA1026, C1orf6, MGC5384, LOC85865, PHAX, MGC11134, FEM1A, LACTB, TIM50L, ARNT, MS4A6A, PPIL1, C20orf3, MRPS15PGGT1B, CXADR, LBP-32, FLJ22004, FLJ32069, UACA, MGC2747, FLJ13187C1orf28, CBX6, C1orf13, NY-BR-1, FLJ20748, KIAA1821, FLJ31751, LSR68, TRAD, USP28, FLJ10702, GBA2, B7-H3, DKFZp547D065, TH1L, TSGA2, RORC, ETL1, FLJ30634, MGC10702, TEX27MGC33602, MGC2555, LOC55893, LOC128439, EDIL3, KIAA0146, RFXANK, HS6ST1, NEK6, FLJ20186, MGC15416HSPC159, SCAMP2, LOC133619, NGEF, C14orf58LOC91012, MGC12972, MGC11034, CYT19KIAA0819, LOC55893PHCA, KCNK6, CRIPT, CDW92MGC3195, GTARPAPOLG, MGC24180, KIAA1126MTA3, MGC24103, moblak, MS4A6A, DAG1, KIAA1394, MGC13114, KIAA1337, FLJ40021, DPP9, KIAA0789ZNF144, TMPIT, MGC13114SYAP1, FBXO32, BOCCD44, LSM10, KIAA1673, CTL2C21orf63MGC2560, ZFP385, TM4SF9, DNAH5, PGGT1B, DKFZp586M1819, ID4, CLIC6, C20orf64, YAP1, FLJ21615, GRP58, LOC149267, C20orf7FLJ37933, FLJ90586, FLJ22626, LOC51242, MGC4604, SDCCAG28, KIAA1321, TEAD2, RPS3A, LOC90701, FLJ32915, FLJ31434, PUNC, TRPS1, MGC45441, LIN7B, DKFZP434H0820FLJ32468, DNALI1, COX412, HOXC9, FLJ20337CLMN, BCAA, OPN4, DGAT2, PRDM6, DKFZp761J1523, KIAA1244, ICMT, FGF11, C21orf97, C20orfl69, VPS18, SIRT2, MGC15677, MGC4604FHOD2, DKFZp547M072, CGI-125, NLN, MAP1LC3AFLJ31842, PGLYRP, FLJ32069, DKFZp547A023, MGC39325, RRP40, KIAA1880, LOC116254LOC51061SYTL2, KIAA0076, KIAA1580, GPT2MGC4840KIAA1345FLJ12577, Tenr, CCT5, FANCF, USP21, KIAA1273, DKFZP434F091, MGC13007MGC16131, SEC5FLJ22215, FBXO22, MGC16491, MGC16028, MGC2601MGC15906, C20orf45C17orf28, IL17BR, STK11IP, SEC61A1, STAU2, FAPP2, FLJ25429, CAC-1, ROCK1, MS4A7, DKFZp434D0215, FLJ20442, HFELOC148523, LOC90353, HIPK2, ERBB2IP, CDKN2B, CGI-09, DPP7, DUSP16, CGN, CLONE24922MSCP, DKFZp547E052, MGC45714, MGC5370, MAP4K1SLC4A11, MGC26568, PPIL2, MGC27034, FBXO30, DKFZp547C195, MIC2L1, DHRSXHTPAP, VIK, FLJ23841, DKFZP434D146, HPS3, IPP, SEMA6ADNAJC5, ULBP2, LOC120224, FLJ11036LOC90580, LOC92906, WDR5, RAB35FLJ10697, MAPT, FLJ14825, KIAA1295, MGC2217, ACTR5, SENP2, LMLN, LTB4DH, MGC11257, MGC15476, SART1, TNNI3, LOC128153, SCDPRO1912, KIAA1896, LOC80298, FLJ20533, SMCR7CGI-69LOC114977KIAA1691, C20orf102, VIP, FBXW5, TRIM35, SLC30A5, JAG1SLC13A3, COQ4, OVCOV1, GLI4, RPC8, FLJ31153, C20orf162, NRP2ENAHARH2LOC55971, FLJ20038CerCAM, UBE4B, LOC57168ALS2CR9, SLC21A11, GPR108MRPL41, KIAA0831KIAA1970, DKFZp762I137INPP4B, ZFP67HSPC189, PF1PCDHB6C2orf9KIAA1468, FLJ14399, DKFZp434G118, KIAA1500, FLJ14681KIAA0869FLJ22558APXL2, MGC16028, APMCF1, LOC90990, PCDH18, DKFZp564J0863, COG1UBE2H, KIAA1970, PCTB, MGC30052, FLJ90575, MMP28, MASS1, MGC13034, RIPK3, CCT4FLJ12519, GOLGA3RCPCP, MGC20983, FLJ35207 EML4, TRUB1MRPL41ZNF213, RPA2, FLJ20813, SAMHD1, KRTAP4-8, C4orf1FBXO8, EPB41L4B, ZNF75A, STK36, PAWR FLII, DKFZp761A052, C20orf23, AKIP, MGC4643, VTI1A, LOC223082, PDK4, PSMB7, KIAA1710, MGC13272, MGC4342, GNG12, N33, FLJ14800, FLJ21924, LOC220074, FLJ22474, DKFZP434P106, FLJ13236, PTENP1, FLJ21159KIAA1441, CGI-85, FAM3D, DKFZP566J2046, LOC116441, TEAD1 LOC51249, PARVA, HSPC230, MGC5442FLJ23091LOC55893, PDCD6IP, OGN, TRIM41, MGC42105, CPNE2, DKFZp547J144, KIAA1784, KIAA1337, SLC30A1RNAC, KIAA0429NRXN3, Spir-2, GGCX, KIAA1694, DNAJA4, CAPN13, NAP1L, RPS27LTMOD4KIAA1557, FLJ21415DKFZP564G092, CLN8PARVA, FLJ40021KIAA1708PC326, NOSTRIN, LOC129642, KIAA1301, CGI-85, MGC13102, LZIC, KIAA2025, FAPP2, FLJ22679, SNX8, ZNT6, DUSP16, PANK2, FLJ14834, DKFZp434C0328, ROD1, FLJ34633, FLJ13391, ARHJ, FLJ11753, B29, OSAP, B2M, CYGB, DERMO1, MIR, WDR20, C20orf155, FLJ32919, MGC2408, CLGSCYL1DKFZp761A132, DKFZp451G182, FLJ90119, FLJ36991, SDCCAG43, PPP1R16A, MGC19764, FLJ13263, GNG2FLJ12517, MRPL20, MGC16212, SRA1, GEMIN7, FLJ37953, HBP1, KIAA1737, CTL2, KIAA1754, FOXA1, MGC13096, HDAC3BOC, FLJ30973, BRUNOL5SEL1L, SPTB, POU4F1, KIAA1337, MIZIP, NAGSCGI-72, PRO1853TRAF4, MGC32124, SNCAIPDKFZp434O0515, SMOC2, FLJ12770LOC113828, FLJ40432DKFZP434K0427, SFPQ, RNB6, BMF, GSH-2, REV1L, SLC27A4C1orf19, SLC5A1KIAA0478, SPPH1, FZD8, MGC26877LOC150379STK36, LIMD1, KIAA1694, FLJ25357ELAVL2, BM-002, ProsteinFLJ20374, STK35, FLJ31434, CHRM1, DLC1, FLJ36155, FLJ21939, MGC21675LOC51320, FCRH3, FLJ10948, MGC27034, MGC14801, MGC11102, SEC14L2KIAA1393, DKFZP434A0225, DKFZp434F054, SHANK2, OSGEP, MGC45474, ARHGAP8, BTCIL1F7GRLF1, DKFZP434B172, MRPL35, PAPOLG, MGC33662, XPO5CTEN, DSCR9, ITGB6FLJ14768, STEAP2KIAA1522, FLJ32069, PCDHB3C20orf136, XRN2MARK1, DKFZp547O146, FLJ12517, FLJ10597GK001, CITED4, IGL@, GALNT13MGC26963, RASAL2FLJ20605, LOC112609, NLGN3, C7orf2, HSPC182, DTNASNX9, ALS2CR9KIAA1219KIAA1190C14orf31HSPC065, KIAA1221, FLJ10252, C4orf7, KIAA1363, NCAG1, NAV1, C14orf28, KLP1, ZDHHC9, MGC2615, SMUG1, PHLDA1, AD-003, BRPF3, ASCL2MGC15523, RELA, ROPN1, FZD4, ZDHHC4, KRTAP3-1, PCDHB16KIAA1036, SLC2A1MGC5P043, FLJ32731AMID, FLJ30277, CKLFSF2, TLR7, SEMA6DNOPE, DKFZP434P0111, SDS3, KSP37, PDCD6SNX14, A1BG, SLC31A1, MK-STYX, SNTG1LOC80298, FLJ25534, MGC10485, FLJ10035, NEUGRIN, BK65A6.2, NKD2, TJP2TRPS1FLJ20753, PPP1R1A, LOC123169, LOC112817, ZNF341, TM4SF9, FLJ90586Spir-1REN, FLJ10210, CEGF3, NOXA1, FLJ14981, RIMS1, PCDH20FLJ20360, DKFZp761H0421, MSX1, DKFZp434F2322FLJ10188, SPP2, MUM2SYT12, pknbeta, MGC11349, RNF40MGC4734, MAP1LC3A, FLJ13687, CNTN3, MGC19604, TLR8, FBXW7, HM13, TLE1AKIP, SMURF2, FLJ21963, MRPL44, PRKAG3, DREV1HSA243666, FENS-1LOC51693 FLJ10486, HAVCR2, HDAC3, AHRR, CXCL14, CGI-09MGC13251DKFZp434E2321, C14orf102KIAA1434, PHCAKIAA1145, FLJ00028, AMOTL1, TMPRSS6, ODF3, MGC4604, DJ667H12.2, VGL2FLJ10052FLJ13881, UK114, DSG2SLC12A4TBCD, MAP1B, OSBPL10GALNT10, DKFZp547I094MGC35352OSBPL6, TRIM7, FLJ30473, MGC2562, DLG1, DKFZp434P0531, KIAA1554ESDNKIAA1910, SEC15BKIAA1172DSCR1L2, PSMB5OSBPP2, GPR34, MGC15098, HDAC5LOC90990, DKFZP564B1023, CASP2NUP133Spir-2, LOC151534, C22orf23, FLJ90811, DKFZp434I1930, NET-2, LOC113026, HOOK3MGC8721, BLVRA, PLA2G12, DAPP1, FBG3 MGC10974, LOC114990, DKFZp547M2010, FLJ20542, LOC144455CG1-94BRUNOL5HKE2, PRND, WFDC3FLJ30990, FLJ23654, KIAA0876, NDUFS1WASL, KRT6IRS, KIAA1684, RU2, DKFZP434K0427, DKFZp434B217, KIAA1549 DKFZp434F2322, MGC4126ENTPD2, GPRC5C, RGNEFFLJ31052CEGF3SYN2, C11ORF30MGC3038, ITGA11KIAA1053LOC57822, LOC130589, RASGRP4, DKFZp434H2111, NFIA DKFZp434C0328, FLJ20209, NDUFS2SENP8SLC2A4RG, p25, C20orfl67KIAA1909, MGC4238, MGC16372, CD5, IGKC, KCNQ4, ZD52F10CCL28, FLJ20539KIAA1357, EPB41L4B, MGC14128, SLC1A5RHEB2, HSPC182, FLJ22527, MGC21621, MGC5370KIAA1130, KIAA1554C9orf11 FLJ31937IMP-2C20orf51, KRTAP17-1, DKFZP434E2318, DKFZP564B1162RPL29, PRO1489HSPA9BKIAA1688, KIAA1324NCOA5, AXIN2, LOC92689, KIAA1272FLJ14642, FLJ37440, FLJ12604, RGS8, MS4A6AZNF216, LOC84570, KIAA1126, SMOC1, TSCOTMGC18257, RDH13, C1QGKIAA1576, ZFP28GNA14, FLJ39155FLJ32069LOC155066, MGC19764FLJ10159, MGC16309LOC55862, PCDHB1437867.00, LOC56851, SNRK, MGC13017, ADAMTS16AGMATPCDHB10, LOC113179, NOL6, C20orf55, PALMD, GFER, BNIP-S, KIAA1337AXIN2, MGC39807, LIP8KIAA1053, MGC45378FLJ11273, FLJ23129DKFZp586I1420KIAA1210COX7B2, TCF7L2, USP21, DKFZp564O1278, FAAHDPCR1NUMBMGC35285JUBEVX1, LMO4AMOTL1, C2orf7TMPRSS3, ARHGEF7CSRP2BP SBBI31, SSBP4, FLJ23654, TABLE 5-continued Up Regulated in UPTG versus HSC CPMDKFZp762K222, DPP9CA5BKIAA1817C14orf92, MYO3A, VIK, CACNG4, NYD-SP21LUC7L, SFRS12, LIPHDIS3, GCC1, FLJ10504, CASP14, KIAA1387, DAB2IP, KIAA2028C20orf40GPR92FLJ32658FLJ25027, LUCRC1, EVC, COG1FLJ25555MOV10 ALDRL6, HTGN29MGC12466, IBA2, MGC15548ADD3, GSN, C14orf50MGC22805MGC39650, KIAA1203FLJ14311, HRMT1L1, MASS1, CGN, IGHG3, ESPN, ZDHHC12, PCDHB4THRSP, FGFR2, LOC91461FLJ25604DRAPC1, ARL8BACH1, KIAA1921, GPR81, KIAA1145ARHGEF7, retSDR3, C20orf6ARFGAP1NSE1TPSG1MRPL4, KIAA1870, X102, KIAA0599, CACNG6, FLJ22301, ZIC2, KIAA0599, MGC4796 HT036, DQX1, SYTL4ICAP-1A, KIAA0350, KIAA0872, GMPPB, FLJ37953, LMLN, NOL6, POLR2J2Hes4, LOC57038, TRPM6, ABCC13, BCAR1FLJ30803FLJ32069KIAA1909, TIMM8BEML4MGC15606MGC35048, NRP2 PCA3, IL17BR, DKFZp727A071, MGC14128, GABRB3, MRP63, PGBD2GATA5, FLJ14735, ENTPD6, SYNE-2PRIC285, MGC2555, LOC90378GLCATS, GCN5L1, DKFZp434F2322, MSCPFLJ30681, ZNFN1A4PRO0971TTTY6C14orf47CTXLFTCD, MGC2835MGC12435, STYXFLJ12076C20orf106TEX11MGC19825, TPM2HOXD10, KIAA1554, FLJ20014, FLJ20748, PPP1R14C, ARHV, ALDOAEGFR-RSC20orf92FLJ14594MSCP, PRO0038SLC25A15, RSP3, PPP1R9A, EPHA7MGC35521GFAP, ICEBERGFOXP3, FLJ33516GPR55, ZNF398, PRO1635FLJ33903FLJ32203, ORMDL3, LOC51315, FLJ32752ELP2LIMD1KIAA1357DOCK1, FLJ14721, STC1ALAS2, HMT-1PADI1, PTPN23FLJ10210, FLJ10826, ELAVL3, LOC90668 FLJ32069, NOL6, LGALS1LOC55971, FLJ20273, SSB1FAD104, GPR107TRA@, SORCS2, LOC91010FGFRL1, UQCR, SEC14L2, DENRST6Ga1NAcI, KISEGLN1, ZNF219SNAP29, TNKS2QP-CSLC4A11, PURB, KIAA1163, FOXP1, C12orf22, TCF7L2, CDH23, FLJ13955KIAA1828, FLJ33008LOC115704, SLC13A3ASB1, DKFZp762I194, CPNE4, GRIN3A, MSTP043, BHLHB5ADMPRBM6, MGC13275, KIAA1889, KRTAP3-3LOXL2, LOC51290, C11orf23FLJ20309, MGC26778NAV1, ARHUFLJ23749, FLJ33071NUMBL, PTPNS1L2MGC3040SMAP-5, MGC2835CDGAPCHFR, FLJ90440, DKFZp434G0522FLJ10300, TRIP11, HSFY, HOOK3, GTF3A, FLJ12634, NEO1TEAD2PTPN2, BCL2L1, KIAA1557 KPNB2, ACPP, CISH, DKFZP434P106, ASPH, DOT1L, FLJ22944SRGAP1, OLFM2, SIN3A, ASB12, CECR7MGC40397NFKBIA, POLRMT, CGI-149C21orf84, MTMR9, GATA4, XYLT1, PCDHB7SEC15L, C20orf160 MGC33302C1orf19, COL12A1, EGLN3, FLJ21032MGC3040, ODZ2, ING5, C12orf2HS6ST2AQP1, MGC10981MGC33607FLJ14399PRACDCAL1, MGC40222, TMOD3, TEFSDS-RS1, LOC115098KIAA1573MLL3, FLJ14103AK3 ARPM1, CARD14MGC12916, ALS2CR12, FLN29, FLJ12697TOB2, N33GTF2I, BHLHB3GPC6, CAMK2D, KRTAP4-13, BDP1, DKFZp761H079, DKFZP564J047CED-6, EB-1, MGC4659 GPR110, DOCK1, FLJ20211, SCN11A, LOC118471, LOC151568 ZFHX2SLA/LP, PCANAP7, HDAC3, POU5F1, GGTL3, C7, FLJ25410, SCAND2, C20orf136, FLJ21616, EB-1, FLJ25067, KIF9KIAA1276, LOC55864, FLJ32771, DKFZp667B1218, DNAJC9LOC51319, FLJ10902, FLJ36525, MESDC2DDX12MGC33993 KIAA1399, LLT1, DKFZP434F091, FLJ12697GPR24, SE70-2, NANSFLJ12571, IL-17RC, TRIM7, NXPH1, ROR2, C20orf60, KLHL5, ZNF265, BECN1SCARA3, PRO1580, MGC35392DKFZP434N178, PEX5R, FLJ31528, LOC135763CLECSF9, MGC41906, FBXO1IZNFN1A4, SPINOFBXO22, IHPK3 C20orf167MAP2FLJ25270, STRBP, MUC13KIAA1878, SNX9MGC26143 KIAA1887, KIAA1712ASB4, BRUNOL4PDE11A, ARG99, FLJ30162, ATP6V1G3, MGC10702, ARSDKCNJ2CAMK2DMGC12335KIAA1617HNTEB-1, GRP58, C21orf59, KIAA1720, LOC221468CCL27CGI-62MGC10204, TNKS1BP1RRP40, FRABINDLX6APOA1FLJ30532, FLJ23403C7orf2 DNER, PDE11A, MAFMGC14276, DLL1, LOC146542, SH3GLB2KIAA1952LOC93109ENDOGLYX1MGC10724, IL4I1, CGI-105, C14orf44, PAX6ASAH2MGC12435, PGA5, and AGPAT3.

TABLE 6

Down Regulated In UPTG Verses UPNTG

CD24, HSPD1, EIF3S6, TIMM17A, DENR, PAI-RBP1, KIAA0101, H2AFZ, SLC38A1, HNRPH1, RPS11, DEK, ZNF131, HSA9761, MGC3077, CD24, CCT6A, RNPC2, ANKT, CSE1L, RABGGTB, HSA9761, SIP, HMGB2, SEMA3F, HINT1, HMGB1, SERP1, RPL27A, FH, DUSP4, SET, KIAA0179, HMGN3, TOP2B, OAT, NUDT4, PCNA, BMI1, SIP, SDCCAG1, PBP, MAC30, SFRS5, ATP1B3, EIF4E, CRABP2, LRPPRC, DKC1, MRP63, STK6, CARD10, MRPS18B, TCF3, TCF3, MGC2747, FLJ20422, IF2, NCL, EIF5, TFAP2B, TIMM9, PPP1CC, ZWINT, HSD17B1, ATP5O, CBX3, CRFG, PXMP4, UBA2, RNASE3L, USP7, LANPL, PTTG1, RANBP7, YES1, CDC2, RBM15, GMPS, PSMD1, TCF3, HSP105B, EMS1, NONO, TOMM20-PENDING, LDHB, DKFZP586L0724, DDX27, JMJ, CENPF, LRPPRC, ID4, EIF1A, PSMC6, ID2, SEC13L, TYMS, LUC7A, SNRPA1, RRM1, RARG-1, SMAP, FEN1, TCN1, ZNF146, ABCE1, DC8, MTCH2, FLJ20152, CCNB1, CKS2, FLJ23445, TDG, DNMT1, MAC30, RPA40, GMNN, APOBEC3B, STMN1, EIF1A, MTHFD1, MGC5560, USP1, ZRF1, EIF5A, WDR3, FLJ20530, RPS21, BAZ1A, MCM6, MICB, OPA1, LAMA5, ECT2, RAD21, RNASEH1, FLJ13081, STXBP3, PAI-RBP1, OSR2, FLJ20006, KIAA0186, C19orf2, NUP107, TAF2, GCSH, FLNB, ZNF363, SEMA4C, RAE1, GSS, NEK2, GTSE1, PAI-RBP1, ABCE1, FLJ20986, MAD2L1, VEGF, LZLP, KIAA1025, KIAA0092, ANP32B, SRRM1, NXT2, TOPBP1, FLJ20485, SFRS7, SMC4L1, CPSF6, LIN7C, FARSL, NDUFB6, FLJ12888, LANPL, ENDOFIN, KR18, FLJ11029, DLG7, WDR12, DC12, CDC5L, SLC35A3, PIGF, PRKRIR, MTO1, CASP6, FLJ11149, FLJ22637, LDHB, PPID, GTPBG3, HMMR, SLC31A1, POLE2, KIAA0984, DJ434O14.5, RAB6KIFL, ASE-1, HNRPA1, FLJ23468, CALR, MELK, SLC25A13, TFDP1, RES4-25, DC13, CGI-111, ARH, FLJ14547, TSN, CYP2B6, PDX1, LCE, FANCG, DHFR, KIAA0020, QDPR, MTIF2, HLXB9, SART3, JAG2, CKAP2, PRC1, SNRPD1, LOC51184, RAN, DLD, PREI3, SRRM2, RAD1, CCNB2, FLJ23277, DDX18, PMSCL1, LEPROTL1, SCGB1D2, TIMM13, C4orf1, KRTHB6, DD5, C1D, PNN, ORC6L, KIAA0170, ASK, DLEU1, SFRS3, SLC19A1, HIP2, PPP2R1B, BIRC5, EPS15, MGC13138, HNRPD, STK6, HSPA8, METAP1, KIAA0776, HSPC128, KIAA0419, MAGOH, CHORDC1, APPBP1, UBL3, RAD51, LOC55871, GLRA2, CUL4A, ARHGAP8, KIAA0648, COX17, SUDD, RAP1GDS1, FLJ14639, BCL9, EZH2, TRIP13, FLJ11210, TOMM70A, PTP4A1, AMD1, DUT, KPNA2, CYP3A4, RFC4, OPA1, RNF6, IBTK, LBR, MGC13138, KIAA0097, KIAA0532, OIP2, VRP, HDAC9, KLC2, FLJ20700, AD24, ALMS1, FLJ21901, DKFZp547P234, FLJ10656, TOP2A, MYC, TAF4, POLR2E, KIAA0528, CRY1, MST4, ETFA, HOXC6, MTX2, HMGCR, RPC5, TOPK, DKFZP564I052, CENTA1, FLJ20758, KCNMA1, KNSL6, CGI-30, MRS2L, PAICS, ZNF85, DJ434O14.5, RABGGTB, HEY1, KIAA0485, KTN1, KIAA1012, CDC20, DKFZP434L0718, CEPT1, MYNN, FLJ10637, ANXA9, RNPS1, RBBP4, SSH-3, LOC90355, CAMLG, KPNB2, FLJ23259, VRK1, FBXO5, HSP70-4, DNAJC9, MYCBP, S164, NTRK3, TAF9, SPG4, DKFZp667G2110, CDKN3, INHBC, PEX11A, CDC27, HMGB3, THOC1, FLJ12151, DKFZp564B0769, HSU79266, DMN, C10orf3, THOC2, NDUFA6, GCSH, PPAT, RHAG, SMC2L1, SE70-2, KPNB2, LSM6, FLJ10377, IL1RN, KIAA0547, FLJ14007, SCLY, KIAA0379, UBE3A, HTATSF1, LOC51685, AGL, BET1, FLJ13782, UMPK, SMARCE1, LSM5, CENPF, EEF1E1, TPT, FLJ10719, IF2, CGI-12, UCHL5, FLJ20628, ERN2, BLM, FLJ21940, PDCD2, STRIN, UMPS, MRPS30, APBA2BP, TCEB1, CREB1, MGC9084, NOLA1, BUB1B, MGC10471, RFC5, RRP4, FLJ13187, CCT5, HSA6591, CHAF1A, FACL3, IMPA1, FLJ23558, CDC25A, CDC5L, BTN2A1, FLJ20422, ELF2, DKFZp586F1019, FLJ22624, LOC51659, CRFG, WHSC2, HN1L, OAZ3, CD1A, CLPX, CABC1, CLASP2, HSPA9B, KIAA0007, SLC1A3, NPM3, SUSP1, SLC16A5, M6A, UBE2J1, TBC1D4, C20orf1, TBXA2R, UVRAG, MLH3, FLJ20331, PEG10, PRPF4B, KIAA0332, MPZL1, KPNB1, FLJ10204, TFAM, FLJ20281, FLJ10604, LAT1-3TM, KIF2, RBM12, MKI67, HRB2, KIAA0056, ZAP3, COX11, SNRPD1, AMD1, TRN-SR, FLJ20641, RB1CC1, KIF4A, FLJ20093, TPR, RAD50, PPP1R12A, HNRPD, PIR51, PSPH, TTC4, HIC2, SLC39A4, RLF, KNSL7, NOL3, ZNF-U69274, EIF4ENIF1, PDCD4, CTSC, CYP2C9, KIAA0677, BCL11A, LOC56906, TIA1, SYN2, RNAC, RDX, FOXM1, HRASLS3, STAG2, HMMR, KIAA0376, CAPN10, CHEK1, NICE-4, MRPL19, TSN, DKFZP434M154, PPID, NEK4, SMC5, MGC1223, SUV39H1, ESPL1, RANBP2, FLJ23018, SNAPC4, LGN, HYA22, JAG2, KIAA0644,

TABLE 6-continued

Down Regulated In UPTG Verses UPNTG

NPR3, FOP, PKMYT1, APPBP2, HSPC135, C20orf20, EIF4E, ZNF239, FLJ20909, CNTNAP2, ZNF292, LIPT1, FZD7, KIAA0971, SSH-3, MRE11A, KIAA0090, PAWR, SMC2L1, CGI-112, SOX13, HBB, KIAA1193, CAP350, RRS1, MTCP1, HBA1, GRPR, LCT, RAD51C, PRKDC, SPAG5, POLQ, BRCA1, GNAI3, FLJ14346, ZNF24, CENPA, E2F3, DDX18, SFRS2, PSP1, FLJ14827, BFAR, FANCC, DMXL1, CUL3, C6orf15, BCLG, SIL, LOC133619, MGC2306, KIAA1096, GMEB2, ASCL1, EBP, FZD3, PRDM2, KNSL1, FJX1, PPP1R3D, SRP72, DKFZP564D0462, CCNF, PAI-RBP1, PRO1496, RBBP6, TEB4, SP192, DCTN4, B4GALT2, SRF, ZNF200, DNCLI1, SCYE1, PPI5PIV, FLJ22087, SLC29A1, FLJ12439, VDR, TIMELESS, TAF15, CGA, FLJ21816, SHMT2, SRISNF2L, DKFZP547E2110, OIP5, MGC2603, FLJ11896, C18B11, IGLJ3, PPARBP, DCX, TAF5, MGC5306, LIM, PTER, PPIL2, FLJ10998, NSEP1, KIAA0332, MCM4, DLAT, KIAA0453, RPL23AP7, TTF1, WRN, TTK, MARK3, SF3B3, FLJ20552, TIMM8A, PANK3, LIN7C, FLJ20225, FLJ10287, MFN2, FLJ21908, REV3L, MGC5566, ZNF42, MSH5, HCAP-G, FLJ20591, SPHK1, E2F1, FLJ14054, CCNE2, MGC4701, C1orf33, BITE, MCM5, KCNK15, AGTPBP1, FLJ20274, CLPTM1, LANCL1, FLJ20125, FLJ11785, BARD1, MYOC, RB1CC1, FLJ23151, RFC1, SLC25A12, FLJ10330, TMPO, KIAA0157, STC2, UBCE7IP5, MGC5306, COL13A1, TMSNB, PTTG3, FLJ40452, MADH6, IF2, SRP72, FLJ20003, USP2, YY1, FLJ23053, KIAA0276, TIA1, PRDM10, OXTR, HRASLS, BAZ1B, M96, SLC7A5, CYP26A1, PB1, TCBAP0758, TLE3, POLD3, LIV-1, HNRPL, FLJ10407, CHAT, UPF3B, RAMP3, TIMM17A, G3BP, PCDH7, FLJ90754, MCLC, EPHB3, STXBP6, CSTF2T, GYG2, PRKCBP1, RRN3, FBXL2, MDM1, PNN, SMPD2, TTF2, TFR2, GDAP2, FLJ10989, MATR3, PRO1598, PAF53, OGT, HNRPH3, H326, VDR, KIAA0843, UTX, KIAA1172, RYBP, FLJ20005, SCML2, SF3B1, KLHL3, NOLC1, ING1L, KIAA1467, ROBO1, TGIF2, C8orf4, NUDE1, PDCD4, FLJ11004, AKR1C1, DKC1, COCH, FLJ20666, HSPC121, FLJ10261, PMFBP1, RAD1, SLC4A4, FGFR2, SMARCC1, BAZ1A, CGI-130, NESG1, FLJ13909, GRM6, FLJ13942, SOX12, FDX1, LGN, GRIN1, BTN2A1, NCBP2, NMU, CDC6, OAZ, CDC7L1, CNNM4, NOL3, FLJ10038, KIR2DS1, KPNB3, SLC4A4, FLJ22390, SLC6A13, NY-REN-24, KIAA0923, LOC113251, SIP, ERCC6, DKFZP586A0522, RAB11B, ZNF197, WHIP, KIAA0040, KIF5C, GTF2H3, PAPA-1, HNRPH3, NDST1, C9orf12, KIAA1069, MAC30, PPP2R1B, ZNF363, KIAA0931, NFRKB, MGC12760, HSU79274, SELP, RAB33B, MYH11, TIAL1, MCM10, DKFZP434F1735, KIAA0553, SAFB, FLJ12455, DRIM, CFLAR, KIAA0542, HTR1B, SMC4L1, TIMP3, MLLT2, ARHGAP1, KIAA0255, WASF1, POP1, KIAA0286, PASK, DACH, SF3B3, CDC2, RCL, IL2RA, IRX5, DUT, FLJ12684, FLJ20640, NSPC1, ABCG1, T, ZNF174, PPP4R2, MGC4, FLJ21596, ZNF11B, FLJ13449, HBA1, E2F3, CDC2, BICD1, RAP2A, CSTF2, LSM8, DYRK1A, FLJ21940, H2AFP, DATF1, ANGPT1, C20orf46, FLJ20147, ZAP, CASP2, KIF14, DDX17, TRIAD3, TAX1BP1, PEX7, KIAA0182, TIMM44, CIAO1, FLJ13490, MED6, FBLN1, SMN1, OR10H3, ARP3BETA, DLAT, TXNRD2, RC3, HUMGT198A, MTHFS, CAT56, CRSP6, DCLRE1A, ACRV1, TAF1, PPAT, SEMA4G, CXCL9, CUL2, AGRN, ZFP100, KIR2DS3, RECQL4, PTPN13, LOC93081, IRF4, IGL@, CYP2B7, CLASP1, MCF2L, KLK5, COPS7B, B3GALT3, DKC1, YES1, CHPPR, MGC21654, TROAP, FLJ23311, MKL1, KIAA0650, MRPS34, SMARCC1, PEX11A, ZNF212, GABRR2, NUP98, SIGLEC7, ZFD25, RRM1, TFIP11, M96, AD024, AP1S2, TIMM17A, GM2A, TAS2R1, RARG, GDI2, FARS1, ROBO4, RINZF, FOXF2, CASP10, CITED1, RPGRIP1, PHTF1, 37870.00, PP35, MGC4659, KIAA0092, EPHB1, KCNJ10, HOXD4, NUP160, PTPRD, PRODH, PTBP2, PFKFB2, SGK2, ACADSB, BRIX, EML4, EDNRA, CHRNB3, NUP155, KIAA0522, SNAPC1, ARIH2, OAS2, SOX10, MFAP4, TCFL4, SH3BP2, NR6A1, MGC2827, HNRPH3, SIP1, FLJ21986, CTH, PDEF, HABP2, RPGR, COQ7, TTTY2, FLJ11767, LOC81691, HSPC111, MGC39851, TAP2, NUFIP1, GABRA4, CDH2, SMTN, ZNF305, C8orf1, ULBP1, VAMP1, FLJ20477, LHX6, CD6, NSBP1, KLF3, SLC13A3, LOC55862, LCK, CDC25C, CGI-32, DKFZP434D193, MBD4, GNB3, BAIAP3, FARS1, CHRNB1, GCAT, KIAA0342, STK18, MPHOSPH10, CRMP1, UNC84A, CACNB1, KIAA1053, KIAA0953, SERPINA5, FLJ20433, SIGLEC6, DKFZp762E1312, LAT, SORD, GGA2, FLJ21945, FGFR4, DBR1, LMNB2, ADCYAP1, NR4A1, LIM, AGC1, FDX1, FLJ20244, ZNF24, DCLRE1B, IL23A, EIF2S1, INCENP, FLJ21820, ZNF264, KIAA0964, CASP8, ORC2L, CHAC, TNFRSF13B, MOST2, ABCB9, DIO3, RABL2A, FAIM, DCT, CLCA1, TRIM29, GK, GNA14, TDPGD, FLJ20186, RAD54L, SSX3, FLJ10193, HT010, HEC, KIR2DL5, CASQ2, TRA@, ZNF335, ING3, HSPC055, ITIH2, BUB1, MADCAM1, AXOT, KIAA0295, RPL17, NRXN1, P2RX5, GASC1, NUP210, ZNF236, RAD21, ANKTM1, EDNRA, HSPD1, CORO2B, NY-REN-58, FKBP1B, AQP8, KIAA0922, SNRPA1, ARIH2, ASGR2, C6orf35, IL1RN, SLC38A3, NFYC, CACNG4, SEZ6L, GLP1R, NUFIP1, G2AN, FLJ13949, FABP7, S100A1, TRIM36, LOC93408, API5, PADI3, TADA3L, EPN2, TNFSF4, MIP, RIPK2, F5, KCNJ3, HADHA, MS4A1, NEK3, KIAA0275, DTR, MNAT1, ZNF223, FNTA, NRCAM, POLG2, ADH6, CAP2, KCNJ5, SFRP1, APOBEC3C, IL7R, P125, UGCGL2, ASIC4, AMFR, HSN44A4A, RAB5A, OXCT, RAB3GAP, D6S1101, OTOR, LTBP1, RIN1, LDB1, PRKAB2, KIAA1006, PLK, PRO2000, MOCS1, RGNEF, PDZ-GEF1, INA, MASP2, RSC1A1, RoXaN, CLDN6, HSAJ2425, KIAA0469, ING4, REM, KIAA0092, SKP2, OGT, CBL, KIAA1240, QKI, ETFDH, PPP2R1B, MDS031, CED-6, SLC11A2, GPX5, CRKL, PC4, FLJ10858, APOC4, CUGBP1, REG1B, DKFZP564B147, C14orf104, PAX4, TRA@, RECQL5, ENG, CDC2L1, FLJ22087, HYA22, DEFA4, GIOT-3, ASPM, ANK3, TNFAIP2, SLIT2, WBSCR20B, EIF5A, PTHLH, ATPW, CASP8AP2, HSPB3, RPS4Y, UNC84A, FLJ20624, CHST5, STARD5, SSX2, IL22, TAF1B, FEM1B, KCNA1, GPR15, C1orf34, CGI-07, WDR8, SLA, HGC6.2, GRIN1, CXorf6, KIAA1034, EDG4, CUL4B, CSPG3, TFEB, P164RHOGEF, FLJ13105, CENPE, APP, MYL6, FLJ23441, PON1, ENDOG, SERPINC1, PGRMC1, TUBB5, CHRD, PAK6, FLJ20045, PELP1, FLJ12735, DXS542, SH2D1A, PRO1728, HOXA6, NEUROD4, CGI-100, FLJ13386, AND-1, TBL3, GZMM, FLJ90005, FGFR1, LOC51231, FNBP1, P11, PPP1R15A, VDR, CPSF6, S164, C20orf14, KIAA0217, SGT, KIAA0332, DKFZP586E1923, FLJ10884, MCF2, MAP4, AAK1, HS3ST3A1, LOC90806, ALDH3A2, MUF1, NCKAP1, FLJ10618, LILRB3, GAGE5, TMEM1, CD6, ADAM22, BM039, NEF3, ITCH, PPP2R2B, PLG, SNAPC1, DXS9879E, MPDZ, CDK3, CD209L, SLC21A9, SHB, Rab11-FIP2, MAP4K5, DGKE, MTMR3, KCNK5, CLCNKA, SGCE, FLJ10565, MCM7, AK5, NCR3, SERPINB4, TPST1, alpha4GnT, NPEPL1, PRLR, MPHOSPH9, IL18RAP, PMSCL1, HS322B1A, TCF2, TPD52, HIVEP2, KRTHB5, KRTAP1-1, DMD, C10ORF6, AGC1, FLJ23436, PTK7, COL9A1, COL4A1, GVIL, EPHB6, AVIL, LOC54550, NASP, OAZIN, SERPINA6, GPR44, VCY, DIAPH2, 384D8-2, MAPK11, GALNT4, PTGES2, WNT2B, STX6, STK17A, PPFIA1, CALCA, CCNA2, DOC2B, NID, BAZ2A, WNT10B, FBXW1B, SPRR3, MINK, B3GNT4, CDK6, BHMT, SRPK2, PGCP, CNK, SSB, CDC6, GART, DLX2, PLEK, PTPN7, UBQLN3, IFI44, TCOF1, FGF16, COPEB, SOCS4, FLJ11222, MRPL12, WDR9, DKFZP434G2226, CLECSF9, NCR3, GPR49, EP400, DKFZP586M0622, PCDHA9, C1QTNF3, STAB1, PRKDC, BEX1, FZD9, CAPN7, BCR, FLJ11577, IGL@, ARR3, PTHLH, AP4S1, ABCG5, SNTG1, CRTAC1, ZNF335, FLJ10979, HSU84971, POLI, KIAA0643, DKFZp434I1916, PPIG, TRG@, MAPK12, ING1L, HIF3A, CDX4, CYHR1, TRAP100, UCHL5, CLOCK, SLC17A7, HFL-EDDG1, ATF7, FLJ20105, HRH4, FALZ, SLC23A1, NRF1, BTN2A2, FLJ20581, DKFZP761H1710, FLJ10376, GLRA3, C20orf30, C4orf6, ELK4, PLCG1, CNR1, KNSL5, KIDINS220, ING4, PPFIBP1, SGSH, PRKAR1B, UBE4B, INSL3, DKFZP434F1735, MTMR8, KRTHA2, MPHOSPH9, SQLE, OGG1, OSMR, AFM, HSPBP1, VGF, HCGIX, U1SNRNPBP, FLJ23447, FLJ10057, PPRB2B, GRIK3, MARK4, WIZ, CORT, MGEA6, BMP7, FLJ10648, BRAP, DKFZP547E1010, C21orf59, STK6, KLK2, GRIN1, HOXB7, SMURF1, PCDH16, BCL11A, SPPH1, FLJ12838, SSR3, KIAA0940, P2RY2, HSU84971, ZNF134, CNTNAP2, ADAM23, MAGEA6, SPAG6, DKFZp761P1010, DTNB, CHAF1B, MLL, DGCR8, MGC3101, SENP3, FLJ12331, LATS1, IPP, FXYD2, FLJ23360, FLJ20898, LUC7A, NDRG4, LIN-28, CXorf15, FLJ13910, ELK1, MGC4294, TBL1Y, FLJ12985, B7H2, FLJ13693, FLJ10945, FLJ20313, DKFZP566C0424, IGHM, TPS1, GFAP, PEX1, NEU3, FLJ10719, NFIC, GTSE1, SIAT7D, PDYN, SELPLG, B7H2, PIGO, SCNN1D, NMBR, NCAM2, YWHAE, SIP1, FLJ14084, PROZ, ATF2, PPM1F, INSM1, CABP5, ZNF124, SP110, SPTA1, MGC2776, BMP8, GAL, SCA7, FLJ11850, FCGR2B, PROSC, PDE4D, MGC11335, AKAP3, CARF, DKKL1-pending, UGT1A1, SHANK2, LSS, GUCY2F, RANBP3, SLC16A7, PIP5K1A, SCAMP-4, LOC63776, SLC7A8, CR2, FLJ20707, FLJ21106, MADH5, CPS1, COL14A1, PROL3, CUL2, CHAF1A, OAS2, SOX10, MFAP4, TCFL4, FLJ12618, SUSP1, MAGEA9, KIAA0322, SLC19A3, AKAP11, USP7, DC11, KIAA0616, BC008967, OR7C2, CACNG3, PELI2, FLJ14050, DMPK, FLJ23071, CCL14, IGHM, BM039, GASC1, BIRC4, MGC5601, KCNK10, SLC22A8, MGC14817, GRCC8, LARGE, ZDHHC11, ANXA13, FLJ14107, FLJ10246, C11orf5, POLA2, SILV, PARD3, LW-1, CCL13, CLCA2, ME1, RAD51C, SSTR3, STK12, ADAMTS2, MRPS12, SMCY, TUBA4, KIAA0794, CCL11, WFDC1, TRY6, MAP2K2, ACOX1, KIAA0874, C1orf16, NRG1, RCN2, CLDN18, MYL3, FLJ13150, LNPEP, SLC25A21, PDE10A, STAG3, TNNI3, CHC1, MAP3K7, OSRF, HMX1, HRG, FLJ11292, PAL,

TABLE 6-continued

Down Regulated In UPTG Verses UPNTG

KIAA1659, VARS2, HSRTSBETA, IL5RA, CYP3A4, FLJ23556, MAPK4, C16orf3, GPD2, HOXA3, MMP7, FLJ10786, C6.1A, KIAA0892, PCDH11Y, TRB@, METL, PRKAA2, ZNF76, FTSJ1, FLJ90130, FLT3, GNAO1, SCNN1G, TAF9L, PRV1, SNX13, CENPJ, CNNM1, FTCD, NEK1, FLJ11336, FLJ14803, C9orf16, HIP1, PPIF, GS3955, NFATC3, DOK1, ROPN1, MAGEC1, HGF, PRLR, CTSL2, NKTR, SAA2, HOXD11, PROX1, MAP3K12, MORF, FLJ10619, SULT2A1, ERF, DKFZP586A0522, KCNQ2, KIAA1387, DFFB, MGC4172, MOCS3, ITGB3, PIB5PA, ZNF117, KCNA4, KIAA0999, HFE, CYP2A6, A2BP1, RASGRP2, AMELY, GABRG3, ITGA8, DUSP3, PTGS1, KIAA0748, CACNA1G, CENPC1, POT1, COL6A1, ST7, FLJ13052, MS4A12, DLG5, TECTA, ETV5, HEY1, NECL1, DICER1, ALOX12P2, KIAA1025, FURIN, WISP2, CSDA, ALDH1A2, USP19, TRG@, SFRS7, CDX2, MRPS31, NSAP1, CUL4B, ABCC2, IQGAP1, WHSC1L1, ALCAM, SERPINB10, MDS028, KOC1, ELF2, DKFZP434A1022, GPM6B, C2GNT3, CYLC1, FLJ11506, CEBPA, LIMK1, CPR2, CLTB, TNR, PLA2G3, GPR30, APOL3, TSKS, HCGIV-6, KCNJ2, MGC5347, MAP1A, PPARD, TMPO, LOC63923, CYP2E1, RYK, PRKAR1B, FLJ11336, FLJ10748, PRO2958, CHN2, CELSR1, LCN1, SLC15A2, USP5, ZFR, CYB5-M, SLC27A5, MJD, KIAA1096, HTR2C, NACA, APC, ELK4, JM1, KCNAB1, GDF2, ST7L, TGT, AMY1A, ESR1, TLX1, TBX1, KIAA0967, KIAA0146, C1QR1, ARHGDIG, KCNIP2, HDAC6, MTHFR, NTRK3, HAVCR1, FLJ22269, PLXNB1, CRACC, EGR4, PMS2L6, POGZ, FLJ21148, FLJ20359, B4GALT1, KIAA1354, CSF3, SLC17A6, PAK2, ZF, CLECSF6, FLJ21120, ZAP3, FLJ20127, VAMP1, DCLRE1C, DRIL2, FLJ11608, SFTPC, GABPB2, ICAM1, PRO2405, TC10, XEDAR, CART, L3MBTL, PMS2L3, R32184_3, TCL1A, MIP-T3, FLJ14639, PLGL, HPGD, MERTK, EIF3S6, PPYR1, RPE, GLS, VAV2, TFAM, SLC6A1, RORA, PLVAP, PCDHB6, HDAC7A, MGC10731, ARTN, HAO1, POU4F3, KCNJ4, ATP9B, F10, LSS, MPP6, TGIF2, ITGA6, KIAA0682, NUDT13, MGC4293, DKFZP564O0523, PACRG, ACLY, FLJ14627, OCM, SLC4A5, HNRPF, KRTHA1, FLJ21940, KIAA0632, SSX3, TNFRSF9, C22orf19, SLC19A1, LSR7, ZFP36L1, SLIT3, DIP13B, C20orf27, ARHGEF2, EST-YD1, PROL5, RAB3B, LAMB4, PPP2R5B, CRYGD, TGM5, ADAM22, AGMAT, PKNOX1, DSC1, TOP1, TU3A, CACNA1G, IDUA, LTBP4, MYRIP, ABLIM1, CALD1, ZNF46, CDKN2C, FLJ20958, RPS8, MAGEB1, KIAA0683, RHAG, BLu, TFF2, XPNPEP2, TYR, FAP48, NCYM, HIF3A, MBNL, LRP16, PLXNC1, LOC51145, C21orf2, ARHGAP8, FLJ32069, FGFR2, NICE-4, PRKWNK1, LOC65243, DIO1, MDM2, PRDM13, CA-11, PSK, TNFSF15, OPRM1, HSPC048, SPN, NBS1, BIRC4, CDC27, HRH2, TRIO, CACNA1I, TFR2, HAN11, NEUROD6, CADPS, MGC12386, ORC5L, TNXB, F2R, PRO2831, CDH18, FLJ11106, DBP, PAX8, DLGI, CDC25A, CDCP1, FLJ10921, HRH4, FLJ20456, IL12B, CACNA1F, E2F5, PRP17, LGALS8, MGC3771, SLC6A3, RAC2, KIAA0286, MGC12488, NR0B1, AD7C-NTP, IGL@, TULP1, PSMD11, COL13A1, UBE3B, FLJ20401, AKAP1, CRTL1, SPF45, FLJ10895, CCL13, COL16A1, CHIA, RAMP2, SSTR1, FYB, TXNDC4, SCAM-1, DYRK1A, KIR3DL2, CNK2, Di-Ras2, MCCC2, KRTAP2-4, KIAA0523, IGHM, ODF2, RXRA, GABRA2, CLST11240, POLR2A, SRY, TAS2R7, BLR1, DKFZP586A2123, FLJ21007, SPON1, ENIGMA, KIAA0140, RPL5, DESC1, DNAJC9, PTK9, MGC10715, SNCA, CEZANNE, TBCE, HOOK1, COVA1, C21orf62, AGXT2L1, SLC24A1, SYCP2, C17orf1A, OR5V1, HCN2, KLF12, AIM1L, LOC51336, PRC17, ITGB3, PRO1992, POMC, PRO0149, B3GAT3, L3MBTL, APG-1, C12orf2, MOX2, ARHGAP11A, ATP5G2, HLA-DOA, GPC4, LOC57406, COL2A1, GABPA, SCN4A, RBP4, PHF7, GRID2, OSBPL7, MRPL9, MYH2, TFPI, FLJ10159, IPF1, IL20RA, THRA, LOX, CMAH, KIAA0616, CYP1A1, MADH5, FLJ40021, FLJ20069, FBXO22, GABRB3, CYP2D6, TNRC4, FLJ22582, NR2C1, PK428, CBFA2T2, KCNK13, DCT, KCNG1, FLJ10648, CENTB1, ADAR3, HTN1, PDCD1, TRIP, EFNB1, TFDP2, ATP2B2, TNFRSF7, MRPL4, PTP4A3, SIGLEC8, PPP3CC, ENTPD5, BAG5, FLJ20047, GLI2, CCL21, EPN1, TONDU, RAP2B, CGI-72, ZNF384, C20orf42, MEF2C, RAB28, TAF1C, USP18, GPR42, HTR2A, PDE4DIP, DKFZP564C196, TXK, H2AFJ, FLJ20623, GPM6A, FOXJ1, MGC29761, IGHM, RAI15, CSTF1, KIAA0800, CSH1, KRT20, RAD51, TAF7L, FLJ10849, PTK9, RGS11, CDH20, FLJ20034, RFRP, FOXD2, HSA9761, PQBP1, DGCR6L, FLJ11132, OR2W1, CRYBA1, LMOD1, DKFZP434J046, PRO0800, SV2B, C12orf3, SGCA, BMX, MHC2TA, RAD51L1, CYB5-M, VIL2, FNBP2, LEC3, RBM9, BRAL1, NGFR, DDX34, MAPK8IP2, ANKTM1, DDEF1, ARL7, STK18, AQP4, MDM2, SYNE-1, FOXO3A, TNNT2, TITF1, ZIC3, PPBP, FLJ12542, SLC18A1, IGKC, HFE, PRO0038, NPPA, IL-17RC, CXCR3, DOM3Z, GADD45A, GL012, CNOT2, TOB2, TFDP1, FLJ21617, MTRF1, APBA2, TTS-2.2, CNOT4, F9, PRO2133, CRABP1, CACNG1, IGFBP5, CTNND2, DKFZP564D166, MYT2, EVI5, HYA22, CHK, HSPC073, RRBP1, FOSL2, FLJ21302, MGC2889, PRKCL1, TSPY, JAG1, NDUFA5, IL1RN, CRH, CXCL11, MYH8, PURG, SLC7A1, KIAA0953, ELAVL2, SP100, KIAA0675, MLLT4, ZNF198, CD38, BHLHB2, LLT1, FLJ10210, PMS2L9, SOCS2, LIN7A, HOXA7, FLJ10661, ELAC2, CYP3A4, P2RX2, MAPK8IP3, ADAM28, NPR3, DEF6, UTRN, PHC3, FBN1, DKFZP566K0524, ZNF132, OR2J2, GJA8, PSIP2, ED1, PP2447, WSX1, LCP1, MAP2K3, KLF1, TFPI, BTN3A1, GCM2, FMR2, DDX3, PRO1768, KIAA1641, HEMK, SLC8A1, LALBA, RBAF600, FLJ10572, MSR1, KPNA4, CIAS1, MEP1B, NR4A2, PKNOX1, GLP1R, FOXP3, dJ222E13.1, KIAA0471, KERA, COL4A3, NPTXR, KIAA0447, ARHGDIA, ACACB, KIAA0847, CASP2, BRIP1, LRP8, IGL@, PCTK2, TFR2, PLA2G5, HSPC056, IL16, FLJ12178, TBX1, KCNJ13, WT1, PRKACG, DKFZp547G183, MYO3A, DSC2, ANAPC2, ALDH1B1, CD1B, MGC14433, GPHN, IGHM, GUCY1A2, HPSE2, GHRH, GGHRH, GTSE1, MSCP, ADAM8, PAPOLG, CGI-14, SIRPB1, RGN, PGGT1B, ELL, RRP4, APOL2, POU3F1, JAM1, SYP, SERPINI1, FLJ12595, NRG2, PDE3B, HIRA, DDX9, LTBP4, FLJ11783, GABARAPL3, DRD3, XP5, FLJ20190, TRPC6, ADRA1A, DSPG3, KIAA0564, KPNB2, DKFZP564O0523, UGT2B15, AP4E1, RGS7, ZNF10, PIWIL2, HLF, CYP4F2, INVS, ITSN1, FCGR3B, ARF4L, REL, RGS20, EPOR, FLJ21168, MSTP9, ULK1, NRF1, TIGD6, GPR88, DUOX2, GP5, SSB3, FSHPRH1, RHOBTB3, C1QBP, CDSN, FSBP, CFDP1, ELK3, TUBD1, KIRREL, BAAT, CEP2, GGA2, KIAA0874, CRB1, FLJ11726, P2Y10, PCDH11Y, GPM6B, FLJ10715, TRIM9, FCAR, FGF22, FLJ13993, DIM1, GIPC2, KIAA0626, SNIP1, Gene Symbol, LARS, C15orf15, KIAA0783, MGC2714, FLJ10036, HSPC154, FLJ10486, FLJ30596, FKBP5, SERF1A, REC14, OCLN, FLJ21924, LOC51249, FRSB, AD034, CCNB1, FAM3B, MLL3, IBA2, SEPP1, C14orf31, HMGB1, C14orf35, MGC4308, FLJ10407, GRCC8, C20orf129, FLJ20060, Spir-1, LANPL, RBBP7, KPNA4, FLJ10486, MKKS, SNX5, SART3, FLJ14494, FLJ21087, HOXB9, NUCKS, PPP4R2, C14orf47, EHF, MGC14439, LOC55871, AP1S2, TRNT1, FLJ25059, MGC10198, KIAA2024, KIAA1309, HSPC014, LAPTM4A, GPR54, ARL6IP2, DNMT3A, DKFZP564B1023, KIAA0114, ATF7IP, HSPCB, HDAC3, FLJ39370, FLJ20093, PP2447, LOC139231, MGC41917, MGC20262, CSRP2BP, LOC51193, GRP58, HEY2, ANLN, UBL5, CDCA7, KIAA1321, KIAA1323, UHRF1, HDAC3, KIAA1911, FLJ00166, KIAA1453, DKFZP434A0131, NY-BR-1, 37865.00, Rpo1-2, MGC5306, BOC, FLJ25804, FLJ14728, BDP1, PSCD3, AF15Q14, HDCMA18P, PRO2000, LOC152518, GART, TRIPIN, DKFZp313A2432, PSA, PGGT1B, MGC4832, LOC85028, FIGNL1, PECR, CBFA2T2, HOXC9, CPSF2, SLC25A19, C20orf45, FLJ32915, ZNF367, PANK1, LOC131118, FLJ14909, MGEA5, TRIM46, Rpo1-2, DKFZP434C245, AKAP10, CDCA1, H326, DKFZp761A078, FLJ20333, NEDD1, AUTL1, TRAP25, KIAA1143, GPHN, LARS, DKFZP434D193, FANCD2, PRO2000, DKFZp313A2432, FLJ12439, MKI67IP, LOC115004, FLJ11220, MCM10, MRPL1, NDUFS8, PHF5A, OAZIN, LOC92345, KIAA1708, KIAA1982, MGC2628, PXMP4, KIAA1804, ELYS, HNRPD, ZNF6, MRPL42, KIAA1287, TRUB1, TOMM22, FLJ25070, SPPH1, ZIC2, C6.1A, CGI-77, MGC33864, MKI67IP, TUBE, VIK, MGC14798, FLJ20354, KIAA0140, GTF2H3, FLJ12787, DLD, ARIH2, KIAA2023, KIAA0864, CDC23, MGC13096, TRF4-2, OSBPL6, MNAB, ROD1, USH1C, MGC16372, FLJ20333, FZD8, MCM10, FLJ23445, WDR4, OFD1, AK2, REV1L, COQ3, ASCL2, EG1, TReP-132, CAB56184, FLJ13081, HELLS, FLJ10378, C20orf16, EPHA8, DTNA, HSU53209, NAGS, LOC84524, LOC91120, LZK1, DKFZP434I092, FLJ14431, FLJ20354, HS6ST2, FLJ20333, KIAA0140, FLJ23476, C14orf31, LOC55871, C14orf75, C20orf42, TBX1, CRMP5, Jade-1, CASPR4, FLJ11132, DKFZp547O146, MRPL50, LOC51193, FUT10, FLJ30655, SELB, KIAA1524, FLJ14813, FLJ38608, TRIM7, SYT12, FANCD2, FLJ25078, FLJ11294, KIAA1357, STRIN, pknbeta, NSD1, DKFZP434B1727, BCRP2, FKSG14, EIF3S9, MGC2744, KIAA1595, C14orf106, LOC144455, KLK12, KIAA1374, BCoR, GABRB3, TIMM22, FLJ25416, BRUNOL5, MGC24665, ARX, DKFZP434K0427, KIAA1915, C7orf11, MtFMT, FLJ21439, MAP2K7, DKFZp434H2111, ARFGEF2, PRO1489, PTPN1, MGC13204, FLJ23322, MGC16386, MGC45866, FLJ30626, CML66, ZNF295, ARL8, LOC115106, MGC12466, SNX5, FLJ22344, MGC10850, AKT2, NCOA5, KIAA1713, MGA, FLJ20032, RNPC2, DKFZP434E2318, MLL3, SYNPR, FLJ10989, C2orf7, LOC115827, LOC91862, MGC13016, USF1, DGKZ, LAMA3, DKFZp564B0769, A2BP1, KIAA1560, LOC221002, BG1, ENT4, RNF3, CHAC, ICAM2, FLJ10493, EIF3S6, TRA@, FLJ25604, TUBGCP6, GATA5, PGS1, HT014,

TABLE 6-continued

Down Regulated In UPTG Verses UPNTG

C20orf6, NAV2, KIAA1357, GABRB3, FLJ10378, HSPC150, ADCY3, BIGM103, MGC3067, APC10, BOC, LOC120379, KPNA4, FKBP7, C14orf50, FLJ22557, NUDT10, DDX17, FLJ22729, TA-NFKBH, FLJ10785, FLJ32745, WHIP, CTLA4, MRPL30, MRPS25, FLJ10498, CDO1, FTCD, SPTB, KIAA1323, DKFZp761F0118, MGC2452, AKAP13, LMLN, LOC112840, FUT10, TP73, PDCD7, KIAA1274, Tenr, CRR9, KIS, SPG7, HSFY, LOC92691, POLH, SMC6, MSCP, FLJ10378, DKFZp434F1819, CSTF3, CPNE4, HINT3, HSPCA, KIAA0982, P53AIP1, ING5, DKFZp434D0513, STI2, SEC14L2, BCL11A, EPI64, FLJ25530, GPR49, IRA1, ARHGEF7, USH1C, RBM6, DSCR8, FLJ35863, NXPH1, MGC46719, MGC10981, ZNF398, CYBB, MGC4170, KRTAP9-4, NCOA6IP, HCAP-G, DMRT2, CORO1A, C12orf22, MLL, KIAA1753, DMRT3, KIAA1557, RAD18, FTCD, EIF2C2, KIF13A, DLL3, KRT19, TRA@, SCAND2, FLJ25286, ZDHHC4, SEC13L, GPR92, ZNF207, FLJ14600, USP2, HDAC9, PRKWNK3, DISPB, CENPH, MGC29667, LOC149420, PRPF18, CHD2, KIAA0599, MGC16824, IRTA1, ZFP28, LOC112840, KIAA1411, LOC51194, SLC4A5, LOC115098, KIAA1720, MGC40397, FLJ36874, NESH, TMF1, LGR6, PF1, MGC16943, TUFM, HERC2, DKFZP434N1511, FLJ12697, NLN, FLJ32827, CSRP2BP, RUFY2, RBM11, UBE2I, YAP, LRP15, CFLAR, OSBPL5, NPD007, ZIC4, OR51E2, MGC17301, PAX6, FLJ12697, MGC35366, U2AF1, TU12B1-TY, BAG2, SLA/LP, BICD2, KIAA1465, DKFZp434G0522, ZNF354B, FLJ10420, DARS, KIAA1337, DKFZP434C0826, KIAA1712, CDGAP, FLJ10324, ARHGEF7, DKFZp434G0625, HES6, MY050, CSNK2A1, MPHOSPH9, HDAC10, KCNJ16, LOC135763, EKN1, ORAOV1, FLJ31528, POU4F1, MGC42174, SYNGAP1, RRP40, MGC10744, FLJ12363, TTC7L1, DKFZP761N09121, ZDHHC11, MGC8721, IRTA2, ODAG, TRPM7, KIAA1878, TM4-B, DKFZp761H039, ADAMTS9, CGI-203, KIAA1881, FLJ20003, SPPL2B, FLJ13386, RPC5, CTLA4, FLJ37034, DKFZp586N2124, DKFZP434D0127, KIAA1966, KIAA1946, MGC20255, SPINO, FLJ90013, ALS2CR7, SH3GLB2, FLJ33962, FLJ23027, PROK1, GABPB1, MIPOL1, MCM6, BAP29, VIT1, SYNGAP1, PELI1, FLJ25477, WBP1, ROCK1, ABTB1, LGI4, WNT5B, CLDN6, FBXO2, C18orf2, GAJ, TRIM7, FLJ13993, PEX5R, CECR6, PR, LOC151648, POSH, HRIHFB2072, SOX7, LOC139231, DKFZP434K0410, SOX6, CHPT1, NUP133, PSG5, FLJ22688, YME1L1, DKFZp313A2432, M11S1, FBXO5, KIAA1444, BCR, EPB41L5, RNPC2, HTATIP2, KIAA0436, NS1-BP, LENG3, GLS, MIXL1, WDR9, DKFZP586M0122, KNSL5, G3BP, KCNJ2, PTBP1, DKFZp434N1415, SEMA6D, LOC63929, PTER, NAV1, FLJ39441, MIDORI, MGC14793, BAT4, FLJ12987, SEPP1, NYD-SP17, ZnTL2, FLJ35725, C6orf12, GSBS, MGC40157, KIAA1458, AUTS2, FBXL12, KIAA1453, C20orf44, MGC20533, PGS1, FLJ11053, MRPS10, EML4, MGC14793, POLR3K, RINZF, MOBP, FLJ12298, PIST, DELGEF, MGC2629, NPHP1, DKFZp434D1428, ARNTL2, NDUFB1, DKFZP667C165, FKSG42, HAL, WBSCR22, MRPS25, DHCR24, LY6G6D, LCHN, DKFZp761A052, DKFZP434G156, TBX3, FLJ21839, BRUNOL4, NYD-TSPG, KIAA1706, STYX, MMD, LOC113521, TRIM35, ZNFN1A4, DKFZP586B0319, KIAA1798, FLJ30829, FLJ14281, DKFZP586G1517, MGC2209, DDHD1, CRSP6, FLJ11252, TRB@, GNAS, FLJ12975, KIAA1458, COL12A1, SPINO, KIAA0478, FLJ20085, SOX7, DRF1, TBDN100, BHMT2, ZFP91, SRMS, MGC15523, KIAA1919, FLJ23816, FLJ11125, C20orf151, STK31, RTBDN, FKSG83, GLI4, FLJ22548, KIAA1912, C20orf42, TRIPIN, NDUFS7, HSPC135, MGC20460, YR-29, SCDGF-B, KCNJ15, CLLD8, ZDHHC5, MGC10724, MGC33215, DKFZP547E052, DEFB118, MGC24039, KIAA1046, FLJ10936, ACMSD, B2M, TGM7, MGC3165, TRPM8, WHIP, LZK1, LOC90990, IRTA2, KIAA1560, NXF2, KIAA1317, DXYS155E, FLJ31528, HSPC154, H19, BAP29, PRKRA, PLAC3, LOC58486, FABP4, LOC130617, JAM3, LOC57019, TF, USP24, FLJ20222, FLJ20354, KIAA1836, MGC3040, SAC2, BARHL1, DSCAML1, STK35, KIAA1337, KIAA1276, LOC115557, FLJ14600, ROCK1, FLJ38359, MGC33215, ATP9B, UBE3B, C7orf3, PRKWNK4, DKFZp434J0617, MAPK1, PRKCE, KIAA2028, GBTS1, KIAA0716, DMRTC2, FLJ10998, FLJ32069, LOC115330, FANCA, DGCR14, KIAA1337, FLJ23577, FLJ22761, FLJ35155, FLJ22329, FLJ14427, FLJ20557, FLJ20321, ROCK1, PPP2R2C, BCoR, FLJ00058, LAMA1, FLJ20898, FLJ31606, PCDHB4, DKFZp547M109, CLASP2, KCNQ5, LOC51240, FKSG79, OAZIN, FLJ13576, MGC4473, LACRT, NAG73, HSA251708, HSJ001348, TRA@, DKFZP434A236, MNAB, HAP1, MGC24995, DKFZP566C134, KIAA1501, MGC13090, C8orf13, GGTL3, FLJ35757, CRYPTIC, C14orf35, KIAA2015, FLJ12303, LOC92033, FLJ20171, FLJ31340, TMPRSS2, RIP60, ZNF272, FLJ20641, RP4-622L5, CENTA2, C20orf64, HHLA2, DPM1, PRKCL2, GNG2, and RTN4IP1.

TABLE 7A

Genes Up Regulated in Un-Passaged Tumorigenic vs. HSC

KRT19, C3, GOLPH2, CRIP1, PTGIS, BF, RAI3, CA12, S100A8, PPL, TUBB, CXADR, NNMT, ITGB5, COL3A1, FN1, C1S, CD14, EFEMP1, COL1A2, GJA1, FLJ20151, LGALS3, TACSTD2, LGALS1, FN1, MUC16, COL1A2, KRT7, RARRES1, DSP, ID4, HRASLS3, S100A11, CYR61, SLPI, C4A, LGMN, S100A9, SERPINB2, MAFB, COBL, WT1, TGFBI, SPUVE, CD24, DKFZp564A176, ANXA2P2, S100A10, ROR1, EGFL6, FN1, MUC1, ALDH1A3, PARVA, CHST1, FN1, TIMP1, MGP, AGR2, KRT18, DC12, CHI3L1, CD24, FLJ20273, ID3, H11, HLA-DQA1, ANXA2, SERPINA3, RAB31, ANXA2, RAB31, EMS1, FER1L3, KIAA1199, CX3CR1, FLJ11619, KLK11, CD24, TIMP2, CCND1, LOC51760, FLRT2, HP, GPRC5B, IL13RA2, APOE, GAS1, PPIC, MAPK13, KIAA0882, APM2, PLAT, MYL9, MYO6, COL3A1, ANXA2, RAB31, IGHG3, PMP22, FAT, S100A8, MARCO, PTPRK, PTPRF, CD163, DF, C4B, COL1A1, IGKC, TFF1, TGM2, CTSL, ITGB5, GALNAC4S-6ST, IF, RARRES2, LAMA2, VCAM1, CD9, ID4, APOC1, PDEF, VIL2, GRIA2, RIG, MET, GNG12, CD163, FLJ22662, CAV1, PRG4, CDH11, IFI27, TM4SF1, NNMT, DUSP4, THBS2, COL6A1, FGFR2, TNXB, A2M, UPK1B, BCHE, IFI30, MAF, KIAA0752, TPD52L1, KRT8, FXYD3, CKAP4, ALDH1A2, ANXA8, BCMP1, ALDH8A1, ASS, EFEMP1, LTF, FLJ20151, T1A-2, SELENBP1, CTSH, GPR64, TJP1, RARRES1, SYN47, PDGFRA, PRSS11, AQP1, COL5A2, EPHA2, ITSN1, SULF1, PTPN3, LGALS2, OGN, CTSB, IER3, FMO1, SNCAIP, SLPI, PTPN2A, MGC2376, GATA6, IL1R1, CD1C, MEIS2, TACC2, C1R, AQP3, LR8, SLC7A8, S100A6, ATIP1, MIG2, TNXB, MAOB, DCAMKL1, DPP7, ANXA3, RBP4, zizimin1, CHI3L1, FARP1, CLMN, BNC, HCA112, CSPG2, CD24, EMS1, CEBPD, IL13RA1, RIL, COL4A5, KDELR3, CAP2, MAF, TFPI2, DOC1, CSPG2, LGI2, Z39IG, CYP1B1, CAV1, ALP, ERBB2, LAMA4, CSPG2, LOC113146, LAMP3, ARGBP2, MNDA, DKFZp564I1922, CAV2, MARCKS, TPM2, LOC92689, GFPT1, N33, SECTM1, WFDC2, CLU, ROR1, TST, EFS2, GUK1, C1QB, CPE, CRYAB, TSTA3, CALB2, EGFR-RS, PPAP2A, PTPRG, SAT, TFAP2C, C2, RCP, SULF1, SFN, LAMB1, IL13RA1, PHT2, BMPR1A, LIM, FLNC, N33, ST5, CSRP2, FLJ23091, PAPSS2, IGSF4, TNFRSF6, STEAP, BACE2, SERPINB7, CALU, PDXK, PPIC, TACC2, CLDN4, GPNMB, RIN2, KIAA0599, LUM, KIAA0790, CARD10, MVP, PDGFRL, RRAS2, KIAA1078, AKAP12, ARHE, RNASE6, BLAME, TM4SF1, T1A-2, KIAA0869, MPZL1, NID2, DDR1, DUSP4, LAMA5, SGCE, UBD, LGALS3BP, ENPP2, SGSH, COPE, KRT5, SEMA3C, IGKC, COX5B, ELOVL1, S100A14, APEG1, ALOX5, TM4SF6, LMNA, DSTN, RAB20, DNAJB2, TYROBP, UPK1B, KDR, P4HB, FLJ11856, C1orf34, ADM, NR2F2, PLXNB2, ITPR3, S100B, SOX9, DCN, EPS8, EFA6R, ZFPM2, PPFIBP2, SERPINF1, NQO1, NMA, AADAC, COL6A2, SERPINE1, MT1X, MGC3047, NCKAP1, DDR1, TLE1, EPN3, TBX3, CDS1, HSPB1, DPP4, CTSB, NEO1, TMEM8, NFIB, FKBP2, TNFRSF11B, FGR, FMOD, P4HA2, TNFRSF12A, ERBB3, NQO1, LAMC1, NQO1, PRO1489, IGFBP3, MYO1C, KIAA1026, SLC6A8, PDE4A, HML2, FLJ21562, C8FW, MS4A6A, KCNK1, C3AR1, AK1, MT2A, KLK10, KIAA0429, IGSF3, ARNT2, DCN, C12orf5, CD24, C4.4A, SFN, CRABP2, VIL2, CLECSF6, HCK, SIX2, TSSC3, CCR7, GFPT2, TUBB-5, ENAH, SLC16A4, C11orf9, FLJ20761, SAR1, GPC1, MYO1D, RGS16, DCN, MT1L, PCDHA12, SGSH, RHBDL2, GLUL, CKMT1, NPAS2, EMP2, DAB2, DSCR1L1, MATN2, BLVRB, PLAB, MT1G, WIT-1, OASIS, PPP1R3C, NQO1, AMOTL2, TNNT1, AZGP1, PARG1, SLC7A7, COL5A2, NEDD4L, DCN, SERPINA1, DFNA5, SAMHD1, IQGAP1, THBD, DPYS, ADAMTS5, MGC10848, NEBL, RAI2, TUFT1, KCNJ15, LIF, CD151,

TABLE 7A-continued

Genes Up Regulated in Un-Passaged Tumorigenic vs. HSC

DAF, IL1R2, NRXN3, HK3, FCN1, CXCL1, CALD1, PCDH7, C1orf13, TRD@, NFIB, VEGFC, CCL22, CD63, CTSZ, KYNU, ADFP, HRH1, CTGF, GRIK2, ANG, KIAA0790, SNK, CST3, SDR1, KIAA0703, MGC35048, ANXA9, YAP1, ADH1B, CLDN1, TIP-1, COL18A1, DOK5, GPRC5C, IGSF4, ABCA8, KDELR3, PPAP2C, KIAA0440, IGF2R, VLDLR, OSBPL10, SLC12A8, NPD009, RPL37A, MAPT, FARP1, LAMP1, DAB2, KRT17, SSH-3, ABCA3, PHLDA1, FBXL2, LOC114990, LOX, ALDH3B1, RIG, SDC4, CGI-38, ZFP36L1, FOLR2, DLG5, PFC, BGN, DSC3, WARS, FLJ21610, MGC2494, PCOLCE, FCER1G, FGF13, MD-2, UGCG, BAG3, MAOA, CAPN2, CCR1, TRIM2, CLU, NR2F6, KIAA1598, GPR65, TRD@, PPARD, HSPA6, KIAA0436, DP1, GRN, ABCA1, CD59, ITGA3, NT5E, SLIT3, CDC42BPB, ZNF144, LTBP2, FER1L3, PCOLCE2, FST, CSTA, CLECSF6, HOMER-3, LDB2, SLC34A2, TEAD3, PMM1, EFEMP2, HN1, FLJ20539, TPM1, CXCL6, MPZL1, DKFZP434B044, GS3955, CHST6, RPL5, IL1RL1, RIS1, SN, CDKN1A, PIGPC1, SLC4A2, SMARCA1, GBP2, RNASE4, EFNA1, MCP, DPP4, HSPA1A, LRP10, GRN, SLC39A1, PFN2, BC-2, WNT2, FLJ23186, TPM1, SIAT4A, RNASE1, PLS3, TIMM17A, DDR1, FLJ20366, EFNB2, PSPHL, MEOX2, KIAA0429, SDC2, MGC10796, SERPINB5, CAST, MYO6, CRIM1, TFPI2, NCF2, FLJ22531, LISCH7, SLC7A11, MGC11242, PKNOX2, RARRES1, FBP1, CLIC4, CAST, C5R1, SPR, BCL6, RIPX, GRN, KIAA0934, HSPB2, SPARCL1, CTSB, S100A11P, IGF1, BCAR3, ASTN, RRAS2, FLJ21562, KIAA0992, FHL2, HLA-DOB, LAMB1, MAP4K4, EFEMP2, KIAA1029, PP1057, SLC7A8, TLR7, MMP15, WDR1, GHR, TJP1, PCDHGC3, MMP19, ARHD, RIL, NOL3, WNT5A, RAB17, F-LAN-1, IGF1, BMPR1A, TLR2, FTS, EPB41L1, TPM1, CD1D, YKT6, GRIM19, WARS, AXL, MIF, CLIC3, MAPK13, SSB1, SEC61A1, PDGFRB, IL10RA, CLTB, PCNP, SNAI2, SGCB, CYP39A1, FLJ90798, SBBI31, FZD2, AMMECR1, SOCS5, KIF1C, S100A13, CLDN7, PBX1, TJP3, RGL, FKBP11, GRP58, EIF5, IGFBP1, FLJ13612, G0S2, TNFAIP1, TIP-1, PSEN2, PPIB, DAG1, ARF4, AHNAK, LOC115207, PCDHGA1, MST1R, SH3GLB1, SC65, MGST3, BMP2, CTSB, TMSB10, TRIM38, ITSN1, MPZL1, ARHC, KIAA1078, PLTP, CRIM1, C11orf24, KIAA0746, MGC2376, COLEC12, BBOX1, WNT2B, HUMPPA, PAM, MAP4, FLJ21918, SLC2A6, MYO1B, NFE2L1, DXS9928E, SLC1A1, TUBGCP2, SULT1A1, QSCN6, LOC51159, PSK-1, CYB5R2, RAI14, L1CAM, KCNMA1, CD1E, HOXC6, THY1, PTOV1, EDG2, SUCLG2, AQP1, DDR1, TMEM4, EDG2, FLJ22833, KCNK15, KIAA0417, TCF21, ASML3B, HSPC163, LAMA4, APOC1, DKFZp761F2014, SLC21A11, CXCL14, FCGR2A, FLJ20967, MRPS12, FLJ13110, KIAA0913, SHC1, DP1, TLE1, SLC2A10, PON2, SPAG4, ITSN1, ACTL7A, RBP1, IL1RAP, C22orf2, ATP1A1, DES, MST1, PHLDA1, KIAA0934, S100A2, ID4, ITGB4, CAST, SLC31A2, C21orf97, CD86, FBXO9, AP1M2, D2S448, ADCY9, PALMD, PTPN21, TRA@, PPIB, EPB41L4B, PNMA2, RSN, SYNGR2, SLI, FYCO1, CLTB, MGC16723, CKAP4, PLEC1, FLJ10521, B4GALT4, ID1, CDA08, OPTN, PTHLH, MYO1B, LIM, TLR5, FLJ23516, CAST, CTSL2, CSF2RA, C14orf58, SLC7A8, TREM2, CST6, ARHN, ST14, PTPN13, SLC5A7, DUSP5, B4GALT4, DKFZp667G2110, TWIST, SC65, PPP2R1B, ITGB5, KIAA1096, EVI5, RAB2, CTSD, SLIT3, KIAA0284, NPY1R, HERPUD1, PAM2, HSD3B1, HPIP, UNC119, KDELR2, FLJ10199, PLOD, GTF2IRD1, SQSTM1, BDKRB2, WSB2, DPP3, LOXL1, SEMA5A, TMP21, CLTB, DNALI1, CXCL13, FZD1, CNN3, KDELR3, ADAMTS2, MD-1, TAT, FLJ20234, DKK1, FLJ10856, TM4SF6, KIAA0152, FBXO2, CLECSF12, PRSS16, KIAA0103, UGDH, YIF1P, P8, SNTB2, GOSR2, KDELR2, D4S234E, HABP4, ANKRD3, CCL18, TEGT, EGFR, ATIP1, EPHB3, H_GS165L15.1, TCEB2, AGRN, NBL1, FLRT3, NPAS2, SCO2, MAOA, NFE2L1, APLP2, MED8, LRP2, SMARCA1, TJP2, p47, FLJ10055, EPS8R1, TGIF, AGRN, SEMACAP3, DSC2, FBLN2, ORMDL2, ADAMTS3, PTGDS, CENTG2, MMP14, SNARK, PTGER3, DPH2L1, PTPN21, DSCR1, PP1665, PTK9, AFFX-HSAC07/X00351_M_at, HAMP, TOB1, FACL3, GMPPB, CSRP2, P4HB, NPC1L1, PIG7, VNN3, ARK5, PODXL, ACADVL, GNPI, FLJ10261, UPLC1, SFN, PEA15, MLCB, SLC31A1, ICAM1, UP, SLC4A4, C11orf17, PTGER3, ZFP103, CYP-M, HMOX1, SLC21A9, TCN1, SLC20A2, RBSK, WNT4, CYBB, ANXA4, DNAJC3, MIRO-2, ARHGEF4, SULT1A3, GOLGA2, PTPRF, NDUFB7, TBC1D2, MSR1, CORO1B, FADD, ATP6V1D, ALDOA, EPLIN, MST1, TDO2, ETV2, CCR5, SERF2, GTPBP1, COL4A2, ASPH, ELMO3, DKFZP564A2416, BAIAP3, APLP2, PDE8A, IFNGR1, GREB1, ANXA2P3, CAPG, PTS, N33, MGC11256, PLA2G4C, HFE, FLJ90798, FLNA, LMNA, IRX5, SRPX, LOC160313, SLC33A1, CSTB, FLJ20152, ATP6V0E, HSPA1A, KRT6A, SAR1, POR, NDUFS8, CCL2, B4GALT1, TMSB4X, FLJ20701, ACTN1, IL4R, F5, CD5L, IGFBP3, ALOX5, AUH, CKAP1, CCR1, KIAA0843, UGTREL1, GAS2L1, AP1M2, RARRES3, PPGB, LY6E, GNB2, CTNND1, FPR1, ALDOA, PC326, KIAA0980, PGM3, DHCR24, PTGDS, LAMB3, ALDH7A1, KIAA0716, TC10, KIAA1096, IL1RN, C11orf24, FDXR, SERPINB3, COL6A1, FLJ20296, DTNA, IGF2R, TRIM36, FLJ22593, IFITM2, ARHD, KIAA0220, OCRL, SDC2, KIF3B, GALNT10, PRKAR1A, VTI1B, PSAP, PTPRO, FGF2, PCSK7, SUCLG2, ERP70, FLJ20254, MLP, CORO2A, IL13RA1, RGS16, MEIS3, FOLR1, LGALS8, LAD1, TGFBR3, NDUFA3, LANO, AKAP, SGPL1, UBXD2, GM2A, PCDHGA10, PACSIN3, CFL1, PAM, GOLGA2, GSTM3, CREB3, C14orf92, IGL@, FLJ21313, SYNE-2, EPHX1, MRPL17, PCDHGC3, MAP3K6, DNCH1, TM7SF1, LARGE, VRP, IL6, KIAA1096, SARS, PSMD8, COX17, GPX4, SULF1, NEU1, ISGF3G, PLP2, CYR61, ATP6V1D, EIF5, FLJ20847, DKFZp761K1423, FLJ11526, EHD1, KMO, KIAA1735, RGS3, SDFR1, ASM3A, FGFR2, FCGR3B, TPM4, CPE, FLOT1, CNGA1, SPHK2, FBXL7, SH3GLB1, LAMP2, EHD1, PLXNB1, VCP, SNCB, ITGAV, FLJ21047, STAT3, PSMC4, CALD1, DES, ALDH3A2, VDR, PAPSS2, MGC13523, ARF1, NDUFA2, PPAP2B, FUS1, ASNA1, TUBB4, MGC4504, RGS19IP1, ATP5H, TSTA3, Cab45, RDH11, ECGF1, TMEM2, GALE, WSB2, NSAP1, WFS1, HSPC003, GOLGA1, SH2D1A, FLJ20986, KRT17, UNC84A, MYL6, LAMC2, FGF18, HS2ST1, RNPEP, TC10, FLJ14675, MGC3178, TM9SF1, GALNS, SORT1, HSPC019, SULT1A3, ENC1, RAB9A, CED-6, C21orf97, HFE, FUCA1, KIAA0674, EHD1, PLAUR, CETN2, TPBG, CYP27A1, MAN1C1, PPP1R13B, ATP5J2, THBS3, FKBP10, YKT6, PIGO, CYP4F12, LRPAP1, ITCH, MLF1, ACTN4, EIF2AK3, PDE4DIP, DZIP1, TUBB4, SEC24D, KIAA0143, ITPK1, FLJ13110, AP2B1, IFITM2, SCN8A, STS, CDC42EP4, ARPC1A, CD2BP2, CACNG4, SULT1A2, TAF10, BRD2, TRAM, HSF2BP, UBC, ADAMTS9, AQP9, RALA, COL15A1, DYSF, LAMB2, RPL5, EHD1, CLCN3, ARF4L, HDLBP, NPR2, HRB, SQRDL, MIG2, NAV2, TBC1D1, TPD52L1, VTN, ARL1, CYB5, LGALS8, COPZ2, FLJ21916, FLJ20421, P4HA1, TBL1X, ANGPTL2, KIAA0992, NRP1, SLC21A11, ICMT, STS, EIF5, PIP5K1C, RDS, PVRL3, PON2, HIG1, DLAT, LOC64182, RNF3, ACAA1, UQCR, FLOT1, TC10, DSTN, TEAD4, RER1, TREM1, IL17R, PLCE1, SLC6A8, HIMAP4, PILR(ALPHA), TRIM38, TXNDC4, CTSK, DSS1, LPHH1, SGCD, PEN-2, KIAA0527, RRAS, CD3D, LANCL2, P2RY6, TUBB, RAC1, AAK1, LOC51762, ALOX5AP, GNB1, FKBP11, RNASEH1, EPB41L1, GPRK5, GPI, HMCS, PTGER3, SSR4, FKBP9, AK3, CBLC, SGPL1, PLCD1, MED8, ALDH3A2, IGSF6, KCNN2, HS3ST3A1, MLCB, TRIM38, FCGR3A, IFI35, ABCA1, DKFZp564A176, FSTL3, MAPKAP1, ENTPD3, FLJ23514, HS3ST1, IGHM, PM5, NDUFB2, TOMM20, ANGPTL2, KRT7, SSH-3, ELOVL1, NPEPL1, NEDD4L, PARVA, PTK2, SEMA3E, NCBP2, KMO, QP-C, ECM2, ATP9A, HMOX2, SMAP, SLC9A3R1, ATP1B1, PCDH7, EDF1, OPCML, NEDD5, FLJ10466, CBX6, CDH6, MAN2B1, CYB5, SLC38A6, FLJ12443, ASPH, MOB, HUMNPIIY20, DC50, PSMD5, LRRFIP1, FLJ22160, PAFAH1B1, DKFZP586L151, BLAME, TAZ, ATP6V0B, APBA2BP, RISC, ADRA1A, PIG3, TNFRSF21, CBFA2T1, EML1, EPIM, APOE, WISP1, CA12, VIL2, RAI, FAAH, ATP6V0D1, CD97, JAG1, STX4A, Cab45, NFE2L2, PPP1R12B, ZMPSTE24, KIAA0500, IL17BR, RRAD, PGM1, CD59, ADAM19, NPEPPS, FJX1, GAA, SOX13, FLJ22638, BAIAP2, DUOX1, TGFA, FLJ20719, LMCD1, BBS4, MARCKS, GM2A, FLJ11200, MAPK3, WWP1, FLJ20152, SMARCA4, PSCA, MCJ, ARF4, SLC35A2, SKD3, CDC42EP4, SLC22A1L, SSH-3, SMARCD3, PDLIM1, IL27w, CGI-135, COX5B, LOXL2, CRK, GOLGB1, PSMD4, MAGED1, CDC42EP1, HSPC171, SEC13L1, KIAA0265, PSEN2, XLKD1, STAB1, FLJ21079, FBLN1, INSM1, FLJ10252, MPDU1, MGC3067, FLJ11181, TPARL, TULIP1, DUSP8, UBXD2, CPD, HSPA4, FLJ11807, GPR1, CTNND1, TNFAIP2, MAGED1, MMP9, CKAP1, UGCGL1, SMP1, FLJ22678, BZRP, COX8, BDKRB1, HOXC4, , H19, NMES1, SMOC2, PIGPC1, TEM8, PTGFRN, FLJ23091, IGKC, ALS2CR9, IMUP, MIG-6, MAL2, SPUVE, YAP1, CXCL16, MYO5B, KIAA1244, PARVA, SYNE-1, FGG, AGR2, KIAA1500, RERG, NTN4, TMPRSS3, ARHU, RHPN2, GLIS2, UGCG, SULF2., BOK, OGN, CLDN1, DKFZp434G171, FAD104, KIAA1165, ShrmL, PTGFRN, AD037, OSAP, LOC51760, MS4A6A, FLJ20273, MS4A6A, FLJ23153, NAP1L, LRG, LOC55971, MGC14859, FLJ30532, UNC5H2, FLJ14299, TCEA3, CTL2, ORF1-FL49, LOC155465, ENAH, OSR-1, SBBI31, DAG1, EDG3, PSK-1, MGC2615, ALS2CR9, DKFZP761L0424, TBX3, FZD4, FLJ20171, DKFZp761P0423, NGEF, TOB1, C1QG, DNALI1, MGC35048, GUK1, DKFZp586C1021, KIAA1500, LOC83468, p25, CCL26, GNG12, SAMHD1, ID4, B4GALT1, DKFZp434D0215, GJB2, FLJ14957, PRO2605, MGC13040, CHDH, ALDOA, FST, TEAD2, KIAA2028, FLRT3, FLJ31842, CDKN2B, MGC16028, IRX3, TEAD1, MGC33662, MS4A6A, SEMA6D,

TABLE 7A-continued

Genes Up Regulated in Un-Passaged Tumorigenic vs. HSC

DKFZp434E2321, PKIB, PKIB, KIAA1671, FLJ22174, LOC128153, COTL1, SAMHD1, MGC24103, UACA, SELM, CGI-85, NAP1L, CAMK2D, C4orf7, BOC, MGC11034, DKFZP564J0863, DKFZP434H0820, PARVA, SPP2, FLJ40432, STEAP2, PDGFA, BACE2, FLJ14834, LOC55971, ANGPTL1, MFI2, KIAA1337, WNT7B, IPP, DKFZp547D065, MGC39325, CTL2, SAMHD1, LNX, MGC26963, KIAA1324, MGC16212, KIAA1921, ALS2CR9, CXCL14, SPPL2A, FLJ14525, ENPP5, MGC29643, TCF21, ECGF1, PCDHB14, CFL2, GRP58, TGFBR3, DKFZp434F2322, FLJ22474, RCP, KIAA1866, MGC10974, PHLDA1, MGC12335, SYTL2, LOC51242, PCDHA10, KIAA1145, KLF15, TMEPAI, GRIA2, LOC92689, SIPL, H19, FAD104, C11orf15, MGC39329, MAFB, BCAR1, RDHL, C14orf50, DRAPC1, RORC, MYEOV, GPR92, DUSP16, GFRA3, ZD52F10, FLJ14735, LOC113026, FLJ20048, CLDN11, CDH24, TLR8, FLJ31052, C(27)-3BETA-HSD, YAP1, EMS1, GATA5, FLJ23420, FLJ10035, IL28RA, MAF, HMT-1, DERMO1, DIRC2, HSPC163, ARHU, LOC114990, MSTP043, CGN, DUSP16, ODZ2, INMT, GPR, CRBPIV, FLJ22558, KIAA1145, TCEB2, LOC55829, SEMA4B, COL12A1, MGC11034, KIAA1576, MTA3, ATP1B1, C20orf155, SDCCAG28, MGC16028, CXADR, CTSB, KIAA0146, MGC33602, CLDN12, RAB23, DKFZp434F2322, PRO2714, BTBD6, MRPS10, SNX9, IL4I1, DKFZP434I1735, LOC91523, AFFX-HSAC07/X00351_M_at, RERG, FLJ14642, FLJ22833, MYO5B, SDCCAG28, RAB10, LBP-32, C14orf31, DLG5, FLJ22415, PCDHB16, MGC10204, C21orf63, DKFZP434K0427, NRP2, KIAA1870, TEAD2, SPTB, FLJ33516, SURF4, NPD007, PCDH20, MGC19825, MGC26818, MGC4604, KIAA1337, ESDN, FLJ23091, MacGAP, CGI-85, C8orf13, FLJ40021, MS4A7, LTB4DH, PLEKHA1, SORCS2, CRIM1, FLJ11200, HS6ST2, FLJ10697, WW45, LOC132671, DCAL1, SNX9, DKFZp761K2222, IGSF9, LOC57168, LOC90701, GPCR1, AK2, FLJ31564, KIAA0599, ANGPTL1, FBXO25, KCNK6, MRPL41, FZD8, UGCGL1, COPZ1, RBMS1, C20orf23, Cab45, TRIM7, OAZIN, FLJ10210, SYTL2, FLJ20442, C20orf139, KIAA1394, C20orf110, MGC1314, C20orf52, CNN3, MacGAP, CAC-1, MAP1B, FLJ40021, PRIC285, RAP2B, TMPIT, KIF1B, GFRA1, DKFZp762A217, XPR1, EMILIN-2, FLJ32069, SMUG1, ARF1, NDUFB10, EHF, NT5E, CORTBP2, FLJ32194, FLJ90440, LOC147700, MGC21874, KRT19, PCDHA10, DTNA, RGC32, ULBP2, H2AFJ, CFL1, MGC2601, DKFZP566F084, SLC26A9, KIAA1404, PX19, APOA1BP, WASL, TLR7, FLJ20739, FLJ25157, FLJ22833, MGC14353, DKFZP566J2046, SNX8, BHLHB5, TAF10, FLJ14594, MRAS, FLJ14511, UBXD1, AMID, ANKRD9, ACTR3, TMEM9, DKFZp761N0624, FLJ20748, ROR2, LOC91461, TLE1, SEC14L2, BAT5, SSB1, E2IG5, KIAA1357, MBC3205, FLJ11046, FLJ14681, HSPC242, DKFZp547A023, CED-6, KIAA1715, TNKS1BP1, ATP1A, EHD4, INADL, FLJ11011, KIF3B, DKFZP434K0427, FLJ32069, CSEN, DKFZp761D0614, MRPL41, PXMP4, LOC84518, LOC115265, LOC51255, ATP6V0B, N4WBP5, GGTL3, MAGI-3, MLLT4, LUC7L, ERO1L, MGC13114, MGC39807, CAPNS1, TRIM47, GPR34, KIAA1200, N33, PSCD3, NSE1, BAL, C20orf24, MGC22805, KIAA1337, CDH11, LOC51248, KIAA1126, FLJ90119, PVRL2, ARHC, SSBP4, DNAJC1, E2IG5, FLJ10702, NUMBL, SET7, BRI3, FLJ32069, FLJ20097, KIAA1870, C14orf31, TP53INP1, NCAG1, GSH-2, FLJ21963, KIAA0599, MPP5, SCDGF-B, AXIN2, CGI-149, CGI-97, MGC19825, DNAJA4, SMOC2, MRPL27, KIAA1542, ARHGEF5, CAMK2D, SLC21A11, FLJ37318, C20orf64, D1S155E, UNC84B, MGC26963, dJ55C23.6, GK001, CPNE4, MGC16491, FHOD2, HTPAP, KIAA2002, PRDM6, FGFR1, DKFZp564B1162, HLA-C, PRDX5, FLJ20623, FLJ20719, C14orf47, MYBBP1A, RDH13, DPP3, PCDHB18, NOL6, JAM1, LOC54516, FLJ10210, NRXN3, MRPL53, KIAA1643, MGC15523, LOC115704, BRI3, GTAR, KIAA1434, MGC33510, FRABIN, UBQLN1, MGC3195, FBXO32, SMP1, FLJ10902, C1orf13, CGI-72, MGC45474, TRIM8, HM13, NFKBIE, FLJ22004, AD-003, MMP24, RBM8A, DNAJC5, C20orf169, NOR1, METL, MGC2747, FLJ14251, DKFZp451G182, KIAA1363, FLJ23393, RNF19, STK35, AMID, MGC4604, FLII, DKFZP566J2046, SNAP29, DKFZp547A023, DKFZp434F2322, SLC17A5, FLJ14117, MGC4342, SLC31A1, MGC2555, KLF2, NKD2, SEC61A1, LOC91012, MSTP028, FLJ20421, MGC40555, KIAA1554, AD-003, SURF4, GALK1, FACL6, DKFZP434D146, GPT2, BRPF3, KIAA1165, SLC30A1, FLJ20542, KIAA1255, JUB, SYNPO2, SURF4, MGC2550, LOC90507, SYNPO2, ARFGAP1, KIAA0599, DNAJB11, UBE2H, C20orf149, PHP14, FLJ23577, FLJ23654, LOC51290, DJ667H12.2, FLJ23277, LOC115098, DKFZp547O146, LACTB, FLJ90575, NEK6, Cab45, MGC13045, SRA1, DPP9, SFRP2, LOC113179, KIAA1784, C20orf149, CGI-09, GBP2, PDK4, HRMT1L1, MGC33993, MESDC2, IDS, RDGBB, RPL17, TEAD2, SEI1, C20orf58, HSPC210, KIAA1163, KIAA1223, RAB18, NFKBIA, SEPP1, B7-H3, MGC33607, CAB56184, SDCBP2, PCDH18, SPEC1, RAB18, SH120, MGC11102, MGC19825, LMLN, REN, CALM2, PPP1R14A, NDUFB9, KIAA1026, MGC20486, FLJ30803, AKIP, LTB4DH, DKFZp547A023, C20orf167, FLJ31937, FLJ20186, APXL2, CFL2, CGI-20, KIAA1437, PVRL2, KIAA1295, KIAA1912, DC-TM4F2, CDW92, RPS27L, CAMK2D, RAB18, FLJ21415, MGC10999, KIAA1896, KIAA1337, CGI-69, and STC1.

TABLE 7B

Genes Down Regulated in Un-passaged Tumorigenic vs. HSC

HSPC053, HOXA9, SPINK2, HOXA9, MPL, KIAA0125, BEX1, FLJ14054, CD69, ANGPT1, AKR1C3, LAGY, TNFSF4, HLA-DQB1, ITM2A, KIT, GUCY1B3, PLAG1, PROML1, MYCN, MLC1, LYL1, MPO, HOXA10, PCDH9, , PLCL2, HLF, SV2, LOC81691, DLK1, HLF, ERG, SOCS2, MYB, PPM1F, PRSS2, BAALC, NPR3, EREG, MMRN, IQGAP2, C17, MPHOSPH9, LOC51659, SELL, MEF2C, TEK, RAB38, FLJ10178, TRY6, NINJ2, FLJ22746, BM046, ICAM2, MLLT3, BCL11A, HMMR, NAP1L3, MPO, AREG, SATB1, LGN, FLJ10713, ERG, PADI5, IGHM, HLA-DQA1, SCHIP1, ARHGEF6, GUCY1A3, TMSNB, TYMS, TAL1, MS4A3, GMFG, FLI1, LPIN1, 6-Sep, C20orf42, TACC3, LOC81558, MCM5, TRAITS, IL8, CXCR4, KIAA0186, RetSDR2, RAMP, MGC2306, LGN, CDW52, HMGA2, PTGER4, NUDT11, ZNF198, PCDH9, FLJ10468, PSIP2, CRHBP, ICAM3, IL12RB2, KIF4A, DKFZp761P1010, FLJ12428, GPR56, CXCL2, PRIM1, BIRC5, PLAC8, TFPI, H3F3B, HBB, NEFH, LMO2, SV2B, ITM2A, BRRN1, MCM2, MLLT3, H2BFQ, DOCK2, UBCE7IP4, ZNFN1A1, BCL11A, DDO, NRIP1, TARBP1, HBB, KIAA1750, F2RL1, NRIP1, FLJ10719, CDC25A, VRK1, DUT, PIP5K1B, NR4A2, BCL11A, BM039, HSPC022, 6-Sep, TOP2A, PDE4B, GIT2, JAM2, KIAA1939, MAP4K1, RUNX3, SELP, ANKT, B4GALT6, BCE-1, HBD, PECAM1, E2F3, FLT3, PIR51, TRAP-1, TFR2, P311, HSU79274, CLDN10, DNMT3B, CDC45L, CDW52, PELI2, MGC861, C1orf29, BRCA1, HHEX, LBR, TOX, ITGA2B, FLJ11712, LOC81691, PPM1F, STAC, CRYGD, MAD2L1, KIAA0379, ITGA4, PLAGL1, TAL1, PF4, ELMO1, ITPR1, RNU2, SNTB1, RAD54L, HCGIV.9, LRMP, BRDG1, ZNF22, CABC1, TEC, NR4A1, FLJ20898, FLJ21276, FLJ10038, ITGA2B, ADA, SSBP2, RRM2, STMN1, PSIP2, DSIPI, NR3C1, RAD51, SCML2, STK17B, LCP2, MCM7, NT5M, FANCG, NR4A2, SCGF, KIAA0916, PRKCB1, STK18, PRSS21, SEMA4D, KIAA0101, DLG7, FLJ10493, KOC1, PDZ-GEF1, ASB9, SCN9A, KIAA0820, FLJ23468, PTGS2, HIS1, GABPB2, KLHL3, PRKCB1, H1FX, PDZ-GEF1, TKT, AKAP7, MST4, PER1, CKAP2, GSTM5, KIAA0582, PRKCH, AMD1, AD024, CD34, SLC27A2, FOXM1, RAGD, MEF2C, LOC51334, EDG6, HMGB2, FLJ22690, CPA3, ANP32B, GNA15, PRC1, CXCL3, SAH, CENPF, PRKACB, KIAA0092, RFC5, MAP4K1, SPN, SORL1, RPS21, ALDH1A1, VRP, TFEC, KIAA0769, SERPINB1, CTSW, KNSL1, CBFA2T3, RNF2, KIAA0711, MSH5, CCNB2, PTPN7, FLJ22794, NASP, WBSCR5, RUNX3, CDC42, NR4A2, MCM6, FLJ10719, HLA-DQB1, C11orf8, BIRC5, NSBP1, PECAM1, WSX1, CCND2, E2F1, UPF3B, LOC129080, STAT5A, KIAA0471, SCARF1, KIAA0239, CASP2, PPBP, SFRS5, MCM5, SERPINB1, HSPC157, DKFZp564B0769, PFAS, C4S-2, BANK, H2BFA, HNRPA1, MPHOSPH9, SMCY, NUDT1, KIAA0841, MFNG, HEC, VWF, TUCAN, RAB33A, FLJ13949, HMMR, SRISNF2L, GNAI1, H4FG, RTP801, DACH, KIAA0918, SYK, CKS2, SLA, HNRPDL, EHD3, SPN, TNFAIP3, MDM1, DJ434O14.3, NASP, PMSCL1, PLAGL1, RPIA, FLJ13912, FLJ20005, HERC1, CDC2, DC11, ACYP1, TALDO1, MYB, TIF1, DKFZp564D0462, IL1B, ING3, AMT, FLJ20047, GGH, PLAGL1, PRKG2, DHFR, AND-1, ATP6V0A2, CDH7, RACGAP1, ITGB3BP, RPS14, TK1, POLA, FLJ20456, 6-Sep, SMC4L1, RYBP, CHAF1A, HCAP-G, EZH2, POLE2, USF2, PRO2198, BCL2, NUP98, ATP2A3, FLJ10604, AMD1, SMARCF1, IL3RA, RUNX1, FLJ12673, KIAA0084, KIAA1157, HMGA1, COX11, HDGFRP3, SS-56, POLQ, GRB10, MSH5, DDX28, RRM1, CEB1, AS3, DNMT1, TCF8, C4ST, LSM5, TRIM22, KEO4, NR2C1, KIAA0092, KIAA0332, KIAA0308, PSIP1, RNF8, NR3C1, TAF5, TTK, RBM8A, MGC12760, KIAA0056, DHFR, ZFP36L2, RASGRP2,

TABLE 7B-continued

Genes Down Regulated in Un-passaged Tumorigenic vs. HSC

HEI10, NAB1, KIAA0170, NAP1L2, KIAA0286, ABCF2, HYA22, PRKACB, LAIR1, 24432, DCK, TFDP2, MGC2217, HOXA10, KIAA1028, DKC1, C11orf2, C11orf21, SKP2, USP1, FUS2, DNAJC9, KIAA1110, GAB2, ZNEU1, M6A, DLEU1, MAC30, DUT, HNRPD, SIAH1, FLJ14280, KIAA0179, TRIP-Br2, DKFZp564B0769, TIEG, PTTG1, FANCA, ESPL1, ING1, BIN2, KIAA0721, HYAL3, CENPA, LRBA, MUTYH, CAPRI, PSMD11, FLJ11222, PDE4D, AKR1C2, BZW2, SLC27A2, ALDH5A1, BIN1, SLK, NFATC1, TFAM, MAPRE2, ABCC4, CA1, RBM15, PRSS3, PRV1, FEN1, PCNA, LOC58504, OIP5, SMC2L1, ITSN2, TOP3A, FLJ23053, TIMM8A, APOBEC3G, TRIM9, RPA1, KNSL7, C5orf6, RBM12, MAC30, UBCE7IP5, CUGBP2, ARHGDIG, NRGN, SHCBP1, CGI-30, CDT1, DGKZ, RAC2, FLJ20272, C20orf42, SLA, MPP1, KIAA0682, DKFZP547E2110, ARHH, KIAA1172, KIAA0265, SOS2, HNRPA0, GIPC2, WASF1, MGC14258, HPRT1, KIAA0443, CD164, KIAA1466, FLJ23151, FLJ10450, DKFZP586A011, BUB1B, C20orf59, TFPI, KIAA0841, DATF1, SLC18A2, MGC14258, CBFB, UBE1L, SNRK, MGC26766, RAD52, SNCA, CHES1, KHK, LRBA, CG018, MBNL, VAV1, BIN1, HIC2, FLJ23018, HSU53209, ELA2, PTGER2, KIAA0555, CYFIP2, MBNL, CLC, AMPD2, CENTB1, PEPP2, ZFP36L2, CENPF, LEPR, C5, FLJ12888, IGLL1, TLK1, AKR1C1, IAPP, TIMELESS, DNAJC6, PRO1331, TIF1, SF3B3, RES4-25, FLJ20641, TPST2, CENTB1, DUT, CD244, EP400, ZWINT, SNCA, GJA4, AVP, MRPL16, MAN2A2, HADHSC, 6-Sep, MAPK14, TAF1C, LY75, MELK, GMNN, NSMAF, BUB1, HGF, PRTN3, AK2, FLJ10335, SFRS5, ZNF215, FLJ12735, MGC5528, GABPB1, GP1BB, MYOZ3, RAB6KIFL, RFC3, OXT, SMC1L1, Nup43, PDGFC, RRP4, HTR1F, HPS4, ICAM4, STRIN, 384D8-2, ANKRD6, ING4, JJAZ1, KIAA0916, FXYD6, KIAA0981, HSPC056, FLJ11294, SPAG5, HSPC047, WFDC1, ORC6L, ZAP, GAPCENA, LMNB2, MGC2603, POLQ, SFRS7, MYOM2, FLJ10156, WEE1, DPH2L1, MIRO-1, POLG2, CHEK1, SRPR, ST7, NEK9, ITM2C, JIK, PAICS, KPNB1, CGI-32, FLJ20105, PTEN, CDC7L1, FLJ13262, ATPAF2, FGFR4, STAG2, UBE1L, FLJ14007, KIAA0308, H2AFY, KIAA0451, FLJ21478, NFE2, GTL3, KATNB1, RIN3, ICAM2, CREB1, ABCB1, MGC4701, ATF1, LOC90355, FLJ10290, FLJ23392, FNBP1, SMARCE1, CES1, KIAA0419, FLJ20035, LOC51320, PRDM2, TIMM9, RAD51, PPM1B, HELLS, CHD4, MORF, TRIP13, NTSR1, LPIN1, MAPRE2, ZNF278, HYA22, CG005, NPAT, MONDOA, LAPTM4B, RRM2, C20orf1, FLJ20010, PRKRIR, SFRS3, DKFZp547I014, MCM3, PCNT2, NAP1L1, FLJ23476, MYBPC2, PA26, C6orf32, MGC13024, OPA1, RBBP4, BIN1, CAMLG, cig5, PLA2G3, KIAA0592, FLJ20094, HNRPH3, GEMIN4, FLJ13386, TKT, DKFZP434B168, PMS1, FMR2, C21orf66, C19orf2, TFPI, DKFZP564O0523, LRMP, PPP2R2B, ZNF135, ZNF198, FBL, SCGF, CEL, LRPPRC, FLJ12903, FLJ10858, KIAA1041, KIAA0800, PCDHA10, JRKL, SUPT3H, ITPR1, POT1, C16orf5, CGI-48, FLJ22002, SFRS11, SYPL, MSH6, ZNF85, DLEU2, LIPT1, RFC4, FLJ10539, LZTFL1, BMI1, CSF1, COX11, UBE2C, LOC93349, ATP2A3, GPC5, F2R, RPL28, TGT, TCERG1, DDX34, LAMP2, CCNF, M96, CDC25C, LANPL, ADCYAP1R1, SUV39H1, FLJ14213, DKFZP434L0718, FLJ21269, PRAX-1, ANP32A, SRRM1, CDC6, FANCE, H2AV, C6orf48, TSN, FBXW3, CEP1, ZNF161, SF3B3, CDC23, SFRS11, CYLN2, IMPDH2, PIGL, H2AFJ, KL, TNFAIP3, MGC2306, Jade-1, CDKN3, FLJ10287, CSNK2A2, OPA1, TRAF5, RPP40, HTATIP2, ANP32A, WTAP, ESRRB, LOC51185, MRE11A, H4FJ, KIAA0097, WAS, HMGB3, MCM10, NBR2, RPL3L, LAPTM4B, FLJ23277, HSA250839, C19orf7, MGC19570, C6orf32, APEX1, KIAA1387, FHL3, CGI-49, TMPO, CGI-127, TBC1D5, RBMX, SF3A3, FLJ10379, HADHSC, IGHG3, LOC254531, SFPQ, FLJ10154, DKFZP434H132, KPNB1, WHSC1, SNCA, CCNB1, CYP3A7, FLJ20244, RAB6IP1, SNRPA, LOC115648, BLM, FLJ20136, SYT11, CAT, USP15, PRPS2, UBE2D2, CENTB2, SRP72, TOPBP1, SIL, MAP2K5, SPG4, RENT2, SCAP1, GP1BA, DNAJC9, TPO, ZNF261, TOP2B, PDCD1, IPW, SNX26, PTTG3, ENO2, CNR1, DDX11, CRLF3, KIAA0092, KIAA0433, NBS1, C20orf67, GP5, KIAA0101, BTBD3, GPRK6, TLK2, FLJ20856, PKD1-like, RECQL5, ARHGEF9, FLJ11210, DKFZP5641052, PLCG2, BITE, HYPH, HNRPA1, ATP11B, LIG1, KIAA1473, PTER, PPP1R16B, FLJ10597, KCND1, FLJ22474, MTMR4, SMC5, FLJ20288, MED6, ULK1, DNM2, ZFHX1B, LRP16, FLJ11184, RNF38, LOH11CR2A, NEDD4, AND-1, ITGA9, CDK2, PGDS, FLJ11896, FLJ13449, LOC93081, MRPS14, ANP32B, FLJ21272, KIAA0555, CDCA4, KIAA1966, FADS1, PRKCN, OGT, TRIP-Br2, KCNE1L, UQCRB, HIF1, SCA7, RAD51C, HDGFRP3, FLJ10565, HINT1, AKR1C1, PTBP2, TCF12, CG005, MPHOSPH9, KIAA0953, OSRF, C14orf94, PNN, NGLY1, LILRA2, CD79B, LANCL1, C20orf16, CCNE2, MTCP1, PPAT, KIAA0800, KIAA1039, MGC5149, FLJ22843, FLJ12610, MRPS31, C14orf2, RUFY2, NCOA6IP, FBXO4, PRKAR2B, TOX, HBOA, PMPCB, LOC51275, GFI1, MGC21654, TGIF2, LARS, DKFZp547P234, NR4A1, KIAA0036, PHKA2, MYST1, HSA9761, AIP1, TFAM, CDC20, CLNS1A, THY28, ZNF145, FLJ20509, FLJ10890, MAX, FLJ20312, ZNF305, C21orf45, ESPL1, ZNF292, VIP, FLJ13902, HA-1, ARTS-1, AS3, H4F1, THEA, FRAG1, DNA2L, KIAA0240, OIP2, ZNF16, GOLGIN-67, GPR44, MTHFD1, IMPA1, GNB2L1, CNGB1, SYPL, PASK, PTDSS1, FLJ11342, MRPS31, CBX8, TTF2, DYRK1A, CR2, RANBP2, FLJ20003, APOBEC3B, BCMSUNL, KIAA0725, PDE4D, PRH1, XPO1, CML2, HYA22, IDN3, KIAA0261, ZNF175, YARS, CDC6, MOAP1, GLRX, ATP2B2, PPAT, FLJ20530, ZFR, COIL, KIAA1100, PER1, PSTPIP2, TXNDC, PP2447, FLJ13197, CIAS1, JMJ, SYT11, H2AV, SPS, CUL3, FLJ23306, SNRPD1, FLJ10876, NBR2, DKFZP434F0318, SP100, NIP30, BANP, SMC2L1, GPR21, CSTF2T, HSA9761, SFPQ, EFNA2, GRB10, RPS20, KCNAB1, FLJ32069, PUM2, RPL17, FLJ20499, HGF, CCND3, CSTG, ABCC1, PIAS1, PPARBP, DC13, SPHAR, SUSP1, C14orf10, NPFF, PFKFB1, PAPOLB, H2AFY, SPRR2C, STAG3, C11orf8, D6S2654E, INVS, ANAPC1, GPHN, DKFZP564O043, TM7SF3, UBE2E1, NAP1L4, RASA1, MGC12909, DIAPH2, FAIM, UCHL1, C10orf2, NUMA1, FLJ10706, SSH3BP1, FLJ23560, ZNF137, MTMR2, ZFD25, PIGN, KIAA0252, MEIS1, SSRP1, ZNF363, NUP50, FLJ10315, UNG, COL6A1, ZNF10, ILF3, DDX28, MGC4170, TSC22, MATR3, ARHGAP11A, LAG3, LOC51231, C21orf33, KIAA0376, ZNF42, RERE, GalNac-T10, NSBP1, CLEC2, RNPS1, MAP4K1, ADSL, SYNGR1, RPL22, FLJ10716, LHX6, FLJ10546, XRCC5, SP192, JJAZ1, INPP5D, HPIP, LOC57019, DKFZp434N062, DEK, EIF4ENIF1, ZFP36L2, FLJ13920, MDS1, KIAA0404, HMGB1, ILF3, SYNGR1, SIAH1, FADS2, KIAA1074, FLJ12788, TAF7, KCNA3, CL640, KHDRBS1, FLJ12377, ED1, MTCP1, FNBP1, EPS15, BHC80, CHD1L, DKFZP434L187, FLJ20477, SCOP, KIAA0470, ME3, QKI, SALL2, SON, CSF3R, HDGFRP3, EIF2C1, P53AIP1, PCTK2, PAI-RBP1, ATRX, HTR2C, CHAF1B, NXT2, Nbak2, CDC14B, CCBL1, GTF3C3, DNMT2, SLC24A1, AND-1, FLJ13373, SET, USP4, CRSP2, NFRKB, P2RX1, SE70-2, CALCRL, DKFZP434D1335, OSBPL3, TUBA1, DKFZp434N062, DNAJC8, ALOX12, RTN3, KIAA0543, DNAJC8, AFFX-r2-Bs-phe-M_at, AXOT, PSMAL/GCP III, WHSC2, DMRT1, TIC, AF311304, NPR3, C14orf93, FLJ10483, IMPACT, TGIF2, TNS, CAPN3, ZNF292, FLJ22557, KIAA0036, CGI-79, H4FA, TFDP2, UBL3, SLC22A6, CGBP, SNRPD1, SCGF, MRPS27, ZNF335, RBBP9, STK12, MAT2A, FLJ11175, KIAA0528, MXD3, CPSF4, HINT1, PPIH, GNAO1, BRD1, KIAA0368, AP1S2, NAP1L1, ST3GALV1, ZNF287, CYP2C8, ZNF291, KIAA0582, GART, EPM2A, , , LOC51194, FLJ21269, EMCN, MGC41269, USP2, HEMGN, MGC24665, ZNFN1A1, CDCA7, SHANK3, Evi1, CDH26, FLJ20171, C4ST3, MGC21854, ST6GalII, CT2, WHIP, MGC16386, FLJ33957, BCL11A, FLJ33069, DKFZp762L0311, ZNF6, DACH, CENPH, EHZF, NIN283, FLJ39957, DKFZP566N034, PTGS1, DKFZP586D0824, KIAA1218, MMP28, NID67, CYYR1, 5'OY11.1, BIC, CDT1, FLJ14503, B3GNT5, SDPR, ITGA4, MGC16179, HOXA7, ROBO4, GNAI1, DJ79P11.1, C1QTNF4, RAD52B, KIAA1726, FLJ30046, ARHGAP9, PRDM16, FANCD2, C21orf91, UHRF1, OAZIN, FKSG14, NIN283, EPB41L5, RAB39B, TFDP2, FLJ12994, PRKACB, FLJ32009, KLHL6, FLJ10493, KIAA0748, FLJ21986, NOG, GPR27, EPC1, STIP-1, CGI-105, MGC12935, FLJ20093, HSAJ1454, EVIN2, KIAA1554, MGC20262, FLJ20354, MGC8721, EKI1, MAML3, SEPP1, TRB@, CHD2, MSI2, DKFZP434A0131, KIAA1554, MGC20262, KIAA1798, TMPO, SYTL4, EHZF, KIAA1337, HNRPD, Rgr, FLJ00026, IRF5, MGC4832, MGC34827, PRAM-1, GAB3, ING3, MGC7036, E11s1, DKFZP761M1511, PRO1635, ZNF367, MYNN, SH2D3C, FLJ11220, HHGP, MCM10, GNG2, FLJ20280, FLJ11252, RPL13, YR-29, KIAA1805, FLJ14642, FLJ12892, CGI-67, OSM, EIF3S6, DKFZp761D221, PAPOLA, MCLC, LOC159090, FLJ20280, KLF12, LOC144455, ALS2, WHSC1, STRIN, UCC1, FANCA, PTPN22, KIAA1677, FLJ23563, MDS006, HMGB1, MGC10744, TIGA1, IL17D, SNURF, LOC221002, CED-6, 1-Sep, CGI-105, LOC134147, FLJ39370, DRLM, LOC85028, P66, CASP2, SLC25A21, MGC10966, FLJ32234, DCLRE1B, CSTF3, ATPAF1, FLJ00026, C6orf33, NY-REN-58, MGC35274, DKFZp571K0837, BRD7, MGC27085, KIAA1084, DKFZp434G0920, MGC45962, MLL, CYYR1, KIAA1387, FLJ23306, AF15Q14, RAMP, CCNB1, HSPC063, FLJ11220, C6orf33, NHP2L1, DKFZp761N1114, CGGBP1, USP16, KIAA1789, DKFZp434C1714, FLJ32194, TIGD3, FLJ32549, MGC20496, LCX, ARHGAP9, STN2, MCM10, GPR114, PPIL3, MJD, UBE3B, WHSC1, LOC51234, CLLD8, C15orf15, TTC7L1, PRO2000, HEMGN, ELAVL4, KIAA1635, CLYBL, NLK, CLLD8, MDM4, MSI2,

TABLE 7B-continued

Genes Down Regulated in Un-passaged Tumorigenic vs. HSC

ASE-1, LSR7, LOC146853, TIGD7, HELLS, LOC159090, TAF9L, DKFZp762O076, FLJ32370, WDR9, HRB2, TIGD2, GAJ, LOC51193, FLJ13614, BAALC, KCNK17, DKFZp313A2432, ARRB1, DKFZp762N0610, DKFZp564B0769, MGC45866, CGI-30, FLJ23277, ROCK1, TRA@, ARRB1, CUL5, DKFZP727C091, FLJ34817, FKBP5, FLJ00058, FLJ90013, FLJ11275, KIAA1211, FLJ13215, HSA9761, EVIN2, DKFZP434C245, MGC16824, HSPC126, HSP70-4, LOC119392, FLJ35382, MMP28, ARIH2, SUV39H2, DKFZp761F0118, FLJ10997, NDUFB1, MNAB, MU, FRSB, KIAA1871, RARA, FLJ11712, MGC5306, FLJ30525, FLJ00005, LOC115330, AMBP, FLJ32942, LOC91768, PECI, KIAA1959, MGC10744, FLJ90013, 5'OY11.1, LOC116349, TSGA14, KIAA1954, HSPC129, KIAA1194, KIAA1238, KHDRBS1, SNRPE, SGKL, FLJ31818, CNOT6L, KIAA0853, MGC39650, FLJ22955, C11ORF30, CKLFSF7, CGI-30, GRCC8, AP3M1, MGC10946, CRSP6, AGS3, DKFZp564B0769, LOC81023, STAF65(gamma), ZRF1, LOC63929, HYPC, LOC90507, bioref, FLJ21438, MGC22679, HP1-BP74, Jade-1, RGM, CYCS, EG1, C20orf92, TPC2, AUTS2, FLJ21918, ZNFN1A1, MAIL, DC6, AUTL1, TAGAP, STARD4, TBRG1, FLJ20354, LSR7, RARA, FLJ14936, FLJ12975, KIAA0379, RIG-I, PPP2CA, MGC15548, HNRPC, ZNF265, TRAP25, DKFZp564D177, MGC33864, HSPC129, PPHLN1, HSPC195, FLJ32020, WWP1, AKIP, TADA2L, DKFZP564I1171, FIGNL1, GRP58, KIAA0141, LOC151648, FLJ20095, FLJ10997, KIAA1545, TIGD7, PRKRA, FLJ20060, DKFZP434G156, FLJ14775, NAV1, RPLP1, B3GNT1, C21orf45, KIAA1586, ELD/OSA1, LOC51249, KIAA1982, FLJ23309, ANAPC1, HINT1, MGC17919, TSGA14, DRLM, MCM6, KIAA1238, KPNA4, AFFX-r2-Bs-thr-3_s_at, IGHG3, YARS, FLJ20309, LU, FLJ10407, MGC14797, KIAA1554, LOC115827, NRM, DNMT3A, MGC4308, KIAA1554, MGC41917, ATE1, TUFM, ROCK1, MATR3, KIAA1311, FGD3, FLJ10876, KIAA1337, ZNFN1A4, PRO2000, SCAP2, FBXO4, CNTN1, MYH11, TRNT1, TCF7L2, CDK5RAP2, DKFZp313A2432, GTF2H3, MGC14439, MGC4730, MGC19570, EIF2S3, RNF3, MGC13204, CHES1, CNNM3, SFRS3, SMBP, TMF1, CSTF3, HBOA, CDCA1, FLJ32745, SPIN, WHSC1L1, DKFZP566I1024, FLJ14906, C20orf24, OSBPL7, NAALADASEL, HSA251708, KIAA0254, LOC144402, FLJ34231, KIAA1228, C20orf72, RANBP2, and NIP30.

TABLE 7C

Genes Up Regulated in Passaged Tumorigenic vs. HSC

FN1, FN1, RAI3, KRT19, FN1, FN1, ITGB5, S100A8, S100P, CA12, TACSTD2, AGR2, S100A2, DC12, DSP, DUSP4, FLJ20151, IGFBP3, S100A9, CXADR, CYR61, BIK, PTPRK, SERPINA3, zizimin1, CD24, SYN47, HRASLS3, LGALS3, FLJ11619, LCN2, RARRES1, GOLPH2, HRY, TFF1, EFEMP1, STHM, IFI27, SFN, MGC4309, ABCC3, DKFZp564A176, CD24, MYO6, KRT7, MUC1, IER3, CTSL2, S100A11, MET, PRO1489, C8orf4, PPL, CD24, GPRC5B, S100A8, COBL, CDS1, TACSTD1, TACC2, KRT18, IL1R2, SOX9, SPUVE, CAV2, TSSC3, C3, CYP1B1, ITGB5, CD9, KRT6A, MAPK13, ARHGAP8, CDKN2A, S100A10, SFN, RDHL, SOX9, CEACAM6, FLJ20273, MGP, CAV1, F3, TGFB1, LGALS1, MYO10, S100A14, INHBA, TM4SF1, CXCL1, TUBB, PPIC, FLJ10052, IL1RN, DPP7, FXYD3, GALNT3, KRT6A, ANXA2, ANXA2, FER1L3, ANXA9, TPD52L1, HRY, PTPN3, EFNA1, C8FW, CDH1, EPS8, CLDN4, PTPRF, CCND1, CALU, GALNAC4S-6ST, DKFZp564I1922, ASS, CAP2, FARP1, CRIP1, LOC51760, HOXA1, MIG2, ANXA2P2, TGM2, MUC16, PAPSS2, SNK, RAI14, CAV1, COL4A5, C4.4A, PTGIS, KIAA1078, SLPI, SAR1, RARRES1, DUSP4, ANXA2, FLJ10901, CD24, KRT6B, EPN3, ADAM9, EPHA2, TFAP2C, BMPR1A, PARVA, SERPINB5, ENAH, MARCKS, FAT, BF, TACC2, FLJ20171, NCKAP1, TONDU, PIGPC1, PARG1, EMS1, CTSL, LIF, EPB41L1, ISG20, ITPR3, LOC90957, CXCL5, PACE4, PHLDA1, HN1, CXCL6, VIL2, C1orf34, GNG12, ALDH1A3, TJP1, TM4SF6, ROR1, FLJ20151, LGMN, DUSP5, IRS1, GFPT1, CD24, ADM, GATA6, LAMC1, NRCAM, CRABP2, ARHE, MCP, YAP1, ADFP, CARD10, COL4A2, EDG2, PTGES, OSBPL10, IGFBP3, KCNK1, RAB20, RIL, NFIB, EFEMP1, CTSH, PDXK, SGK, DEFB1, KRT17, RAB25, HUMPPA, C12orf5, DLG5, KIAA0869, SLC1A1, PPP1R14B, KDELR3, RAB31, DDR1, TSTA3, CDH3, TFPI2, PPAP2C, SLC12A8, TM4SF1, FLJ22662, DDR1, S100A6, DD96, KIAA1078, VEGF, ARHGAP8, ELF3, RAB31, RIG, MAL, COL4A1, HBP17, LOC113146, ERBB3, RHCG, NR2F6, EMS1, MUC4, PLAB, STEAP, S100A7, NET1, FLJ11856, MGC5395, GPR48, DLAT, RIN2, NFIB, CEACAM6, CORO2A, TIMM17A, CLMN, FLJ13593, FARP1, E2IG4, IL1RL1, DSTN, CYB5R2, TIMP2, KRT8, GFPT2, POLR2J, SLC6A14, ANXA3, LAMB1, FLJ21918, MGC10796, EPB41L4B, G0S2, SDC4, CCL20, TLE1, LAMC2, NMU, SPAG4, TRIM7, RAB31, EGFR, ZNF339, MGC35048, PLAT, PITX1, ZFP36L1, GMFB, PHLDA1, BNC, SLC11A2, LAMB3, TFPI2, FLJ22408, SAT, LAMP1, POR, TGFA, MYO6, KCNMA1, TPM2, TUFT1, GPR87, BZW1, KDELR3, ANKRD3, EGFR-RS, AKR1B10, RBP1, CDKN2A, CLDN1, AKAP12, SLC7A5, SEMA3C, ERBB2, GPR64, PLXNB1, COX5B, MGC11242, FACL3, PPARD, PPAP2A, EMP2, CASK, MT1H, TMPRSS4, PDEF, KDELR2, FLJ21610, TMEM8, GSTT1, KREMEN2, ECT2, PFN2, MT1X, MT2A, HAIK1, CNN3, PTK2, IL1A, S100A13, NDRG1, MID1, TNFRSF11B, SOCS5, MATN2, ME1, SEMA3F, ARHD, PP35, ZNF144, MLPH, PDZK1, SCD, CRYAB, HSPC163, RRAD, IGSF3, PCBD, ITSN1, IL13RA1, UGCG, EDG2, ANXA8, SSSCA1, LAMA5, KIAA0436, KIAA0599, ENDOG, SLC6A8, CALD1, FLJ11183, MGC3101, UMPK, EFA6R, NQO1, PTK9, MT1L, ELF3, CST6, ST5, NETO2, KIAA0802, MYO1B, NOTCH3, PTK6, KIAA1416, MYO1C, SUCLG2, KRT17, RHBDL2, AMOTL2, COL7A1, IL20RA, CD14, CEBPD, SMARCA1, ESDN, TNFRSF6, FLJ20591, PEG10, FOXA1, KIAA1026, FLJ21870, PBEF, TOB1, AQP3, LISCH7, TGIF, MYO1B, MPZL1, DDR1, CP, IQGAP1, P4HA2, BMPR1A, NEBL, PLEK2, EPHB4, AK3, BHLHB3, IL6, TAZ, PLS3, OSR2, SH3YL1, NQO1, PPAP2A, UP, SBBI31, KDELR2, KIAA0790, FLJ10292, SLC2A1, AQP6, P2RY2, MTAP, FLJ10718, DAF, MOB, MKLN1, TM4SF6, SQSTM1, OCRL, C21orf97, NMB, FLJ23186, SDC1, RIS1, PTPRF, KLK10, SCEL, MGST3, CSTB, HOMER-3, PON2, CASK, SSH-3, DPP4, HSPB1, MGC2376, LOC92689, RARRES1, LTBP2, BNIP3, HMCS, TGM2, TNC, ITCH, MRPS12, CTSB, SUCLG2, PPIC, SLC31A1, MGC14480, KIAA0440, EGFR, AK3, SRD5A1, FBP1, FLJ13984, UBE2H, H2BFL, MGC3103, NPD009, FCGBP, CDK5, ANG, TEAD3, DPP4, PRRG1, NQO1, KIAA0429, SUCLG2, IF2, ERO1L, CLDN3, SERPINE1, SFN, FHL2, HS3ST1, PDE8A, CLDN8, BAP29, RRAS2, RPL5, PIG11, PPFIBP2, DNAJB2, RRAS2, NID2, TOPK, MRPL19, NT5E, FN1, KIAA0103, CED-6, MAP4K4, PRSS8, COL13A1, G1P2, ROR1, UGCG, BCAR3, ISG20, CYP24, LIM, LOC57228, SERPINE1, SLC7A8, TJP3, ESR1, NPAS2, CKAP4, CLDN7, UCHL3, KIAA0143, RBSK, FJX1, NOL3, SLC39A4, FLJ12910, BNIP3, PLP2, FLJ22531, FLJ22028, JAM1, LMNA, KIAA0644, CUGBP1, VNN3, LAMC1, CX3CL1, THBS1, NUP50, SLC31A2, NNMT, THBS1, AMMECR1, KMO, MAPK13, KIAA1695, RCP, GTF2IRD1, ARPC1A, MMP7, DKFZP434E2135, IF2, GLDC, PRSS11, TJP1, ATF3, PAX8, IL13RA1, ATP6V1C1, TST, SHANK2, ANK1, CRIP2, ChGn, GAS2L1, EPHB3, N33, CD59, GEM, EIF5, CENTG2, OAZ3, ASPH, SRPK2, B3GNT3, EDNRA, HSPC159, BACE2, ATP6V1C1, DP1, EHD1, DNAJB1, YKT6, KLF8, DDEF2, SRD5A1, RALA, CYP1B1, GPNMB, DKFZP564A022, FGFR3, ACP1, FLJ20366, TLR5, SCD, KIAA0882, KIAA1028, SC4MOL, MPZL1, RALGPS1A, SAR1, PTCH, SDR1, PDE4A, CELSR1, F12, FGF2, GCNT3, SNCAIP, DDR1, PBEF, MMP14, EGLN1, ELOVL1, ADCY9, FST, KIAA0716, HSPA1A, CNGA1, HNMT, KIAA0984, SIRPB2, HRH1, ITGA3, FASTK, LDLR, RGS20, MRPS17, ELMO3, AP1M2, TEGT, SH3GLB1, SMARCA1, UNC84A, GJB3, CAST, DKFZP564F0522, SLC19A2, HK2, ID1, ARNTL2, EVI5, KLK11, KIAA0703, NPAS2, MEIS2, CRIM1, GCLM, PARD3, EML1, RAD23B, AP1M2, S100A11P, YWHAZ, PON2, MTCH2, FLJ23153, TUBB-5, CDH6, SCD, KRT5, RNASEH1, LHX1, UBE2D1, TMEFF1, MGC4171, PGM3, KLC2, TNF, HSKM-B, IDH3A, KIAA0874, FLJ11773, PSMD5, HGD, PPP1R13B, TNFRSF12A, FLJ13841, MBLL39, SH3BP5, FLJ22418, CETN2, CAST, IF2, LLGL2, SPATA2, SYNGR2, SLC16A1, FBXO26, C1orf27, ITGB5, LOC113251, KIAA1029, FLJ20623, SELENBP1, PCDH1, DAG1, TMSB10, SUDD, STK17A, LAD1, SQSTM1, THBS1, ARNT2, CGI-115, TRIP13, DSTN, CTNND1, SOX13, SFTPA2, SLC2A10, CGI-141, MT1G, COL4A6, CTNNAL1, RIL, IL1RAP, SNRPD3, MAOB, G1P3, PIK3R3, FLJ21511, NAV2, CLDN3, VEGF, KIAA1609, MEF2A, SCARA3, CPD, FER1L3, KMO, NY-REN-45, JAG2, OSBPL2, YIF1P, FLJ10055, PSMD12, GRIT, LOC113251, FBXL2, PRSS16,

TABLE 7C-continued

Genes Up Regulated in Passaged Tumorigenic vs. HSC

PTPRG, FOXE1, EML1, GUK1, RHO6, TPBG, HRB, H_GS165L15.1, FLJ12571, MGC29643, SBBI26, MARCKS, PSMB3, SLC11A2, FZD2, KIAA0220, TMEPAI, MTRR, HMGE, BCL6, STK39, CELSR2, KIAA0895, ACP1, E2IG5, KDELR3, CYP-M, ANXA10, ANK3, CLIC4, KRTHB6, TSTA3, MLF1, TES, ASPH, PAPSS2, SLC20A2, RGS19IP1, NFIB, NPD009, HOXB7, FLJ10134, APOE, KIAA1219, KIAA0173, PODXL, IGFBP1, HSPCA, MAK, C11orf5, HIG2, CRIM1, FKBP2, HSPA1B, FLJ20624, CPD, ITCH, ENSA, UNC84A, KIAA0062, EPPB9, FLJ10851, STK6, PSCA, PTP4A1, DNAJC3, FLJ13782, CKTSF1B1, UAP1, KRT15, AXL, HMGCS1, GNPI, PRKCI, MGC5509, MAGED2, CD63, FLJ11856, ADAM10, KIAA0934, DXS9928E, SYNE-2, IFNGR1, SLC7A11, RIG, PP1057, LOXL2, SPOCK, PTPRF, PACSIN3, ATP11A, STK24, CAPN2, C4BPA, FLJ11149, TMP21, CYP2E1, COL4A1, PTP4A1, KIAA0937, PKP2, ARF4, KLF5, HSPA4, NPC1L1, ATP5J2, MSLN, TLE1, ARK5, SS18, SNARK, LOC56902, KIAA1630, JAG1, KIAA0843, C1S, MAP4K3, TAZ, PTHLH, RHEB2, NEDD5, HOXB7, MGC24447, EIF2AK3, UGTREL1, MIG2, ADK, GAL, FTH1, FTS, PEN-2, TNFRSF11B, CGI-148, MGC11061, LAMP1, MGC39851, CPD, MGC11061, NCOA3, CDC42BPB, C11orf24, MAP3K8, MGC3038, TRA@, IRS3L, CLTB, SC65, KIAA0471, PTS, POLR2K, CED-6, BLZF1, TRIM36, SPR, AP1S1, EVA1, LIMK1, TIMP1, KIAA0923, NDUFS8, EMP1, BFSP1, JAG1, GOCAP1, BID, RIL, CGI-90, CLTB, RIG-I, ANGPTL4, ATP11A, ITGAV, IL1RAP, SH2D1A, FLJ22693, INSIG1, FKBP10, FLJ20847, DUSP14, VDR, IFRD1, TOMM22, POLR2K, IGFBP4, HSD11B2, PTHR2, PREI3, FLJ10769, AFAP, ENC1, MFN1, CD24, H2BFT, TRIM2, HIP2, JAG2, DAF, FLJ10099, CRK, YES1, DLG5, RARRES2, LIPG, APXL, FLJ20113, CYP51, CALM1, MKI67, PLS1, VIP32, WARS, ABCA1, RASAL1, CDC42EP4, MYO1D, CRA, H2BFB, KIAA0790, BOP1, TACSTD2, KPNA2, SGSH, RPP20, LAMP2, GRSF1, CBLC, ZNF165, SCAMP1, PLOD2, GSTM3, CLTB, C2orf6, MST1R, GSPT1, CLCA2, SGCE, CHST3, CDC42EP4, NPC1, TPM4, HEBP2, WBSCR21, HMGCR, ARL7, FLJ20623, DHFR, FLJ23548, IL8, DKFZP564F013, SECTM1, RAD23B, CFLAR, POU2F3, ITPK1, IGSF4, CBX3, RHOBTB3, PDP, HSPA4, WFDC2, TRIM16, ARHD, KIAA0632, TCN1, ITGB4, KIF5B, SGPL1, RAD1, EIF2S2, CYC1, IL1R1, HARC, KIAA0779, SLC25A13, PPARG, RAB17, PLEC1, DKFZP564A2416, C20orf97, DDX26, ALDH3A2, CGI-12, BAG3, EPB41L1, GS3955, FLJ20986, C14orf92, PP35, BTF, KRT7, FLJ20457, G10, EPS8R2, LOC160313, MGC2376, KIAA0429, GOLGA2, GOSR2, COX17, FLJ21313, FLJ10300, EIF5, SKD3, ADK, NPEPL1, SLC35A3, FLJ20186, YWHAZ, UBE2A, CYB561, NR2F2, ELK1, FLJ13397, LAMP2, SGSH, FDPS, FLJ10534, PIK3R3, SPINT1, FLJ11619, FLJ20989, ATIP1, SORD, PP, HCCS, SLC1A1, FLJ20739, SLC6A8, RBBP8, GRIK3, CALU, KIAA0644, SAA2, KIAA0934, USP18, TXNL2, FLJ10521, FBXO3, SSBP1, MGC3067, CGI-100, MRPL13, PIG7, KIF3B, KIAA1735, DAAM1, ADAM17, IL5RA, TPD52L1, PPP2R3A, RAB9A, PAWR, HIPK3, PPP3CB, EPHA1, GFPT1, KIAA0431, C7orf14, BNIP1, LMCD1, ATP6V1G1, COPB2, KIAA0265, RPL5, FLJ20234, OBP2B, MIR16, CTNND1, ATP6V0E, DHCR24, FRK, MGC5178, IQGAP1, HFE, DKFZP434J214, ACTL7A, APBB2, LANO, PMM2, HMGE, ARHGEF4, NPTX1, CTSB, RPA3, NET-7, ARHGAP6, FLJ20637, FLRT3, FLJ10407, RTP801, NR6A1, NR5A2, PTPN12, ZNF217, TEB4, CALD1, HSPC111, DP1, SNAI2, STS, ANXA4, BRIX, MGC16723, MCP, FLJ22055, C1orf28, ACTN1, TMEM4, FLJ20401, SE57-1, SH3GLB1, CDYL, OAZIN, PRO1855, H41, RAB22A, FLJ10326, PEX13, SH3BP5, MIF, SOAT1, MRS2L, CDC6, PEPP3, FLJ14675, TPD52, CTBP2, SPINK1, PPP2R1B, SELT, TNFAIP1, IFRD1, SORT1, ATP1B1, QSCN6, PDK1, SNX16, VIL2, PMM1, CIB1, FLJ22195, SLC27A5, PCNP, TNFRSF10B, CDR2, FLJ21657, MTX1, SLC38A1, BC-2, PEX3, CIAO1, PLXNB2, ROD1, RPL39L, TAF1B, ZF, C12orf22, DDX26, ME1, NPEPPS, DNAJB1, SLC39A1, ATIP1, MGC2742, BBOX1, FAM3C, FBXL11, EGR1, LIN7C, UBE2G1, MCP, TMPRSS3, MARCKS, LOC56902, GRAF, ALS2CR3, KIAA0680, FZD6, SPON1, HSPC111, CCNB1, P2RX5, B4GALT4, GOLGA2, p47, KOC1, RAB2, TM4SF9, MGAT4A, HS2ST1, CD44, FLJ20315, TCFL4, PCMT1, BHLHB2, VRP, RBSK, FLJ10829, HES2, EKI1, ZRF1, C2orf6, TUBGCP2, PFTK1, BZW1, CYR61, NOL3, PTGES, CGI-100, BM039, SCRIB, DDX3, SVIL, SMC6, NET-6, KIAA1023, ATOX1, IER5, IL1R2, STX6, PKP3, PITX1, ETV2, MCCC2, MRPL33, MGC2494, BPGM, C22orf2, ACTR2, BCL10, TRAM, B7, FLJ12439, DKFZp564A176, PHKA1, SLC33A1, TGOLN2, HRC, LGALS8, FLJ22940, OBP2A, STOML2, IFNGR1, POLR2J2, DKFZP586B0923, SLC2A4RG, NDUFA8, KIAA0964, FLJ11269, TMPRSS2, PLEKHA1, UGT2B28, ARL1, PFDN2, IGLJ3, FLJ23516, KIAA1609, WSB2, KIAA1598, YES1, KIAA0284, ATP6V1D, VMP1, C22orf5, HSPA6, MUC1, MAPK9, PARD3, APG12L, RAB5C, PAK6, LSM1, INSIG1, NDUFS6, ALDH3B2, TNFSF10, CHML, UBE2V1, IGF2R, ITGB5, SEC61G, LOC55831, OPTN, ORMDL2, GABRP, DPP3, FLJ20967, POP3, GPC1, ANXA2P3, PRDX4, CHPPR, DKFZP434G2311, LGALS3BP, UEV3, KRAS2, TM4SF11, FLJ10116, CTBP2, CALU, USP3, P4HA1, SLC22A1L, FER, SLC1A7, PCDHA12, ENC1, FLJ14251, PPP2R3A, FLJ20069, DDXx, STK6, PLA2G5, ZYG, PPFIA1, AFFX-HUMGAPDH/M33197_5_at, AK1, GNA11, WWP1, HRY, SMURF1, FOP, DHCR7, GCSH, HDGF, NCBP1, ETEA, KIAA1096, GMPS, TGFBR3, HSF2BP, ZFP103, GLA, MGC4309, SYNE-1, CDKN2B, ENAH, ARHGEF7, CD2AP, ARF4, CHD1L, MGC8974, ZMPSTE24, PSMB5, ACR, GSK3B, NEDD4L, KPNA4, VIL2, CDC42EP2, UNC119, EPS8R1, KIAA0143, FLJ22709, LOC55862, YWHAE, BAZ1A, WIT-1, IL13RA1, ITGB8, OS4, LRP3, DRIL1, FASN, TXN, RASAL2, NCOA3, JUP, AUH, NEK2, GEMIN6, PSMD11, RECQL, MAP7, SNX4, TPD52, KLK8, INPP5E, KIF1C, ORC5L, CDA, C20orf35, FLJ13189, B4GALT4, CDK5R1, C1orf16, ATP6V1D, KIF5B, CTNND2, CGGBP1, SQLE, PTP4A1, CSNK2A1, LIFR, PLSCR1, SRI, CDC20, PSMB7, C20orf18, NAT1, KLK5, KPNA1, PELI1, TRIM29, YWHAZ, KLF4, FLJ21916, LTF, DAPK2, DHCR7, RNMT, RXRA, SPAG1, DDX21, CKTSF1B1, OXTR, KIAA1096, COL16A1, CELSR2, KIAA0111, TPARL, MLCB, STS, DKFZP586C1619, TPSB2, MEIS3, APBB2, HSPC121, ASK, ABCB6, RBMS2, DKFZp762N1910, CCNE1, FLJ22347, TEAD4, PPIB, NDUFS8, TMG4, BUB1, RRAS2, NOC4, SSH-3, TAX1BP1, EPN2, ISGF3G, MRPL17, AHNAK, TBL1X, EIL1, B4GALT1, SPHK1, PPIF, TINCR, DSC2, KIAA1096, SSR1, ATP9A, OSBPL1A, COX8, EIF2S1, SIP1, ACPP, FLJ20085, SMARCA4, SSTR1, UNG2, C1GALT1, PRKCL2, CABYR, FLJ10232, SLC4A7, ARHGEF5, GLUD1, MED8, MAP2K1, PPM1B, NET1, PPP2R3A, RHEB2, PME-1, FLJ20591, FLJ22595, SPS, CPSF5, MGC5466, SLC35A2, PLOD2, DKFZP434B103, APPBP2, TFIP11, FLJ10252, MRPS16, KCNK1, GOLGA5, PAIP1, CHPPR, PA200, APP, FLJ23338, FLJ13852, RHEB2, PK428, BAIAP2, LAMC2, C7orf10, LANCL2, ITGB1, HCCS, TPM1, FACL3, MRPS15, EPPB9, ITGB1, FLJ10199, CSPG6, COPS7A, KRTHA6, SGPL1, EML4, AHCYL1, TPD52, SHC1, EPLIN, TUBB1, GAS2L1, MPZL1, IDH3A, CYP4B1, CGI-96, TM9SF2, FER1L4, C10orf3, FLJ23537, LGALS8, P2RY6, ALDOA, PEX7, EBNA1BP2, DKFZP566C134, NPEPPS, PDE4DIP, GSG1, FLJ20485, MTIF2, PCTAIRE2BP, FLJ23510, LAMP1, KIAA0020, GMFB, ACTR2, HLCS, P4HB, CYCS, PSMD8, TIMM17A, MFTC, TXNL2, PNAS-4, CGI-60, PMP22, TONDU, GGPS1, FLJ20604, TAT, FLJ10803, CLN5, NRP2, RPN1, KIAA1718, CALM1, NOV, MAOA, TPS1, FLJ20555, KIAA0649, TSLL2, OSBPL11, TPM2, MRPL40, TCF-3, H2BFT, SLC4A7, SURF2, LZ16, KIAA0471, DPM1, DNAJA2, COG5, DKFZP434G2226, DC50, TCEB1, ACLY, DUSP3, ROD1, NCOA3, NFATC4, GAN, UNC84A, UCHL5, FLJ11850, RPP38, MYCBP, PDEF, DKFZP586N0721, KLK6, TPI1, PSMC2, SLC16A1, TEAD1, VEGF, NDUFS1, BS69, MAGEA3, TLE2, HSPC051, FN1, BAZ1A, FLJ22584, SEC23B, , , , NMES1, MAL2, PIGPC1, LOC55971, FLJ20171, ShrmL, LOC91523, FLJ22474, H19, RHPN2, MIG-6, KLF, KIAA1165, YAP1, MGC4309, SYNE-1, CDKN2B, ENAH, CTL2, ALS2CR9, TMEPAI, IMUP, DKFZP564J0863, UGCG, MGC12335, ITGB6, CYP4X1, GLIS2, FLJ20273, FLJ31842, LOC55971, TMEPAI, SYT13, SPUVE, KIAA1244, HSJ001348, MGC29643, BOK, TEM8, FLJ30532, LBP-32, DKFZP761L0424, FLJ23153, EDG3, IL20RA, MYO5B, GJB2, MYEOV, PTK2, KIAA2028, SBBI31, FLJ10052, AGR2, FGG, FAD104, LOC120224, CLDN1, LOC51760, IRX3, C20orf100, CLDN12, MGC4734, ERO1L, FLJ40432, MGC33630, NTN4, KIAA1522, SLC4A11, ESDN, DKFZp434C0328, PTGFRN, EHF, MFI2, PRO1489, TCEA3, GNG12, TMPRSS3, TEAD2, GJB6, ALS2CR9, DDEF1, CFL2, LOC116238, KIAA1671, SDCCAG43, MGC35048, TOB1, LRG, DKFZP761P0423, C20orf129, SMOC2, FZD4, RDHL, WNT7B, MGC14839, DJ667H12.2, TEAD1, RDHL, FLJ14957, ZIC2, HSPC163, DLG5, FLJ14735, FLJ20048, WW45, FLJ90440, LOC92689, DAG1, LOC55971, B4GALT1, HAS3, PIGR, SNX9, AK2, PRO2605, UGCGL2, CDH24, GFRA3, FLJ13593, CP, CRBPIV, FHOD2, MGC26963, LOC129642, UACA, YAP1, FLJ23420, IL28RA, PSA, DKFZP434D0215, PPP1R14C, PTGFRN, E2IG5, C14orf31, FLJ10052, BCAR1, MGC22805, DKFZp434G171, MGC11034, KIAA1870, FLJ22415, FLJ34633, GPR54, CHDH, FST, KIAA1708, UBE2H, DDEF1, WASL, FLJ14408, CXCL16, PARVA, DKFZP434H0820, CASPR3, RAB10, PDP, ANLN, FLJ25157, NETO2, OLD35, UBQLN1, LOC58489, FLJ23867, E2IG5, ATP11A, CD44, DNAH5, LOC128153, PHLDA1, IPP, DUSP16, COL12A1, MGST1, PLEKHA1, KIAA2025, LTB4DH, FLJ20739, FLJ22174, MGC24180, DKFZp761N0624, IRAK2, ALS2CR9, MGC39329, AKAP2, C14orf50, MGST1, UGCGL1, KLK7,

TABLE 7C-continued

Genes Up Regulated in Passaged Tumorigenic vs. HSC

FLJ31937, DIRC2, FLJ10035, MGC11034, SOX7, PARVA, LOC139231, GPCR1, SDCCAG28, GPR92, LOC147184, LOC113026, MGC14798, LOC147700, DKFZP434A1315, FLJ10702, LTB4DH, PYPAF3, RBMS1, SLC30A1, MTA3, ARL8, KIAA1688, RASAL2, PDK1, XPR1, SULF2., STEAP2, H41, METL, FBXO32, TLE1, DDEF1, GPT2, MRPL30, FLJ14117, DKFzp434E2321, MGC26963, SAT, ORF1-FL49, GRP58, MGC33662, NT5E, FLJ31052, RNAC, CGI-85, CTL2, STC1, SCD, DKFZP434K0427, SCARA3, MGC14128, BCCIP, MGC3195, TGFBR3, PXMP4, KIAA1500, Spir-1, ARHGEF12, DKFZP434A0225, LOC55829, C20orf24, HSPC242, CAMK2D, FAD104, ZD52F10, HS6ST2, HLCS, FLRT3, SDCCAG28, KLF15, C20orf139, FLJ39155, MGC1314, C20orf24, FLJ14511, CGI-20, EDG8, MGC10765, C7orf3, MGC14801, FLJ10697, ATP1B1, EHF, JUB, FLJ11200, MacGAP, H4FH, MGC11102, RORC, COL12A1, PRO1853, MGC13096, SPTB, FLJ32115, DKFZP566F084, SEMA4B, DKFZP434A0225, BTC, PCDHB14, CGI-09, EMS1, PCDHB16, KIAA1384, SCEL, GRP58, KIAA1357, CAC-1, SURF4, FLJ11011, LMLN, ARL6IP2, OCLN, C17orf28, INPP4B, C14orf31, FLJ22558, FLJ10116, KIAA1363, DAB2IP, MGC35352, GK001, PDGFA, SNX8, MGC22805, LOC114990, ELP2, CXADR, LOC120224, ST6Ga1NAcI, MGC35403, MGC39350, KPNB2, DSCR1L2, FLJ20333, PPP1R1B, EIF2C2, PX19, BPNT1, AD-003, LACTB, FLJ36445, ULBP2, GUK1, KIAA1321, SPP2, CRB3, FLJ90586, NDUFB9, PDK4, FLJ30973, HSPC228, MacGAP, DEFB118, DKFZp761K2222, ASPH, MGC45474, UBQLN1, TRAF4, DKFZp761K2222, DJ667H12.2, AFFX-HUMGAPDH/M33197__5_at, C12orf22, RHOBTB3, MGC33974, KPNB2, C9orf5, FLJ32421, FLJ25604, COQ4, FLJ20281, FLJ13391, TEAD2, ELL2, RPS3A, FLJ33516, ESPN, DKFZP434A0225, KIAA1684, TRA@, SEC61A1, DKFZP434K0427, PRIC285, KIAA1870, AMN, LOC151242, FLJ20686, FLJ10210, FLJ22415, MGC19764, CGI-97, CDW92, NAT5, KIAA1126, CLMN, RAB18, MRPS15, JAM1, TEAD2, ENAH, KIAA1228, ACTR3, PCDHA10, ATP5A1, GNPNAT1, CL25084, LOC51260, CNN3, TFDP1, FLJ31528, KIAA1434, FLJ10902, MGC14289, GGTL3, SYTL2, MGC21874, TIM50L, PHCA, PSCD3, KIAA1026, INADL, DNAJC5, AD037, FLJ11046, KIAA1804, KIAA1337, PPARD, KIF1B, MIR16, ROD1, SLC2A13, CFL2, GDF1, MRPL36, SLC26A9, LOC51290, CABYR, HSPC159, SPPL2A, ABCC3, BTBD6, SMURF2, STK35, CGI-85, ZAK, DKFZp434B1231, KCNK6, PCDHB2, Spir-1, KIAA0146, ZNF265, COPZ1, FLJ20421, C11orf15, DKFZp761D0614, KRT19, RAB23, MGC16491, FLJ40432, MGC10981, C20orf45, CTEN, MGC30022, NUCKS, MGC13251, MRPL27, FLJ90586, MGC16028, FLJ90165, SHMT1, FLJ14525, BACE2, ABLIM2, FLJ20719, SCGB3A1, MGC2477, FLJ20038, MGC29643, FLJ30829, C20orf155, PGK1, FLJ37440, RBM8A, FBXO22, KIAA1219, KIAA1200, KIF3B, MGC19825, AK5, C22orf20, FLJ10378, INADL, HSPCA, EIF5A2, RAB18, BCL2L13, MBC3205, UBE2H, FLJ20354, SLC5A7, FLJ30532, C14orf47, TMPIT, EHD4, FLJ13089, MGC17299, IDS, CED-6, MGC27277, LOC137392, FXYD6, MGC22825, CPM, SNX9, MGC19764, TLR7, FENS-1, SDCBP2, NUDT5, MGC11102, SEC24A, CGI-141, NKD2, EFG1, ANAPC11, MYO5B, MGC14833, LOC85865, EPB41L4B, FLJ21415, KCNC4, GSBS, TEAD2, LOC115548, MAGI-3, C9orf5, CLONE24922, MRPS15, RGNEF, CORTBP2, FLJ20354, HSPC121, NOC4, KIAA1673, MGC14595, MGC2560, MGC2408, MRPL14, APOA1BP, FLJ14681, MGC13102, KIAA1437, KIAA1126, MGC13034, CSEN, SH120, VIP, PRO2000, SLC31A1, AD003, CALM2, HT002, RAP2A, EML4, WDR5, MPP5, LOC90990, MGC2560, FLJ14431, ARHGEF5, HCC8, TCEB2, FLJ13187, FLJ90575, FLJ10525, FLJ23393, HOXB9, LOC84661, dJ55C23.6, HFE, MGC13040, WDR20, MRPL4, FLJ25604, DKFZP566C134, LOC55871, CGI-09, MRPS23, MRPL47, MGC13045, ERK8, KIAA1500, HPS3, CRYPTIC, SBBI31, MGC14353, CGI-20, FHOD2, PPP1R14A, REPS1, MAPKAP1, V-1, FBXO25, BNIP-S, MGC13114, EKN1, GPR24, RCP, FLJ12806, MGC2747, OBP2A, HM13, C21orf97, FLJ14909, C9orf10, STYX, THOC3, RDGBB, PFKFB4, FLJ21924, KIAA1295, ZDHHC9, STXBP5, RPE, UBE2H, PCDHB18, FLJ20303, NPD007, N4WBP5, FLJ20333, FLJ12747, SURF4, C20orf45, FLJ12787, LOC90507, FLJ10839, EPB41L4B, FLJ37953, BAP29, MRPL50, MGC10999, C9orf5, TBDN100, STK35, FRABIN, JUB, PRO2714, MLLT4, MGC40214, CPNE4, FLJ22233, MIZIP, MGC14859, MRPS24, HPS3, FLJ23841, FLJ23577, HSPCA, MRPS10, FLJ14251, SSR3, MGC13186, KIAA1453, HN1, HOOK3, ATP1B3, MRPL50, MAP4K1, LOC90120, D1S155E, DKFZP564O0463, FLJ23816, CFTR, MGC40555, MGC20781, FLJ20085, NOPE, FLJ14825, MSP, LMO7, C7orf2, MRPL32, FLJ10074, MAK3P, KRT6IRS, DKFZp547A023, SAMHD1, HSPC043, FLJ10597, FACL6, LGR6, SORCS2, MGC4840, RAB35, MGC10911, and MLL3.

TABLE 7D

Genes Down Regulated in Passaged Tumorigenic vs. HSC

MEF2C, HSPC053, HOXA9, PRG1, RetSDR2, GMFG, AIF1, AIF1, HLA-DPB1, PLCL2, ICAM2, HLA-DPA1, PTPRC, SPINK2, SPARC, CUGBP2, PTGER4, CECR1, CDW52, CCND2, LYZ, SELL, CD69, HOXA9, ITM2A, HLA-DQB1, ITM2B, LYL1, KIAA0125, LMO2, ARHGEF6, KIAA0084, MPL, RGS2, LAGY, QKI, EVI2B, ZNFN1A1, DOCK2, HLA-DRB3, NAP1L3, HLA-DPA1, KIT, HF1, HLF, LST1, ANGPT1, CD53, LST1, FLJ14054, SELPLG, LST1, BM046, TUBA3, HLA-DQA1, BCE-1, CDW52, FLJ10178, PRKACB, PRKCB1, IQGAP2, CHES1, GUCY1B3, PSCDBP, HLA-DRA, LAPTM5, PRG1, MEF2C, SLC2A5, LST1, FHL1, MAP4K1, TNFSF4, PLAC8, HLA-DQB1, IGFBP7, PCDH9, MAP4K1, EVI2A, SATB1, MLC1, SSBP2, FLI1, CLIC2, CLECSF2, LY75, NDN, HLA-DRB1, FLJ21276, DLK1, GLUL, NUDT11, BEX1, SH3BGRL, PRKCB1, MPHOSPH9, LST1, HLA-DQB1, FLJ22690, UQCRH, FLJ22746, HLA-DRB3, SLC2A3, NPIP, BCL11A, MPO, RUNX3, ERG, SV2, HLF, MMRN, CYFIP2, HLA-DRB4, PECAM1, CORO1A, MOX2, SEPP1, BAALC, 6-Sep, ITM2B, LCP2, PELI2, C17, IGHM, LRMP, PPP1R16B, HLA-DRB5, HBB, DJ971N18.2, LOC51186, SCGF, ERG, LAPTM5, P311, SAMSN1, ITGA4, DJ434O14.3, IGFBP7, TFEC, HA-1, MAGED1, PLCB1, SOCS2, CG018, PDE4B, MHC2TA, PADI5, USF2, CUGBP2, VIM, HLA-DRB6, TFPI, BIRC1, PTGS1, HFL2, SCDGF-B, LSP1, NRLN1, MPO, KIAA1939, PTGS1, MS4A3, HPIP, FLJ20220, HLA-DPA1, NCF4, MAPRE2, ZFP, BANK, TOX, CXCR4, IGHM, RUNX3, HCLS1, LOC81558, ARHGDIB, TRO, SCHIP1, CRHBP, KIAA1750, BCL2, FLJ20950, FLJ10097, DAB2, BASP1, JAM2, FLJ21616, HHEX, ITM2C, SPRY1, SERPING1, SLA, EBI2, ZNF42, DSIPI, FLJ10038, PECAM1, 6-Sep, CASP1, RB1, TACC3, 13CDNA73, 6-Sep, MAPRE2, FCER1A, BTK, LOH11CR2A, LRMP, PLAGL1, MICAL, TCF4, CLGN, H1FX, WASPIP, LAIR1, ZNF175, INSR, FLJ20456, C11orf8, KIAA0443, AKAP7, TAL1, HLA-DRA, HRB2, PLEK, RAGD, PLAGL1, ALDH1A1, B4GALT6, GLIPR1, GAB2, KIAA1157, PPM1F, WAS, SETBP1, MUF1, C6orf32, MYOZ3, TUCAN, RNU2, KLHL3, TSC, PKIA, MLLT3, NEFH, DKFZp564B0769, PPM1F, SNTB1, PCDH9, CRYGD, MPP1, ABCB1, KIAA1110, ALEX3, ATP2A3, KIAA0308, MAGEH1, BIMLEC, CTSW, SORL1, FLJ20898, MCM5, COL4, D244, PPP1R16B, MAGED1, ASC, GIPC2, RASSF2, LOC81691, SCGF, PTEN, 24432, STAT5A, 6-Sep, SLC24A1, UBE1L, CD83, TAHCCP1, GNA15, NR3C2, KIAA0053, INPP5D, CPA3, GYPC, SYK, PRKACB, RUNX1, RIN3, TRB@, NPIP, CABC1, HLA-B, PGDS, CD34, SPN, LOC58504, MAGEL2, TBXAS1, MFNG, LOC91316, TRAP-1, RECK, TCEA2, FLJ20136, ARHGAP6, AMT, CAT, ADARB1, PTEN, LCP1, CCL3, SCN9A, RASGRP2, DKFZP586I2223, SS-56, SLA, C4S-2, PDGFC, LILRA2, RAGD, HNRPDL, ZNF288, ITGA2B, LOC81691, HBD, SELP, C6orf32, PDZ-GEF1, CPT1A, KLF2, ZNF198, TACC1, HBB, B1, CIAS1, HNRPA0, HLA-DQA1, KIAA0308, MYO1F, PRO1331, RAB33A, TNS, NAP1L2, CERK, MGC4170, ADA, RNASE3, NFE2, ANKRD6, AKR1C3, CDC42, HIS1, TRIM22, BIN1, ICAM4, IL12RB2, CSF2RB, EPB41L3, BRDG1, TNRC5, CIRBP, RPLP2, AMPD2, SFRS7, EDG6, BRCA1, MSN, HLA-DQB1, C5orf5, GSTM5, ITPR1, IL16, AIF1, NFATC1, LILRB2, FGF23, STAC, RPL22, PTEN, LRBA, PFAS, CGI-116, DKFZP586A0522, MGC13024, GALC, ABCG1, MGC45806, ELF1, SAP18, ALDH5A1, ELA2, GATM, CHC1L, KIAA0918, LOC51334, FOSB, PRO2198, TEC, SLC1A4,

TABLE 7D-continued

Genes Down Regulated in Passaged Tumorigenic vs. HSC

CAD, KIAA1028, VAV1, LOC57100, C11orf21, SLC1A4, TRPV2, EPB41L2, FBN1, CD48, GIT2, CSF3R, DNAJC6, BIN1, KIAA0582, ARL4, SH3BGRL, GLS, FXYD6, PF4, SCGF, NEK9, PKD2, MATK, BIN1, NSBP1, MSH5, PRKG2, NT5M, PML, CD37, SF3A2, PLSCR4, CSK, HA-1, NUDT1, SIAH1, MEIS1, IGLJ3, HLX1, SV2B, DKFZP586I2223, KEO4, ENPP2, CTSF, IL1B, PSMB10, IL1B, ZFP36L2, SFPQ, FLJ11175, ATP2A3, STK10, FLJ22021, MYOM2, PTENP1, MGC861, HERC1, Jade-1, BTEB1, KIAA1102, NPTX2, UCHL1, LYN, COL5A1, ZNF215, MGC2217, SRISNF2L, LOH11CR2A, RERE, COL5A1, RAP1B, CLDN15, VWF, HHEX, SMARCA2, SMCY, UBCE7IP4, LOC115207, KPNB1, ZNF22, STOM, C16orf5, ICAM2, KIAA1102, CENTB1, DKFZP434C171, ITGAM, TFPI, CASP1, CLN2, TAL1, AASS, SAH, FLJ11712, FXYD5, KIAA0303, FBXL5, SFRS5, FNBP1, FLJ11749, MAGE-E1, SNRK, SPN, CTSS, SIAT1, SCARF1, HSPC047, CD38, VAMP5, SF3B3, FLJ10374, FHL1, PTPRCAP, LRBA, DUSP6, PTPRC, KIAA0092, PLA2G4A, RBM5, FLJ21478, PLCB2, GOLGIN-67, RBM8A, OXCT, HEM1, DUSP6, CRI1, RAB6IP1, IMPDH2, C21orf33, LOC93349, EMP3, NASP, MGC40204, PTGER2, COL5A1, SPARC, NISCH, SIGLEC5, CSTF2T, HGF, SNX10, DACH, NINJ2, MGC12760, KIAA1332, NPIP, KIAA0379, LYN, H2AFY, PACAP, PLCG2, PDE4D, LOC129080, FLJ11753, KIAA0447, BCL2A1, FUS2, PTPN7, WASF1, ZNF42, C18orf1, UROD, KIAA0303, NRGN, RNASE2, FLJ23056, FYN, DEFCAP, PTPN22, MAPKAPK3, ZFP36L2, AF1Q, NCF4, CDH7, DJ971N18.2, PA26, ANXA6, PHGDH, MCL1, LEPROTL1, HUMMHCW1A, TNFRSF14, STK17B, CGI-49, MGC14258, PSIP2, CRI1, FLJ35827, CCRL2, PTPRN2, CES1, SCA1, FLJ21865, KIAA0798, BIA2, HLA-DQB1, UCP2, DPYSL2, FLJ11259, FLJ20312, KIAA0240, GTL3, C6orf48, AK2, TFR2, FLJ13949, MAX, CHKL, FLJ12668, ALDH2, NUCB2, HPIP, RNF8, C1orf21, AS3, ZNEU1, FLJ11323, FLJ23506, LOC115648, KCND1, STMN1, BTN3A3, MAP4K1, ALG12, ATP5G2, PET112L, TIAF1, KIAA1043, TRPC1, THY28, SYT11, HSU79274, PRPF8, CLC, PCNT2, H2AFY, DAPK1, CCL4, RPL28, IFRG28, CCND3, C14orf94, MGC3035, 6-Sep, GNB5, KIAA0916, EIF3S7, LENG4, FACL5, AP1S2, MCM5, DKFZp434N062, AIP1, PROS1, CIRBP, REC8, SLK, C11orf2, dJ222E13.1, H2AV, NEK1, BNIP2, FLJ13197, ITGA4, FLJ21269, KIAA0708, IMPA1, FLJ12750, SLC18A2, EMR1, KIAA0239, RPS9, ARHH, MCJ, ALTE, KCNE1L, ABCB1, RPL22, KIAA0841, LOC58486, SNX26, ADAMTS1, USP4, STXBP1, ITGA2B, C5orf6, RBM10, FLJ21439, KHK, OS4, MAPK14, NIP30, KIAA0471, SLC16A7, RIN3, DDX28, HPIP, RNASE6, ADSL, ARHG, GNG7, HLA-C, RHOBTB1, CACNB2, DATF1, PDZ-GEF1, RPL13, TALDO1, DGKG, FLJ22794, PTPN6, SYT11, C5, FLJ22349, FGFR4, CGBP, PROL2, LARS, RPL3, JIK, MGC45806, MGC2488, MGC2752, TYMS, PECAM1, NSMAF, ABCC1, LEPR, MYB, LAIR1, LOC57209, EP400, ALCAM, ZNF187, FLJ13386, KPNB1, LTA4H, HGF, PPI628, NRIP1, GNAO1, IL3RA, CD79B, CENTB1, ZNF261, ST18, FGF9, CDK10, RAI17, STARD5, OXT, PML, KATNB1, ASMTL, NEDD4, ACTA2, MBNL, FLJ31821, PER1, MOAP1, DCK, DXS1283E, SNCA, AD7C-NTP, MYBPC2, STX8, ATPAF2, ACYP1, RAD51L1, CLIPR-59, FACL4, AASS, RAC2, MGC2306, SLC27A2, FLJ23018, RGS1, NAP1L1, ELAC2, LOC51185, SGKL, PCDH16, TRAF5, KIAA0682, DGKZ, FLJ10539, PIGN, FLJ10647, NCOA1, LBR, GFI1, MAN2A2, KRTAP2-4, HLA-C, FLJ35827, PCDHA10, HLA-A, APLP2, SFRS5, FLJ13262, WTAP, EFNA2, C12orf8, CCND2, PTPRC, MPPE1, HMGA2, CLK2, SWAP70, PRO1843, FLJ14280, FLJ23277, KIAA1172, PRCP, MADD, SMARCA2, WASF2, MGC5149, CDC42, PLEK, SMARCF1, RCD-8, ATP9B, IHPK2, IGHG3, DHRS4, EEF2, QARS, KIAA0841, ADRA2A, RPL29, GCNT1, UBL3, GRB10, IMP-2, ABCA5, HSPC157, TNFRSF5, H2AV, JM4, TBXA2R, SLC1A4, RPS6KA5, IGLL1, MGC8721, PEPP2, USP7, PSMB8, ARHGDIG, HLA-A, RBM10, NAP1L1, KIAA1393, AVP, KIAA1018, RPL28, RES4-22, NAP1L1, ST13, KIAA0186, MBNL, HEXA, KIAA0555, FLJ20189, MN1, TSPYL, USF2, APLP2, ZNF135, HPS1, RPS21, MAP2K5, HSD17B8, PROSC, NAP1L1, DUT, KIAA0170, TPK1, NY-REN-34, RBIG1, IL16, AKR7A2, STK10, PRP17, WWP2, PTD015, CAPRI, ARHGAP8, FLJ20856, APPBP2, LRRN1, MDM1, HLA-DMB, CGI-30, COX11, DDX28, ACK1, TM7SF3, FLJ23554, SDCCAG8, FLJ20094, MMP28, MUTYH, CA1, AKR7A2, WDR6, DYRK1A, DPH2L1, RBPMS, FLJ20005, MAP2K5, C4ST, FLJ22059, FLJ20202, H2BFQ, CAMLG, CHAF1A, ABLIM1, MAPK11, RAP140, DUT, ITSN2, EHHADH, DKFZP547E2110, H2AFJ, MGC4659, RPL13, KCNA3, BC008967, CASP1, NMI, NBEA, NUMA1, DEF6, PRAX-1, TBC1D5, KIAA0332, NEW1CP, KIAA0769, CENTB2, CKIP-1, EIF4A2, OAZ, ARH, KIAA0467, C19orf7, KCNAB2, TTLL1, FLJ10597, SF3A2, FLJ11222, PSTPIP2, BCL11A, SPHAR, GLIPR1, KIAA0555, MMP2, EIF4A1, STOM, ALOX12, FLJ11588, RBAF600, PROSC, CUB, VIL, FLJ12707, M6A, TCIRG1, HTR1F, RICH1, F13A1, CACNA2D3, RRP4, TAF7, ZNF134, HSU53209, LZTFL1, TKT, LILRA2, ZNF302, FLJ13114, ZNF177, PURA, DKFZp547I014, TXN2, TLR3, BHC80, MGC5139, PTPNS1, ZNF145, THTPA, BTBD3, MDS010, KIAA0924, ZNF292, ITGB2, TJP4, GPRK6, CYLN2, ENPP4, ALB, RPS20, FOXO1A, ADH5, CTSS, FLJ23221, C11orf8, TNFSF13, TOLLIP, KIAA1449, HINT1, GLTSCR2, KIAA1052, FLJ10260, RAB3GAP, HINT1, TAPBP, CHD5, LOC57406, TP53TG1, SRP46, MS4A4A, NUP62, PIM1, ZNF42, COG4, ADPRTL1, ZNF289, CATSPER2, TXNIP, PDE4DIP, HSA250839, FUT4, HSPA1L, GALT, MGC4278, APEX1, FN5, STRIN, USP11, SPP1, NPFF, CEP1, GAPCENA, HLA-E, SCAND2, CG005, VRP, BRAP, GPR56, MLH1, GPR105, OGT, C1R, BTN3A1, FLJ14107, PACS1, MGC26766, FLJ22378, APOBEC3C, CG005, CA11, QDPR, DUT, ALDH6A1, FLJ10450, BST1, NGLY1, FLJ12057, FECH, ZNF137, SERPINB1, EZH1, CASP1, MGC3265, CXorf7, TRG@, DKFZp564B0769, KIAA0616, D1S155E, MN7, C18orf1, NSBP1, NXF1, FHL1, TOP3A, TARBP1, KIAA0766, RRAS, SEMA4D, CEBPA, TIP120A, IL15, HADHSC, HIRIP3, CTBP1, DVL2, RBM12, RAD54L, NYD-SP15, PHC1, KIAA1042, IGL@, NPR3, HRMT1L1, FLJ20551, MYST1, LOC51231, TCF12, KIAA0543, MKPX, LOC51157, SYNGR1, AKR1A1, SCOP, LRRN1, FY, AMY1A, PHEMX, KIAA0930, MAP3K3, FLJ10631, ZNF85, APOL3, MAPK12, TRG@, POLD1, LDOC1, POLA, TPST2, WASF3, RPL11, MKL1, FLJ22242, PTPRM, AMHR2, FLJ20288, TERF2, DOK4, KCNAB1, DISC1, FLJ22494, LOC91316, VIP, POLR2A, RGS19, C12orf6, RPS9, LIG1, NASP, ARHGEF9, MANBA, SARM, SRPR, CDH9, MRPL16, FLJ20509, SNRPN, HLA-E, NTS, ZNF232, FLJ12903, PHKA2, MSH5, PURA, ATP9B, TRIM28, FLJ12768, ME2, IDS, MPHOSPH9, DIA1, ADAM8, HADHSC, STX12, COX15, RPA2, SHANK1, GGA1, LANCL1, UBE3A, SOX11, LAT, BCL7A, DKFZp434K1210, BRAP, SMARCC2, DKFZP434H132, NHP2L1, FLJ11294, FLJ12270, KIAA1649, SRP46, PSMB9, GGA1, MGC4368, TOP2B, PTK2B, FLJ13912, EZH1, THRA, BAX, NAG, MERTK, HADHA, SRRM2, HNRPH3, GNG7, HSPC018, FLJ22573, HPCAL4, MBC2, MAPK4, FLJ10716, ITGAL, NFRKB, MRP63, DKFZP434L187, GABARAP, CHD4, DKFZP564D172, FGL2, LOC57019, KIAA0478, NTSR1, LPIN1, USP4, KIAA0391, ASGR1, KIAA0174, TBXA2R, TRAP95, FLJ22649, NEK3, ZNF271, SIL1, 76P, CYLD, CD164, TINF2, ZNF220, DAB2, HRIHFB2206, SF3A3, TRO, FLJ13373, UBE4B, GC20, ADAM28, PHKB, BCAS3, MGC14258, RAD52, HLA-F, KIAA0721, MRC1, CHD1L, LMOD1, FLJ10315, CHRNA7, NAP1L1, BIP5PA, GADD45A, RPL35A, LPIN1, TFPI, FLJ14213, KIAA0746, KIAA0981, C22orf4, PP1044, ABCF2, FLJ10379, RASSF1, FLJ23392, RPS8, DAB2, FLJ14011, CDC2L2, GAD1, MGC17330, FLJ23342, HEI10, NPDC1, KIAA0710, BIRC1, KIAA0349, SF3B3, MST4, IRAK3, CD81, LOC57406, FLJ12610, SF1, SLC27A2, KIAA0804, KIAA1055, GTF2F1, SEPX1, SCAMP2, PPP3CB, U5-200KD, HMGN2, F2, PCBP3, FLJ20721, ING4, HADHSC, KIAA0286, TREX1, ATP11B, RUFY2, SUPT3H, SFRS11, PIAS1, HBOA, HAS1, HYMAI, NUP210, TGT, FLJ11896, CIDEB, TRHDE, FLJ90524, TOX, KIAA0261, GSTM2, GAS7, MBD1, KIAA1305, PPP2R2B, CDT1, FLJ11164, TMPRSS2, TYROBP, G6PT1, PRIM1, GP5, DKFZP566H073, RPS14, CCNG1, FANCG, CMAH, SORBS1, KIAA0800, C1QTNF3, UBCE7IP5, FXR1, ZNF334, CNN2, RFC5, ACAA2, GNB1, FLJ22757, CDKN1C, UROD, KIAA1028, HD, CTSG, CLNS1A, P2RX1, TACC1, ADH5, RPL13A, ZNF363, PRKCH, AF020591, LOC51659, PER1, TFPI, TSN, BMI1, KIAA0625, MLLT2, TAF1C, DHFR, SLC23A1, HAGE, NAP1L4, EGFL3, SCA2, FLJ20489, SNAP25, USF2, CRYL1, GG2-1, EDN3, TRPC1, AP1S2, ERCC1, KIAA0582, RPL15, LOC54103, FLJ22557, CGI-127, CSNK2A2, ZNF278, EDG5, IPW, RASGRP2, SAE1, KIAA0725, RTN2, CTNS, FLJ20274, FLJ10276, LTBP4, FLJ10539, HYAL3, MTL5, MGEA6, BNIP3L, PARVB, MGC15523, KCNK7, IGHM, PASK, KIDINS220, PCM1, KIAA0092, ASB9, MAP3K4, CD1B, COL6A1, HCA127, ZNF262, GG2-1, CAPN3, SAP18, EIF3S5, ZNF337, EIF4A1, DBT, CROT, FLJ10474, FLJ10483, CBX8, TABLE 7D-continued Genes Down Regulated in Passaged Tumorigenic vs. HSC DKFZP586M1523, CCRL1AP, FLJ14153, KIAA0397, COL2A1, CD164, TLE4, PRO2730, ATM, RFX5, KIAA0515, FLJ20542, HYPH, ERG-1, DBH, SCML2, GNAO1, WDR13, GCA, FLJ23323, FLJ11362, CGBP, MGAT1, HMGB2, NDUFA6, KIAA0515, KIF13A, OPA1, BRD1, ATP2B4, PSME1, KIAA0931, HPS4, KIAA1966, DKFZP564J0123, DBY, HUMNPIIY20, MAT2A, DFFB, FLJ20294, ADSL, CSTF2T, , ZNFN1A1, LOC51194, FLJ21269, DJ79P11.1, BCAT1, MGC21854, DKFZP586D0824, EMCN, C21orf91, SDPR, PRO1635, ITGA4, FLJ20171, ROBO4, ZNF6, DRLM, TAGAP, PRDM16, ST6GalII, GNAI1, EHZF, MGC10966, ARHGAP9, HEMGN, GNG2, LOC83690, PTGS1, MGC41924, USP2, FLJ33069, CT2, C4ST3, PRAM-1, FLJ32122, SLC11A3, BIC, TNFSF13B, FLJ37080, FLJ35564, KIAA1913, CDH26, BCL11A, FLJ30046, MGC7036, DKFZP566N034, RARA, C1orf21, PAG, SH2D3C, FLJ00026, STIP-1, FLJ39957, KLHL6, VIK, FLJ34922, SHANK3, FLJ00026, PTPN22, HRB2, ZDHHC2, DKFZP566K1924, SYTL4, DACH, FLJ21986, EVIN2, GAB3, CYYR1, MMP28, EHZF, FLJ00058, LOC93589, KLF12, CLLD8, KIAA1218, MGC16179, HS3ST3B1, ARHGAP9, LOC144402, LOC114928, FLJ39370, PRKACB, MGC13105, Ells1, CGI-145, EPB41L5, RAB39B, LOC145553, HRB2, SDCCAG33, ARRB1, EEF1A1, MGC12992, BBX, DAP10, CMG2, GPR27, GBP5, FLJ20202, UCC1, RAD52B, KIAA1554, AKNA, TBXAS1, a1/3GTP, JAK3, B2M, MGC20496, CLLD8, ALEX3, FLJ21438, MJD, FLJ22570, AP1S2, TFDP2, P5CR2, C1orf21, KIAA1554, Evil, MGC8721, FACL5, CYSLTR1, CTSS, Rgr, NID67, FLJ32194, MGC45400, KIAA1789, DCP1B, MGC4251, CPXM, SMBP, PARVG, ESRRBL1, C6orf33, MGC20262, C6orf33, MGC27027, LOC51234, ZNF33A, RGS18, KIAA1607, TIGA1, HOXA7, NAALADASEL, ATP8B2, CLYBL, DKFZP727G051, KIAA1214, WHIP, IRF5, UBL5, KIAA1946, GLTSCR2, CMG2, OSM, KIAA0748, FLJ11113, FLJ12994, ERO1-L(BETA), NUCB2, KIAA1337, DEF6, POLH, FLJ11712, LOC91526, TTYH2, ACRBP, MAML3, FLJ00012, C6orf37, MYH11, C9orf24, HNRPD, CCNDBP1, DKFZP434L0117, GPR114, ANKH, MGC13170, NOG, CXorf10, C1QTNF4, NAV1, RPIB9, DKFZp571K0837, SFXN1, KIAA1497, PHACS, PAPOLA, ELAC1, MDS006, FLJ14167, LOC136895, CGGBP1, MGC45962, CGI-85, AUTS2, FXYD5, FLJ32009, FGD3, HSAJ1454, GRP58, KIAA1954, ELD/OSA1, PRex1, MGC11324, FLJ90013, NIN283, HCA127, DKFZP564D1378, HMGB1, TRB@, MGC4796, ASE-1, YR-29, FLJ25476, CGI-67, STK33, SLC25A21, ZNFN1A1, DRLM, PP2135, STMN3, CAMK2G, MGC16169, DC6, GCNT1, PRO1635, STRIN, DLC1, DKFZp761D221, FLJ10656, ZNFN1A4, SENP7, MGC34827, MGC15619, FLJ32942, RPL28, FLJ00005, FLJ23462, DKFZp762L0311, FLJ30726, MGC3200, ARRB1, EIF3S7, HSA9761, FLJ11896, MGC10744, KIAA1309, WDR9, KIAA1587, MIR, FLJ12953, MGC12921, LOC130617, NAV1, HPSE, FLJ20085, KIAA1982, KCNK17, KIAA1495, LOC64744, AUTL1, LOC91689, SEPP1, PPP2CA, KHDRBS1, DREV1, MGC35274, SNRPE, LOC91689, KIAA0853, FLJ13215, TACC1, MGC20262, MGC17515, MGC40157, DKFZP572C163, PRPF8, HINT1, FUSIP1, MEF2D, C20orf24, TADA2L, NIN283, FS, HSPC063, ALS2, NHP2L1, LGALS12, MGC10986, KIAA1871, DKFZP434A0131, KIAA1949, DTNBP1, GPHN, SUV39H2, BRD7, FLJ32001, HYPC, EEF2K, ESRRB, ZNF226, IL18BP, CSRP2BP, HEMGN, FOXP1, SGKL, FLJ11220, TRIM4, FLJ21918, KIAA1545, MGC2474, CDCA7, HSPC002, LOC115294, LOC119710, GTF3A, TAGAP, TCF7L2, FLJ22690, OAZIN, TRAP1, MGC42174, MGC9850, KIAA1632, HSU53209, BIVM, BAALC, WHSC1, C16orf5, KIAA1238, MRS2L, CGI-105, ZDHHC2, LOC143903, DKFZp762N0610, NSE1, OSBPL7, HAVCR2, ASAHL, KIAA1798, TLR4, MGC10946, PRex1, FLJ31340, TAHCCP1, C20orf141, FLJ20313, TAF9L, FRSB, PRKRA, P66, KIAA0141, RARA, BANP, FLJ00007, DTNBP1, LRP5, KIAA1337, MGC29667, WHSC1, MMP28, EVIN2, Cab45, CED-6, PTER, ZNFN2A1, NDP52, CHES1, KIAA1635, NFAT5, FLJ32332, HTRA3, MAP4K1, KIAA1337, AP1S2, FLJ23306, HP1-BP74, KIAA1218, BTBD4, DKFZp761F0118, MGC16703, BAZ2B, MU, FLJ13614, MYO15B, OAZIN, LOC92799, CANX, SUFU, KIAA1954, AGS3, LAPTM4A, HP1-BP74, FLJ23467, FLJ12892, MGC40042, KIAA1143, RPL11, LSR7, CENPJ, NY-REN-58, NRM, FLJ23563, WASF2, AMBP, NIP30, EIF2AK4, MGC15429, TTC7L1, NICN1, FXC1, FLJ20793, SOC, RPL13, HYPC, CLONE24945, MGC24663, TEM7R, FLJ14768, DKFZp667M2411, STARD9, FOXP1, ELP3, KIAA1337, CDA017, PPP6C, PAK1, FLJ10876, EPC1, ZNF397, C21orf63, KIAA1805, MIR, CYYR1, DKFZp564B0769, EPSTI1, MDM4, MGC23947, MGC14421, SDCCAG33, DKFZp762O076, LOC93109, STN2, HSMPP8, FLJ20265, LOC85028, MGC15435, 1-Sep, MGC41917, MSI2, Jade-1, IL17D, MGC2752, MATR3, PRKRA, DKFZp434C1714, MGC4415, DKFZP727C091, MY038, FLJ35453, FLJ30794, DJ462O23.2, FLJ90130, FLJ22283, EEF2, LOC155066, ATPAF1, FLJ23499, STAM2, LOC85028, FLJ21709, LOC51279, TRA@, JAM3, SIAT6, KIAA1453, EIF2S3, LSR7, ROCK1, DKFZP566I1024, FANCD2, MEF-2, MGC2664, MGC15548, ZNF75A, HSPC126, EIF3S5, RBM7, FLJ20280, GSTA4, SEPP1, TIGD3, DKFZP434A1319, MCLC, MGC14136, DKFZP762N2316, LOC115330, D4ST-1, UCP4, PRMT6, LAK, NIN, FLJ10997, RAB4B, LMO4, RRN3, CENPH, FLJ23277, GBTS1, FLJ90013, LOC115509, PP2135, FLJ36175, SPINO, PAIP2, DKFZp761G0122, ATF7IP, WBP1, MGC29937, MGC9564, CASP2, TIGD7, C4S-2, MGC25181, LOC89887, KIAA1387, FLJ22283, GIT2, MIR, SSBP3, LOC159090, U5-200KD, FLJ10997, ZNF295, PGBD1, HEL308, POLH, AP3M1, NORE1, SEMA6D, PPID, CUL5, LOC91663, FLJ13171, BAT4, RPLP1, KIAA1630, CT2, HSPC182, HMGB1, FLJ20280, FKBP5, EIF3S6, C15orf15, TRPC7, FLJ31153, TA-KRP, MGC17919, AP2A1, C20orf132, SECP43, PPIL2, FLJ14494, YARS, MGC10974, CLN6, C20orf81, U2AF1, KIAA1238, FLJ23861, LOC144455, DKFZp564D177, NIP30, TBC1D1, ZNF265, and PPP4R2.

TABLE 8

Some Solid Tumor Stem Cell Cancer Markers

Bmi-1, eed, easyh1, easyh2, rnf2, yy1, smarcA3, smarckA5, smarcD3, smarcE1, mllt3, frizzled 2, frizzled 6, frizzled 7, mf2, Frizzled 1, Frizzled2, Frizzled4, Frizzled10, Frizzled6, FZD1, FZD2, FZD3, FZD4, FZD6, FZD7, FZD8, FZD9, FZD10, WNT2, WNT2B, WNT3, WNT5A, WNT10B, WNT16, AXIN1, BCL9, MYC, (TCF4),, SLC7A8, IL1RAP, TEM8, TMPRSS4, MUC16, GPRC5B, SLC6A14, SLC4A11, PPAP2C, CAV1, CAV2, PTPN3, EPHA1, SLC1A1, CX3CL1, ADORA2A, MPZL1, FLJ10052, C4.4A, EDG3, RARRES1, TMEPAI, PTS, CEACAM6,, NID2, STEAP, ABCA3, CRIM1, IL1R1, OPN3, DAF, MUC1, MCP, CPD, NMA, ADAM9, GJA1, CD14, SLC19A2, ABCA1, PCDH7, ADCY9, SLC39A1, NPC1, ENPP1, N33, GPNMB, LY6E, CELSR1, LRP3, C20orf52, TMEPAI, FLVCR, PCDHA10, GPR54, TGFBR3, SEMA4B, and PCDHB2.

TABLE 9

The Alpha-catenin and E-cadherin Cancer Stem Cell Gene Signatures

| Cancer stem cell gene signatures | Low to undetectable expression | Elevated expression |
|---|---|---|
| CTNNA1 Signature 1 | CTNNA1, LNX, ARMCX3, D2S448, TUSC1, GLUL, RB1, BEX2, SLC12A2, GALC, NGFRAP1, FGF13, KIAA1102, SLC1A4, DNAJD1 | CAV1, CAV2, IGFBP3, S100A2, CXCL5, MET, FOXQ1, CDKN2A, MFHAS1, IL27RA, KLRF1, PKCA, UPP1, SLC7A5, ARNTL2, PRSS1 /// PRSS2 /// PRSS3, PRSS3, VNN1, RAB38, ZBED2, MYEOV, MAL, IMP-3, DHRS9 |
| CTNNA1 Signature 2 | CTNNA1, NCSTN, LNX, ARMCX3, D2S448, TUSC1, GLUL, RB1, BEX2, SLC12A2, GALC, NGFRAP1, FGF13, KIAA1102, SLC1A4, DNAJD1 | EDG2, CAV1, CAV2, DCBLD2, IGFBP3, S100A2, CXCL5, MET, FOXQ1, CDKN2A, MFHAS1, IL27RA, KLRF1, PKCA, UPP1, CTSL2, SLC7A5, ARNTL2, PRSS1///PRSS2///PRSS3, PRSS3, VNN1, RAB38, ZBED2, MYEOV, MAL, IMP-3, DHRS9 |
| CTNNA1 Signature 3 | CTNNA1, NCSTN, LNX, ARMCX3, D2S448, GLUL, RB1 | EDG2, CAV1, CAV2, DCBLD2, IGFBP3, S100A2, CXCL5, MET, FOXQ1, CDKN2A, MFHAS1, CTSL2 |
| CTNNA1 Profile 4 (295 array) | CTNNA1, NCSTN, TUSC1, GLUL, FGF13, SLC12A2, GALC, SLC1A4, DNAJD1, RB1, ARMCX3, NGFRAP1, KIAA1102 | EDG2, CAV1, CAV2, DCBLD2, CDKN2A, FOXQ1, IGFBP3, S100A2, MFHAS1, IL27RA, CTSL2, MET, PKCA, UPP1, ARNTL2, PRSS3, VNN1, RAB38, MAL, ZBED2, MYEOV, IMP-3, KLRF1, SLC7A5, DHRS9 |
| CTNNA1 Profile 5 (286 array) | CTNNA1, NCSTN, D2S448, GLUL, FGF13, GALC, SLC1A4, DNAJD1, RB1, ARMCX3, NGFRAP1, KIAA1102 | EDG2, CAV1, CAV2, CDKN2A, IGFBP3, S100A2, MFHAS1, IL27RA, CTSL2, MET, PKCA, UPP1, PRSS1///PRSS2///PRSS3, PRSS3, VNN1, RAB38, MAL, ZBED2, IMP-3, KLRF1, SLC7A5, CXCL5, DHRS9 |
| CDH1 Signature 1 | CDH1, MMP7, Nov, FOSL1, IL1R2, SFRP1, KRT6B, G0S2, IL8, B3GNT5, FGFBP1 | FLJ20152, ARNT, CYFIP2, C17orf27, TAP1, RNASEL, LOC57168 |
| CDH1 Signature 2 | CDH1, MMP7, Nov, FOSL1, IL1R2, SFRP1, KRT6B, G0S2, IL8, B3GNT5, FGFBP1 | SHC1, FLJ20152, ARNT, CYFIP2, C17orf27, TAP1, RNASEL, LOC57168 |
| CDH1 Signature 3 | CDH1, MMP7, Nov, FOSL1, IL1R2 | SHC1, FLJ20152 |
| CDH1 Profile 4 (295 array) | CDH1, MMP7, Nov, FOSL1, IL1R2, SFRP1, KRT6B, IL8, B3GNT5, FGFBP1 | SHC1, FLJ20152, ARNT, CYFIP2, C17orf27, TAP1, RNASEL, LOC57168 |
| CDH1 Profile 5 (286 array) | CDH1, MMP7, Nov, FOSL1, IL1R2, SFRP1, KRT6B, G0S2, IL8, FGFBP1 | SHC1, FLJ20152, CYFIP2, TAP1 |

Table 9 shows alpha-catenin and E-cadherin cancer stem cell gene signatures as distinct, yet both reveal the loss, as compared to normal human breast epithelium, of essential components of cell-cell contacts known as adherens junctions. Cancer stem cells that possess signature 1 gene expression display undetectable or low levels of alpha-catenin (CTNNA1) expression, and cancer stem cells that possess signature 2 gene expression display undetectable or low levels of e-cadherin (CDH1) expression. E-cadherin is a cell-surface receptor involved in homophilic cell-cell adhesion and epithelial polarity. E-cadherin interacts directly with beta-catenin, which in addition to its function at cell junctions, is an essential component of the Wnt signaling pathway. Beta-catenin in turn interacts with alpha-catenin, and alpha-catenin binds to polymerized actin to anchor cell junctions to the cell cytoskeleton (Bienz, 2004, Cur. Biol. 15:R64; Kobielak & Fuchs, 2004, Nat. Rev. Mol. Cell Biol. 5:614). Reduced levels of either alpha-catenin or e-cadherin protein can disrupt cell-cell adhesion, and genetic deletions of alpha-catenin in mice reveals epithelial polarity defects and epidermal hyperplasia that are accompanied by epithelial invaginations resembling precancerous lesions. Both mutations and decreased expression levels of alpha-catenin and e-cadherin characterize many different human cancers, including tumors of the breast and colon. Reduced expression of e-cadherin or alpha-catenin often correlates with metastasis. Furthermore, levels of e-cadherin influence signaling by beta-catenin, and loss of e-cadherin expression might allow for sustained activation of Wnt signaling, which itself is well-known to be involved in certain human cancers as described herein (Kobielak & Fuchs, 2004, Nat. Rev. Mol. Cell Biol. 5:614; Hazan et al., 2004, Annals NY Acad. Science 1014:155-163; Mohammad, 2005, J. Pathol. 205:130-144).

The Alpha-catenin Cancer Stem Cell Gene Signature.

In addition to the undetectable or low levels of alpha-catenin expression in cancer stem cells the present invention further identifies the increased and decreased expression as compared to normal breast epithelium of a diverse group of genes that have various physiological functions and that are implicated to varying degrees in the development, maintenance, and/or progression of human cancers. In some embodiments of the present invention the undetectable or low levels of alpha-catenin expression is accompanied by undetectable or low level expression of one or more of a distinct set of genes comprising: nicastrin (NCSTN); ligand of numb-protein X (LNX); armadillo repeat containing, X-linked 3 (ARMCX3); melanoma associated gene (D2S448); tumor suppressor candidate 1 (TUSC1); glutamine synthase (GLUL); retinoblastoma 1 (RB1), brain expressed X-linked 2 (BEX2); solute carrier family 12, member 2 (SLC12A2); galactosylceramidase (GALC); nerve growth factor receptor associated protein 1 (NGFRAP1); fibroblast growth factor 13 (FGF13); KIAA1102; solute carrier family 1, member 4 (SLC1A4); and DnaJ homolog, subfamily D, member 1 (DNAJD1) and elevated expression of one or more of a distinct set of genes comprising: endothelial differentiation, lysophosphatidic acid G-protein coupled receptor 2 (EDG2); caveolin 1 (CAV1); caveolin 2 (CAV2); discoidin, CUB and LCCL domain containing 2 (DCBLD2); insulin-like growth factor binding protein 3 (IGFBP3); S100A2; CXCL5; c-Met (MET); forkhead box Q1 (FOXQ1); cyclin-dependent kinase inhibitor 2A (CDKN2A); malignant fibrous histiocytoma amplified sequence 1 (MFHAS1); interleukin 27 receptor, alpha (IL27RA); killer cell lectin-like receptor subfamily F, member 1 (KLRF1); protein kinase C, alpha (PKCA); uridine phosphorylase 1 (UPP1); cathepsin L2 (CTSL2); solute carrier family 7, member 5 (SLC7A5); aryl hydrocarbon receptor nuclear translocator-like 2 (ARNTL2); protease, serine, 1, 2, and 3 (PRSS1, PRSS2, PRSS3); vanin 1 (VNN1); RAB38; zinc finger, BED domain containing 2 (ZBED2); myeloma overexpressed gene (MYEOV); MAL; IGF-II mRNA-binding protein 3 (IMP-3); and dehydrogenase/reductase SDR family, member 9 (DHRS9). In another embodiment the undetectable or low levels of alpha-catenin expression further comprises undetectable or low level expression of one or more of the genes: NCSTN; LNX; ARMCX3; D2S448; TUSC1; GLUL; RB1; BEX2; SLC12A2; GALC; NGFRAP1; FGF13; KIAA1102; SLC1A4; and DNAJD1. In another embodiment the undetectable or low levels of alpha-catenin is accompanied by the elevated expression of one or more of the genes: EDG2; CAV1; CAV2; DCBLD2; IGFBP3; S100A2; CXCL5; MET; FOXQ1; CDKN2A; MFHAS1; IL27RA; KLRF1; PKCA; UPP1; CTSL2; SLC7A5; ARNTL2; PRSS1; PRSS2; PRSS3; VNN1; RAB38; ZBED2; MYEOV; MAL; IMP-3; and DHRS9. In further embodiments of the present invention signature 1 cancer stem cells display undetectable or low level expression of one or more of the genes: alpha-catenin; NCSTN; LNX; ARMCX3; D2S448; TUSC1; GLUL; RB1; BEX2; SLC12A2; GALC; NGFRAP1; FGF13; KIAA1102; SLC1A4; and DNAJD1 and increased expression of one or more of the genes: EDG2; CAV1; CAV2; DCBLD2; IGFBP3; S100A2; CXCL5; MET; FOXQ1; CDKN2A; MFHAS1; IL27RA; KLRF1; PKCA; UPP1; CTSL2; SLC7A5; ARNTL2; PRSS1; PRSS2; PRSS3; VNN1; RAB38; ZBED2; MYEOV; MAL; IMP-3; and DHRS9. Alternatively, signature 1 cancer stem cells comprises: 1) undetectable or low level expression of two or more of the genes: alpha-catenin; NCSTN; LNX; ARMCX3; D2S448; TUSC1; GLUL; RB1; BEX2; SLC12A2; GALC; NGFRAP1; FGF13; KIAA1102; SLC1A4; and DNAJD1 or 2) elevated expression of two or more of the genes: EDG2; CAV1; CAV2; DCBLD2; IGFBP3; S100A2; CXCL5; MET; FOXQ1; CDKN2A; MFHAS1; IL27RA; KLRF1; PKCA; UPP1; CTSL2; SLC7A5; ARNTL2; PRSS1; PRSS2; PRSS3; VNN1; RAB38; ZBED2; MYEOV; MAL; IMP-3; and DHRS9.

In some embodiments of the present invention the undetectable or low levels of alpha-catenin expression is accompanied by undetectable or low level expression of one or more of a distinct set of genes comprising: nicastrin (NCSTN); ligand of numb-protein X (LNX); armadillo repeat containing, X-linked 3 (ARMCX3); melanoma associated gene (D2S448); glutamine synthase (GLUL); and retinoblastoma 1 (RB1), and elevated expression of one or more of a distinct set of genes comprising: endothelial differentiation, lysophosphatidic acid G-protein coupled receptor 2 (EDG2); caveolin 1 (CAV1); caveolin 2 (CAV2); discoidin, CUB and LCCL domain containing 2 (DCBLD2); insulin-like growth factor binding protein 3 (IGFBP3); S100A2; CXCL5; c-Met (MET); forkhead box Q1 (FOXQ1); cyclin-dependent kinase inhibitor 2A (CDKN2A); cathepsin L2 (CTSL2); and malignant fibrous histiocytoma amplified sequence 1 (MFHAS1). In another some embodiment the undetectable or low levels of alpha-catenin expression is accompanied by undetectable or low level expression of one or more of the genes: NCSTN; LNX; ARMCX3; D2S448; GLUL; and RB1. In another some embodiment the undetectable or low levels of alpha-catenin is accompanied by the elevated expression of one or more of the genes: EDG2; CAV1; CAV2; DCBLD2; IGFBP3; S100A2; CXCL5; MET; FOXQ1; CDKN2A; CTSL2; and MFHAS1. In further some embodiments of the present invention signature 1 cancer stem cells display undetectable or low level expression of one or more of the genes: alpha-catenin; NCSTN; LNX; ARMCX3; D2S448; GLUL; and RB1 and increased expression of one or more of the genes: EDG2; CAV1; CAV2; DCBLD2; IGFBP3; S100A2; CXCL5; MET; FOXQ1; CDKN2A; CTSL2; and MFHAS1. Alternatively, signature 1 cancer stem cells display: 1) undetectable or low level expression of two or more of the genes: alpha-catenin; NCSTN; LNX; ARMCX3; D2S448; GLUL; and RB1 or 2) elevated expression of one or more of the genes: EDG2; CAV1; CAV2; DCBLD2; IGFBP3; S100A2; CXCL5; MET; FOXQ1; CDKN2A; CTSL2; and MFHAS1.

Signature 1 cancer stem cell gene expression can encompass decreased expression of Nicastrin (NCSTN). Nicastrin is an essential component of the multimeric gamma-secretase complex that includes presenilins as its catalytic subunit. Intramembrane proteolysis by gamma-secretase is required for the normal processing of many receptor-like proteins including: Notch, where it leads to intracellular signaling during tissue development and renewal; beta-amyloid precursor protein (APP), where it contributes to the generation of amyloid beta peptides that accumulate in Alzheimer's disease; and E-cadherin, where both interactions with and cleavage by the gamma-secretase complex regulate the stability of adherens junctions. Nicastrin is involved in stabilizing presenilin and is thus required for gamma-secretase activity (Baki et al., 2001, PNAS 98:2381; Marambaud et al., EMBO J. 21:1948; Yan et al., 2004, J. Neurosci. 24:2942. However, Nicastrin can also play an inhibitory role as fibroblasts from heterozygous nicastrin mice unexpectedly display increased gamma-secretase activity compared to the complete absence of activity in the knock out mice (Li et al., 2003, J. Biol. Chem. 278:33445). Thus decreased expression of Nicastrin can first increase gamma-secretase activity, increasing proliferative signaling via Notch and decreasing cellular adhesion via cleavage of E-cadherin, suggesting that further decreases in expression of nicastrin or gamma-secretase inhibitors can slow tumor growth and inhibit metastasis.

Signature 1 cancer stem cell gene expression can also include decreased expression of Ligand of numb-protein X (LNX). LNX is a RING finger-type E3 ubiquitin ligase that targets the cell fate determinant Numb for ubiquitylation and proteasomal degradation. During cell division Numb controls cell fate by its asymmetric localization to a single daughter cell and subsequent regulation of Notch signaling. Decreased degradation of Numb is proposed to disrupt this asymmetric localization (Nie et al., 2002, EMBO J. 21:93; Nie et al., 2004, J. Biol. Chem. 279:20807). Thus the decreased expression of LNX in cancer stem cells can contribute to the self-renewal of tumorigenic stem cells over the generation of non-tumorigenic daughter cells.

Signature 1 cancer stem cell gene expression further comprises decreased expression of ARMCX3, a member of the armadillo repeat (arm) family of proteins implicated in embryogenesis, tissue maintenance, and cancer. Expression of arm family members is significantly reduced in various human carcinomas suggesting a role in suppressing tumors of epithelial origin (Kurochkin et al., 2001, Biochem. Biophys. Res. Commun. 280:340).

Signature 1 cancer stem cell gene expression further comprises decreased expression of Melanoma associated gene (MG50). MG50 is a melanoma antigen which encodes epitopes recognized by human cytolytic T lymphocytes and is a possible IL-1 receptor antagonist (Mitchell et al., 2000, Cancer Res. 60:6448).

Signature 1 cancer stem cell gene expression further comprises decreased expression of Glutamine synthase (GLUL). GLUL catalyzes the ATP-dependent conversion of glutamate and ammonia to glutamine, an abundant amino acid essential for cellular growth. Although highly expressed in a subset of cells, such as astrocytes and pericentrally located hepatocytes, involved in controlling levels of potentially toxic glutamate and ammonia, the majority of cells express low levels of GLUL for the production of glutamine. GLUL is over-expressed in liver tumors with beta-catenin mutations, suggesting regulation by the Wnt signaling pathway. GLUL is, however, considered a dispensable enzyme for tumors though its induction and could help provide glutamine for quickly proliferating tumor cells and enhance tumor growth rates (Medina et al., 2001, Am. Soc. Nut. 131:2539 S; Leoppen et al., 2002, Cancer Res. 62:5685).

Signature 1 cancer stem cell gene expression also comprises decreased expression of Retinoblastoma 1 (RB1), a well-characterized tumor suppressor that is mutated in inherited retinoblastoma and functionally inactivated in a large number of cancers. RB1 acts as a critical transcriptional regulator of cell cycle progression and differentiation, and its loss can contribute to uncontrolled cancer stem cell proliferation (Yamasaki & Pagano, 2004, Curr. Opin. Cell Biol. 16:623).

The alpha-catenin gene expression signature further comprises the decreased expression of brain expressed X-linked 2 (BEX2); solute carrier family 12, member 2 (SLC12A2); galactosylceramidase (GALC); nerve growth factor receptor associated protein 1 (NGFRAP1); fibroblast growth factor 13 (FGF13); KIAA1102; solute carrier family 1, member 4 (SLC1A4); DnaJ homolog, subfamily D, member 1 (DNAJD1) and tumor suppressor candidate 1 (TUSC1). BEX2 (also designated as p75NTR-associated cell death executor 5; NADE5) and NGFRAP1 (also designated as NADE and BEX3) are adaptor proteins for p75 neurotrophin receptor signaling and promote the induction of apoptosis (Mukai et al., 2000, J. Biol. Chem. 275:17566-70; Mukai et al., 2003, Vitam. Horm. 66:385-402; Roux & Barker, 2002, Prog. Neurobiol. 67:203-33). SLC12A2 is an ubiquitously expressed sodium-potassium-chloride co-transporter with an important role in epithelial salt secretion, cell volume regulation, and neuronal membrane potential (Hebert et al., 2004, Pflugers Arch. 447:580-93) and is one of several genes whose loss-of-function causes antenatal and classic Bartter syndrome (Hebert, 2003, Curr. Opin. Nephrol. Hypertens. 12:527-32). GALC encodes a beta-galactocerebrosidase that catalyzes the lysosomal hydrolysis of specific galactolipids including galatosylceramide, one of the major glycosphingolipids of myelin. GALC is defective in Krabbe disease (globoid-cell leukodystrophy; GLD) in which 90% of patients are infants with fatal cerebral demyelination (Rafi et al., 1995, Hum. Mol. Genet. 4:1285-9; Boggs et al., 2004, Glycoconj. J. 21:97-110). FGF13 is a member of the fibroblast growth factor family implicated in a diverse array of cellular processes including proliferation, apoptosis, cell survival, chemotaxis, cell adhesion, differentiation, and migration (Bottcher & Niehrs, 2005, Endocr. Rev. 26:63-77; Greene et al., 1998, Eur. J. Neurosci. 10:1911-25). KIAA1102 a hypothetical human protein at LOC22998. SLC1A4 is a ubiquitous neutral amino acid transporter (Zerangue & Kavanaugh, 1996, J. Biol. Chem. 271:27991-4). And lastly, DNAJD1 is a heat shock protein 40 homolog molecular chaperone. DNAJD1 expression is lost in many primary ovarian tumors, conferring of them resistance to chemotherapeutic agents (Shridhar et al., 2001, Cancer Res. 61:4258-65).

Signature 1 cancer stem cell gene expression comprises increased expression of Endothelial differentiation gene 2 (EDG2). EDG2 belongs to a family of G-protein coupled receptors with high affinity for lysophosphatidic acid (LPA), a bioactive phospholipid that stimulates cell proliferation over differentiation, morphological changes, and tumor cell invasion. LPA promotes growth of ovarian tumors and is found at high concentrations in patients with ovarian carcinomas, suggestive of an important role in ovarian cancers. Elevated levels of LPA have also been detected in patients with endometrial and cervical cancers (Mills and Moolenaar, 2003, Nat. Rev. Cancer 3:582). Increased expression of EDG2 in a population of cancer stem cells can implicate responsiveness to LPA more broadly in initiating tumorigenesis. However, increased expression level of EDG2 is associated with decreased cell growth rates via LPA-independent induction of apoptosis (Fang et al., 2000, Annals NY Acad. Science 188) suggesting that antagonizing LPA-dependent signaling but enhancing LPA-independent apoptosis must be balanced to counter tumor cell growth.

Signature 1 cancer stem cell gene expression further comprises increased expression of both caveolin-1 (CAV1) and caveolin-2 (CAV2). The caveolins are integral membrane proteins that serve both structural and regulatory roles at plasmalemmal invaginations called caveolae. Caveolae have been implicated in a range of cellular functions including vesicular transport, cholesterol homeostasis, and compartmentalization of signal transduction. Caveolin-1 has tumor suppressor properties and is mutated or lost in some breast cancers. Conversely caveolin-1 is up-regulated in gastrointestinal and prostate cancers and is associated with metastasis in the latter. The recent identification of a secreted form of caveolin with the ability to stimulate cell viability and clonal growth can help explain these contradictory results (Cohn et al., 2004, Physiol. Rev. 84:1341; Williams & Lisanti, 2005, Am. J. Physiol Cell Physiol. 288:C494-0506.) Thus targeting extracellular forms of caveolin can inhibit proliferation of cancer stem cells with increased expression of these proteins.

Signature 1 cancer stem cell gene expression additionally comprises increased expression of Discoidin, CUB and LCCL domain containing 2 (DCBLD2), a type-I transmembrane protein structurally similar to the neurophilins, cell surface receptors for VEGF and semaphorins. Increased expression of DCBLD2 is found in lung cancer cells upon acquisition of a metastatic phenotype and in lung cancers that have a high frequency of metastatic lesions (Kobuke et al., 2001, J. Biol. Chem. 276:34105; Koshikawa et al., 2002, 21:2822-8). Thus increased expression of DCBLD2 in type 1 tumor stem cells can indicate an increased metastatic potential.

Signature 1 cancer stem cell gene expression further comprises increased expression of Insulin-like growth factor binding protein 3 (IGFBP3). IGFBP3 is the main binding partner for insulin-like growth factor (IGF)-I, which regulates cell proliferation and survival. IGFBP-3 both directly counteracts the mitogenic effects of IGF and mediates growth inhibition and apoptosis by other growth factors and hormones. And in vitro IGFBP-3 alone can stimulate cell proliferation through its interactions with the EGF receptor and mitogen-activated protein kinase (MAPK) signaling. High levels of circulating IGFBP-3 are associated with an increased risk of premenopausal breast cancer, however, to date most evidence points to IGFBP-3 playing a protective role against various cancers (Schedlich & Graham, 2002, 59:12-22; Ali et al., 2003, Horm. Metab. Res. 35:726-33; Renehan et al., 2004, 363:1346; Vestey et al., 2005, Breast Cancer Res. 7:R119).

Signature 1 cancer stem cell gene expression also comprises increased expression of S100A2. The S100 family of Ca2+ binding proteins is implicated in various cellular functions including Ca2+ homeostasis and cell growth. Furthermore, the expression of many S100 proteins is altered in human cancers. Expression of S100A2 is increased in several cancers including non-small cell lung carcinoma (NSCLC), where it is often associated with DeltaNp63 and can be linked to metastatic potential. The role and importance of the S100 proteins in cancer, however, is not yet clear (Diederichs et al., 2004, Cancer Res. 64:6654-9; Emberley et al., 2004, Biochem. Cell Biol. 82:508-15; Smith et al., 2004, Br. J. Cancer 91:1515-24).

Signature 1 cancer stem cell gene expression further comprises increased expression of CXCL5, a lipopolysaccharide-inducible chemokine that recruits neutrophils of the immune system and is pro-angiogenic. Over-expression of CXCL5 has been linked to the growth of human adrenocortical carcinomas and can contribute to the self-renewal of hematopoietic stem cells (Keane et al., 2001, Am. J. Respir. Crit. Care Med. 164:2239; Schteingart et al., 2001, J. Clin. Endocrinol. Metab. 86:3968; Choong et al., 2004, Cytokine 25:239-45; Pold et al., 2004, Cancer Res. 64:1853). Thus increased expression of CXCL5 by cancer stem cells can contribute to stem cell self-renewal and/or help maintain tumors via angiogenesis.

Signature 1 cancer stem cell gene expression comprises increased expression of c-Met, a receptor tyrosine kinase activated by the secreted hepatocyte growth factor/scatter factor (HGF/SF). c-Met controls cell proliferation, dissociation, and migration during embryogenesis and aberrant activation of these processes in human cancer contributes to tumor growth and metastasis. Met activation phosphorylates beta-catenin, a modification that promotes loss of beta-catenin association with alpha-catenin at cell junctions decreasing cellular adhesion and making beta-catenin available for Wnt mediated signaling (Tokunou et al., 2001, Am. J. Pathol. 158:1451; Birchmeier et al., 2003, Nat. Rev. Mol. Cell Biol. 4:915; Biez, 2004, Curr. Biol. 15:R64; Boccaccio et al., 2005, Nature 434:396; and Ma et al., 2005, Cancer Res. 65:1479).

Signature 1 cancer stem cell gene expression additionally comprises increased expression of forkhead box Q1 (FOXQ1). The forkhead family is a diverse group of winged helix transcription factors involved in numerous aspects of development, and their deregulation contributes to human cancer. FOXQ1 is required for proper differentiation of epidermal hair shafts in mice and is overexpressed in colorectal adenocarcinoma and lung carcinoma cell lines as well as pancreatic cancers. The role overexpression of FOXQ1 plays in carcinogenesis is as yet unclear (Bieller et al., 2001, DNA Cell Biol. 20:555-61; Hong et al., 2001, Genesis 29:163-71; Cao et al., 2004, Cancer Biol. Ther. 3:1081-9).

Signature 1 cancer stem cell gene expression also comprises increased expression of cyclin-dependent kinase inhibitor 2A (p16INK4). p16INK4 is an inhibitor of activated cyclin-Cdk complexes that control the $G_1$ checkpoint of the mammalian cell cycle, and has been identified as a potent inhibitor of cdk4-mediated phosphorylation of the tumor suppressor protein retinoblastoma (Rb). p16INK4 is a tumor suppressor that is inactivated in a number of human cancers (Okamoto et al., 1994, PNAS 91:11045; Kim et al., 2005, Int. J. Oncol. 26:1217-26).

Signature 1 cancer stem cell gene expression further comprises increased expression of Malignant fibrous histiocytoma amplified sequence 1 (MRHAS1). MRHAS1 is located on chromosome 8p23.1, a region that is amplified in some solid tumors and that is translocated in hematological malignancies and head and neck squamous carcinomas. MRHAS1 itself is translocated in a B-cell lymphoma cell line, and both wild-type and chimeric MRHAS1 possess tumorigenic properties in a nude mouse model (Tagawa et al., 2005, Oncogene 23:2576-81).

Signature 1 cancer stem cell gene expression further comprises increased expression of cathepsin L2 (CTSL2). CTSL2 is a thymus and testis-specific lysosomal cyteine proteinase member of the peptidase C1 family and is misexpressed in colorectal, breast, ovarian, and renal carcinomas (Santamaria et al., 1998, Cancer Res. 58:1624-30).

The alpha-catenin gene expression signature further comprises the elevated expression of interleukin 27 receptor, alpha (IL27RA); killer cell lectin-like receptor subfamily F, member 1 (KLRF1); protein kinase C, alpha (PKCA); uridine phosphorylase 1 (UPP1); solute carrier family 7, member 5 (SLC7A5); aryl hydrocarbon receptor nuclear translocator-like 2 (ARNTL2); protease, serine, 1, 2, and 3 (PRSS1, PRSS2, PRSS3); vanin 1 (VNN1); RAB38; zinc finger, BED domain containing 2 (ZBED2); myeloma overexpressed gene (MYEOV); MAL; IGF-II mRNA-binding protein 3 (IMP-3); and dehydrogenase/reductase SDR family, member 9 (DHRS9). IL27RA is a class I cytokine receptor involved in regulating adaptive immunity and critical to the generation of a Th1 response (Chen et al., 2000, Nature 407:916-20; Robinson & O'Garra, Immunity 16:755-8). KLRF1 is a type II transmembrane glycoproteins with a single extracellular C-type lectin-like domain. KLRF1 is expressed by natural killer (NK) cells and other hematopoietic cells that bind MHC class I molecules to distinguish tumor or virus-infected cells from normal host cells (Roda-Navarro et al., 2001, Biochim. Biophys. Acta. 1520:141-6; Natarajan et al., 2002, Annu. Rev. Immunol. 20:853-5). PKCA is a member of a family of serine- and threonine-specific protein kinases activated by calcium and diacylglycerol that phosphoylate a wide range of protein targets involved in numerous cellular signaling pathways. Several PKC isoforms are upregulated in human cancers (Shen, 2003, Curr. Drug Targets Cardiovasc. Haematol. Disord. 3:301-7; Lahn et al., 2004, Oncol. 67:1-10). Uridine phosphorlyase (UPP1) is a critical enzyme in the pyrimidine salvage pathway catalyzing the reversible phosphorolysis of uridine to uracil. UPP1 is overexpressed in several tumor cell lines and in primary tumors associated with metastases (Watanabe & Uchida, 1995, Biochem. Biophys. Res. Commun 2:265-72; Miyashita et al., 2002, Cancer 94:2959-66; Sahin et al., 2005, Pancreas 30:158-67). SLC7A5 is a cationic amino acid transporter (Closs et al., 1993, J. Biol. Chem. 268:7538-44). ARNTL2 is a member of the basic helix-loop-helix PER-ARNT-SIM family of transcription factors that control diverse physiological processes including circadian rhythms and cell proliferation (Schoenhard et al., 2002, Am. J. Physiol. Cell Physiol. 283:C103-14; Yeh et al., 2003, Oncogene 22:5306-14). PRSS1, PRSS2, and PRSS3 are serine proteases secreted by the pancreas of which PRSS1 is mutated in 80% of patients with symptomatic hereditary pancreatitis (Szmola et al., 2003, J. Biol. Chem. 278:48580-9; Howes et al., 2005, Clin. Lab Med. 25:39-59). VNN1 is an epithelial ectoenzyme member of the vanin family of proteins and plays a role in the glutathione-dependent response to oxidative-stress (Martin et al., 2001, Immunogenet. 53:296-306; Berruyer et al., 2004, Mol. Cell. Biol. 24:7214-24). RAB38 is a small GTP binding protein member of the RAS oncogene family that regulates intracellular vesicle trafficking. A point mutation in the GTP binding domain of RAB38 in melanocytes produces the oculocutaneous albinism of chocolate mice (Loftus et al., 2002, PNAS 99:4471-6; Osanai et al., 2005, Biol. Chem 286:143-53). ZBED2 is a zinc finger protein containing a BED finger domain, a domain proposed to play a role in altering local chromatin architecture (Mahajan et al., 2002, Mol. Cell Biol. 22:6883-94). MAL is a hydrophobic integral membrane protein of the MAL family of proteolipids and is involved in the formation, maintenance, and function of glycosphingolipid-enriched myelin and membrane microdomains (Frank, 2000, Prog. Neurobiol. 60:531-44). IMP-3 is localized to the nucleolus where it binds to and represses translation of the 5' UTR of the insulin-like growth factor II leader 3 mRNA during late mammalian development. Furthermore, IMP-3 is a sensitive and specific marker for carcinomas and high-grade dysplastic lesions of the pancreatic ductal epithelium (Nielsen et al., 1999, Mol. Cell Biol. 19:1262-70; Yantiss et al., 2005, Am. J. Surg. Pathol. 29:188-95). DHRS9 is a retinol dehydrogenase/reductase of the SDR superfamily that converts retinol to retinaldehyde, the first of two reactions in the formation of all-trans retinoic acid, which mediates the various biological functions of vitamin A including visual transduction, cell growth, and embryonic development. Expression of DHRS9 is reduced in colon adenomas, carcinomas, and in seven carcinoma cell lines and appears to be regulated by APC (Markova et al., 2003, Mol. Genet. Metab. 78:119-35; Jette et al., 2004, J. Biol. Chem. 279:34397-405).

It should be understood the signatures described above are optimized and some signatures of the present invention. The present invention is not limited to the use of these particular signatures. Any combination of one or more markers that provides useful information can be used in the methods of the present invention. For example, it should be understood that one or more markers can be added or subtracted from the above signatures, while maintaining the ability of the signatures to yield useful information (e.g., more information than would be obtained in the absence of testing).

The E-cadherin Cancer Stem Cell Gene Signature.

In addition to the undetectable or low levels of E-cadherin expression in cancer stem cells the present invention further identifies the increased and decreased expression as compared to normal breast epithelium of a diverse set of genes with a range of physiological functions that are implicated in the development, maintenance, and/or progression of human cancers. In some embodiments of the present invention the undetectable or low levels of E-cadherin expression further comprises undetectable or low level expression of one or more of the following genes: matrix metalloproteinase 7 (MMP7); nephroblastoma overexpressed gene (Nov); FOS-like antigen 1 (FOSL1); interleukin 1 receptor, type II (IL1R2), secreted frizzled-related protein 1 (SFRP1); keratin 6B (KRT6B); putative lymphocyte G0/G1 switch gene (G0S2); interleukin 8 (IL8); UDP-GlcNAc:betaGal beta-1,3-N-acetylglucosaminyltransferase 5 (B3GNT5); and fibroblast growth factor binding protein 1 (FGFBP1) and elevated expression of one or more of the genes comprising: SHC (Src homology 2 domain containing) transforming protein 1 (SHC1); FLJ20152; aryl hydrocarbon receptor nuclear translocator (ARNT); cytoplasmic FMR1 interacting protein 2 (CYFIP2); chromosome 17 open reading frame 27 (C17orf27); transporter 1, ATP-binding cassette, sub-family B (TAP1); RNASEL; and similar to aspartate beta hydroxylase (LOC57168). In another embodiment the undetectable or low levels of E-cadherin expression further comprises undetectable or low level expression of one or more of the genes: MMP7; Nov; FOSL1; IL1R2; SFRP1; KRT6B; G0S2; IL8; B3GNT5; and FGFBP1. In another embodiment the undetectable or low levels of E-cadherin expression further comprises elevated expression of one or more of the genes: SHC1; FLJ20152; ARNT; CYFIP2; C17orf27; TAP1; RNASEL; and LOC57168. In further embodiments of the present invention signature 2 cancer stem cells comprise undetectable or low level expression of one or more of the genes: E-cadherin; MMP7; Nov; FOSL1; IL1R2; SFRP1; KRT6B; G0S2; IL8; B3GNT5; and, FGFBP1 and further comprises elevated expression of one or both of the genes: SHC1; FLJ20152; ARNT; CYFIP2; C17orf27; TAP1; RNASEL; and LOC57168. Alternatively signature 2 cancer stem cells comprise 1) undetectable or low level expression of one or more of the genes: E-cadherin; MMP7; Nov; FOSL1; IL1R2; SFRP1; KRT6B; G0S2; IL8; B3GNT5; and FGFBP1 or 2) elevated expression of one or more of the genes: SHC1; FLJ20152; ARNT; CYFIP2; C17orf27; TAP1; RNASEL; and LOC57168.

In some embodiments of the present invention the undetectable or low levels of E-cadherin expression further comprises undetectable or low level expression of one or more of the genes: matrix metalloproteinase 7 (MMP7); nephroblastoma overexpressed gene (Nov); FOS-like antigen 1 (FOSL1); and interleukin 1 receptor, type II (IL1R2), and elevated expression of one or more of the genes comprising: SHC (Src homology 2 domain containing) transforming protein 1 (SHC1) and FLJ20152. In another more some embodiment the undetectable or low levels of E-cadherin expression further comprises undetectable or low level expression of one or more of the genes: MMP7; Nov; FOSL1; and IL1R2. In another embodiment the undetectable or low levels of E-cadherin expression further comprises elevated expression of one or both of the genes: SHC1 and FLJ20152. In further some embodiments of the present invention signature 2 cancer stem cells comprise undetectable or low level expression of one or more of the genes: E-cadherin; MMP7; Nov; FOSL1; and IL1R2, and further comprises elevated expression of one or both of the genes: SHC1 and FLJ20152. Alternatively signature 2 cancer stem cells comprise 1) undetectable or low level expression of one or more of the genes: E-cadherin; MMP7; Nov; FOSL1; and IL1R2 or 2) elevated expression of one or more of the genes: SHC1 and FLJ20152.

Signature 2 cancer stem cell gene expression comprises the decreased expression of matrix metalloproteinase 7 (MMP7). Matrix metalloproteinases (MMPs) are secreted proteolytic enzymes involved in the turnover of the extracellular matrix during tissue formation and remodeling. Overexpression and secretion of MMPs by tumor cells is thought to contribute to inappropriate degradation of both the extracellular matrix and basement membranes, liberating bioactive molecules that can stimulate cellular growth and aiding tumor cell invasion and metastasis (Hamacher et al., 2004, Dtsch. Med. Wocherschr. 129:1976-80; Mott & Werb, 2004, Curr. Opin Cell Biol. 16:558-64).

Signature 2 cancer stem cell gene expression further comprises the decreased expression of nephroblastoma overexpressed gene (Nov). Nov was identified as the insertion site of the myelobastosis-associated virus 1-N in avian nephroblastoma and belongs to a family of secreted proteins associated with the extracellular matrix that play various biological roles including cell proliferation, chemotaxis, and cellular adhesion. Nov has been implicated in cell cycle control and slowing cell growth. Consistent with this notion, high levels of Nov expression are associated with less aggressive brain tumors, and levels of Nov decrease with progression of adrenocortical tumors to a malignant state (Martinerie et al., 2001, J. Clin. Endocrinol. Metab. 86:3929-40; Gellhaus et al., 2004, J. Biol. Chem. 279:36931).

Signature 2 cancer stem cell gene expression additionally comprises the decreased expression of FOS-like antigen 1 (FOSL1). Dimers of Jun and Fos proteins, including FOSL1, make up the transcription factor activator protein-1 (AP-1). AP-1 is linked to a large number of often competing cellular functions including cell transformation, proliferation, differentiation, and apoptosis that are determined by a complex network of extracellular and intracellular signaling pathways. FOSL1 differs from c-Fos in not contain transactivation domains essential for cellular transformation induced by AP-1 (Matsuo et al., 2000, Nat. Genet. 24:184-7; Ameyar et al., 2003, Biochimie 85:747-52).

Signature 2 cancer stem cell gene expression also comprises the decreased expression of interleukin 1 receptor, type II (IL1R2), a non-signaling decoy receptor for IL-1 with both secreted and membrane bound forms. IL-1 is a potent pro-inflammatory cytokine that can stimulate the production of pro-tumorigenic cytokines such as the angiogenic and mitogenic cytokine IL-8 (Bourke et al., 2003, J. Immunol. 170: 5999; Cui et al., 2003, J. Immunol. 171:6814; Pantschenko et al., 2003, Int. J. Oncol. 23:269-84). Thus restoration of IL1R2 expression levels in this population of cancer stem cells can help to counteract both inflammation and tumor growth.

The E-cadherin gene expression signature further comprises decreased expression of secreted frizzled-related protein 1 (SFRP1); keratin 6B (KRT6B); putative lymphocyte G0/G1 switch gene (G0S2); interleukin 8 (IL8); UDP-GlcNAc:betaGal beta-1,3-N-acetylglucosaminyltransferase 5 (B3GNT5); and fibroblast growth factor binding protein 1 (FGFBP1). SFRP1 is a secreted frizzled-related protein that binds to Wnt proteins and modulates signaling (Uren et al., 2000, J. Biol. Chem. 275:4374-82). SFRP1 can promote apoptosis and is downregulated or hypermethylated in various carcinomas (reviewed in Kawano & Kypta, 2003, 116:2527-34). KRT6B is a member of the keratin gene family expressed in epithelial cells and strongly induced in stratified epithelia undergoing excessive cell proliferation or abnormal differentiation (Takahashi et al., 1995, J. Biol. Chem. 270:18581-92). G0S2 encodes a small basic phosphoprotein that plays a role in the commitment of cells to enter the G1 phase of the cell cycle (Cristillo et al., 1997, DNA Cell Biol. 16:1449-58). IL8 is a potent pro-inflammatory, chemoattractant, and pro-angiogenic CXC chemokine (Dumitrascu, 1996, Rom J. Intern. Med. 34:159-72; Rosenkilde & Schwartz, 2004, APMIS 112: 481-95). B3GNT5 encodes a type II membrane enzyme of the beta-1,3-N-acetylglucosaminyltransferase family that transfers GlcNAc to glycolipid substrates (Togayachi et al., 2001, J. Biol. Chem. 276:22032-40) and is strongly linked to tumor invasion and metastasis (Chakraborty & Pawelek, 2003, 20:365-73). FGFBP1 binds and activates both acidic and basic members of the fibroblast growth factor family, which have been implicated in a diverse array of cellular processes including proliferation, apoptosis, cell survival, chemotaxis, cell adhesion, differentiation, and migration (Bottcher & Niehrs, 2005, Endocr. Rev. 26:63-77).

Signature 2 cancer stem cell gene expression further comprises the increased expression of SHC (Src homology 2 domain containing) transforming protein 1 (SHC1). SHC1 is an adaptor protein that is a key mediator of the insulin-like growth factor (IGF-1) and epithelial growth factor (EGF) pathways that regulates cell proliferation, differentiation, and apoptosis. Three isoforms of SHC1 are expressed from the same gene, p46 Shc, p52 Shc, and p66 Shc, and whereas the p46 and p52 isoforms are overexpressed in gastric cancers (Yukimasa et al., 2005, Int. J. Oncol. 26:905-11) a variant allele of p66 Shc can decrease the risk of breast cancer (Wagner et al., 2004, Carcinogenesis 25:2473).

Signature 2 cancer stem cell gene expression further comprises the increased expression of FLJ20152 a hypothetical human protein at L0054463.

The E-cadherin gene expression signature further comprises elevated expression of aryl hydrocarbon receptor nuclear translocator (ARNT); cytoplasmic FMR1 interacting protein 2 (CYFIP2); chromosome 17 open reading frame 27 (C17orf27); transporter 1, ATP-binding cassette, sub-family B (TAP1); RNASEL; and similar to aspartate beta hydroxylase (L0057168). The aryl hydrocarbon (Ah) receptor, a member of the basic helix-loop-helix PER-ARNT-SIM transcription factor family, binds environmental pollutants, including polycyclic aromatic hydrocarbons, and regulates expression of genes involved in xenobiotic metabolism through interaction with specific xenobiotic response elements (XREs; Reyes et al., 1992, Science 256:1193-5). CYFIP2 interacts with the fragile X mental retardation protein (FMRP), an RNA-binding protein associated with polysomes, and acts as an effector of Rac1, a small GTP-binding protein cytoskeletal regulator, to antagonize FMRP function (Schenck et al., 2003, Neuron 38:843-5; Schenck et al., 2001, PNAS 98:8844-9). TAP1 is a member of the ATP-binding cassette (ABC) transporter superfamily. TAP1 is localized to the endoplasmic reticulum and cis-golgi and is involved in the presentation of degraded cytoplasmic protein peptides to the MHC class I molecule of the cellular immune system (Townsend & Trowsdale, 1993, 4:53-61). RNASEL is an endoribonuclease induced by interferon and activated by 5' phosphorylated, 2',5'-linked oligoadenylates that is implicated in both the actions of interferon as well as basic homeostatic RNA stability in mammalian cells (Zhou et al., 1993, Cell 72:753-65). Mutations in RNASEL can increase the risk of prostate cancer (Silverman, 2003, Biochem. 42:1805-12).

It should be understood the signatures described above are optimized and represent some signatures of the present invention. The present invention is not limited to the use of these particular signatures. Any combination of one or more markers that provides useful information can be used in the methods of the present invention. For example, it should be understood that one or more markers can be added or subtracted from the above signatures, while maintaining the ability of the signatures to yield useful information (e.g., more information than would be obtained in the absence of testing).

Additional solid tumor stem cells cancer markers can be identified, for example, using the methods described in Example 4 below.

Another aspect of the present invention is the means and methods for classifying tumors based upon the profiling of solid tumor samples by comparing a gene expression pattern of a cancer sample to a cancer stem cell gene expression signature. This invention for the first time has discovered tumor stem cell gene expression signatures that are predictors of distant metastases and death. The microarray data of the present invention identifies cancer stem cell markers likely to play a role in breast or colon cancer development, progression, and/or maintenance while also identifying individual predictor genes and gene signatures useful in classifying tumors, such as breast and colon tumors, into low and high risk of, for example, metastasis and death. Classification based on the detection of differentially expressed polynucleotides and/or proteins that comprise a cancer gene profile when compared to a cancer stem cell gene signature can be used to predict clinical course, predict sensitivity to chemotherapeutic agents, guide selection of appropriate therapy, and monitor treatment response. Furthermore, following the development of therapeutics targeting such cancer stem cell markers, detection of the cancer gene signatures described in detail herein will allow the identification of patients likely to benefit from such therapeutics.

As described herein, the invention employs methods for clustering genes into gene expression profiles by determining their expression levels in two different cell or tissue samples. The invention further envisions using these gene profiles as compared to a cancer stem cell gene signature to predict clinical outcome including, for example, metastasis and death. The microarray data of the present invention identifies gene profiles comprising similarly and differentially expressed genes contained on the Affymetrix HG-U133 array between two tissue samples including between tumor stem cells and normal breast epithelium, non-tumorigenic tumor cells and normal breast epithelium, and tumor stem cells and non-tumorigenic tumor cells. These broad gene expression profiles can then be further refined, filtered, and subdivided into gene signatures based on various different criteria including, but not limited to, fold expression change, statistical analyses (e.g. t-test P value from multiple compared samples), correlation with expression of other genes, biological function (e.g. cell cycle regulators, transcription factors, proteases, etc.), some therapeutic targets (e.g. genes encoding extracellular membrane associated proteins suitable for antibody based therapeutics), identified expression in additional patient samples, and ability to predict clinical outcome.

Thus in some embodiments of the present invention the genes differentially expressed in tumor stem cells versus normal breast epithelium are subdivided into different cancer stem cell gene signatures based on their fold expression change. For example genes with from 2 to 2.5 fold elevated (or reduced, or both elevated and reduced) expression in tumor stem cells comprise a cancer stem cell gene signature, genes with from 2.5 to 3 fold elevated (or reduced, or both) expression comprise another cancer stem cell gene signature. Alternatively, all genes above a certain fold expression change are included in a cancer stem cell gene signature. For example, all genes with a 2 fold or more reduced (or elevated, or both) expression in tumor stem cells can comprise one cancer stem cell gene signature, all genes with a 3 fold or more reduced (or elevated, or both) expression in tumor stem cells can comprise another cancer stem cell gene signature, and so on. In other embodiments, the genes differentially expressed in tumor stem cells versus normal breast epithelium are filtered by using statistical analysis. For example, all genes with elevated (or reduced, or both) expression with a t-test P value across samples from 0.01 and 0.005 can comprise one cancer stem cell gene signature, all genes with elevated (or reduced, or both) expression with a t-test P value across samples of 0.005 and 0.001 can comprise another cancer stem cell gene signature, and so on. Furthermore, gene expression analysis of independent patient samples or different cell lines can be compared to any cancer stem cell gene signature generated as described above. A cancer stem cell gene signature can be modified, for example, by calculating individual phenotype association indices as described (Glinsky et al., 2004, Clin. Cancer Res. 10:2272) to increase or maintain the predictive power of a given cancer stem cell gene signature. In addition a cancer stem cell gene signature can be further narrowed or expanded gene by gene by excluding or including genes based on various criteria (e.g. inclusion of a some therapeutic target or exclusion based of a biologically unrelated target).

In yet further embodiments, a broad gene expression profile such as those generated by the Affymetrix HG-U133 array analyses of the present invention can be further refined, filtered, subdivided, etc. into gene signatures based on two or more different criteria. In some embodiments of the present invention the genes differentially expressed in tumor stem cells versus normal breast epithelium are subdivided into different cancer stem cell gene signatures based on their fold expression change as well as their biological function. For example, all genes involved in cell cycle regulation with 3 to 3.5 fold elevated (or reduced, or both) expression in tumor stem cells versus normal breast epithelium can comprise one cancer stem cell gene signature, all genes involved in cell cycle regulation with 3.5 to 4 fold elevated (or reduced, or both) expression in tumor stem cells versus normal breast epithelium can comprise another cancer stem cell gene signature, all genes encoding extracellular membrane associated proteins with 4 fold or more elevated (or reduced, or both) expression in tumor stem cells versus normal breast epithelium can comprise another cancer stem cell gene signature, all genes encoding extracellular membrane associated proteins with 5 fold or more elevated (or reduced, or both) expression in tumor stem cells versus normal breast epithelium can comprise yet another cancer stem cell gene signature.

In some embodiments, the genes differentially expressed in tumor stem cells are divided into cancer stem cell gene signatures based on the correlation of their expression with a chosen gene in combination with their fold or percentage expression change. Specifically, in some embodiments the microarray analysis of the invention was used to identify a solid tumor stem cell signature, the alpha-catenin gene signature, based on genes with expression levels that correlate with alpha-catenin expression and display a fold or percentage expression change in tumor stem cells with undetectable or low levels of alpha-catenin compared to normal breast tissue and alpha-catenin non-deficient tumor stem cells. Genes with undetectable to low expression in tumor stem cells comprising low to undetectable alpha-catenin expression were identified as having a positive correlation, from 0.9 to 1, with alpha-catenin expression in all tumor stem cells as well as expression levels lower by 90% or more in tumor stem cells comprising low to undectable alpha-catenin compared to normal breast tissue and alpha-catenin non-deficient tumor stem cells. Genes with elevated expression in tumor stem cells comprising low to undetectable alpha-catenin expression were identified as having a negative correlation, from −0.9 to −1, with alpha-catenin expression in all tumor stem cells as well as expression levels in tumor stem cells comprising low to undectable alpha-catenin that are 9 fold or more than in normal breast tissue and alpha-catenin non-deficient tumor stem cells. Together these genes comprise the alpha-catenin signature 1 (Table 9). A second alpha-catenin signature (alpha-catenin signature 2) was then generated by further including genes that slightly violated the fold or expression change criteria described above but were subjectively determined to be therapeutically and/or biologically related genes: one gene with undetectable to low expression and three genes with elevated expression (underlined in Table 9). A third alpha-catenin signature (alpha-catenin signature 3) was then generated by excluding genes from alpha-catenin signature 2: nine genes with undetectable to low expression and fifteen genes with elevated expression (Table 9). The alpha-catenin signature 2 was compared against gene expression analysis from the two independent cancer patient populations: 295 consecutive early breast cancer patients from the Netherlands Cancer Institute and 286 lymph node negative breast cancer patients from the Erasmus Medical Center producing alpha-catenin profile 4 and alpha-catenin profile 5, respectively (Table 9).

In other embodiments the microarray analysis of the invention was used to identify a solid tumor stem cell signature, the E-cadherin gene signature, based on genes with expression levels that correlate with E-cadherin expression and display a fold or percentage expression change in tumor stem cells with undetectable or low levels of E-cadherin compared to normal breast tissue and E-cadherin non-deficient cells. Genes with undetectable to low expression in tumor stem cells comprising low to undetectable E-cadherin expression were identified as having a positive correlation, from 0.9 to 1, with E-cadherin expression in all tumor stem cells as well as expression levels lower by 85% or more in tumor stem cells comprising low to undectable E-cadherin compared to normal breast tissue and E-cadherin non-deficient tumor stem cells. Genes with elevated expression in tumor stem cells comprising low to undetectable E-cadherin expression were identified as having a negative correlation, from −0.9 to −1, with E-cadherin expression in all tumor stem cells as well as expression levels in tumor stem cells comprising low to undectable E-cadherin expression that are 2.5 fold or more than in normal breast tissue and E-cadherin non-deficient tumor stem cells. Together these genes comprise the E-cadherin signature 1. A second E-cadherin signature (E-cadherin signature 2) was then generated by further including genes that slightly violated the fold or expression change criteria described above but were subjectively determined to be therapeutically and/or biologically interesting genes: one gene with elevated expression (underlined in Table 9). A third E-cadherin signature (E-cadherin signature 3) was then generated by excluding genes from E-cadherin signature 2 that were subjectively determined not to be therapeutically and/or biologically interesting genes: six genes with undetectable to low expression and six genes with elevated expression (Table 9). The E-cadherin signature 2 was then compared against gene expression analysis from the two independent cancer patient populations: 295 consecutive early breast cancer patients from the Netherlands Cancer Institute and 286 lymph node negative breast cancer patients from the Erasmus Medical Center producing E-cadherin profile 4 and E-cadherin profile 5, respectively (Table 9).

The invention further embodies the use of these cancer stem cell gene signatures to predict clinical outcome including, but not limited to, metastasis and death. Any independent patient population that includes gene expression analysis (e.g. microarray analysis, immunohistochemical analysis, etc) or tumor samples suitable for gene expression analysis (e.g. frozen tissue biopsies, paraffin embedded tumor tissue samples, etc) along with determined clinical parameters or ongoing monitoring of clinical parameters including, for example, lymph node status, metastasis, death, etc. can be used to assess the ability of a cancer stem cell gene signature to predict clinical outcomes. In some embodiments the invention tests the ability of the alpha-catenin and E-cadherin tumor stem cell gene signatures to predict metastasis and death in two independent cancer patient populations: 295 consecutive early breast cancer patients from the Netherlands Cancer Institute (van de Vijver et al., 2002, N. Eng. J. Med. 347:1999) and 286 lymph node negative breast cancer patients from the Erasmus Medical Center (Wang et al., 2005, Lancet 365:671). Many statistical analyses can be used to determine predictive ability. These include, for example, Kaplan-Meier survival analysis, Cox proportional hazard survival analysis, chi-square analysis, and multivariate analysis. In some embodiments of the present invention, Cox proportional hazard survival analysis of the 295 consecutive early breast cancer patients from the Netherlands Cancer Institute and chi-square analysis of the 286 patients from the Erasmus Medical Center were used to identify cancer stem cell gene signatures significantly predictive of clinical outcome.

Correlation and Cox proportional hazard survival analysis of microarray data from 295 consecutive early breast cancer patients from the Netherlands Cancer Institute (van de Vijver et al., 2002, N. Eng. J. Med. 347:1999) identified 125 patient tumors with a gene expression profile (alpha-catenin profile 4) that positively correlated with the alpha-catenin signature 2, and showed alpha-catenin signature 2 as significantly predictive of metastasis with a univariate hazard ratio of 1.15 per 0.1 correlation ($P=5.9\times10^{-4}$) and significantly predictive of death with a univariate hazard ratio of 1.24 per 0.1 correlation ($P=3.7\times10^{-7}$). Furthermore, correlation and chi-square analysis of the microarray data from 286 lymph-node negative breast cancer patients from the Erasmus Medical Center (Wang et al., 2005, Lancet 365:671) revealed that patient tumors with a gene expression profile (alpha-catenin profile 5) that correlated with the alpha-catenin signature 2 (n=77) had an increased risk of metastasis (P=0.67). Thus a tumor stem cell gene signature, such as the alpha-catenin expression signature 2 provides a gene signature for tumors with high risk of metastasis and death, and is thus a gene signature that predicts a poor prognosis. Although any particular gene of the alpha-catenin expression signature 2 can or can not have either reduced expression or elevated expression in a tumor sample, the expression level and its relationship with the other genes in the signature creates a unique solid tumor stem cell signature that can be used to classify a tumor sample.

A similar comparison using the E-cadherin gene expression signature described above was again used to assess clinical outcome as summarized in Table 10. Correlation and Cox proportional hazard survival analysis of microarray data from 295 consecutive early breast cancer patients from the Netherlands Cancer Institute identified 240 patient tumors with a gene expression profile (E-cadherin profile 4) that positively correlated with the E-cadherin signature 2, and showed E-cadherin signature 2 as predictive of metastasis with a univariate hazard ratio for metastasis of 0.981 per 0.1 correlation (P=0.59) and predictive of death with a univariate hazard ratio of 0.938 per 0.1 correlation (P=0.1). Combining the alpha-catenin and E-cadherin gene expression signatures was also predictive of metastasis in patients (univariate hazard ratio for metastasis of 1.28 per 0.1 correlation ($P=4.2\times10^{-4}$)). In addition, correlation and chi-square analysis of microarray data from 286 lymph-node negative breast cancer patients from the Erasmus Medical Center (Wang et al., 2005, Lancet 365:671) showed that patient tumors with a gene expression profile (E-cadherin profile 5) that correlated with the E-cadherin gene signature 2 (n=198) had an increased risk of metastasis (P=0.57).

TABLE 10

Statistical Analysis of Metastasis and Death Prediction by the Alpha-Catenin and E-Cadherin Gene Signatures

| Gene expression signature | Death 295 patients (Netherlands Cancer Institute) | | Metastasis 295 patients (Netherlands Cancer Institute) | | Metastasis 286 patients (Erasmus Medical Center) |
|---|---|---|---|---|---|
| | P value | Hazard ratio (per 0.1) | P value | Hazard ratio (per 0.1) | P value |
| CDH1 | 0.1 | 0.938 | 0.59 | 0.981 | 0.57 |
| CTNNA1 | 3.7e−7 | 1.24 | 0.00059 | 1.15 | 0.67 |
| CDH1 + CTNNA1 | 6.6e−5 | 1.37 | 0.00042 | 1.28 | |

The invention for the first time identifies the alpha-catenin gene signature as a predictor of poor clinical outcome. In certain embodiments of the present invention the alpha-catenin signature is used clinically to classify tumors as low or high risk and to assign a tumor to a low or high-risk category. The alpha-catenin signature can further be used to provide a diagnosis, prognosis, and/or select a therapy based on the classification of a tumor as low or high risk as well as to monitor a diagnosis, prognosis, and/or therapy over time. If it is known that a patient has a tumor that expresses the genes comprising the alpha-catenin signature and thus has a poor prognosis, a more aggressive approach to therapy can be warranted than in tumors not falling within the alpha-catenin subclass. For example, in patients where there is no evidence of disease in lymph nodes (node-negative patients), a decision must be made regarding whether to administer chemotherapy (adjuvant therapy) following surgical removal of the tumor. While some patients are likely to benefit from such treatment, it has significant side effects and can be avoided by patients with low risk tumors. Presently it is difficult or impossible to predict which patients would benefit. Knowing that a patient falls into a poor prognosis category can help in this decision. Furthermore, detecting expression of an alpha-catenin gene profile that is highly correlated with the alpha-catenin signature of the present invention can provide information related to tumor progression. It is well known that as tumors progress, their phenotypic characteristics can change. The invention thus contemplates the possibility that breast tumors can evolve from expressing an alpha-catenin gene profile that is highly correlated with a cancer stem cell gene signature to not (or vice versa) either in response to therapy or in response to lack of therapy. Thus detection of an alpha-catenin gene profile that either correlates with or fails to correlate with an alpha-catenin gene signature can be used to detect such progression and alter therapy accordingly.

It is well known in the art that some tumors respond to certain therapies while others do not. At present there is very little information that can be used to determine, prior to treatment, the likelihood that a specific tumor will respond to a given therapeutic agent. Many compounds have been tested for anti-tumor activity and appear to be effective in only a small percentage of tumors. Due to the current inability to predict which tumors will respond to a given agent, these compounds have not been developed into marketed therapeutics. This problem reflects the fact that current methods of classifying tumors are limited. However, the present invention offers the possibility of identifying tumor subgroups and characterizing tumors by a significant likelihood of response to a given agent. Tumor sample archives containing tissue samples obtained from patients that have undergone therapy with various agents are available along with information regarding the results of such therapy. In general such archives consist of tumor samples embedded in paraffin blocks. These tumor samples can be analyzed for their expression of polypeptides that are then compared to the polypeptides encoded by the genes comprising an alpha-catenin signature of the present invention. For example, immunohistochemistry can be performed using antibodies that bind to the polypeptides. Alternatively these tumor samples can be analyzed by their expression of polynucleotides that are then compared to the polynucleotides comprising an alpha-catenin signature of the present invention. For example, RNA can be extracted from the tumor sample and RT-PCR used to quantitatively amplify mRNAs that are then compared to the polynucleotides comprising an alpha-catenin signature. Tumors belonging to an alpha-catenin subclass can then be identified on the basis of this information. It is then possible to correlate the expression of an alpha-catenin profile with an alpha-catenin signature predicated response of the tumor to therapy, thereby identifying particular compounds that show a superior efficacy against tumors of this subclass as compared with their efficacy against tumors overall or against tumors not falling within the alpha-catenin subclass. Once such compounds are identified it will be possible to select patients whose tumors fall into an alpha-catenin subclass for additional clinical trials using these compounds. Such clinical trials, performed on a selected group of patients, are more likely to demonstrate efficacy. The reagents provided herein, therefore, are valuable both for retrospective and prospective trials.

In the case of prospective trials, detection of expression of one or more of the genes or encoded polypeptides in a cancer stem cell profile, such as an alpha-catenin profile, that correlates with a cancer stem cell signature, such as an alpha-catenin signature, can be used to stratify patients prior to their entry into the trial or while they are enrolled in the trial. In clinical research, stratification is the process or result of describing or separating a patient population into more homogeneous subpopulations according to specified criteria. Stratifying patients initially rather than after the trial is frequently some (including by regulatory agencies such as the U.S. Food and Drug Administration involved in the approval process for a medication), and stratification is frequently useful in performing statistical analysis of the results of a trial. In some cases stratification can be required by the study design. Various stratification criteria can be employed in conjunction with detection of expression of one or more cancer stem cell gene profiles that correlate with a cancer stem cell signature, such as an alpha-catenin gene signature. Commonly used criteria include age, family history, lymph node status, tumor size, tumor grade, etc. Other criteria that can be used include, but are not limited to, tumor aggressiveness, prior therapy received by the patient, estrogen receptor (ER) and/or progesterone (PR) positivity, Her2/neu status, or p53 status. Ultimately, once compounds that exhibit superior efficacy against cancer gene profile tumors that are highly correlated with a cancer stem cell gene signature, such as the alpha-catenin signature, are identified, reagents for detecting expression of the gene profile can be used to guide the selection of appropriate therapy for additional patients. Thus, by providing reagents and methods for classifying tumors based on their expression of a cancer gene profile that is compared to a cancer stem cell gene signature, the present invention provides a means to identify a patient population that can benefit from potentially promising therapies that have been abandoned due to inability to benefit broader or more heterogenous patient populations and further offers a means to individualize cancer therapy.

Information regarding the expression of cancer stem cell signature genes, such as the alpha-catenin signature genes, is thus useful even in the absence of specific information regarding their biological function or role in tumor development, progression, and maintenance. Although the reagents disclosed herein find particular application with respect to breast cancer, the invention also contemplates their use to provide diagnostic and/or prognostic information for other cancer types including but not limited to: biliary tract cancer; bladder cancer; brain cancer including glioblastomas and medulloblastomas; cervical cancer; choriocarcinoma; colon cancer; ondometial cancer; esophageal cancer; gastric cancer; hematological neoplasms including acute lymphocytic and myelogenous leukemia; multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and modullar carcinoma; and renal cancer including adenocarcinoma and Wilms tumor.

In other embodiments of the present invention, a cancer stem cell gene signature, such as an alpha-catenin signature, can be used experimentally to test and assess lead compounds including, for example, small molecules, siRNAs, and antibodies for the treatment of cancer. For example tumor cells from a patient can be screened for expression of a particular solid tumor stem cell gene signature, such as the alpha-catenin gene signature, and then transplanted into the xenograft model described herein and the effect of test compounds, such as for example antibodies against one or more cancer stem cell markers described herein, tested for effects on tumor growth and survival. Furthermore a cancer gene profile can be determined following treatment and the cancer gene profile compared to a cancer stem cell gene signature to assess the effectiveness of the therapy and in turn guide a future treatment regimen. In addition the efficacy of test compounds can be assessed against different tumor subclasses. For example test compounds can be used in xenografts of tumors that express a cancer gene profile that is highly correlated with a cancer stem cell signature, such as the alpha-catenin gene signature, versus tumors having a gene profile that does not correlate with a cancer stem cell gene signature, or that express another gene signature such as, for example, an E-cadherin gene signature. Any differences in response of the different tumor subclasses to the test compound are determined and used to optimize treatment for particular classes of tumors.

The cancer stem cell gene signatures, such as the alpha-catenin gene signatures, were identified from genes that are expressed at decreased or at elevated levels in tumor stem cells compared to normal breast epithelium. Thus in certain embodiments expression levels of mRNA, or amplified or cloned version thereof, are determined from a tumor sample by hybridization to polynucleotides that represent each particular gene comprising a cancer stem cell gene signature. Some polynucleotides of this type contain at least about 20 to at least about 32 consecutive basepairs of a gene sequence that is not found in other gene sequences. Even more some are polynucleotides of at least about 50 to at least about 400 basepairs of a gene sequence that is not found in other gene sequences. Such polynucleotides are also referred to as polynucleotide probes in that they are capable of hybridizing to sequences of the genes, or unique portions thereof, described herein. The sequences can be those of mRNA encoded by the genes, the corresponding cDNA to such mRNAs, and/or amplified versions of such sequences. In one some embodiment of the invention a cancer stem cell gene profile is detected by polynucleotide probes that comprise a cancer stem cell gene signature, such as an alpha-catenin signature, immobilized on an array (such as a cDNA microarray).

In another some embodiment of the invention, all or part of the disclosed polynucleotides of a cancer stem cell gene signature, such as an alpha-catenin gene signature, can be amplified and detected by methods such as the polymerase chain reaction (PCR) and variations thereof, such as, but not limited to, quantitative PCR (Q-PCR), reverse transcription PCR (RT-PCR), and real-time PCR (including means of measuring the initial amounts of mRNA copies for each sequence in a sample). Real-time RT-PCR or real-time Q-PCR can be used. Such methods utilize one or two primers that are complementary and hybridize to portions of a disclosed sequence, where the primers are used to prime nucleic acid synthesis. The newly synthesized nucleic acids are optionally labeled and can be detected directly or by hybridization to a polynucleotide of the invention. Additional methods to detect expressed nucleic acids include RNAse protection assays, including liquid phase hybridizations, and in situ hybridization of cells or tissue samples.

In yet other embodiments of the invention, gene expression can be determined by analysis of protein expression. Protein expression can be detected by use of one or more antibodies specific for one or more epitopes of individual gene products (proteins), or proteolytic fragments thereof, of a cancer stem cell gene signature, such as an alpha-catenin signature, in a tumor sample. Detection methodologies suitable for use in the practice of the invention include, but are not limited to, immunohistochemistry of cells in a tumor sample, enzyme linked immunosorbent assays (ELISAs) including antibody sandwich assays of cells in a tumor sample, mass spectroscopy, immuno-PCR, FACS, and protein microarrays.

It is envisioned that any patient tumor sample can be analysed, a tumor profile determined and then compared to a cancer stem cell gene signature. The alpha-catenin gene expression signature, an example of a solid tumor stem cell gene signature, was discovered from a comparison of gene expression of cancer stem cells against a non-tumorigenic tissue, such as, for example, normal breast tissue, and its prognostic ability was identified from microarray analysis of unfractionated, and thus heterogenous, breast tumor samples normalized against a reference set of tumor samples (van't Veer et al., 2002, Nature 415:530; van de Vijver et al., 2002, N. Eng. J. Med. 347:1999) or to a target intensity (Wang et al., 2005, Lancet 365:671). Thus unfractioned tumor samples, including but not limited to a solid tissue biopsy, fine needle aspiration, or pleural effusion can be analysed for generating a cancer gene profile in a tumor sample and comparing the profile to a cancer stem cell gene signature. More selective samples that are isolated from a heterogenous patient sample such as, for example, by isolating tumorigenic cancer cells or by laser capture microdissections can also be used. Alternatively the sample can permit the collection of cancer cells as well as normal cells for analysis so that the gene expression patterns for each sample can be determined and compared to a cancer stem cell signature.

In addition to the solid tumor stem cell gene signatures, one or more individual genes that comprise the signatures are significantly predictive of metastasis and death in the 295 patients from the Netherlands Cancer Institute suggesting that one or more of these genes can be used in place of an entire solid tumor stem cell gene signature as described above. In the case of the alpha-catenin gene signature it was discovered that the following genes GALC, CTSL2, FOXQ1, MYEOV, RB1, and SLC7A5 were significantly predictive of metastases and death. Expression of low to undetectable levels of GALC compared to a reference set of expression across all tumor samples (described in van't Veer et al., 2002, Nature 415:530 and van de Vijver et al., 2002, N. Eng. J. Med. 347:1999) was significantly predictive of metastasis with a univariate hazard ratio of 0.632 per 0.1 correlation ($P=8.1 \times 10^{-3}$) and significantly predictive of death with a univariate hazard ratio of 0.583 per 0.1 correlation ($P=5.4 \times 10^{-3}$). Expression of elevated levels of CTSL2 compared to the reference set was significantly predictive of metastasis with a univariate hazard ratio of 1.52 per 0.1 correlation ($P=1.7 \times 10^{-6}$) and significantly predictive of death with a univariate hazard ratio of 1.86 per 0.1 correlation ($P=4.0 \times 10^{-11}$). Expression of elevated levels of FOXQ1 compared to the reference set was significantly predictive of metastasis with a univariate hazard ratio of 1.44 per 0.1 correlation ($P=1.7 \times 10^{-3}$) and significantly predictive of death with a univariate hazard ratio of 1.73 per 0.1 correlation ($P=1.6 \times 10^{-5}$). Expression of elevated levels of MYEOV compared to the reference set was significantly predictive of metastasis with a univariate hazard ratio of 1.76 per 0.1 correlation ($P=2.2 \times 10^{-2}$) and significantly predictive of death with a univariate hazard ratio of 2.09 per 0.1 correlation ($P=5.9 \times 10^{-3}$). Expression of elevated levels of RB1 compared to the reference set was significantly predictive of metastasis with a univariate hazard ratio of 0.72 per 0.1 correlation ($P=1.6 \times 10^{-2}$) and significantly predictive of death with a univariate hazard ratio of 0.664 per 0.1 correlation ($P=6.8 \times 10^{-3}$). Expression of elevated levels of SCL7A5 compared to the reference set was significantly predictive of metastasis with a univariate hazard ratio of 3 per 0.1 correlation ($P=2.6 \times 10^{-4}$) and significantly predictive of death with a univariate hazard ratio of 3.52 per 0.1 correlation ($P=1.1 \times 10^{-4}$).

In addition, several of the genes comprising the E-cadherin gene expression signature were predictive alone including some with low to undetectable expression: IL8 and KRT6B and some with elevated expression: RNASEL and C17orf27. Expression of low to undectable levels of IL8 compared to the reference set was significantly predictive of metastasis with a univariate hazard ratio of 1.17 per 0.1 correlation ($P=5.2 \times 10^{-2}$) and significantly predictive of death with a univariate hazard ratio of 1.3 per 0.1 correlation ($P=3.0 \times 10^{-3}$). Expression of low to undetectable levels of KRT6B compared to the reference set was significantly predictive of metastasis univariate hazard ratio of 1.35 per 0.1 correlation ($P=3.9 \times 10^{-2}$) and significant predictive of death with a univariate hazard ratio of 1.54 per 0.1 correlation ($P=4.7 \times 10^{-3}$). Expression of elevated levels of RNASEL compared to the reference set was significantly predictive of metastasis with a univariate hazard ratio of 0.655 per 0.1 correlation ($P=3.7 \times 10^{-2}$) and significantly predictive of death with a univariate hazard ratio of 0.498 per 0.1 correlation ($P=1.4 \times 10^{-3}$). Elevated expression levels of C17orf27 compared to the reference set was significantly predictive of metastasis with a univariate hazard ratio of 2.35 per 0.1 correlation ($P=1.5 \times 10^{-2}$) and significantly predictive of death with a univariate hazard ratio of 3.19 per 0.1 correlation ($P=3.1 \times 10^{-3}$).

IV. Detection of Solid Tumor Stem Cell Cancer Markers

In some embodiments, the present invention provides methods for detection of expression of stem cell cancer markers (e.g., breast cancer stem cell cancer markers). In some embodiments, expression is measured directly (e.g., at the RNA or protein level). In some embodiments, expression is detected in tissue samples (e.g., biopsy tissue). In other embodiments, expression is detected in bodily fluids (e.g., including but not limited to, plasma, serum, whole blood, mucus, and urine). The present invention further provides panels and kits for the detection of markers. In some embodiments, the presence of a stem cell cancer marker is used to provide a prognosis to a subject. The information provided is also used to direct the course of treatment. For example, if a subject is found to have a marker indicative of a solid tumor stem cell (see, e.g. Tables 4-9), additional therapies (e.g., hormonal or radiation therapies) can be started at an earlier point when they are more likely to be effective (e.g., before metastasis). In addition, if a subject is found to have a tumor that is not responsive to hormonal therapy, the expense and inconvenience of such therapies can be avoided.

The present invention is not limited to the markers described above. Any suitable marker that correlates with cancer or the progression of cancer can be utilized. Additional markers are also contemplated to be within the scope of the present invention. Any suitable method can be utilized to identify and characterize cancer markers suitable for use in the methods of the present invention, including but not limited to, those described in illustrative Example 4 below. For example, in some embodiments, markers identified as being up or down-regulated in solid tumor stem cells using the gene expression microarray methods of the present invention are further characterized using tissue microarray, immunohistochemistry, Northern blot analysis, siRNA or antisense RNA inhibition, mutation analysis, investigation of expression with clinical outcome, as well as other methods disclosed herein.

In some embodiments, the present invention provides a panel for the analysis of a plurality of markers. The panel allows for the simultaneous analysis of multiple markers correlating with carcinogenesis and/or metastasis. Depending on the subject, panels can be analyzed alone or in combination in order to provide the best possible diagnosis and prognosis. Markers for inclusion on a panel are selected by screening for their predictive value using any suitable method, including but not limited to, those described in the illustrative examples below.

1. Detection of RNA

In some embodiments, detection of solid tumor stem cell cancer markers (e.g., including but not limited to, those disclosed in Tables 4-9) are detected by measuring the expression of corresponding mRNA in a tissue sample (e.g., breast cancer tissue). mRNA expression can be measured by any suitable method, including but not limited to, those disclosed below.

In some embodiments, RNA is detection by Northern blot analysis. Northern blot analysis involves the separation of RNA and hybridization of a complementary labeled probe.

In still further embodiments, RNA (or corresponding cDNA) is detected by hybridization to an oligonucleotide probe). A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

2. Detection of Protein

In other embodiments, gene expression of stem cell cancer markers is detected by measuring the expression of the corresponding protein or polypeptide. Protein expression can be detected by any suitable method. In some embodiments, proteins are detected by immunohistochemistry. In other embodiments, proteins are detected by their binding to an antibody raised against the protein. The generation of antibodies is described below.

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In some embodiments, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to cancer markers is utilized.

In other embodiments, the immunoassay described in U.S. Pat. Nos. 5,599,677 and 5,672,480; each of which is herein incorporated by reference.

3. cDNA Microarray Technology cDNA microarrays consist of multiple (usually thousands) of different cDNAs spotted (usually using a robotic spotting device) onto known locations on a solid support, such as a glass microscope slide. The cDNAs are typically obtained by PCR amplification of plasmid library inserts using primers complementary to the vector backbone portion of the plasmid or to the gene itself for genes where sequence is known. PCR products suitable for production of microarrays are typically from 0.5 and 2.5 kB in length. Full length cDNAs, expressed sequence tags (ESTs), or randomly chosen cDNAs from any library of interest can be chosen. ESTs are partially sequenced cDNAs as described, for example, in Hillier, et al., 1996, 6:807-828. Although some ESTs correspond to known genes, frequently very little or no information regarding any particular EST is available except for a small amount of 3' and/or 5' sequence and, possibly, the tissue of origin of the mRNA from which the EST was derived. As will be appreciated by one of ordinary skill in the art, in general the cDNAs contain sufficient sequence information to uniquely identify a gene within the human genome. Furthermore, in general the cDNAs are of sufficient length to hybridize, selectively, specifically or uniquely, to cDNA obtained from mRNA derived from a single gene under the hybridization conditions of the experiment.

In a typical microarray experiment, a microarray is hybridized with differentially labeled RNA, DNA, or cDNA populations derived from two different samples. Most commonly RNA (either total RNA or poly A+ RNA) is isolated from cells or tissues of interest and is reverse transcribed to yield cDNA. Labeling is usually performed during reverse transcription by incorporating a labeled nucleotide in the reaction mixture. Although various labels can be used, most commonly the nucleotide is conjugated with the fluorescent dyes Cy3 or Cy5. For example, Cy5-dUTP and Cy3-dUTP can be used. cDNA derived from one sample (representing, for example, a particular cell type, tissue type or growth condition) is labeled with one fluorophore while cDNA derived from a second sample (representing, for example, a different cell type, tissue type, or growth condition) is labeled with the second fluorophore. Similar amounts of labeled material from the two samples are cohybridized to the microarray. In the case of a microarray experiment in which the samples are labeled with Cy5 (which fluoresces red) and Cy3 (which fluoresces green), the primary data (obtained by scanning the microarray using a detector capable of quantitatively detecting fluorescence intensity) are ratios of fluorescence intensity (red/green, R/G). These ratios represent the relative concentrations of cDNA molecules that hybridized to the cDNAs represented on the microarray and thus reflect the relative expression levels of the mRNA corresponding to each cDNA/gene represented on the microarray.

Each microarray experiment can provide tens of thousands of data points, each representing the relative expression of a particular gene in the two samples. Appropriate organization and analysis of the data is of key importance, and various computer programs that incorporate standard statistical tools have been developed to facilitate data analysis. One basis for organizing gene expression data is to group genes with similar expression patterns together into clusters. A method for performing hierarchical cluster analysis and display of data derived from microarray experiments is described in Eisen et al., 1998, PNAS 95:14863-14868. As described therein, clustering can be combined with a graphical representation of the primary data in which each data point is represented with a color that quantitatively and qualitatively represents that data point. By converting the data from a large table of numbers into a visual format, this process facilitates an intuitive analysis of the data. Additional information and details regarding the mathematical tools and/or the clustering approach itself can be found, for example, in Sokal & Sneath, Principles of numerical taxonomy, xvi, 359, W. H. Freeman, San Francisco, 1963; Hartigan, Clustering algorithms, xiii, 351, Wiley, New York, 1975; Paull et al., 1989, J. Natl. Cancer Inst. 81:1088-92; Weinstein et al. 1992, Science 258:447-51; van Osdol et al., 1994, J. Natl. Cancer Inst. 86:1853-9; and Weinstein et al., 1997, Science, 275:343-9.

Further details of the experimental methods used in the present invention are found in the Examples. Additional information describing methods for fabricating and using microarrays is found in U.S. Pat. No. 5,807,522, which is herein incorporated by reference. Instructions for constructing microarray hardware (e.g., arrayers and scanners) using commercially available parts can be found at "http://" followed by "cmgm.stanford.edu/pbr-own/" and in Cheung et al., 1999, Nat. Genet. Supplement 21:15-19, which are herein incorporated by reference. Additional discussions of microarray technology and protocols for preparing samples and performing microarray experiments are found in, for example, DNA arrays for analysis of gene expression, Methods Enzymol, 303:179-205, 1999; Fluorescence-based expression monitoring using microarrays, Methods Enzymol, 306: 3-18, 1999; and M. Schena (ed.), DNA Microarrays: A Practical Approach, Oxford University Press, Oxford, UK, 1999. Descriptions of how to use an arrayer and the associated software are found at "http://" followed by "cmgm.stanford.edu/pbrown/mguide/a -rayerHTML/ArrayerDocs.html", which is herein incorporated by reference.

4. Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject can visit a medical center to have the sample obtained and sent to the profiling center, or subjects can collect the sample themselves and directly send it to a profiling center. Where the sample comprises previously determined biological information, the information can be directly sent to the profiling service by the subject (e.g., an information card containing the information can be scanned by a computer and the data transmitted to a computer of the profiling center using an electronic communication system). Once received by the profiling service, the sample is processed and a profile is produced (e.g., expression data), specific for the diagnostic or prognostic information desired for the subject.

The profile data is then prepared in a format suitable for interpretation by a treating clinician. For example, rather than providing raw expression data (e.g. examining a number of the markers described in Tables 4-9), the prepared format can represent a diagnosis or risk assessment for the subject, along with recommendations for particular treatment options. The data can be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject can chose further intervention or counseling based on the results. In some embodiments, the data is used for research use. For example, the data can be used to further optimize the inclusion or elimination of markers as useful indicators of a particular condition or stage of disease.

5. Kits

In yet other embodiments, the present invention provides kits for the detection and characterization of cancer (e.g. for detecting one or more of the markers shown in Tables 4-9, or for modulating the activity of a peptide expressed by one or more of markers shown in Tables 4-9). In some embodiments, the kits contain antibodies specific for a cancer marker, in addition to detection reagents and buffers. In other embodiments, the kits contain reagents specific for the detection of mRNA or cDNA (e.g., oligonucleotide probes or primers). In some embodiments, the kits contain all of the components necessary and/or sufficient to perform a detection assay, including all controls, directions for performing assays, and any necessary software for analysis and presentation of results.

Another embodiment of the present invention comprises a kit to test for the presence of the polynucleotides or proteins, e.g. in a tissue sample or in a body fluid, of a solid tumor stem cell gene signature, such as the alpha-catenin signature. The kit can comprise, for example, an antibody for detection of a polypeptide or a probe for detection of a polynucleotide. In addition, the kit can comprise a reference or control sample; instructions for processing samples, performing the test and interpreting the results; and buffers and other reagents necessary for performing the test. In certain embodiments the kit comprises a panel of antibodies for detecting expression of one or more of the proteins encoded by the genes of the alpha-catenin signature. In other embodiments the kit comprises pairs of primers for detecting expression of one or more of the genes of the solid tumor stem cell gene signature signature. In other embodiments the kit comprises a cDNA or oligonucleotide array for detecting expression of one or more of the genes of the solid tumor stem cell gene signature.

6. In Vivo Imaging

In some embodiments, in vivo imaging techniques are used to visualize the expression of cancer markers in an animal (e.g., a human or non-human mammal). For example, in some embodiments, cancer marker mRNA or protein is labeled using a labeled antibody specific for the cancer marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the cancer markers of the present invention are described below.

The in vivo imaging methods of the present invention are useful in the diagnosis of cancers that express the solid tumor stem cell cancer markers of the present invention (e.g., in breast cancer). In vivo imaging is used to visualize the presence of a marker indicative of the cancer. Such techniques allow for diagnosis without the use of an unpleasant biopsy. The in vivo imaging methods of the present invention are also useful for providing prognoses to cancer patients. For example, the presence of a marker indicative of cancer stem cells can be detected. The in vivo imaging methods of the present invention can further be used to detect metastatic cancers in other parts of the body.

In some embodiments, reagents (e.g., antibodies) specific for the cancer markers of the present invention are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference).

In other embodiments, antibodies are radioactively labeled. The use of antibodies for in vivo diagnosis is well known in the art. Sumerdon et al., (Nucl. Med. Biol 17:247-254 [1990] have described an optimized antibody-chelator for the radioimmunoscintographic imaging of tumors using Indium-111 as the label. Griffin et al., (J Clin Onc 9:631-640 [1991]) have described the use of this agent in detecting tumors in patients suspected of having recurrent colorectal cancer. The use of similar agents with paramagnetic ions as labels for magnetic resonance imaging is known in the art (Lauffer, Magnetic Resonance in Medicine 22:339-342 [1991]). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetiium-99m (6 hours), and indium-111 (3.2 days), of which gallium-67, technetium-99m, and indium-111 are preferable for gamma camera imaging, and gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 [1980] for In-111 and Tc-99m, and by Scheinberg et al. (Science 215:1511 [1982]). Other chelating agents can also be used, but the 1-(p-carboxymethoxybenzyl) EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 [1982]) for labeling of albumin with In-111, but which can be adapted for labeling of antibodies. A suitable method of labeling antibodies with Tc-99m which does not use chelation with DPTA is the pre-tinning method of Crockford et al., (U.S. Pat. No. 4,323,546, herein incorporated by reference).

A some method of labeling immunoglobulins with Tc-99m is that described by Wong et al. (Int. J. Appl. Radiat. Isot., 29:251 [1978]) for plasma protein, and recently applied successfully by Wong et al. (J. Nucl. Med., 23:229 [1981]) for labeling antibodies.

In the case of the radiometals conjugated to the specific antibody, it is likewise desirable to introduce as high a proportion of the radiolabel as possible into the antibody molecule without destroying its immunospecificity. A further improvement can be achieved by effecting radiolabeling in the presence of the specific stem cell cancer marker of the present invention, to insure that the antigen binding site on the antibody will be protected.

In still further embodiments, in vivo biophotonic imaging (Xenogen, Almeda, Calif.) is utilized for in vivo imaging. This real-time in vivo imaging utilizes luciferase. The luciferase gene is incorporated into cells, microorganisms, and animals (e.g., as a fusion protein with a cancer marker of the present invention). When active, it leads to a reaction that emits light. A CCD camera and software is used to capture the image and analyze it.

V. Antibodies and Antibody Fragments

The present invention provides isolated antibodies and antibody fragments (e.g., Fabs). In some embodiments, the present invention provides monoclonal antibodies or antibody fragments that specifically bind to an isolated polypeptide comprised of at least five, or at least 15 amino acid residues of the stem cell cancer markers described herein (e.g., as shown in Tables 4-9). These antibodies or antibody fragments find use in the diagnostic, drug screening, and therapeutic methods described herein (e.g. to detect or modulate the activity of a stem cell cancer marker peptide).

An antibody, or antibody fragment, against a protein of the present invention can be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method can be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant can be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), can be used.

Examples of myeloma cells include NS-1, P3U1, SP2/0, AP-1 and the like. The proportion of the number of antibody producer cells (spleen cells) and the number of myeloma cells to be used can be about 1:1 to about 20:1. PEG (e.g., PEG 1000-PEG 6000) can be added in concentration of about 10% to about 80%. Cell fusion can be carried out efficiently by incubating a mixture of both cells at about 20° C. to about 40° C., or about 30° C. to about 37° C. for about 1 minute to 10 minutes.

Various methods can be used for screening for a hybridoma producing the antibody (e.g., against a tumor antigen or autoantibody of the present invention). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20% or 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., e.g., 37° C., for about 5 days to 3 weeks, e.g., 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against a cancer marker of the present invention) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies can be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. can be coupled to a hapten in a weight ratio of about 0.1 parts to about 20 parts, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant can be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, a stem cell cancer marker of the present invention (further including a gene having a nucleotide sequence partly altered) can be used as the immunogen. Further, fragments of the protein can be used. Fragments can be obtained by any methods including, but not limited to expressing a fragment of the gene, enzymatic processing of the protein, chemical synthesis, and the like. The antibodies and antibody fragments can also be conjugated to therapeutic (e.g. cancer cell killing compounds). In this regard, the antibody directed toward one of the stem cell cancer markers is used to specifically deliver a therapeutic agent to a solid tumor cancer cell (e.g. to inhibit the proliferation of such sell or kill such a cell).

VI. Drug Screening

In some embodiments, the present invention provides drug screening assays (e.g., to screen for anticancer drugs). The screening methods of the present invention utilize stem cell cancer markers identified using the methods of the present invention (e.g., including but not limited to, the stem cell cancer markers shown in Tables 4-9). For example, in some embodiments, the present invention provides methods of screening for compound that alter (e.g., increase or decrease) the expression of stem cell cancer marker genes. In some embodiments, candidate compounds are antisense agents or siRNA agents (e.g., oligonucleotides) directed against cancer markers. In other embodiments, candidate compounds are antibodies that specifically bind to a stem cell cancer marker of the present invention. In certain embodiments, libraries of compounds of small molecules are screened using the methods described herein.

In one screening method, candidate compounds are evaluated for their ability to alter stem cell cancer marker expression by contacting a compound with a cell expressing a stem cell cancer marker and then assaying for the effect of the candidate compounds on expression. In some embodiments, the effect of candidate compounds on expression of a cancer marker gene is assayed by detecting the level of cancer marker mRNA expressed by the cell. mRNA expression can be detected by any suitable method. In other embodiments, the effect of candidate compounds on expression of cancer marker genes is assayed by measuring the level of polypeptide encoded by the cancer markers. The level of polypeptide expressed can be measured using any suitable method, including but not limited to, those disclosed herein. In some embodiments, other changes in cell biology (e.g., apoptosis) are detected.

Specifically, the present invention provides screening methods for identifying modulators, i.e., candidate or test compounds or agents (e.g., proteins, peptides, peptidomimetics, peptoids, small molecules or other drugs) which bind to, or alter the signaling or function associated with the cancer markers of the present invention, have an inhibitory (or stimulatory) effect on, for example, stem cell cancer marker expression or cancer markers activity, or have a stimulatory or inhibitory effect on, for example, the expression or activity of a cancer marker substrate. Compounds thus identified can be used to modulate the activity of target gene products (e.g., stem cell cancer marker genes) either directly or indirectly in a therapeutic protocol, to elaborate the biological function of the target gene product, or to identify compounds that disrupt normal target gene interactions. Compounds which inhibit the activity or expression of cancer markers are useful in the treatment of proliferative disorders, e.g., cancer, particularly metastatic cancer or eliminating or controlling tumor stem cells to prevent or reduce the risk of cancer.

The invention provides assays for screening candidate or test compounds that are substrates of a cancer markers protein or polypeptide or a biologically active portion thereof. In another embodiment, the invention provides assays for screening candidate or test compounds that bind to or modulate the activity of a cancer marker protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are some for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds can be presented in solution (e.g., Houghten, Biotechniques 13:412-421 [1992]), or on beads (Lam, Nature 354:82-84 [1991]), chips (Fodor, Nature 364: 555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249: 404-406 [1990]; Cwirla et al., Proc. Natl. Acad. Sci. 87:6378-6382 [1990]; Felici, J. Mol. Biol. 222:301 [1991]).

In some embodiments, an assay is a cell-based assay in which a cell that expresses a stem cell cancer marker protein or biologically active portion thereof is contacted with a test compound, and the ability of the test compound to the modulate cancer marker's activity is determined Determining the ability of the test compound to modulate stem cell cancer marker activity can be accomplished by monitoring, for example, changes in enzymatic activity. The cell, for example, can be of mammalian origin.

The ability of the test compound to modulate cancer marker binding to a compound, e.g., a stem cell cancer marker substrate, can also be evaluated. This can be accomplished, for example, by coupling the compound, e.g., the substrate, with a radioisotope or enzymatic label such that binding of the compound, e.g., the substrate, to a cancer marker can be determined by detecting the labeled compound, e.g., substrate, in a complex.

Alternatively, the stem cell cancer marker is coupled with a radioisotope or enzymatic label to monitor the ability of a test compound to modulate cancer marker binding to a cancer markers substrate in a complex. For example, compounds (e.g., substrates) can be labeled with $^{125}$I, $^{35}$S $^{14}$C or $^{3}$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a stem cell cancer marker substrate) to interact with a stem cell cancer marker with or without the labeling of any of the interactants can be evaluated. For example, a microphysiometer can be used to detect the interaction of a compound with a cancer marker without the labeling of either the compound or the cancer marker (McConnell et al. Science 257:1906-1912 [1992]). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and cancer markers.

In yet another embodiment, a cell-free assay is provided in which a cancer marker protein or biologically active portion thereof is contacted with a test compound and the ability of the test compound to bind to the stem cell cancer marker protein or biologically active portion thereof is evaluated. Some biologically active portions of the cancer markers proteins to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET)

(see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule can simply utilize the natural fluorescent energy of tryptophan residues. Labels are chosen that emit different wavelengths of light, such that the 'acceptor' molecule label can be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in 1 5 the assay should be maximal. An FRET binding event can be conveniently measured through standard fluorometric detection means well known in the art (e.g., using a fluorimeter).

In another embodiment, determining the ability of the stem cell cancer markers protein to bind to a target molecule can be accomplished using real-time Biomolecular Interaction Analysis (BIA) (see, e.g., Sjolander and Urbaniczky, Anal. Chem. 63:2338-2345 [1991] and Szabo et al. Curr. Opin. Struct. Biol. 5:699-705 [1995]). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In some embodiments, the target gene product or the test substance is anchored onto a solid phase. The target gene product/test compound complexes anchored on the solid phase can be detected at the end of the reaction. The target gene product can be anchored onto a solid surface, and the test compound, (which is not anchored), can be labeled, either directly or indirectly, with detectable labels discussed herein.

It can be desirable to immobilize stem cell cancer markers, an anti-cancer marker antibody or its target molecule to facilitate separation of complexed from non-complexed forms of one or both of the proteins, as well as to accommodate automation of the assay. Binding of a test compound to a stem cell cancer marker protein, or interaction of a cancer marker protein with a target molecule in the presence and absence of a candidate compound, can be accomplished in any vessel suitable for containing the reactants. Examples of such vessels include microtiter plates, test tubes, and micro-centrifuge tubes. In some embodiments, a fusion protein can be provided which adds a domain that allows one or both of the proteins to be bound to a matrix. For example, glutathione-S-transferase-cancer marker fusion proteins or glutathione-S-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target protein or cancer marker protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of cancer markers binding or activity determined using standard techniques. Other techniques for immobilizing either cancer markers protein or a target molecule on matrices include using conjugation of biotin and streptavidin. Biotinylated cancer marker protein or target molecules can be prepared from biotin-NHS (N-hydroxy-succinimide) using techniques known in the art (e.g., biotinylation kit, Pierce Chemicals, Rockford, EL), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with stem cell cancer marker protein or target molecules but which do not interfere with binding of the stem cell cancer markers protein to its target molecule. Such antibodies can be derivatized to the wells of the plate, and unbound target or cancer markers protein trapped in the wells by antibody conjugation. Methods for detecting such complexes, in addition to those described above for the GST-immobilized complexes, include immunodetection of complexes using antibodies reactive with the cancer marker protein or target molecule, as well as enzyme-linked assays which rely on detecting an enzymatic activity associated with the cancer marker protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284-7 [1993]); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit 11:141-8 [1998]; Hageand Tweed J. Chromatogr. Biomed. Sci. Appl 699:499-525 [1997]). Further, fluorescence energy transfer can also be conveniently utilized, as described herein, to detect binding without further purification of the complex from solution.

The assay can include contacting the stem cell cancer markers protein or biologically active portion thereof with a known compound that binds the cancer marker to form an assay mixture, contacting the assay mixture with a test compound, and determining the ability of the test compound to interact with a cancer marker protein, wherein determining the ability of the test compound to interact with a cancer marker protein includes determining the ability of the test compound to preferentially bind to cancer markers or biologically active portion thereof, or to modulate the activity of a target molecule, as compared to the known compound.

To the extent that stem cell cancer markers can, in vivo, interact with one or more cellular or extracellular macromolecules, such as proteins, inhibitors of such an interaction are useful. A homogeneous assay can be used can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, cancer markers protein can be used as a "bait protein" in a two-hybrid assay or three-hybrid assay (see, e.g., U.S. Pat. No. 5,283,317; Zervos et al., Cell 72:223-232 [1993]; Madura et al., J. Biol. Chem. 268.12046-12054 [1993]; Bartel et al., Biotechniques 14:920-924 [1993]; Iwabuchi et al., Oncogene 8:1693-1696 [1993]; and Brent WO 94/10300; each of which is herein incorporated by reference), to identify other proteins, that bind to or interact with cancer markers ("cancer marker-binding proteins" or "cancer marker-bp") and are involved in cancer marker activity. Such cancer marker-bps can be activators or inhibitors of signals by the cancer marker proteins or targets as, for example, downstream elements of a cancer markers-mediated signaling pathway.

Modulators of cancer markers expression can also be identified. For example, a cell or cell free mixture is contacted with a candidate compound and the expression of cancer marker mRNA or protein evaluated relative to the level of expression of stem cell cancer marker mRNA or protein in the absence of the candidate compound. When expression of cancer marker mRNA or protein is greater in the presence of the candidate compound than in its absence, the candidate compound is identified as a stimulator of cancer marker mRNA or protein expression. Alternatively, when expression of cancer marker mRNA or protein is less (i.e., statistically significantly less) in the presence of the candidate compound than in its absence, the candidate compound is identified as an inhibitor of cancer marker mRNA or protein expression. The level of cancer markers mRNA or protein expression can be determined by methods described herein for detecting cancer markers mRNA or protein.

A modulating agent can be identified using a cell-based or a cell free assay, and the ability of the agent to modulate the activity of a cancer markers protein can be confirmed in vivo, e.g., in an animal such as an animal model for a disease (e.g., an animal with prostate cancer or metastatic prostate cancer; or an animal harboring a xenograft of a prostate cancer from an animal (e.g., human) or cells from a cancer resulting from metastasis of a prostate cancer (e.g., to a lymph node, bone, or liver), or cells from a prostate cancer cell line.

This invention further pertains to novel agents identified by the above-described screening assays (See e.g., below description of cancer therapies). Accordingly, it is within the scope of this invention to further use an agent identified as described herein (e.g., a cancer marker modulating agent, an antisense cancer marker nucleic acid molecule, a siRNA molecule, a cancer marker specific antibody, or a cancer marker-binding partner) in an appropriate animal model (such as those described herein) to determine the efficacy, toxicity, side effects, or mechanism of action, of treatment with such an agent. Furthermore, novel agents identified by the above-described screening assays can be, e.g., used for treatments as described herein (e.g. to treat a human patient who has cancer).

VII. Cancer Therapies

In some embodiments, the present invention provides therapies for cancer (e.g., breast cancer). In some embodiments, therapies target cancer markers (e.g., including but not limited to, those shown in Tables 4-9).

A. Antisense Therapies

Candidate therapeutic agents also find use in drug screening and research applications. In some embodiments, the present invention targets the expression of stem cell cancer markers. For example, in some embodiments, the present invention employs compositions comprising oligomeric antisense compounds, particularly oligonucleotides (e.g., those identified in the drug screening methods described above), for use in modulating the function of nucleic acid molecules encoding stem cell cancer markers of the present invention, ultimately modulating the amount of cancer marker expressed. This is accomplished by providing antisense compounds that specifically hybridize with one or more nucleic acids encoding cancer markers of the present invention. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that can be engaged in or facilitated by the RNA. The overall effect of such interference with target nucleic acid function is modulation of the expression of cancer markers of the present invention. In the context of the present invention, "modulation" means either an increase (stimulation) or a decrease (inhibition) in the expression of a gene. For example, expression can be inhibited to potentially prevent tumor proliferation.

It is some to target specific nucleic acids for antisense. "Targeting" an antisense compound to a particular nucleic acid, in the context of the present invention, is a multistep process. The process usually begins with the identification of a nucleic acid sequence whose function is to be modulated. This can be, for example, a cellular gene (or mRNA transcribed from the gene) whose expression is associated with a particular disorder or disease state, or a nucleic acid molecule from an infectious agent. In the present invention, the target is a nucleic acid molecule encoding a stem cell cancer marker of the present invention. The targeting process also includes determination of a site or sites within this gene for the antisense interaction to occur such that the desired effect, e.g., detection or modulation of expression of the protein, will result. Within the context of the present invention, a some intragenic site is the region encompassing the translation initiation or termination codon of the open reading frame (ORF) of the gene. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes can have two or more alternative start codons, any one of which can be preferentially utilized for translation initiation in a particular cell type or tissue, or under a particular set of conditions. In the context of the present invention, "start codon" and "translation initiation codon" refer to the codon or codons that are used in vivo to initiate translation of an mRNA molecule transcribed from a gene encoding a tumor antigen of the present invention, regardless of the sequence(s) of such codons.

Translation termination codon (or "stop codon") of a gene can have one of three sequences (i.e., 5'-UAA, 5'-UAG and 5'-UGA; the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which refers to the region between the translation initiation codon and the translation termination codon, is also a region that can be targeted effectively. Other target regions include the 5' untranslated region (5' UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The cap region can also be a some target region.

Although some eukaryotic mRNA transcripts are directly translated, many contain one or more regions, known as "introns," that are excised from a transcript before it is translated. The remaining (and therefore translated) regions are known as "exons" and are spliced together to form a continuous mRNA sequence. mRNA splice sites (i.e., intron-exon junctions) can also be some target regions, and are particularly useful in situations where aberrant splicing is implicated in disease, or where an overproduction of a particular mRNA splice product is implicated in disease. Aberrant fusion junctions due to rearrangements or deletions are also some targets. It has also been found that introns can also be effective, and therefore some, target regions for antisense compounds targeted, for example, to DNA or pre-mRNA.

In some embodiments, target sites for antisense inhibition are identified using commercially available software programs (e.g., Biognostik, Gottingen, Germany; SysArris Software, Bangalore, India; Antisense Research Group, University of Liverpool, Liverpool, England; GeneTrove, Carlsbad, Calif.). In other embodiments, target sites for antisense inhibition are identified using the accessible site method described in U.S. Patent WO0198537A2, herein incorporated by reference.

Once one or more target sites have been identified, oligonucleotides are chosen that are sufficiently complementary to the target (i.e., hybridize sufficiently well and with sufficient specificity) to give the desired effect. For example, in some embodiments of the present invention, antisense oligonucleotides are targeted to or near the start codon.

In the context of this invention, "hybridization," with respect to antisense compositions and methods, means hydrogen bonding, which can be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. It is understood that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired (i.e., under physiological conditions in the case of in vivo assays or therapeutic treatment, and in the case of in vitro assays, under conditions in which the assays are performed).

Antisense compounds are commonly used as research reagents and diagnostics. For example, antisense oligonucleotides, which are able to inhibit gene expression with specificity, can be used to elucidate the function of particular genes. Antisense compounds are also used, for example, to distinguish between functions of various members of a biological pathway.

The specificity and sensitivity of antisense is also applied for therapeutic uses. For example, antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides are useful therapeutic modalities that can be configured to be useful in treatment regimes for treatment of cells, tissues, and animals, especially humans.

While antisense oligonucleotides are a some form of antisense compound, the present invention comprehends other oligomeric antisense compounds, including but not limited to oligonucleotide mimetics such as are described below. The antisense compounds in accordance with this invention can comprise from about 8 to about 30 nucleobases (i.e., from about 8 to about 30 linked bases), although both longer and shorter sequences can find use with the present invention. Particularly some antisense compounds are antisense oligonucleotides, e.g., those comprising from about 12 to about 25 nucleobases.

Specific examples of some antisense compounds useful with the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, modified oligonucleotides that do not have a phosphorus atom in their internucleoside backbone can also be considered to be oligonucleosides.

Some modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Some modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other some oligonucleotide mimetics, both the sugar and the internucleoside linkage (i.e., the backbone) of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science 254:1497 (1991).

In some embodiments, the oligonucleotides have phosphorothioate backbones and oligonucleosides with heteroatom backbones, and in particular —$CH_2$—, —NH—O—$CH_2$—, —$CH_2$—N($CH_3$)—O—$CH_2$—[known as a methylene (methylimino) or MMI backbone], —$CH_2$—O—N($CH_3$)—$CH_2$—, —$CH_2$—N($CH_3$)—N($CH_3$)—$CH_2$—, and —O—N($CH_3$)—$CH_2$—$CH_2$—[wherein the native phosphodiester backbone is represented as —O—P—O—$CH_2$—] of the above referenced U.S. Pat. No. 5,489,677, and the amide backbones of the above referenced U.S. Pat. No. 5,602,240. Also some oligonucleotides have morpholino backbone structures of the above-referenced U.S. Pat. No. 5,034,506.

Modified oligonucleotides can also contain one or more substituted sugar moieties. Some oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Particularly some are O[$(CH_2)_n$O]$_m$$CH_3$, O$(CH_2)_n$O$CH_3$, O$(CH_2)_n$N$H_2$, O$(CH_2)_n$$CH_3$, O$(CH_2)_n$ON$H_2$, and O$(CH_2)_n$ON[$(CH_2)_n$$CH_3$)]$_2$, where n and m are from 1 to about 10. Other some oligonucleotides comprise one of the following at the 2' position: $C_1$ to $C_{10}$ lower alkyl, substituted lower alkyl, alkaryl, aralkyl, O-alkaryl or O-aralkyl, SH, S$CH_3$, OCN, Cl, Br, CN, $CF_3$, OC$F_3$, SO$CH_3$, S$O_2$$CH_3$, ON$O_2$, N$O_2$, $N_3$, N$H_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A some modification includes 2'-methoxyethoxy(2'-O—$CH_2$$CH_2$O$CH_3$, also known as 2'-O-(2-methoxyethyl) or 2'-MOE) (Martin et al., Helv. Chim. Acta 78:486 [1995]) i.e., an alkoxyalkoxy group. A further some modification includes 2'-dimethylaminooxyethoxy (i.e., a O$(CH_2)_2$ON$(CH_3)_2$ group), also known as 2'-DMAOE, and 2'-dimethylaminoethoxyethoxy (also known in the art as 2'-O-dimethylaminoethoxyethyl or 2'-DMAEOE), i.e., 2'-O—$CH_2$—O—$CH_2$—N$(CH_3)_2$.

Other some modifications include 2'-methoxy(2'-O—$CH_3$), 2'-aminopropoxy(2'-O$CH_2$$CH_2$$CH_2$N$H_2$) and 2'-fluoro (2'-F). Similar modifications can also be made at other positions on the oligonucleotide, particularly the 3' position of the sugar on the 3' terminal nucleotide or in 2'-5' linked oligonucleotides and the 5' position of 5' terminal nucleotide. Oligonucleotides can also have sugar mimetics such as cyclobutyl moieties in place of the pentofuranosyl sugar.

Oligonucleotides can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently some base substitutions, even more particularly when combined with 2'-O-methoxyethyl sugar modifications.

Another modification of the oligonucleotides of the present invention involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, (e.g., hexyl-S-tritylthiol), a thiocholesterol, an aliphatic chain, (e.g., dodecandiol or undecyl residues), a phospholipid, (e.g., di-hexadecyl-rac-glycerol or triethylammonium 1,2-di-O-hexadecyl-rac-glycero-3-H-phosphonate), a polyamine or a polyethylene glycol chain or adamantane acetic acid, a palmityl moiety, or an octadecylamine or hexylamino-carbonyl-oxycholesterol moiety.

One skilled in the relevant art knows well how to generate oligonucleotides containing the above-described modifications. The present invention is not limited to the antisense oligonucleotides described above. Any suitable modification or substitution can be utilized.

It is not necessary for all positions in a given compound to be uniformly modified, and in fact more than one of the aforementioned modifications can be incorporated in a single compound or even at a single nucleoside within an oligonucleotide. The present invention also includes antisense compounds that are chimeric compounds. "Chimeric" antisense compounds or "chimeras," in the context of the present invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide can serve as a substrate for enzymes capable of cleaving RNA:DNA or RNA:RNA hybrids. By way of example, RNaseH is a cellular endonuclease that cleaves the RNA strand of an RNA:DNA duplex. Activation of RNaseH, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the present invention can be formed as composite structures of two or more oligonucleotides, modified oligonucleotides, oligonucleosides and/or oligonucleotide mimetics as described above.

The present invention also includes pharmaceutical compositions and formulations that include the antisense compounds of the present invention as described below.

B. Genetic Therapies

The present invention contemplates the use of any genetic manipulation for use in modulating the expression of stem cell cancer markers of the present invention. Examples of genetic manipulation include, but are not limited to, gene knockout (e.g., removing the cancer marker gene from the chromosome using, for example, recombination), expression of antisense constructs with or without inducible promoters, addition of a heterologous gene (e.g. controlled by an inducible promoter), and the like. Delivery of nucleic acid construct to cells in vitro or in vivo can be conducted using any suitable method. A suitable method is one that introduces the nucleic acid construct into the cell such that the desired event occurs (e.g., expression of an antisense construct).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Some methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the some gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors can be administered to a subject in a variety of ways. For example, in some embodiments of the present invention, vectors are administered into tumors or tissue associated with tumors using direct injection. In other embodiments, administration is via the blood or lymphatic circulation (See e.g., PCT publication 99/02685 herein incorporated by reference in its entirety). Exemplary dose levels of adenoviral vector can be, e.g., $10^8$ to $10^{11}$ vector particles added to the perfusate.

C. Antibody Therapy

In some embodiments, the present invention provides antibodies that target tumors that express a stem cell cancer marker of the present invention (e.g., those shown in Tables 4-9). Any suitable antibody (e.g., monoclonal, polyclonal, or synthetic) can be utilized in the therapeutic methods disclosed herein. In some embodiments, the antibodies used for cancer therapy are humanized antibodies. Methods for humanizing antibodies are well known in the art (See e.g., U.S. Pat. Nos. 6,180,370, 5,585,089, 6,054,297, and 5,565,332; each of which is herein incorporated by reference).

In some embodiments, the therapeutic antibodies comprise an antibody generated against a stem cell cancer marker of the present invention, wherein the antibody is conjugated to a cytotoxic agent. In such embodiments, a tumor specific therapeutic agent is generated that does not target normal cells, thus reducing many of the detrimental side effects of traditional chemotherapy. For certain applications, it is envisioned that the therapeutic agents will be pharmacologic agents that will serve as useful agents for attachment to antibodies, particularly cytotoxic or otherwise anticellular agents having the ability to kill or suppress the growth or cell division of endothelial cells. The present invention contemplates the use of any pharmacologic agent that can be conjugated to an antibody, and delivered in active form. Exemplary anticellular agents include chemotherapeutic agents, radioisotopes, and cytotoxins. The therapeutic antibodies of the present invention can include a variety of cytotoxic moieties, including but not limited to, radioactive isotopes (e.g., iodine-131, iodine-123, technicium-99m, indium-111, rhenium-188, rhenium-186, gallium-67, copper-67, yttrium-90, iodine-125 or astatine-211), hormones such as a steroid, antimetabolites such as cytosines (e.g., arabinoside, fluorouracil, methotrexate or aminopterin; an anthracycline; mitomycin C), vinca alkaloids (e.g., demecolcine; etoposide; mithramycin), and antitumor alkylating agent such as chlorambucil or melphalan. Other embodiments can include agents such as a coagulant, a cytokine, growth factor, bacterial endotoxin or the lipid A moiety of bacterial endotoxin. For example, in some embodiments, therapeutic agents will include plant-, fungus- or bacteria-derived toxin, such as an A chain toxins, a ribosome inactivating protein, α-sarcin, aspergillin, restrictocin, a ribonuclease, diphtheria toxin or pseudomonas exotoxin, to mention just a few examples. In some embodiments, deglycosylated ricin A chain is utilized.

In any event, it is proposed that agents such as these can, if desired, be successfully conjugated to an antibody, in a manner that will allow their targeting, internalization, release or presentation to blood components at the site of the targeted tumor cells as required using known conjugation technology (See, e.g., Ghose et al., Methods Enzymol., 93:280 [1983]).

For example, in some embodiments the present invention provides immunotoxins targeted a stem cell cancer marker of the present invention. Immunotoxins are conjugates of a specific targeting agent typically a tumor-directed antibody or fragment, with a cytotoxic agent, such as a toxin moiety. The targeting agent directs the toxin to, and thereby selectively kills, cells carrying the targeted antigen. In some embodiments, therapeutic antibodies employ crosslinkers that provide high in vivo stability (Thorpe et al., Cancer Res., 48:6396 [1988]).

In other embodiments, particularly those involving treatment of solid tumors, antibodies are designed to have a cytotoxic or otherwise anticellular effect against the tumor vasculature, by suppressing the growth or cell division of the vascular endothelial cells. This attack is intended to lead to a tumor-localized vascular collapse, depriving the tumor cells, particularly those tumor cells distal of the vasculature, of oxygen and nutrients, ultimately leading to cell death and tumor necrosis.

In some embodiments, antibody based therapeutics are formulated as pharmaceutical compositions as described below. In some embodiments, administration of an antibody composition of the present invention results in a measurable decrease in cancer (e.g., decrease or elimination of tumor).

D. RNAi Therapies

In other embodiments, RNAi is used to regulate expression of the stem cell cancer markers of the present invention (e.g. those shown in Tables 4-9). RNAi represents an evolutionary conserved cellular defense for controlling the expression of foreign genes in most eukaryotes, including humans. RNAi is triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired structure characterized by two nucleotide 3'-overhangs. Following the introduction of a small RNA, or RNAi, into the cell, it is believed the sequence is delivered to an enzyme complex called RISC(RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments.

Chemically synthesized siRNAs have become powerful reagents for genome-wide analysis of mammalian gene function in cultured somatic cells. Beyond their value for validation of gene function, siRNAs also hold great potential as gene-specific therapeutic agents (Tuschl and Borkhardt, Molecular Intervent. 2002; 2(3):158-67, herein incorporated by reference).

The transfection of siRNAs into animal cells results in the potent, long-lasting post-transcriptional silencing of specific genes (Caplen et al, Proc Natl Acad Sci U.S.A. 2001; 98: 9742-7; Elbashir et al., Nature. 2001; 411:494-8; Elbashir et al., Genes Dev. 2001; 15: 188-200; and Elbashir et al., EMBO J. 2001; 20: 6877-88, all of which are herein incorporated by reference). Methods and compositions for performing RNAi with siRNAs are described, for example, in U.S. Pat. No. 6,506,559, herein incorporated by reference.

siRNAs are extraordinarily effective at lowering the amounts of targeted RNA, and by extension proteins, frequently to undetectable levels. The silencing effect can last several months, and is extraordinarily specific, because one nucleotide mismatch between the target RNA and the central region of the siRNA is frequently sufficient to prevent silencing Brummelkamp et al, Science 2002; 296:550-3; and Holen et al, Nucleic Acids Res. 2002; 30:1757-66, both of which are herein incorporated by reference.

E. Pharmaceutical Compositions

The present invention further provides pharmaceutical compositions (e.g., comprising a small molecule, antisense, antibody, or siRNA that targets the stem cell cancer markers of the present invention). The pharmaceutical compositions of the present invention can be administered in a number of ways depending upon whether local or systemic treatment is desired and upon the area to be treated. Administration can be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders can be desirable.

Compositions and formulations for parenteral, intrathecal or intraventricular administration can include sterile aqueous solutions that can also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions can be generated from a variety of components that include, but are not limited to, preformed liquids, self-emulsifying solids and self-emulsifying semisolids.

The pharmaceutical formulations of the present invention, which can conveniently be presented in unit dosage form, can be prepared according to conventional techniques well known in the pharmaceutical industry. Such techniques include bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention can be formulated into any of many possible dosage forms such as, but not limited to, tablets, capsules, liquid syrups, soft gels, suppositories, and enemas. The compositions of the present invention can also be formulated as suspensions in aqueous, non-aqueous or mixed media. Aqueous suspensions can further contain substances that increase the viscosity of the suspension including, for example, sodium carboxymethylcellulose, sorbitol and/or dextran. The suspension can also contain stabilizers.

In some embodiments of the present invention the pharmaceutical compositions can be formulated and used as foams.

Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level can also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention can additionally contain other adjunct components conventionally found in pharmaceutical compositions. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Certain embodiments of the invention provide pharmaceutical compositions containing (a) one or more compounds that modulate the activity of a stem cell cancer marker (e.g. antibody, small molecule, siRNA, anti-sense, etc.) and (b) one or more other chemotherapeutic agents. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). Anti-inflammatory drugs, including but not limited to nonsteroidal anti-inflammatory drugs and corticosteroids, and antiviral drugs, including but not limited to ribivirin, vidarabine, acyclovir and ganciclovir, can also be combined in compositions of the invention. Other chemotherapeutic agents are also within the scope of this invention. Two or more combined compounds can be used together or sequentially.

Dosing is dependent on severity and responsiveness of the disease state to be treated, with the course of treatment lasting from several days to several months, or until a cure is effected or a diminution of the disease state is achieved (e.g. reduction in tumor size). Optimal dosing schedules can be calculated from measurements of drug accumulation in the body of the patient. The administering physician can easily determine optimum dosages, dosing methodologies and repetition rates. Optimum dosages can vary depending on the relative potency of individual oligonucleotides, and can generally be estimated based on $EC_{50}$s found to be effective in in vitro and in vivo animal models or based on the examples described herein. In general, dosage is from 0.01 µg to 100 g per kg of body weight, and can be given once or more daily, weekly, monthly or yearly. The treating physician can estimate repetition rates for dosing based on measured residence times and concentrations of the drug in bodily fluids or tissues. Following successful treatment, it can be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

VIII. Transgenic Animals Expressing Cancer Marker Genes

The present invention contemplates the generation of transgenic animals comprising an exogenous cancer marker gene of the present invention or mutants and variants thereof (e.g., truncations or single nucleotide polymorphisms) or knock-outs thereof. In some embodiments, the transgenic animal displays an altered phenotype (e.g., increased or decreased presence of markers) as compared to wild-type animals. Methods for analyzing the presence or absence of such phenotypes include but are not limited to, those disclosed herein. In some embodiments, the transgenic animals further display an increased or decreased growth of tumors or evidence of cancer.

The transgenic animals of the present invention find use in drug (e.g., cancer therapy) screens. In some embodiments, test compounds (e.g., a drug that is suspected of being useful to treat cancer) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al., 1985, PNAS 82:4438-4442). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873, 191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, 1976, PNAS 73:1260). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., 1985, PNAS 82:6927). Transfection is easily and efficiently obtained by culturing the blastomeres on a monolayer of virus-producing cells (Stewart, et al., 1987, EMBO J., 6:383).

Alternatively, infection can be performed at a later stage. Virus or virus-producing cells can be injected into the blastocoele (Jahner et al., 1982, Nature 298:623). Most of the founders will be mosaic for the transgene since incorporation occurs only in a subset of cells that form the transgenic animal. Further, the founder can contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 [1990], and Haskell and Bowen, 1995, Mol. Reprod. Dev., 40:386).

In other embodiments, the transgene is introduced into embryonic stem cells and the transfected stem cells are utilized to form an embryo. ES cells are obtained by culturing pre-implantation embryos in vitro under appropriate conditions (Evans et al., 1981, Nature 292:154; Bradley et al., 1984, Nature 309:255; Gossler et al., 1986, PNAS 83:9065; and Robertson et al., 1986, Nature 322:445). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes can also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science, 1988, 240:1468). Prior to the introduction of transfected ES cells into the blastocoel, the transfected ES cells can be subjected to various selection protocols to enrich for ES cells which have integrated the transgene assuming that the transgene provides a means for such selection. Alternatively, the polymerase chain reaction can be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., truncation mutants). Methods for homologous recombination are described in U.S. Pat. No. 5,614,396, incorporated herein by reference.

Experimental

The following examples are provided in order to demonstrate and further illustrate certain some embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); and ° C. (degrees Centigrade).

EXAMPLE 1

Establishing and Analyzing a Solid Tumor Cell Xenograft Model

This example describes the generation of tumors in mice using human solid tumor cells from humans and the analysis of these tumors.

Materials and Methods

Mouse preparation. 8-week old female NOD-SCID mice were anesthetized by an intra-peritoneal injection of 0.2 ml Ketamine/Xylazine (300 mg Ketamine combined with 20 mg Xylazine in a 4 ml volume. 0.02 ml of the solution was used per 20 g mouse). Dilution to 200 μl was done using HBSS. Mice were then treated with VP-16 (etoposide) via an intra-peritoneal injection (30 mg etoposide dose per 1 kg mouse, diluted in serum-free HBSS for a final injection volume of 200 μl). At the same time, estrogen pellets were placed subcutaneously on the back of the mouse's neck using a trocar. All tumor injections/implants were done 5 days after this procedure. In the following procedures, mice were anesthetized as described above.

Primary tumor specimen implantations. For the implantation of fresh specimens, samples of human breast tumors were received within an hour after surgery. The tumors were cut up with scissors into small pieces, and the pieces were then minced with a blade to yield 2×2 mm-size pieces. Mincing was done in sterile RPMI 1640 medium supplemented with 20% Fetal Bovine Serum (FBS) under sterile conditions on ice. The tumor pieces were washed with serum-free HBSS before implantation. A 2-mm incision was then made in the mid abdomen area, and using a trocar, one to two small tumor pieces were implanted in the region of the upper right and upper left mammary fat pats (right below the second nipple on both sides). A 6-0 suture was wrapped twice around the MFP-Nipple allowing it to hold the implanted pieces in place. Sutures were removed after 5 days. Nexaban was used to seal the incision and mice were monitored weekly for tumor growth.

Pleural effusions injections. For the injection of the pleural effusions, cells were received shortly after thorocentesis and washed with serum-free HBSS. Cells were then suspended in serum free-RPMI/Matrigel mixture (1:1 volume) and then injected into the upper right and left mammary pads using an 18 G needed. 0.2 ml containing 1-2 million cells were typically injected. The site of the needle injection was sealed with Nexaban to prevent any cell leakage.

Preparation of Single Cell Suspensions of Tumor Cells. Prior to Digestion with collagenase, Xenograft tumors or primary human tumors were cut up into small pieces and then minced completely using sterile blades. To obtain single cell suspensions, either pleural effusion cells or the resulting tumor pieces were then mixed with ultra-pure Collagenase III in HBSS solution (200-250 U Collagenase per ml) and allowed to incubate at 37° C. for 3-4 hours. Pipetting with a 10 ml pipette was done every 15-20 minutes. At the end of the incubation, cells were filtered through a 45 μl nylon mesh and washed with RPMI-20% FBS, then washed twice with HBSS. Cells to be injected were then suspended in HBSS/Matrigel mix (1:1 volume) and injected into the area of the mammary fat pad as described above. Nexaban was used to seal the injection site.

Cell staining for flow-cytometry. Cells were counted and then transferred to a 5 ml tube, washed twice with HBSS with 2% Heat-inactivated calf serum (HICS) (5 min @1000 rpm), then re-suspended in 100 μl (per $10^6$ cells) of HBSS with 2% HICS. 5 ml of Sandoglobin solution (1 mg/ml) was then added and incubated on ice for 10 minutes, after which the sample was washed twice with HBSS 2% HICS and re-suspended in 100 ml (per $10^6$ cells) of HBSS 2% HICS. Antibodies (using appropriate dilution per antibody) were then added and incubated for 20 minutes on ice, and then washed twice with HBSS 2% HICS. When needed, a secondary antibody addition was conducted by re-suspending in 100 ul (per $10^6$ cells) of HBSS 2% HICS, and then adding 1-4 ml of secondary antibody (depending on the secondary antibody and its concentration), followed by a 20 minute incubation. When streptavidin was used, cells were re-suspended in 100 ul (per $10^6$ cells) of HBSS 2% HICS and then 1 ul of strepavidin conjugated with the indicated fluorescent dye was added, followed by a 20 minute incubation. The cells were washed twice with HBSS 2% heat-inactivated fetal calf serum (HICS) and re-suspended in 0.5 ml (per million cells) of HBSS 2% HICS that contained 7AAD (1 mg/ml final concentration).

Flow-cytometry. The antibodies used were anti-CD44 (APC, PE or Biotin), anti-CD24 (PE or FITC), anti-B38.1 (APC), anti-ESA-FITC (Biomeda, Calif.), anti-H2K$^d$, (Santa Cruz Products, Santa Cruz, Calif.). Lineage marker antibodies were anti-CD2, -CD3-CD10, -CD16, -CD18, -CD31, -CD64 and -CD140b. Unless noted, antibodies were purchased from Pharmingen (San Diego, Calif.). Antibodies were directly conjugated to various fluorochromes depending on the tests. In all tests, mouse cells and/or Lineage$^+$ cells were eliminated by discarding H2K$^{d+}$ (class I MHC) cells or Lineage$^+$ cells during flow-cytometry. Dead cells were eliminated using the viability dye 7-AAD. Flow-cytometry was performed on a FACSVantage (Becton Dickinson, San Jose, Calif.). Side scatter and forward scatter profiles were used to eliminate cell doublets. Cells were routinely sorted twice and the cells were re-analyzed for purity, which typically was greater than 95%.

In solid tumors, it has been demonstrated that only a small proportion of the tumor cells are able to form colonies in an in vitro clonogenic assay[21-24,101-103] (Southam & Brunschwig, 1961, Cancer 14:971-8; Wodinsky et al., 1967, Cancer Chemother. Rep. 51:415-21; Bergsagel & Valeriote, 1968, Cancer Res 28:2187-96; Fialkow, 1976, Birth Defects Orig. Artic Ser. 12:123-32; Hamburger & Salmon, 1977, Science 197:461-3; Heppner, 1984, Cancer Res. 44:2259-65; Weisenthal & Lippman, 1985, Cancer Treat. Report 69:615-48). Furthermore, large numbers of cells must typically be transplanted to form tumors in xenograft models. One possible explanation for these observations is that every cell within a tumor has the ability to proliferate and form new tumors but that the probability of an individual cell completing the necessary steps in these assays is small. An alternative explanation is that only a rare, phenotypically distinct subset of cells has the capacity to significantly proliferate and form new tumors, but that cells within this subset do so very efficiently (Reya et al., 2001, Nature 414:105-11). To distinguish between these possibilities it is necessary to identify the clonogenic cells in these tumors with markers that distinguish these cells from other non-tumorigenic cells. This has been accomplished in acute myelogenous leukemia (AML), where it was demonstrated that a specific subpopulation of leukemia cells (that expressed markers similar to normal hematopoietic stem cells) was consistently enriched for clonogenic activity in NOD/SCID immunocompromised mice while other cancer cells were depleted of clonogenic activity (Lapidot et al., 1994, Nature 17:645-8; Larochelle et al., 1996, Nat. Med. 2:1329-37; Bonnet & Dick, 1997, Nat. Med. 3:730-7). Such tests have not been reported in solid cancers.

To investigate the mechanisms of solid tumor heterogeneity, a mouse model was developed that was a modification of the NOD/SCID immunodeficient mouse model in which human breast cancers were efficiently propagated in the mouse mammary fat pad (Sakakibara et al., 1996, Cancer J. Si. Am. 2:291-300). In the present application, it was shown that solid tumors contain a distinct population of cells with the exclusive ability to form tumors in mice. These cells are referred to as tumorigenic cells or cancer initiating cells since they consistently formed tumors while other cancer cell populations were depleted of cells capable of tumor formation. Cell surface markers were identified which can distinguish between these cell populations. These findings provide a new model of breast tumor biology in which a defined subset of cells drives tumorigenesis, as well as generating tumor cell heterogeneity. The prospective identification of this tumorigenic population of cancer cells allows for the identification of molecules expressed in these cells that can then serve as targets to eliminate this critical population of cancer cells.

Tumor specimens and engraftment rate. Human breast cancer specimens obtained from primary or metastatic sites in 9 different patients (designated tumors 1-9; T1-T9) all engrafted in the NOD/SCID mice. (Table 1). In one case, the cancer cells were obtained from a primary breast tumor (T2) while in other cases the cells were obtained from metastatic pleural effusions (T1, T3-T9). Some tests were conducted on cells after they had been passaged once or twice in mice (designated Passage 1 & 2) while other tests were conducted on unpassaged fresh or frozen tumor samples obtained directly from patients. When using human cancer cells from tumors passaged in mice, contaminating mouse cells were removed by eliminating H2K$^+$ cells [mouse histocompatability class I (MHC)].

TABLE 1

| Tumor | Origin | Formation In mice | Passage In mice | Diagnosis |
|---|---|---|---|---|
| 1 | Metastasis | Yes | Yes | Infiltrating ductal carcinoma |
| T2 | Breast Primary | Yes | Yes | Adenocarcinoma |
| T3 | Metastasis | Yes | Yes | Invasive lobular carcinoma |
| T4 | Metastasis | Yes | No | Invasive lobular carcinoma |
| T5 | Metastasis | Yes | Yes | Invasive lobular carcinoma |
| T6 | Metastasis | Yes | Yes | Inflammatory breast carcinoma |
| T7 | Metastasis | Yes | Yes | Invasive lobular carcinoma |
| T8 | Metastasis | Yes | Yes | Inflammatory breast carcinoma |
| T9 | Metastasis | Yes | Yes | Adenocarcinoma |

Table 1 presented the results of engraftment of human breast cancers into NOD/SCID mice. Mice were injected with unsorted T1 and T3 cells, and a 2 mm piece of T2. Cells from T4-T9 were isolated by flow cytometry as described in FIG. 1. All 9 tumors tested engrafted in the NOD/SCID mouse model. Except for T2 which was a primary breast tumor, all other tumors were metastases. All of the tumors were passaged serially in mice except for T4.

Identification of tumorigenicity markers. Breast cancer cells were heterogeneous with respect to expression of a variety of cell surface-markers including CD44, CD24, and B38.1. CD24 and CD44 are adhesion molecules, while B38.1 has been described as a breast/ovarian cancer-specific marker (Kufe et al., 1983, Cancer Res. 43:851-7; Uchida et al., 2000, PNAS 97:14720-5; Ahrens et al., 2001, Oncogene 20). To determine whether these markers could distinguish tumorigenic from non-tumorigenic cells, flow-cytometry was used to isolate cells that were positive or negative for each marker from first passage T1 or T2 cells. When $2\times10^5$-$8\times10^5$ cells of each population were injected, all injections of CD44$^+$ cells (8/8), B38.1$^+$ cells (8/8), or CD24$^{-/low}$ cells (12/12) gave rise to visible tumors within 12 weeks of injection, but none of the CD44$^-$ cell (0/8), or B38.1$^-$ cell (0/8) injections formed detectable tumors (Table 2). Although no tumors could be detected by palpation in the locations injected with CD24$^+$ cells, 2 of 12 mice injected with CD24+ cells did contain small growths at the injection site that were detected upon necropsy. These growths most likely arose from the 1-3% of CD24− cells that invariably contaminate the sorted CD24+ cells, or alternatively from CD24+ cells with reduced proliferative capacity (Table 2). Because the CD44+ cells were exclusively B38.1+, we focused on the CD44 and CD24 markers in subsequent tests.

Figure 6:
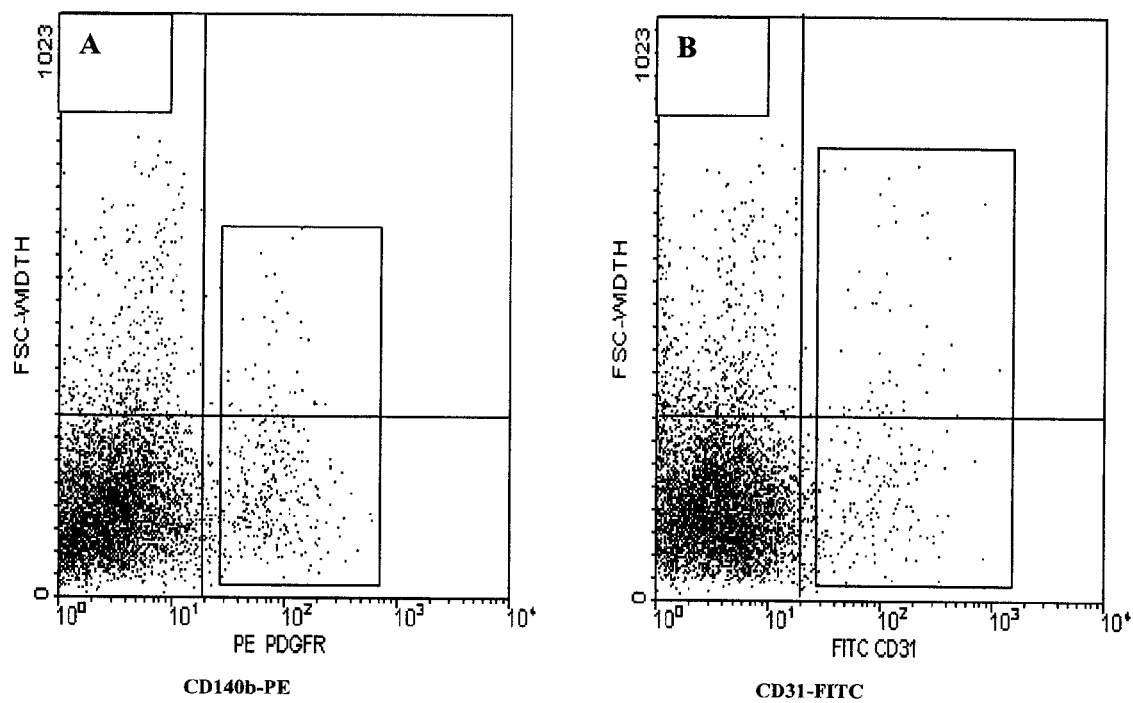
FIG. 6 shows the isolation of normal tumor fibroblasts and endothelial cells.

Several antigens associated with normal cell types (Lineage markers; CD2, CD3, CD10, CD16, CD18, CD31, CD64, and CD140b) were found not to be expressed by the cancer cells based on analyses of tumors that had been passaged multiple times in mice. By eliminating Lineage+ cells from unpassaged or early passage tumor cells, normal human leukocytes, endothelial cells, mesothelial cells and fibroblasts were eliminated. By microscopic examination, the Lineage− tumor cells had the appearance of neoplastic cells (FIG. 6).

Table 2 shows the results of cells isolated by flow cytometry as described in FIG. 1 based upon expression of the indicated marker and assayed for the ability to form tumors after injection into the mammary fat pads of NOD/SCID mice. For 12 weeks, mice were examined weekly for tumors by observation and palpation, then all mice were necropsied to look for growths at injection sites that were too small to palpate. The number of tumors that formed/the number of injections that were performed is indicated for each population. All tumors were readily apparent by visual inspection and palpation except for tumors from the CD24+ population that were only detected upon necropsy.

Depending on the tumor, 11% to 35% of the Lineage− cancer cells in tumors or pleural effusions were CD44+ CD24$^{-/low}$ (FIG. 4a-1f). CD44+CD24$^{-/low}$ Lineage− cells or other populations of Lineage− cancer cells that had been isolated from nine patients were injected into the mammary fat pads of mice (Table 3). When injecting unsorted, passaged T1 or T2 cells, $5\times10^4$ cells consistently gave rise to tumors, but $10^4$ cells gave rise to tumors in only a minority of cases. In contrast, as few as $10^3$ T1 or T2 CD44+CD24$^{-/low}$ Lineage− cells gave rise to tumors in all cases (Table 3). In T1 and T2, up to $2\times10^4$ cells that were CD44+Lineage− but CD24+ failed to form tumors. These data suggest that the CD44+CD24$^{-/low}$ Lineage− population is 10-50 fold enriched for the ability to form tumors in NOD/SCID mice relative to unfractionated tumor cells. Whether the CD44+CD24$^{-/low}$Lineage− cells were isolated from passaged tumors (T1, T2, T3) or from unpassaged cancer cells obtained directly from patients (T1, T4-T6, T8, T9), they were enriched for tumorigenic activity. Note that T7 was the only one of 9 cancers studied that did not fit this pattern (FIG. 4f). Other than T7, CD24+Lineage− cancer cells in both unpassaged and passaged tumors were unable to form new tumors (Table 3). Therefore, the xenograft and unpassaged patient tumors were composed of similar populations of phenotypically diverse cancer cell types, and in both cases only the CD44+CD24$^{-/low}$Lineage− cells had the capacity to proliferate to form new tumors (p<0.001).

TABLE 2

| | Tumors/Injections | | |
|---|---|---|---|
| Cells/Injection | $8\times10^5$ | $5\times10^5$ | $2\times10^5$ |
| Passsaged T1 | | | |
| CD44− | 0/2 | 0/2 | — |
| CD44+ | 2/2 | 2/2 | — |
| B38.1− | 0/2 | 0/2 | — |
| B38.1+ | 2/2 | 2/2 | — |
| CD24+ | — | — | 1/6 |
| CD24− | — | — | 6/6 |
| Passaged T2 | | | |
| CD44− | 0/2 | 0/2 | — |
| CD44+ | 2/2 | 2/2 | — |
| B38.1− | 0/2 | 0/2 | — |
| B38.1+ | 2/2 | 2/2 | — |
| CD24+ | — | — | 1/6 |
| CD24− | — | — | 6/6 |

TABLE 3

| # of cells per injection | $5\times10^5$ | $10^5$ | $5\times10^4$ | $2\times10^4$ | $10^4$ | $5\times10^3$ | $10^3$ | 500 | 200 | 100 |
|---|---|---|---|---|---|---|---|---|---|---|
| Mouse passage 1 | | | | | | | | | | |
| Unsorted | 8/8 | 8/8 | 10/10 | | 3/12 | | 0/12 | | | |
| CD44+CD24+ | | | | 0/10 | 0/10 | 0/14 | 0/10 | | | |
| CD44+CD24$^{-/low}$ | | | 10/10 | 10/10 | 14/14 | 10/10 | | | | |
| CD44+CD24$^{-/low}$ ESA+ | | | | | | | 10/10* | 4/4 | 4/4 | 1/6 |
| CD44+CD24$^{-/low}$ ESA− | | | | | | | 0/10* | 0/4 | 0/4 | 0/6 |
| Mouse passage 2 | | | | | | | | | | |
| CD44+CD24+ | | | | | 0/9 | | | | | |
| CD44+CD24$^{-/low}$ | | | | | 9/9 | | | | | |
| Patients' tumor cells | | | | | | | | | | |
| CD44+CD24+ | | 0/3 | 0/4 | 0/8 | 1/13 | 0/2 | | | | |
| CD44+CD24$^{-/low}$ | | 3/3 | 4/4 | | 11/13 | 1/1 | | | | |
| CD44+CD24$^{-/low}$ ESA+ | | | | | | | 2/2 | 2/2 | | |
| CD44+CD24$^{-/low}$ ESA− | | | | | | | 2/2# | 0/2 | | |

As shown in Table 3, tumorigenic breast cancer cells were highly enriched in the ESA+CD44+CD24−/low population. Cells were isolated from first passage (designated Mouse Passage 1) Tumor 1, Tumor 2 and Tumor 3, second passage Tumor 3 (designated mouse Passage 2), unpassaged cells obtained from 6 different patients, T1, T4, T5, T6, T8 and T9, (designated Patients' tumor cells). CD44+CD24+Lineage− populations and CD44+CD24−/lowLineage− cells were isolated by flow-cytometry as described in FIG. 1. The indicated number of cells of each phenotype was injected into the breast of NOD/SCID mice. The frequency of tumorigenic cells calculated by the modified maximum likelihood analysis method is ~$5/10^5$ if single tumorigenic cells were capable of forming tumors, and every transplanted tumorigenic cell gave rise to a tumor (Porter & Berry, 1964, Br. J. Cancer 17). Therefore, this calculation can underestimate the frequency of the tumorigenic cells since it does not take into account cell-cell interactions and local environment factors that can influence engraftment. In addition to the markers that are shown, all sorted cells in all tests were Lineage−, and the tumorigenic cells from T1, T2, and T3 were further selected as B38.1+. The mice were observed weekly for 4-6½ months, or until the mice became sick from the tumors. #Tumor formation by T5 ESA-CD44+CD24−/lowLINEAGE− cells was delayed by 2-4 weeks. *2,000 cells were injected in these tests.

FIG. 1 shows isolation of tumorigenic cells. Flow cytometry was used to isolate subpopulations of Tumor 1 (a, b), Tumor 3 (c), Tumor 5 (d), Tumor 6 (e) and Tumor 7 cells (f) that were tested for tumorigenicity in NOD/SCID mice. T1 (b) and T3 (c) had been passaged (P) once in NOD/SCID mice while the rest of the cells were frozen or unfrozen samples obtained directly after removal from a patient (UP). Cells were stained with antibodies against CD44, CD24, Lineage markers, and mouse-H2K (for passaged tumors obtained from mice), and 7AAD. Dead cells (7AAD+), mouse cells (H2K+) and Lineage+ normal cells were eliminated from all analyses. Each plot in FIG. 1 depicts the CD24 and CD44 staining patterns of live human Lineage− cancer cells, and the frequency of the boxed tumorigenic cancer population as a percentage of cancer cells/all cells in each specimen is shown.

In three of the tumors, further enrichment of tumorigenic activity was possible by isolating the ESA+ subset of the CD44+CD24−/low population. ESA (Epithelial Specific Antigen, Ep-CAM) has been used in the past to distinguish epithelial cancer cells from benign reactive mesothelial cells (Packeisen et al., 1999, Hybridoma 18:37-40). When ESA+CD44+CD24−/lowLineage− cells were isolated from passaged T1, as few as 200 cells consistently formed tumors of approximately 1 cm about 5-6 months after injection whereas 2000 ESA−CD44+CD24−/lowLineage− cells or 20,000 CD44+CD24+ cells always failed to form tumors (Table 3). Ten thousand unsorted cells formed tumors in only 3 of 12 mice. This suggests that the ESA+CD44+CD24−/lowLineage− population was more than 50 fold enriched for the ability to form tumors relative to unfractionated tumor cells (Table 3). The ESA+CD44+CD24−/lowLineage− population accounted for 2-4% of first passage T1 cells (2.5-5% of cancer cells). The ESA+CD44+CD24−/lowLineage− population (0.6% of cancer cells) from unpassaged T5 cells was also enriched for tumorigenic activity compared to ESA− CD44+CD24−/lowLineage− cells, but both the ESA+ and ESA− fractions had some tumorigenic activity (Table 3). Among unpassaged T5 cells, as few as 1000 ESA+CD44+CD24−/lowLineage− cells consistently formed tumors.

In order to determine whether the difference in tumorigenicity of the cell populations was due to differences in cell cycle, populations were analyzed by flow-cytometry. Comparison of the cell cycle status of tumorigenic and non-tumorigenic cancer cells from T1 revealed that both exhibited a similar cell cycle distribution (FIGS. 2a, 2b). Therefore, neither population was enriched for cells at a particular stage of the cell-cycle, and the non-tumorigenic cells were able to undergo at least a limited number of divisions in the xenograft model.

Figure 2:
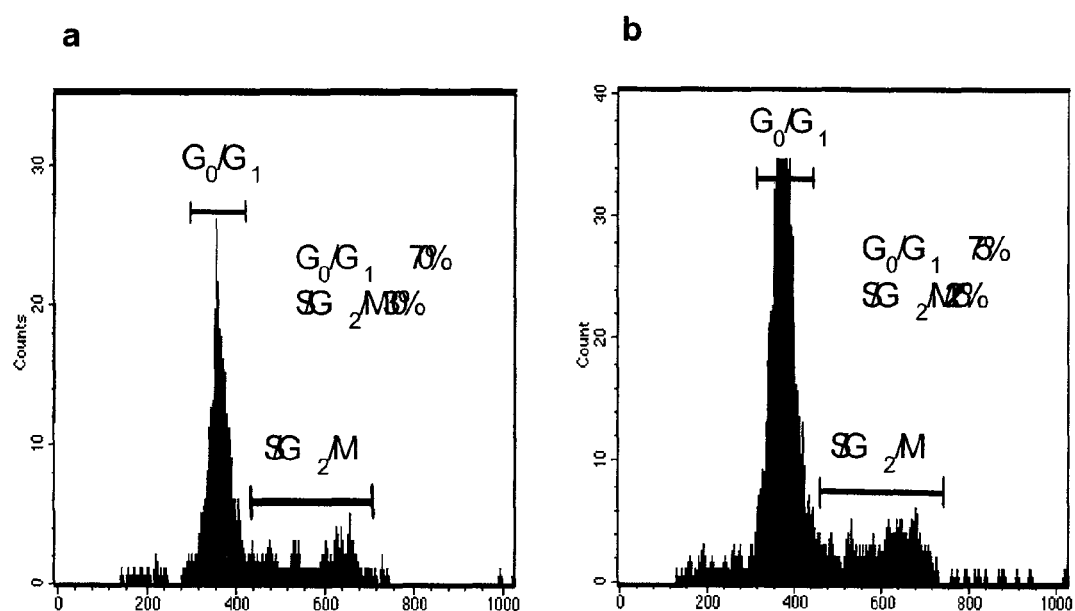
FIG. 2 shows the DNA content of tumorigenic and non-tumorigenic breast cancer cells.

FIG. 2 shows the DNA content of tumorigenic and non-tumorigenic breast cancer cells. The cell cycle status of the ESA+CD44+CD24−/lowLineage− tumorigenic cells (a) and the remaining Lineage− non-tumorigenic cancer cells (b) isolated from T1 were determined by hoechst 33342 staining of DNA content (20). The tumorigenic and non-tumorigenic cell populations exhibited similar cell cycle distributions Six months after inoculation, the injection sites of 20,000 tumorigenic CD44+CD24−/lowLineage− cells and 20,000 CD44+CD24+Lineage− cells were examined by histology. The CD44+CD24−/lowLineage− injection sites contained tumors approximately 1 cm in diameter while the CD44+CD24+Lineage− injection sites contained no detectable tumors (FIG. 6c). Only normal mouse mammary tissue was seen by histology at the sites of the CD44+CD24+Lineage− injections (FIG. 3a), whereas the tumors formed the CD44+CD24−/lowLineage− cells contained malignant cells as judged by hematoxylin and eosin stained sections (FIG. 3b). Even when CD44+CD24+Lineage− injection sites from 58 mice, each administered 1,000-50,000 cells, were examined after 16-29 weeks, no tumors were detected. Furthermore, the tumorigenic and non-tumorigenic populations were indistinguishable morphologically. Both the tumorigenic and non-tumorigenic subsets of Lineage− cells from passaged and unpassaged tumors contained >95% cancer cells as judged by Wright staining or Papanicolaou staining and microscopic analysis. By histology, the CD44+CD24−/lowLineage− cells and the rest of the Lineage− cells had the appearances of epithelial cancer cells (FIGS. 3d, 3e).

Figure 3:
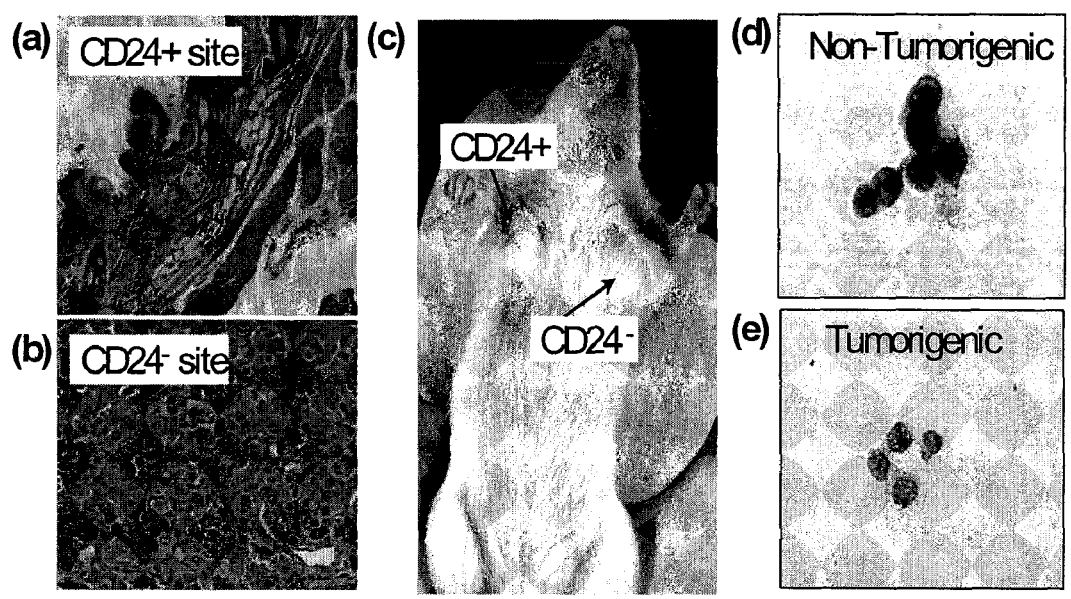
FIG. 3 shows histology from the $CD24^+$ injection site (a), (20× objective magnification) revealed only normal mouse tissue while the $CD24^{-/low}$ injection site (b), (40× objective magnification) contained malignant cells. (c) A representative tumor in a mouse at the $CD44^+CD24^{-/low}$ Lineage$^-$ injection site, but not at the $CD44^+CD24^+$Lineage$^-$ injection site. T3 cells were stained with Papanicolaou stain and examined microscopically (100× objective). Both the non-tumorigenic (c) and tumorigenic (d) populations contained cells with a neoplastic appearance, with large nuclei and prominent nucleoli.

FIG. 3 shows histology from the CD24+ injection site (a), (20× objective magnification) revealed only normal mouse tissue while the CD24−/low injection site (b), (40× objective magnification) contained malignant cells. (c) A representative tumor in a mouse at the CD44+CD24−/lowLineage− injection site, but not at the CD44+CD24+Lineage− injection site. T3 cells were stained with Papanicolaou stain and examined microscopically (100× objective). Both the non-tumorigenic (c) and tumorigenic (d) populations contained cells with a neoplastic appearance, with large nuclei and prominent nucleoli.

The tumorigenic population is capable of generating the phenotypic heterogeneity found in the initial tumor. The ability of small numbers of CD44+CD24−/lowLineage− tumorigenic cells to give rise to new tumors was reminiscent of the organogenic capacity of normal stem cells. Normal stem cells self-renew and give rise to phenotypically diverse cells with reduced proliferative potential. To test whether tumorigenic breast cancer cells also exhibit these properties, tumors arising from 200 ESA+CD44+CD24−/lowLineage− T1 or 1,000 CD44+CD24−/lowLineage− T2 cells were dissociated and analyzed by flow-cytometry. The heterogeneous expression patterns of ESA, CD44 or CD24 in the secondary tumors resembled the phenotypic complexity of the tumors from which they were derived (FIGS. 7a,7b vs 7e,7f). Within these secondary tumors, the CD44+CD24−/lowLineage− cells remained tumorigenic, while other populations of Lineage− cancer cells remained non-tumorigenic (Table 3). Thus tumorigenic cells gave rise to both additional CD44+CD24−/low−Lineage− tumorigenic cells as well as to phenotypically diverse non-tumorigenic cells that recapitulated the complexity of the primary tumors from which the tumorigenic cells had been derived. These CD44$^+$CD24$^{-/low}$Lineage$^-$ tumorigenic cells from T1, T2 and T3 have now been serially passaged through four rounds of tumor formation in mice, yielding similar results in each passage with no evidence of decreased tumorigenicity. These observations suggest that CD44$^+$CD24$^{-/low}$Lineage$^-$ tumorigenic cancer cells undergo processes analogous to the self-renewal and differentiation of normal stem cells.

Figure 4:
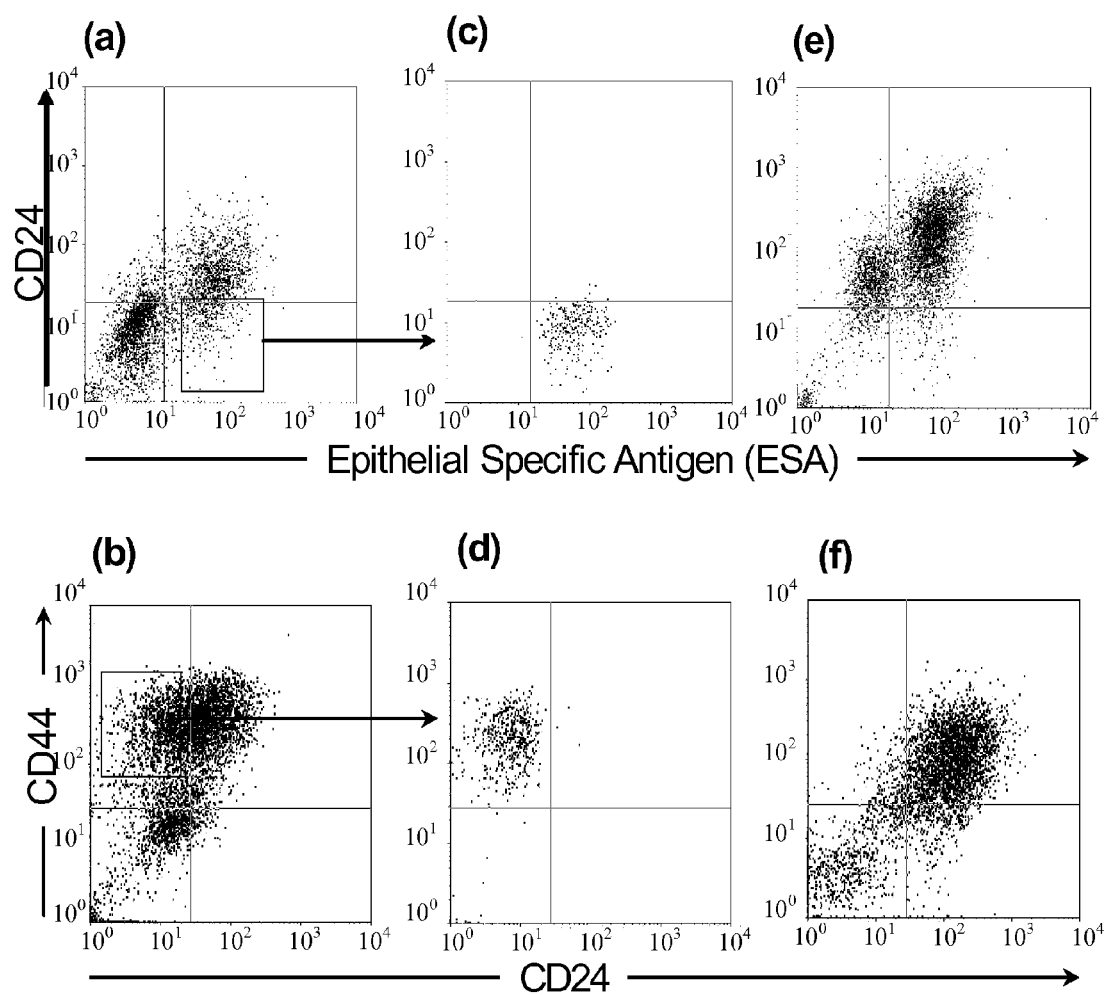
FIG. 4 shows the phenotypic diversity in tumors arising from CD44+CD24−/lowLineage− cells.

FIG. 4 shows the phenotypic diversity in tumors arising from CD44+CD24−/lowLineage− cells. The plots depict the CD24 and CD44 or ESA staining patterns of live human Lineage− cancer cells from Tumor 1 (a, c and e) or Tumor 2 (b, d and f). T1 CD44+Lineage− cells (a) or T2 Lineage− cells (b) were obtained from tumors that had been passaged once in NOD/SCID mice. ESA+CD44+CD24−/lowLineage− tumorigenic cells from T1 (c) or CD44+CD24−/lowLineage− tumorigenic cells from T2 (d) were isolated and injected into the breasts of NOD/SCID mice. Panels (e) and (f) depict analyses of the tumors that arose from these cells. In both cases, the tumorigenic cells formed tumors that contained phenotypically diverse cells similar to those observed in the original tumor.

Figure 5:
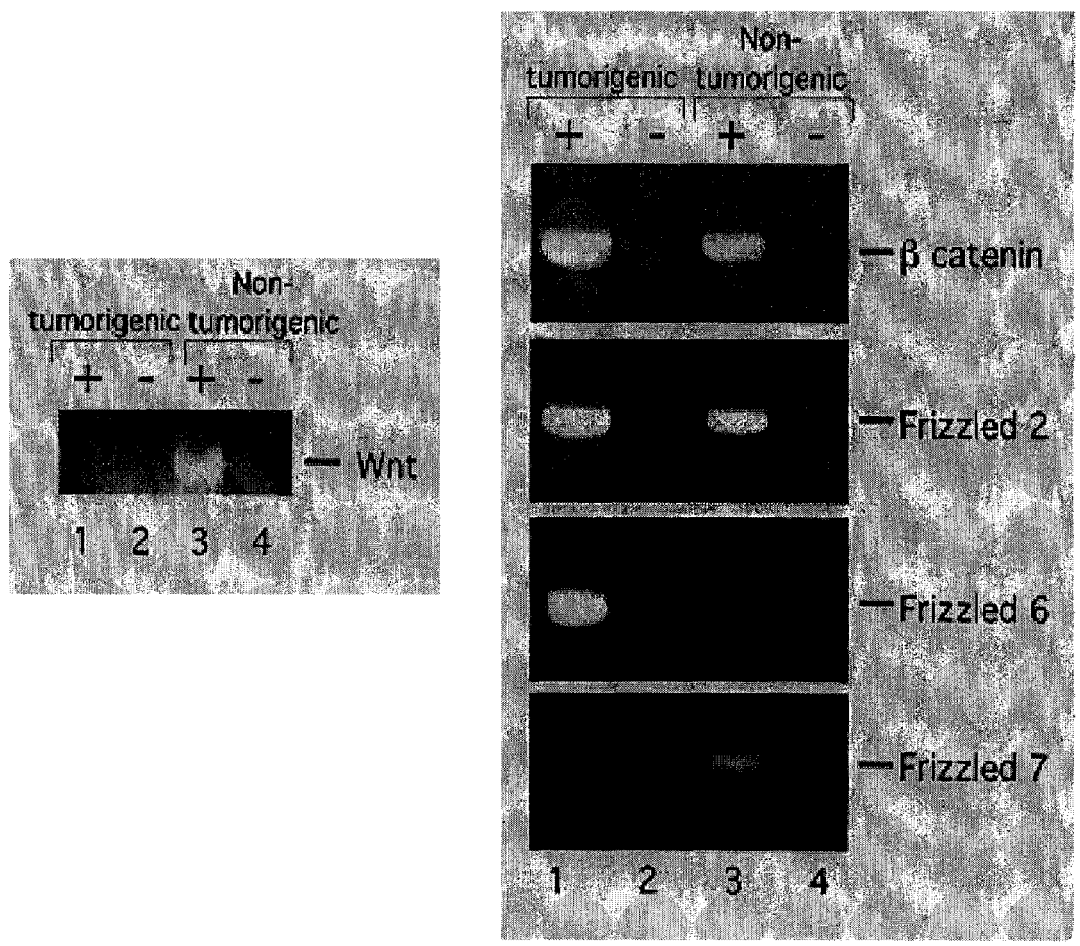
FIG. 5 shows the expression of Wnt (left panel) and Frizzled (right panel).

Expression of Wnt pathway genes in subpopulations of breast cancer tumor cells. The Frizzled proteins are receptors for the growth/survival factors of the Wnt family. In some normal stem cells, Wnt is known to play a role in proliferation, survival and differentiation. In certain situations, stimulation of Wnt can promote stem cell self-renewal. Upon activation, Wnt induces the stabilization of β-catenin. Flow cytometry using an antibody against β-catenin demonstrates that Tumor 1 cells express this protein (FIG. 5). Immunohistochemistry shows that the β-catenin is located in the cytoplasm and the nucleus, indicating that the protein is active (data not shown). Different Wnt proteins specifically activate different frizzled receptors (Taipale & Beachy, 2001, Nature, 411:349). Since the Wnt signaling pathway appears to play a critical role in proliferation of both normal and breast cancer cell proliferation, the expression of Wnt pathway genes in Tumor 1 tumorigenic cells and non-tumorigenic cells was examined (FIG. 5). To do this, one hundred ESA$^+$B38.1$^+$ CD24$^{-/lo}$LINEAGE$^-$ (tumorigenic) or non-tumorigenic tumor cells were isolated. RT-PCR using nested primers for each of the frizzled proteins was done. These results demonstrate that the tumorigenic cells expressed frizzled 2 and 6, while the non-tumorigenic cells expressed frizzled 2 and 7 (FIG. 5). These tests have been repeated twice with identical results. Next, members of the Wnt family expressed by the breast cancer cells were identified. RNA was isolated from 10,000 stem and non-tumorigenic cells. There are more than 20 known members of the Wnt family, making it difficult to analyze expression of particular Wnts in breast cancer tumors. Therefore RT-PCR was performed using degenerate primers that recognize all known Wnt genes and cloned and sequenced the resultant cDNA. Surprisingly, we were able to detect expression of cDNA only by the non-tumorigenic cells (FIG. 5). This was confirmed doing RT-PCR at the ten-cell level. Frizzled 6 expression was detected in nine of ten tumorigenic samples, and only one of ten non-tumorigenic cell samples. The cDNA was cloned, and sequencing revealed that these cells expressed Wnt 3A, 4, 7A, 7B, 10B, and 11. Wnt signals have been implicated in the growth of both breast cancer cells and normal endothelial cells. While not necessary to understand to practice the present invention, this suggests that the non-tumorigenic cells promote tumor formation both by stimulation of breast cancer stem cells and vessel formation via the Wnt pathway. This model fits very well with known observations that it is much easier to grow breast cancers using pieces of tissue as opposed to individual cells (Bergsagel & Valeriote, 1968, Cancer Res. 28:2187-96).

FIG. 5 shows the expression of Wnt (left panel) and Frizzled (right panel). In regard to the left panel, RT-PCR was done using degenerate Wnt primers with RNA isolated from 10,000 cells of the indicated type. + or − indicates whether RT was used. Right panel. RNA was isolated from one hundred breast cancer cells or breast cancer stem cells isolated by flow cytometry as described in FIG. 1. RT-PCR was done using nested primers to detect the indicated mRNA. Control RT-PCR reactions omitting RT were negative.

To confirm the RT-PCR results for the expression of frizzled proteins, an Affymetrix microarray was probed with cDNA made from Tumor 1, Tumor 2 and Tumor 3 cancer stem cells. All three tumors expressed Frizzled 2 & 6. In addition, Tumors 2 & 3 appeared to express frizzled 4.

Isolation of normal cells from a tumor. Efforts were then made to determine whether sufficient normal cells could be isolated from a tumor to do molecular studies with these cells. Normal fibroblast and endothelial cells from a patient's tumor (approximately 3 cm in size) were isolated by flow cytometry. 2% of the tumor cells were CD31$^+$ endothelial cells and 8% were CD140b$^+$ fibroblasts (FIG. 6). Nine thousand fibroblasts and two thousand endothelial cells were collected when 1/45 of the tumor was used for flow cytometry. By extrapolation, it would have been possible to isolate approximately 90,000 endothelial cells and 405,000 fibroblasts from the entire tumor.

FIG. 6 shows the isolation of normal tumor fibroblasts and endothelial cells. Tumors were dissociated as described in the methods section and tumor cells were stained with cytochrome labeled with antibodies against -CD2, -CD3, -CD16, -CD18, -CD45, -CD64, and anti-B38.1-APC (to eliminate hematopoietic cells and tumor cells respectively), anti-CD140b-PE and anti-CD31-FITC. A: the box shows the sorting gate for fibroblasts, which are Lineage$^-$ CD31$^-$ CD140b$^+$ cells. B: the box shows the sorting gate for endothelial cells, which are CD31$^+$ Lineage$^-$ cells.

Figure 7:
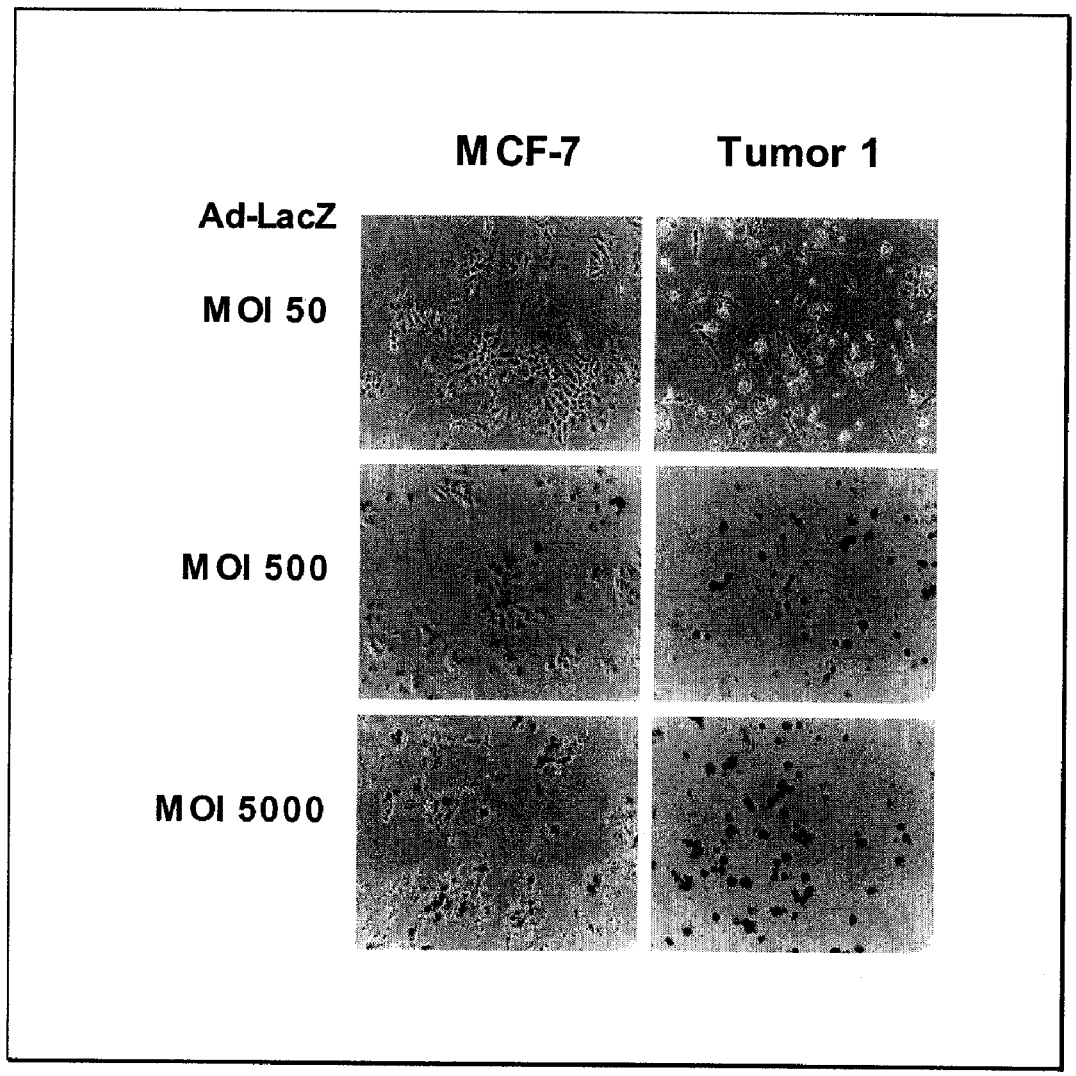
FIG. 7 shows infection of breast cancer stem cells with an adenovirus vector.

Infection of breast cancer stem cells with an adenovirus vector. Since the xenograft tumors can only be grown briefly in tissue culture, conventional transfection methods are generally not useful for gene expression studies and only viral vectors have the potential to efficiently transduce the breast cancer stem cells. Therefore, the ability of adenovirus vectors to infect T1 breast cancer stem cells was tested. To do this, groups of 10,000 breast cancer stem cells or control MCF-7 cells were infected with 0, 50, 500, or 5,000 LacZ adenovirus particles. FIG. 7 shows that we could easily transduce greater than 90% of the stem cells and they were more easily infected with the adenovirus vector than were the control MCF-7 cells. This demonstrates that we can use adenovirus vectors to transduce the stem cells with recombinant genes.

FIG. 7 shows infection of breast cancer stem cells with an adenovirus vector. Flow cytometry was used to isolate CD44$^+$ CD24$^{-/low}$Lineage$^-$ cells. The Tumor 1 stem cells or control MCF-7 cells were infected with 0, or 500, or 5,000 LacZ adenovirus particle/cell. Two days later, the cells were stained with X-gal. Note that the Tumor 1 stem cells were easily infected by the adenovirus vector.

The following data is a description of work that has been done studying hematopoietic stem cells. It illustrates fundamental stem cell properties, and it also demonstrates how the isolation of stem cells enables one to first characterize these cells and then to do molecular and biochemical studies to functionally characterize them.

Adult stem cell numbers are strictly regulated. The regulation of hematopoietic stem cell (HSC) homeostasis is not well understood. We screened for genetic polymorphisms that were linked to differences between mouse strains in the numbers of long-term reconstituting HSCs or restricted progenitors in the bone marrow. AKR/J mice had significantly higher frequencies and numbers of both HSCs and restricted progenitors in their bone marrow than C57BL/Ka-Thy-1.1 mice. The C57BL/Ka-Thy-1.1 alleles were partially dominant. A locus on chromosome 17, including the H-2 complex, was significantly linked to the frequency of long-term self-renewing HSCs but showed no evidence of linkage to the frequency of restricted progenitors. Conversely, a chromosome 1 locus exhibited suggestive linkage to restricted progenitor frequencies but was not linked to HSC frequency. This demonstrates that there are distinct genetic determinants of the frequencies of HSCs and restricted progenitors in vivo. The AKR/J chromosome 17 locus was not sufficient to increase HSC frequencies when bred onto a C57BL background. This suggests that to affect HSC frequencies, the product(s) of this locus likely depend on interactions with unlinked modifying loci. The present invention demonstrates that stem cell expansion is under tight genetic regulation in an animal.

Genomic analysis of hematopoietic stem cells. Hematopoietic stem cells (HSCs) have self-renewal capacity and multilineage developmental potentials. The molecular mechanisms that control the self-renewal of HSCs are still largely unknown. A systematic approach using bioinformatics and array hybridization techniques to analyze gene expression profiles in HSCs was done. To enrich mRNAs predominantly expressed in uncommitted cell lineages, 54 000 cDNA clones generated from a highly enriched population of HSCs and a mixed population of stem and early multipotent progenitor (MPP) cells were arrayed on nylon membranes (macroarray or high-density array), and subtracted with cDNA probes derived from mature lineage cells including spleen, thymus, and bone marrow. Five thousand cDNA clones with very low hybridization signals were selected for sequencing and further analysis using microarrays on glass slides. Two populations of cells, HSCs and MPP cells, were compared for differential gene expression using microarray analysis. HSCs have the ability to self-renew, while MPP cells have lost the capacity for self-renewal. A large number of genes that were differentially expressed by enriched populations of HSCs and MPP cells were identified. These included transcription factors, signaling molecules, and previously unknown genes.

Bmi-1 is required for HSC self-renewal. The gene expression analysis of HSCs allowed us to identify genes potentially important for self-renewal. After analysis of the gene expression data, we began mechanistic studies to identify important stem cell regulatory genes. A central issue in stem cell biology is to understand the mechanisms that regulate self-renewal of HSCs, which is required for hematopoiesis to persist for the lifetime of the animal. We found that adult and E14.5 fetal mouse and adult human hematopoietic stem cells express the proto-oncogene bmi-1. The number of fetal liver HSCs, as measured by flow cytometry, was normal in loss of function bmi-1 mice, and the bmi-1$^{-/-}$ HSCs were able to migrate normally towards a chemokine gradient. In post-natal bmi-1$^{-/-}$ mice, the number of HSCs, but not early progenitor cells was markedly reduced. Both fetal liver and bone marrow cells obtained from bmi-1$^{-/-}$ mice were able to contribute only transiently to hematopoiesis when transplanted into lethally irradiated recipients. There was no detectable self-renewal of adult hematopoietic stem cells, indicating a cell autonomous defect in bmi-1$^{-/-}$ mice. This study indicates that expression of bmi-1 is essential for the generation of self-renewing adult hematopoietic stem cells. See the manuscript by Park et al., "Bmi-1 is required for maintenance of adult self-renewing hematopoietic stem cells" Nature (2003).

Summary: The xenograft model developed by this laboratory has made possible the analysis of human breast cancer cells at the cellular level. Although cancer cell lines have proven useful for many studies, the cell lines are adapted to the unique conditions imposed by tissue culture and many of their properties clearly differ from the cancer cells in patients' tumors (Porter & Berry, 1964, Br. J. Cancer 17; Brown, 1997, Oncol. Res. 9:213-5). Recently, the size of primary breast cancer tumors prior to resection has markedly decreased. This has made biological and biochemical studies using patient samples difficult. It is contemplated that the xenograft model described in the preliminary results ameliorates this problem. Preliminary results suggest that the xenograft tumors appear to recapitulate the phenotypic and biological diversity seen in the original patients' tumors. Although there can be some differences in the mouse and human tumors due to environmental factors, the NOD/SCID model described here is the best available model of human breast cancer. Results demonstrate that breast cancer cells reliably engraft in this xenograft model and in the early passages reflect the cellular and biological diversity found in the original human tumor. These tests also show that different populations of cancer cells can differ in their ability to form tumors.

EXAMPLE 2

Characterizing the Wnt/β-catenin Pathway in Human Breast Cancer Tumors Using Systems and Methods of the Present Invention This Example provides illustrative screening methods using the systems and methods of the present invention. This example describes, for example, how one could characterize the Wnt/β-catenin pathway in human breast cancer tumors using the xenograft model described above. The Wnt/β-catenin pathway plays a role in the proliferation and self-renewal of normal stem cells. Although a significant percentage of human breast cancers appear to have constitutive activation of this critical pathway, unlike colon cancer, it has not been definitively established what role this pathway plays in the pathology of this disease in humans (Candidus et al., 1996, Cancer Res. 56:49-52; Sorlie et al., 1998, Hum. Mutat. 12:215; Jonsson et al., 2000, Eur. J. Cancer 36:242-8; Schlosshauer et al., 2000, Carcinogenesis 21:1453-6; Lin et al., 2000, PNAS 97:4262-6; Wong et al., 2002, J. Pathol. 196: 145-53). The xenograft model described above can be used to characterize the biological consequences of this pathway in human breast cancer tumors. These tests are done using cancer cells directly after removal from patients and early passage xenograft tumors.

The function of the Wnt/frizzled/β-catenin signaling pathway in multiple patients' tumors. Rationale: Almost 90% of colon cancers contain mutations that result in activation of β-catenin. The most common mutations are in the APC gene, which is involved in targeting β-catenin for degradation, or mutations in the β-catenin protein itself (Webster et al., 2000, Genes Chromosomes Cancer 28:443-53; Taiple & Beachy, 2001, Nature 411:349-54). These latter mutations prevent degradation. Although the cancer cells in many breast tumors appear to have constitutively active of β-catenin, in contrast to colon cancer, mutations in the APC gene or β-catenin itself account for only 6-10% of these cases (Candidus et al., 1996, Cancer Res. 56:49-52; Sorlie et al., 1998, Hum. Mutat.

12:215; Jonsson et al., 2000, Eur. J. Cancer 36:242-8; Schlosshauer et al., 2000, Carcinogenesis 21:1453-6; Lin et al., 2000, PNAS 97:4262-6; Wong et al., 2002, J. Pathol. 196: 145-53). Examination of the Wnt/β-catenin signaling pathway in breast cancer cells should lead to new insights into the pathogenesis of this disease. There are a large number of Wnt proteins that are thought to differentially bind to different Frizzled receptors (Nusse et al., 1991, Cell 64:231; Nusse, 1992, J. Steroid Biochem. Mol. Biol. 43:9-12; Cadigan & Nusse, 1997, Genes & Dev. 11:3286-305; Nusse, 1999, Trends Genet. 15:1-3; Taiple & Beachy, 2001, Nature 411: 349-54). Only a subset of Wnts, and by inference Frizzled receptors, can activate β-catenin. Normally, β-catenin is bound to E-cadherin at the cell membrane. Cytoplasmic β-catenin forms a complex with the APC and Axin proteins and facilitates β-catenin phosphorylation by GSK3β (Sorlie et al., 1998, Hum. Mutat 12:215; Jonsson et al., 2000, Eur. J. Cancer 36:242-8; Webster et al., 2000, Genes Chromosomes Cancer 28:443-53). The phosphorylated β-catenin is then degraded via the ubiquitin degradation pathway. However, upon activation of frizzled receptors by a Wnt, β-catenin is stabilized. The protein then translocates to the nucleus where it forms a complex with the LGLS/BCL9, PYGO and TCF proteins to activate transcription (Korinek et al., 1998, Mol. Cell. Biol. 18:1248-56; Kramps et al., 2002, Cell 109:47-60). We believe that our xenograft model and cellular assays are unique and powerful tools for understanding this critical pathway. We analyze 10 tumors that have constitutive β-catenin signaling and 10 that do not. These studies give new insights into the mechanisms by which the Wnt pathway is activated and the consequences of this activation in human breast cancer.

In mice, ectopic expression of various Wnt proteins results in breast tumor formation, while in humans activated β-catenin in breast cancer cells is associated with expression of cyclin D1 and poor prognosis (Nusse & Varmus, 1982, Cell 31:99-109; Nusse, 1991, Curr. Topics Microbiol. Immunol. 171:43-65; Nusse, 1992, J. Steroid Biochem. Mol Biol. 43:9-12; Lin et al., 2000, PNAS 97:4262-6). However, it is not known whether continuous β-catenin signaling is necessary for tumorigenic breast cancer cells to form tumors. There are several possible roles that constitutive β-catenin signaling can play in human breast cancer. First, it can be necessary for continued proliferation and/or viability of the tumorigenic cancer cells. Next, it can be necessary for the initiation of the tumor, but subsequent mutations bypass the need for β-catenin signaling. Third, it can make the cancer cells more resistant to chemotherapy due to the activation of downstream targets such as cyclin D1. Fourth, constitutive β-catenin signaling accelerates cancer cell growth, but is not necessary for tumorigenicity. Finally, the role of β-catenin signaling in tumor formation might differ in tumors with and without constitutive activation of β-catenin. For example, the former tumors might require β-catenin signaling whereas the latter tumors might require Wnt signals from other tumor cells or they might be independent of β-catenin because they have constitutive activation of downstream targets such as c-myc and/or cyclin D1. The tests described here are designed to distinguish between these possibilities using a novel xenograft model of human cancer. The data shows that the xenograft model virtually recapitulates a human breast tumor. Thus, this model allows us to study the Wnt pathway in de novo human tumors in as physiological conditions as possible.

Is β-catenin signaling required for tumor formation by cancer cells isolated from multiple patients? The tests here determine whether the β-catenin pathway is obligate for breast cancer cell growth or whether activation is not required for tumor formation but does increase the rate of proliferation of the cancer cells. Although the xenograft tumors appear to closely resemble human tumors, over time selection pressure result in tumors that are adapted to the mouse environment. The cancer cells in such tumors differ in some ways with the cancer cells that made up the original human tumors. We identify cancer cells from five different xenograft tumors and five unpassaged tumors that have activated β-catenin (cytoplasmic and/or nuclear expression by immunohistochemistry) and cancer cells from five xenograft tumors and five unpassaged tumors that do not (membrane-associated expression by immunohistochemistry). We select tumors that are heterogeneous for important prognostic features that include estrogen receptor/progesterone receptor (ER/PgR), primary tumor vs. metastatic tumor, wild type vs. mutant p53, and amplification of Her2/neu.

To identify cells that have constitutive activation of β-catenin, we take advantage of the observation that this results in stabilization of β-catenin and accumulation of the protein in the cytoplasm and nucleus. When not activated, β-catenin is associated with the plasma membrane. We therefore analyze the breast cancer cell population from each of the tumors using immunohistochemistry to determine the sub-cellular localization of β-catenin and using flow cytometry to determine the amount of β-catenin expressed by each population of cells. To do this, we use flow cytometry to isolate the Lineage⁻ cancer cells from multiple tumors. Viably frozen xenograft or patient tumor cells are used for this analysis. The cancer cells then are stained with an anti-β-catenin-FITC antibody for immunohistochemistry and flow cytometry analysis using the antibody manufacturer's protocol (Transduction Laboratories). Cells with activated β-catenin have cytoplasmic/nuclear localization and increased levels of the protein.

To determine the role of β-catenin signaling in tumorigenesis, Lineage⁻ cancer cells isolated from each of the 20 tumors are infected with either an adenovirus vector or a lentivirus vector that contains a dominant-negative (dn) TCF4-IRES-GFP minigene or a control GFP virus (for details of virus construction and use, see Clarke et al., 1995, PNAS 92:11024-8). The adenovirus vector expresses the dnTCF4 transiently for 1-3 weeks, while the lentivirus vector expresses the dnTCF4 permanently. The dnTCF4 adenovirus has already been made using a dnTCF4 minigene (a gift from Eric Fearon). The dnTCF4 forms a complex with β-catenin thereby inhibiting transcriptional transactivation by the activated β-catenin. Note that the dnTCF4 blocks signaling from all members of the TCF family that mediate β-catenin signaling (Eric Fearon, personal communication). Limiting dilution tests are done to determine the ability of the transduced cells to form colonies in vitro and tumors in vivo. The tests here are done using cancer cells isolated from either patient or human tumors by flow-cytometry. By eliminating the lineage cocktail to eliminate the normal cells, colony formation in tissue culture and tumor formation in mice by cancer cells can be measured (The possible contributions of normal stromal cells to the growth of tumorigenic cells are analyzed as described below in aim 2B). To determine the role of β-catenin signaling on cancer cell growth and viability, five sets of 1,000, 5,000, 20,000, 50,000 and 100,000 Lineage⁻ cancer cells from each of the tumors infected with the dnTCF4 viruses (either the adenovirus or lentivirus vectors) and control viruses are cultured in vitro in medium containing the Notch ligand Delta and the number of colonies that form are determined. The colonies in a control tissue culture plate are stained with cytokeratin to confirm that they arose from neoplastic cells (Ethier et al., 1993, Cancer Res 53:627-35). Two days after infection the cells are examined with a fluorescent microscope to confirm that greater than 90% of the cells were transduced by the virus. Similarly, in vivo limiting dilution tests are done to determine whether the dnTCF4 viruses affect tumor formation by the cancer cells isolated from the different patients. After infection, ten sets of 5,000, 20,000, 50,000 and 100,000 Lineage⁻ cancer cells are isolated by flow-cytometry and then infected with the dnTCF4 adenovirus or control adenovirus. The infected cells are injected into the breast of NOD/SCID mice. We then determine the number of cancer cells needed to form tumors in each group, the time needed to form tumors in each group, the rate of growth of each group, and the size of the tumors that form in each group. This allows us to determine whether β-catenin is necessary for tumor formation by cancer cells that do or do not have constitutively activated β-catenin.

Subsequent tests depend on the results of the in vivo and in vitro limiting dilution tests. If inhibition of β-catenin transcriptional transactivation blocks tumor formation or slows tumor growth, then we begin to test whether downstream β-catenin targets such as cyclin D1 or c-myc are required for tumorigenicity (Lin et al., 2000, PNAS 97:4262-6; Yu et al., 2001, Nature 411:1017-21; Wong et al., 2002, J. Pathol. 196: 145-53). To do this, we infect the Lineage– cancer cells isolated by flow-cytometry and infect the cells with either the control or dnTCF4 adenovirus as well as a control gfp vector, a c-myc-IRES-gfp retrovirus vector, a cyclin D1-IRES-rfp retrovirus vector, or both the myc-IRES-gfp and the cyclin D1-IRES-rfp retrovirus vectors. Infected cells are isolated by flow cytometry, and then ten sets of 5,000, 10,000, 20,000, 50,000 or 100,000 Lineage– cancer cells of each test group are injected into mice. The mice are analyzed weekly for the formation of tumors, and the rate of growth of each test group. This allows us to determine whether enforced expression of either c-myc and/or cyclin rescues the cells from inhibition of β-catenin signaling.

If inhibition of β-catenin does not have any discernable effects on tumor formation, we first confirm that both of the dominant-negative viruses are inhibiting expression of the dnTCF4 minigene. If not, we use another method to inhibit the β-catenin pathway. In addition to RNA-i and antisense approaches (Sazani et al., 2001, Nucl. Acid Res. 29:3965-74; Caplen et al., 2001, PNAS 98:9742-7; Martinez et al., 2002, Cell 110:563-74; Paul et al., 2002, Nat. Biotech. 29:505-8), overexpression of Axin (which targets β-catenin for degradation) can be used to inhibit β-catenin (Hedgepeth et al., 1999, Mol. Cell Biol. 19:7147-57; Spink et al., 2000, EMBO 19:2270-9). If β-catenin signaling was inhibited and there was minimal or no effect on tumor formation, then we determine whether there are more subtle changes on the cancer stem cells. Expression of cyclin D1, whose expression is induced by β-catenin, has been associated with resistance to chemotherapy. Therefore, we treat mice with Adriamycin (8 mg/kg) or Taxol (60 mg/kg) five days after the dnTCF4-transduced or control cancer stem cells were injected into mice to determine whether inhibition of β-catenin enhance the efficacy of chemotherapy. The effect on tumor formation and tumor growth rate is determined as described above.

Expected results. Although cancer cells in a significant number of breast tumors have a constitutively active β-catenin signaling pathway, it is not known whether this pathway is essential for malignant transformation. If the Wnt/β-catenin pathway is necessary for the cancer cells to form tumors, then dominant-negative inhibitors block the ability of cancer cells to form tumors. If constitutive β-catenin signaling enhances tumor cell growth after malignant transformation but is not necessary for tumor formation, then the dominant-negative inhibitor slow growth of the tumor cells but not block tumor formation. If oncogenic mutations subsequent to tumor initiation make the cells independent of Wnt signaling, then the dominant-negative inhibitor do not affect tumor formation or growth. Finally, it is possible that constitutive activation of the Wnt pathway contributes to resistance to apoptosis and therefore makes the cells resistant to chemotherapy.

In a model of mouse cancer, a brief inhibition of c-ras or c-myc activity in cancer cells transformed by these genes resulted in a permanent loss of tumorigenicity (Chin et al., 1999, Nature 400:468-72; Jain et al., 2002, Science 297:102-4). If this is also true for β-catenin signaling, then transient inhibition of signaling by the adenovirus inhibit tumor formation. If inhibition of β-catenin signaling inhibits tumorigenicity, but the cells remain viable and restoration of β-catenin signaling enables them to form tumors, then the adenovirus vector slow tumor formation whereas the lentivirus vector inhibit tumor formation. If β-catenin signaling increases the rate of proliferation but is not obligate for tumorigenicity, then both viral vectors delay tumor formation and slow the growth of the tumors. If some tumors rely on β-catenin signaling and others rely on other pathways or have constitutive activation of downstream effectors of β-catenin signaling, then some tumors are affected by the viral vectors while others do not. The tests described above allow us to answer these critical questions using a unique model recapitulates human tumors. These tests for the first time delineate the biological function(s) of β-catenin signaling in de novo human breast cancers.

The lentivirus can be made using other envelopes until one is found that infects the cells efficiently (Hughes et al., 2002, Mol. Ther. 5:16-24; Wang et al., 2002, PNAS 94:10705-10).

Note that with the lentivirus vector, infection efficiency can only be in the range of 30-70%. This would mean that a significant number of tumor cells would remain that could form tumors. However if inhibition of β-catenin signaling inhibits tumor formation, then the resultant tumors would not express gfp. Flow cytometry is used to measure gfp-expressing cells in the tumors infected with the dnTCF4 and control viruses. The tumors arising from the dnTCF4 group have a marked decrease in such cells if β-catenin signaling does play a role in tumor formation.

Does inhibition of β-catenin signaling alter the phenotype of tumorigenic breast cancer cells? One of the informative markers useful for the separation of tumorigenic and non-tumorigenic breast cancer cells is CD44. Interestingly, CD44 is one of the target genes that is transcriptionally upregulated by β-catenin and epithelial stem cells, but not their differentiated progeny, are felt to express this marker (Liu et al., 1997, PNAS 94:10705-10; van de Wetering et al., 2002, Cell 111: 241-50). We contemplate that inhibition of β-catenin signaling result in the differentiation of the tumorigenic breast cancer cells and cause them to lose expression of CD44. We further contemplate that the CD44⁻ non-tumorigenic cancer cells do not have active β-catenin. To test this, we use flow-cytometry to isolate ESA⁺CD44⁺CD24⁻$^{/low}$Lineage– cancer cells from Tumor 1, Tumor 2 and Tumor 3 and infect them with the dnTCF4 adenovirus or a control adenovirus. The cells are cultured in tissue culture medium containing soluble Delta. We have found that this medium allows the tumorigenic cells to grow in tissue culture for 1-3 weeks. The cells are monitored for growth in vitro over a 3-week period. In addition, 1, 3 and 7 days after infection, the dnTCF4 adenovirus or a control adenovirus infected cells are analyzed by flow-cytometry for the expression of ESA, CD44 and CD24.

Next, we determine if there is a difference in β-catenin signaling in the tumorigenic cancer cells, the CD44$^+$ cancer cells, or the CD44$^-$ cancer cells. To do this, we use flow-cytometry to isolate ESA$^+$CD44$^+$CD24$^{-/low}$Lineage– tumorigenic cancer cells, CD44$^+$ cancer cells, and CD44$^-$ non-tumorigenic cancer cells from tumor 1, tumor 2 and tumor 3. Each population of cells are stained with an anti-β-catenin antibody that has been conjugated with APC. Each population of cells are analyzed by fluorescent microscopy to determine whether the β-catenin is membrane bound (not constitutively active), and by flow-cytometry to determine the amount of the protein in the cells. The level of β-catenin is associated with activity. In addition, we use commercially available antibodies that recognize phosphorylated and unphosphorylated β-catenin. The phosphorylated form is marked for degradation while the unphosphorylated form is active (van Noort et al., 2002, J. Biol. Chem. 277:17901-5; van Noort et al., 2002, Exp. Cell Res. 274-72). These tests allow us to determine whether CD44 expression and β-catenin signaling are linked in patients' cancer cells.

CD44 is one of the best markers that allows one to distinguish tumorigenic cancer cells from non-tumorigenic cancer cells. Since CD44 is transcriptionally activated by β-catenin, then inhibition of β-catenin signaling result in downregulation of CD44.

Does the differential expression of the frizzled proteins affect breast cancer stem cell fate in Tumor 1? Data suggest that in Tumor 1, the tumorigenic stem cells express frizzled 2 and 6, whereas the non-tumorigenic neoplastic cells express Wnt 3, 4, 7A, 7B, 10B, and 11. This suggests a paracrine system in this particular tumor where the non-tumorigenic cells might drive the proliferation of the cancer stem cells. Preliminary data also suggest that in Tumor 1, the tumorigenic stem cells express frizzled 2 and 6, whereas the non-tumorigenic neoplastic cells express frizzled 2 and 7. It is possible that differential expression of frizzled genes plays a role in cancer cell fate decisions. The other possibility is that differential expression of these genes is a function of differentiation or immortality but does not directly regulate cell fate decisions in this tumor. This Example illustrates systems of the present invention that find use in distinguishing between these possibilities.

Tumor 1 tumorigenic cells express frizzled 6 and non-tumorigenic cancer cells express frizzled 7. It is possible that frizzled 6 enhances and frizzled 7 inhibits the proliferation or self-renewal of the cancer cells. To test this possibility, in vitro and in vivo clonogenic assays are done. Tumor 1 tumorigenic and non-tumorigenic cancer cells are infected with a lentivirus vector that expresses either frizzled 6-IRES-GFP or frizzled 7-IRES-GFP. A lentivirus is used rather than an adenovirus since the former virus can infect and stably transduce a high proportion of primary cells, whereas adenovirus transduction is often transient. It is conceivable that expression of frizzled 6 confers the ability to self renew to the cancer cells. If so, infection of stem cells and/or non-tumorigenic cells with a lentivirus vector containing a frizzled 6-IRES-GFP minigene can enhance tumorigenicity of the stem cell or allow the previously non-tumorigenic cells to form tumors. Conversely, enforced expression of frizzled 7 can inhibit tumorigenicity. After infection with either the frizzled or control virus, limiting dilution tests are done to determine whether enforced expression of each gene alters the ability of each population of cancer cells to form tumors.

These tests allow us to determine whether enforced expression of frizzled 6 increases stem cell proliferation and/or self-renewal or expression of frizzled 7 inhibits tumorigenic cancer cell proliferation and/or self-renewal. To test this possibility, we isolate the tumorigenic ESA$^+$CD44$^+$CD24$^{-/low}$Lineage$^-$ cancer cells and the other Lineage$^-$, non-tumorigenic cancer cells are isolated by flow-cytometry from each of the tumors. First, immunohistochemistry are done using the anti-β-catenin antibody to determine whether there is a difference in the amount of active β-catenin in the tumorigenic and non-tumorigenic cells. Next, we determine the amount of phosphorylated (inactivated) and non-phosphorylated (active) β-catenin the tumorigenic and non-tumorigenic cells (van Noort et al., 2002, J. Biol. Chem. 277:17901-5).

Next, in vitro assays are designed to determine the affects of each gene on colony formation by tumorigenic and non-tumorigenic cancer cells in tissue culture. After isolation by flow cytometry, each population of cells are infected with an identical MOI of either the frizzled 6/GFP, frizzled 7/GRP or a control GFP virus. Triplicate cultures of 100, 500, 1,000 and 5,000 cells are placed in tissue culture medium. The total number of GFP$^+$ colonies as well as the total number of colonies and the number of GFP$^+$ colonies are counted on days 3, 7, 14, 21 and 28. At the end of 21 days, we attempt to pass the cells to determine whether expression of the particular frizzled gene affects self-renewal.

The influence of enforced expression of each frizzled gene on the ability of the neoplastic cells to form tumors in the NOD/SCID mice are determined Normally, 200 Tumor 1 cells are required to form a tumor. Therefore, the frizzled 6, frizzled 7 or a control GFP lentivirus are used to infect 50, 100, 500, 1,000, 5,000, and 10,000 tumorigenic cancer cells or non-tumorigenic cancer cells. The cells are injected into the immunodeficient mice. The number of cells needed to form tumors and the rate of tumor growth are monitored. After the tumors have reached one centimeter in size, they are excised and analyzed by flow cytometry for expression of GFP. By comparing the percentage of cells infected by the GFP virus and frizzled/GFP virus, we are able to estimate the efficiency of infection and the affect of the latter virus on proliferation. These tests are replicated three times.

Predicted Results In Tumor 1, different populations of cells express different frizzled proteins, and the non-tumorigenic cells appear to preferentially express Wnt proteins. This suggests that certain populations of non-tumorigenic cells promote tumor formation through Wnts. If β-catenin signaling is downregulated in the non-tumorigenic cells and active in the tumorigenic subset, this is detected by the immunohistochemistry analysis of the expression patterns of phosphorylated & unphosphorylated β-catenin in the non-tumorigenic and tumorigenic cancer cells respectively. If there is no affect of the particular frizzled/GFP virus, then a similar percentage of cells would express GFP in each group and there is no difference in the number of cells needed to form a tumor. If the particular frizzled virus decreases or increases tumorigenicity or proliferation, then tumors infected with frizzled/GFP virus would have fewer or more GFP$^+$ cells and/or would require more or fewer cells to form tumors, respectively.

If necessary, a Feline Leukemia Virus lentivirus based vector system is used. This latter vector efficiently transduces non-replicating cells, and results in prolonged expression of transgenes. We can infect cells using a tet-inducible dnTCF-IRES-GFP lentivirus flanked by gene insulators or a control GFP lentivirus. 1-2 days prior to harvesting tumors, the transgene is activated. GFP$^+$ breast cancer stem cells are harvested and transplanted into the breasts of NOD/SCID mice. We continue to induce the expression of the transgene in the mice, and we are able to monitor them for the ability of the cells to form tumors.

The β-catenin signaling pathway differs in the cancer cells isolated from cancers with and without constitutively activated β-catenin. Rationale: Unlike colon cancer, mutations in the β-catenin signaling pathway have been detected in only a minority of breast cancer cells. However, these studies have concentrated only on APC and β-catenin. Using the systems and methods of the present invention, we closely examine the β-catenin pathway in each of the tumors that were analyzed at the biological level in specific aim 1A.

Does the Wnt pathway differ in cancer cells isolated from different tumors? In these experiments, we characterize the Wnt/β-catenin pathway in each of the tumors. To do this, we use RT-PCR to amplify the coding sequence of β-catenin, each of the frizzled proteins, the low-density lipoprotein-related Wnt receptors, APC, TCF family members, Axin, and Bcl-9 expressed by the cancer cells from each of the 10 tumors with constitutive activation of β-catenin. RT-PCR products of the expressed genes are sequenced to determine whether there are mutations in any of the genes. Any possible mutant genes are confirmed by repeated sequencing of an independent RT-PCR sample. If mutations are found, we determine whether the mutations result in the constitutive activation of the Wnt/β-catenin pathway. To do this, the mutated gene-IRES-GFP are cloned into the pCDNA3 eukaryotic expression vector. For example, if we find a mutant frizzled 2, then HEK 293 cells (which do not have activated β-catenin; Gazit et al., 1999, Oncogene 18:5959-66) are transfected with the mutant frizzled 2-IRES-GFP expression vector or a control IRES-GFP vector. Cells are stained with an anti-β-catenin-PE antibody and fluorescent microscopy is done to determine whether the mutant frizzled 6 causes cytoplasmic/nuclear localization of β-catenin, indicating activation of signaling. This assay allows us to determine whether mutation of components of the β-catenin pathway result in aberrant signaling in human breast cancer stem cells.

Expected results. Although constitutively active β-catenin is seen in the cancer cells in a significant number of breast cancer tumors, the mechanism is not known. There are differences in the signaling pathway in different tumor cells that are detected by these studies. If a mutation in a Wnt receptor or β-catenin modifier is present, then the sequencing studies detect this difference. If autocrine stimulation is present, then we see expression of one of the Wnt ligands by the cancer cells.

Does Wnt expression by different populations of tumor cells in some tumors drive breast cancer cell growth? Perhaps more so than any other type of cancer, a breast cancer tumor contains a heterogeneous population of normal cells including mesenchymal (stromal) cells, inflammatory cells, and endothelial cells that interact with malignant cells to modulate tumor growth and invasion. The purpose is to begin to understand the role of the Wnt pathway in such interactions. We contemplate that normal stromal elements including mesenchymal and endothelial cells produce different Wnts that influence tumor cell proliferation and invasion. Just unpassaged tumors are analyzed since the xenograft tumors would be expected to have infiltrating normal mouse stromal cells and analysis of the mouse cells would be too complicated. Purification of these cells by flow-cytometry allow both molecular and biological analysis of these cells without first placing the cells in tissue culture. This is particularly important since the normal cells are known to change expression of genes when cultured in vitro.

The normal stromal cells are thought to play a role in the proliferation of breast cancer cells. It is also likely that the cell-cell interactions between cancer cells contribute to tumor growth. Wnt signaling is one of the major pathways that normal tissue cells use to talk to each other. Therefore, it is important to understand how this pathway is regulated in tumors. Specific Wnt proteins can activate specific frizzled receptors. Some frizzled receptors signal through β-catenin, while others signal through different pathways. To understand how the various populations of tumor cells within a tumor might talk to the tumorigenic breast cancer cells through this pathway, we must first determine which frizzled and Wnt genes are expressed by the normal cells and the cancer cells from multiple patients' tumors. Therefore, we identify the Wnt pathway genes that are expressed by each population of normal cells and the cancer cells isolated from the 5 patients' tumor samples that have constitutive β-catenin signaling and the cancer cells from 5 patients' tumors that do not have constitutive activation of this protein.

Since our evidence suggests that there are differences in the expression of Wnt and frizzled genes in the different populations of cancer cells, it is important to isolate the different phenotype subsets of cells in the cancer to do these tests. This is because the apparently tumorigenic population of cells is a minority population, and the genes that these cells express might otherwise be missed in the analyses. Therefore, flow-cytometry is used to isolate tumorigenic and non-tumorigenic breast cancer cells, as well as normal endothelial cells and fibroblasts from the patients' original tumor. This is done as described in preliminary results and aim 1. RNA is isolated from pools of 35,000 of each population of cells and then linear amplification is done to make sufficient probe for the microarray analysis (Ramalho-Santos et al., 2002, Science 298:597-600; Ivanova et al., 2002, Science 107:3823; Terskikh et al., 2002, Blood 99:488-98; Akashi et al., 2003, Blood 101:383-9). To determine which frizzled and Wnt genes are expressed by the each population of cells found in each tumor, we probe an affymetrix microarray chip (3 chips for each cell type) that includes the Wnt and frizzled genes (the newly released U133 chip has the majority of these genes). Results are confirmed by quantitative RT-PCR of the different populations of cancer cells isolated from the primary tumors with and without activated β-catenin in the cancer cells. Real time RT-PCR is done to determine the level of expression of each of the frizzled and Wnt genes by different populations of normal and neoplastic tumor cells. To do this, we make PCR primers for detection each of these genes. Each set of primers span at least one exon so RT-PCR can be used to detect expression of the mRNA in different populations of tumor cells. Flow-cytometry is used to isolate the tumorigenic population of cells identified in each of the tumors. Real-time PCR then is used to measure the expression of each of the Wnt pathway-related RNAs by each respective cell population identified in the microarray analysis (reviewed in Bustin, 2000, J. Mol. Endocrinol. 25:169-93). To do the real-time PCR gene expression analysis, mRNA is purified from $3 \times 10^4$ cells (isolated by flow-cytometry). Part of the RNA is used to directly measure RNA amount by the Ribogreen RNA quantitative method (Molecular Probes, Eugene, Oreg.), and part used to measure rRNA and GAPDH expression (a control housekeeping gene) via the Taqman real-time RT-PCR assay. Taken together, these control measurements allow us to normalize expression of the genes of interest between the different populations of cells (Bustin, 2000, J. Mol. Endocrinol. 25:169-93). Although fewer cells can be used in this assay, analysis of RNA isolated from $3 \times 10^4$ cells should result in a more accurate measurement of gene expression.

Each frizzled receptor expressed by the different populations of cancer cells from each tumor is analyzed for the ability to activate β-catenin and transform cells when stimulated by each of the different Wnt genes that are expressed by different populations of cells within a tumor. Two biological systems are used for these studies. First, we use HEK 293 cells transfected with each individual frizzled identified in this screen to test the ability of the identified Wnts to activate β-catenin through the frizzled proteins expressed by the tumorigenic cells. Next, we use a mammary epithelial cell line to determine whether a particular Wnt or frizzled gene is able to transform the cell line.

To measure the biochemical functions of the different Wnt and Frizzled proteins expressed by the breast cancer cells, we use a transient transfection assay as described by Gazit et al., 1999, Oncogene 18:5959-66. In this assay, HEK 293T cells are transiently transfected with a frizzled minigene or a control minigene and aTCF-luciferase or control reporter minigene. To test the ability of a particular Wnt protein to stimulate β-catenin signaling, a second group of HEK 293T cells are transfected with each of the Wnt genes expressed by the various populations of tumor cells. The frizzled-transfected cells are mixed with the Wnt-transfected cells to measure paracrine activation of a particular frizzled receptor expressed by the breast cancer stem cells activates β-catenin when stimulated by a particular Wnt protein expressed by one of the various populations of tumor cells.

The C57MG cell line is used to determine whether activation of particular frizzled receptors by particular Wnts causes morphological transformation (Wong et al., 1994, Mol. Cell Biol. 14:6278-86). These cells undergo morphologic transformation when exposed to Wnt-1, Wnt-2, Wnt-3A, Wnt-6 and Wnt-7A, but not Wnt4, Wnt-5A, Wnt-5B and Wnt-7B. These data suggest that the non-transforming Wnts signal differently than the transforming Wnts, or that they signal through different receptors not expressed by the C57MG cells. Therefore, to fully characterize the functions of the different frizzled and Wnt proteins expressed by the cancer cells in the patients' tumors, we must first determine which frizzled genes are expressed by the C57MG cells. The cells are transfected with minigenes that express any frizzled genes expressed by tumorigenic breast cancer cells but not expressed by the C57MG cells. Next, cells are cultured in the presence of lethally irradiated fibroblasts or HEK 293T cells transfected with individual Wnt genes that were expressed by the different populations of tumor cells. The cells are analyzed for morphological transformation as described by Shimizu et al., 1997, Cell Growth Diff. 8:1349-58.

Next, we characterize the in vivo response of cancer cells from the different patients' tumors to different Wnts made by the tumor cells. The Wnt proteins are often found in the extracellular matrix and difficult to prepare in soluble forms. Therefore, we make control HEK 293 cell lines that express each of the Wnts made by the various types of tumor cells present in 2 patients' tumors. To do this, we first analyze HEK 293 cells to determine whether they constitutively make any of the Wnt proteins. Next, we stably transfect the HEK 293 cells with each of the Wnts made by the patients' tumor cells. To determine the affect of Wnt stimulation in the breast cancer cells by each of its ligands in vivo, 0, 10, 50, 100, 200, 500 and 1,000 Tumor 1 stem cells are mixed with 500,000 lethally irradiated control 293 cells or 293 cells transfected with one or more relevant Wnt minigenes and then injected into immunodeficient mice. Each injection is done in five mice. The mice then are monitored weekly for tumor formation. If a particular Wnt stimulates self renewing cell division, then either fewer cells are needed to initiate a tumor and/or tumors form more quickly. Conversely, if the ligand induces commitment to differentiation, then more cells are required to form a tumor and/or tumors take longer to form.

Expected results. The interaction of cancer cells with the normal stromal cells in tumors is thought to be critical for tumor formation and metastasis (Hanahan & Weinberg, 2000, Cell 100:57-70). The Wnt pathway is one of the central pathways by which cells in normal tissues communicate (Cadigan & Nusse, 1997, Genes & Dev. 11:3286-305). It is therefore likely that such communications are maintained to some extent in tumors. The models described in this proposal for the first time enable such studies to be conducted using patients' tumor cells. If the stromal cells indeed promote tumor growth through Wnt signaling, then the various populations of stromal cells make specific Wnts that provide a proliferative signal for the tumorigenic cancer cells.

To minimize these problems, all tests are done in triplicate with different numbers of cells. Expression of a control RNA of a known quantity is used to construct a standard curve to analyze the data (reviewed in Bustin, 2002, J. Mol. Endocrinol. 25:169-193). If necessary, new PCR primers are made, or RT is done with gene specific primers recognizing a different part of the mRNA (oligo dT primers are used for the RT reaction initially).

Summary: These tests using the systems and methods of the present invention provide means for comprehensive detail the molecular mechanisms by which the β-catenin pathway is activated in vivo in tumorigenic populations of breast cancer cells obtained directly from multiple patients' tumors, and the biological consequences of this activation in de novo breast cancer cells.

EXAMPLE 3

Localization of β-Catenin in Tumorigenic Cells

Figure 8:
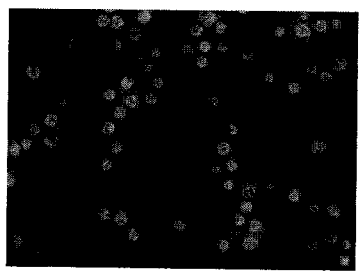
FIG. 8 shows subcellular localization of β-catenin.
Figure 8:
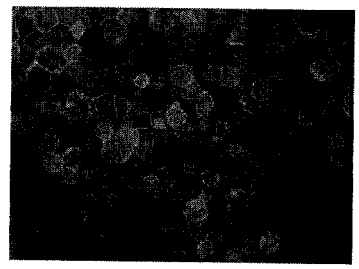
Figure 8:
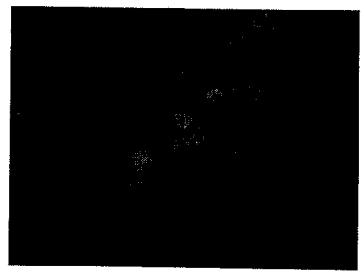

In normal hematopoietic cells, nuclear β-catenin is found only in the stem cell compartment. Reya et al. further demonstrate that β-catenin signaling is necessary for normal stem cells to self-renew. A recently completed analysis of the subcellular localization of β-catenin in tumorigenic and non-tumorigenic tumor 1 breast cancer cells further supports this notion. Normally, the subcellular distribution of β-catenin is heterogeneous in cancer cells. In some cells, the protein is located primarily in the outer membrane, while in others primarily in the nucleus. The subcellular distribution of the protein differs in the tumorigenic and non-tumorigenic cancer cells. The β-catenin is primarily located in the cytoplasm of the non-tumorigenic cancer cells, while it is primarily in the nucleus of the tumorigenic cells (FIG. 8). Since upon activation by a Wnt signal, β-catenin translocates from the cell membrane to the nucleus to activate downstream target genes, this data supports the hypothesis that Wnt signaling plays a role in the self-renewal of breast cancer stem cells.

FIG. 8 shows subcellular localization of β-catenin. A FITC labeled anti-β-catenin antibody was used to stain (A) colon cancer cells, which have a constitutively activated β-catenin, (B) non-tumorigenic T1 breast cancer cells, and (C) tumorigenic breast cancer cells. The tumorigenic and non-tumorigenic cancer cells were isolated by flow cytometry as described in the PNAS manuscript by Al-Hajj et al. Note that the β-catenin is located primarily in the nucleus of the colon cancer cells and the breast cancer stem cells, but it is primarily located on the surface of the non-tumorigenic cells.

Figure 9:
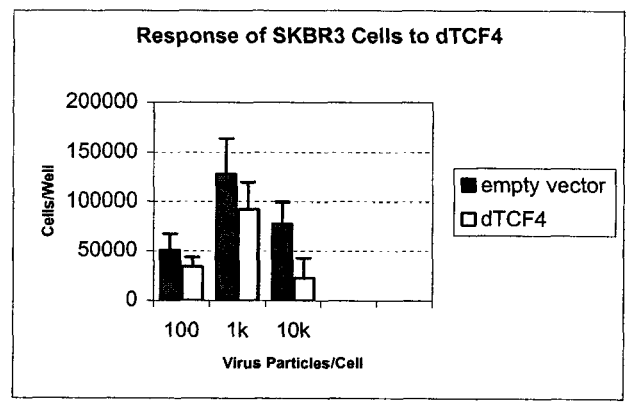
FIG. 9 shows inhibition of β-catenin signaling in cancer cells.
Figure 9:
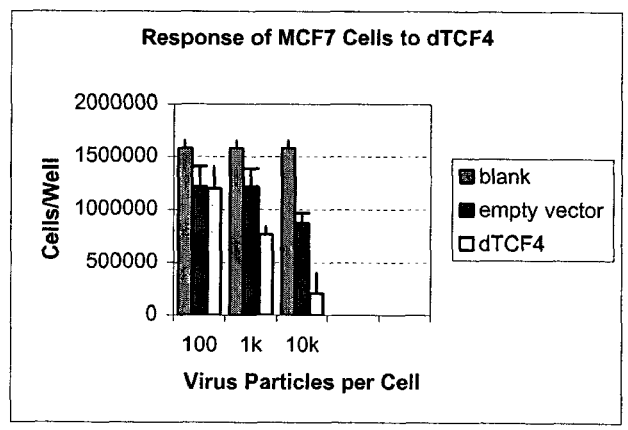
Figure 9:
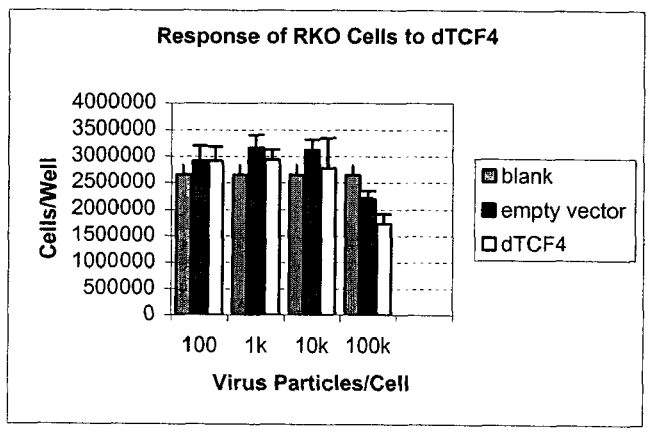

To begin to understand the biological consequences of β-catenin signaling in breast cancer, we have tested our dominant negative TCF-4 (dTCF4) adenovirus vector in several cell lines. This adenovirus acts to inhibit β-catenin signaling. Two different breast cancer cell lines, SKBR3 and MCF7, and a gastrointestinal tract cancer cell line, RKO, were infected with the dTCF4 adenovirus or a control adenovirus (empty vector). Four days after infection, the number of viable cells in each group was determined. As shown in FIG. 9, the breast cancer cells infected with the dTCF4 adenovirus, but not the control adenovirus, died. These data show that the Wnt pathway does play a role in human breast cancer.

FIG. 9 shows inhibition of β-catenin signaling in cancer cells. Triplicate cultures of SKBR3 cells (A), MCF7 cells (B) and RKO cells (C) were infected with either an control adenovirus (empty vector) or an adenovirus vector that expresses a dominant-negative TCF4 minigene (dTCF4). With increasing virus concentrations, SKBR3 cells and MCF7 cells, but not RKO cells, lost viability. Note that the virus titers resulting in cell death were those needed to efficiently infect most of the target cells with a control GFP virus (data not shown). This experiment has been repeated with similar results.
The observation that β-catenin is located primarily in the nucleus in the tumorigenic but not the non-tumorigenic cancer cells taken together with the observation that inhibition of β-catenin signaling affects the viability of some breast cancer cell lines shows that like normal stem cells, Wnt signals can play a role in the self-renewal of cancer stem cells.

EXAMPLE 4

Identifying Stem Cell Cancer Markers

This Example describes how various stem cell cancer markers were identified using microarray screens. The results of these screens were processed and the names of the differentially expressed genes are reported in Tables 4-9 (see above).

In order to generate gene expression profiles, human breast tumorigenic cells which were initially isolated. A series of samples were accumulated from human breast tumors or normal tissues. These were generated as follows. Three passaged breast tumors—breast tumor cells from patient 1, 2, 3 were engrafted on mice. Each tumor was engrafted on three mice to make the triplicate tumors. The breast tumorigenic cells were then isolated from these tumors. Two or three unpassaged breast tumors from three patients SUM, PE13, PE15 were labeled and sorted into tumorigenic cells (TG) or non-tumorigenic cells (NTG). Both PE15-TG and PE15-NTG were triplicate. Two or three normal breast samples were from breast reduction patients. Breast epithelial cells (Breast) were isolated with flow cytometry and used for microarray. Two or three normal colon samples were collected freshly from colon patients. Colon epithelial cells (Colon) were isolated with flow cytometry and used for microarray. Two or three normal stem cell samples (normal bone marrow) were collected from bone marrow donors. Hematopoietic stem cells (HSC) were isolated with flow cytometry. Probes were made from the following were made from the various cells types for use in the microarray analysis.

In order to perform the various microarray screens Affymetrix HG-U133 gene chips were used. The normalized gene expression intensity was used to generate the data that was collected in a number of large tables. The results in these tables was processed and used to generate Tables 4, 5, 6, 7a, 7b, 7c, 7d and 8, which present the names of the genes found to be differentially expressed. For tables 4-6, candidate cancer markers were sorted by identifying genes whose expression was greater or less than 1.5 fold in unpassaged breast tumorigenic cells comparing to non-tumorigenic cells or the normal stem cells (HSC). Table 6 shows only those genes found to be down regulated in UPTG vs. UPNTG. Table 5 shows only those genes found to be up regulated in UPTG vs.

HSC. Table 4 shows only those genes found to be up regulated in UPTG vs UPNTG. For tables 7a, 7b, 7c and 7d, cancer markers were generated from the larger tables by standard T-test. These tables were sorted based on T-score is <0.01 and ratio is more than 2 fold. Table 7a shows only those genes found to be up regulated in UPTG vs. HSC. Table 7b shows only those genes found to be down regulated in UPTG vs. HSC. Table 7c shows only those genes found to be up regulated in PTG vs HSC. Table 7d shows only those genes found to be down regulated in PTG vs HSC.

EXAMPLE 5

Isolation and Enrichment of Cancer Stem Cells Based on Signature 1 and Signature 2 Cancer Stem Cell Markers This example describes methods for isolating and enriching for tumorigenic cancer stem cells from solid tumors based on the differential expression of signature 1 and signature 2 cancer stem cell markers identified by the present invention. Methods of identifying additional cancer stem cell markers using isolated signature 1 and signature 2 cancer stem cells are also provided.

Tumor cells from a patient sample (solid tumor biopsy or pleural effusion) or from a solid tumor passaged in a xenograft mouse model are removed under sterile conditions. Tissue samples are cut up into small pieces and then minced completely using sterile blades. Single cell suspensions are then obtained by enzymatic digestion and mechanical disruption. Specifically, pleural effusion cells or the minced tumor pieces are mixed with ultra-pure collagenase III in culture medium (200-250 units of collagenase per mL) and incubated at 37° C. for 3-4 hours with pipetting up and down through a 10-mL pipette every 15-20 min. Digested cells are filtered through a 45 ul nylon mesh, washed with RPMI/20% FBS, and washed twice with HBSS.

Single cell tumor suspensions are sorted into tumorigenic and non-tumorigenic cells based on cell surface markers. Cells are counted, washed twice with HBSS containing 2% heat-inactivated calf serum (HICS), and resuspended at $10^6$ cells per 100 ul. Antibodies are added and the cells incubated with antibody for 20 min on ice followed by two washes with HBSS/2% HICS. Antibodies include anti-ESA (Biomeda, Foster City, Calif.), anti-CD44, anti-CD24, and Lineage markers anti-CD2, -CD3, -CD10, -CD16, -CD18, -CD31, -CD64, and -CD140b (collective referred to as Lin; PharMingen, San Jose, Calif.). Antibodies are directly conjugated to fluorochromes to positively or negatively select cells expressing these markers. In tissue collected from xenografts, mouse cells are eliminated by selecting against H2 Kd+ cells. Dead cells are eliminated by using the viability dye 7AAD. Flow cytometry is performed on a FACSVantage (Becton Dickinson, Franklin Lakes, N.J.). Side scatter and forward scatter profiles are used to eliminate cell clumps.

In some embodiments, cancer stem cells are isolated and enriched based on their expression levels of transmembrane proteins identified by the alpha-catenin gene expression signature. Antibodies are generated against the extracellular domains of the transmembrane proteins showing increased gene expression in the alpha-catenin signature, including c-Met, EDG2, and DCBLD2 using standard techniques, and the generated antibodies are then purified and directly labeled with fluorochromes. Solid tumor cells are dissociated and incubated with labeled antibodies against ESA, CD44, CD24, Lineage markers, c-Met, EDG2, and DCBLD2 as described above. Flow cytometry is then used to select for cells expressing high levels of ESA, CD44, c-Met, EDG2, and DCBLD2 and select against cells expressing CD24 and Lineage markers. Alternatively, ESA+, CD44+, CD24−/low, and Lin− cells are first isolated as described above, and this population of cancer stem cells (Al-Hajj et al., 2003) is incubated with labeled antibodies against c-Met, EDG2, and DCBLD2 followed by flow cytometry to positively select cells expressing high levels of c-Met, EDG2, and DCBLD2 Thus is obtained a tumor cell population enriched for ESA+, CD44+, CD24−/low, Lin−, c-Met+, EDG2+, and DCBLD2+ signature 1 type cancer stem cells.

The tumorigenicity of cells isolated based on an alpha-catenin gene expression signature is then determined 5,000, 1,000, 500, and 100 isolated ESA+, CD44+, CD24−/low, Lin−, c-Met+, EDG2+, and DCBLD2+ cancer stem cells versus identical numbers of ESA+, CD44+, CD24−/low, and Lin− cancer stem cells or unsorted dissociated tumor cells are injected into the mammary fat pads of NOD/SCID mice. Five days before cell injections, mice are prepared by treatment with 30 mg/kg VP-16 via intraperitoneal injection and the placement of estrogen pellets subcutaneously. The number of injected cells required for consistent tumor formation in mice is used to determine the fold enrichment for tumorigenic versus non-tumorigenic cells based on isolating signature 1 cancer stem cells.

In another embodiment cancer stem cells are isolated and enriched based on differential expression of transmembrane proteins identified by the E-cadherin gene expression signature. Antibodies are generated against the extracellular domains of the transmembrane proteins showing decreased gene expression in the E-cadherin gene signature, including IL1R2 and E-cadherin, using standard techniques, and once generated the antibodies are purified and directly labeled with fluorochromes. Solid tumor cells are dissociated and incubated with labeled antibodies against ESA, CD44, CD24, Lineage markers, IL1R2, and E-cadherin as described above. Flow cytometry is then used to select for cells expressing high levels of ESA and CD44 and select against cells expressing E-cadherin, IL1R2, CD24, and Lineage markers.

Alternatively, ESA+, CD44+, CD24−/low, and Lin− cells are first isolated as described above, and this population of cancer stem cells (Al-Hajj et al., 2003) is incubated with labeled antibodies against E-cadherin and IL1R2 followed by flow cytometry to select against cells expressing high levels of E-cadherin and IL1R2. Thus is obtained a tumor cell population enriched for ESA+, CD44+, CD24−/low, Lin−, IL1R2−, and E-cadherin− signature 2 type cancer stem cells.

The tumorigenicity of the cells isolated based on an E-cadherin gene expression signature is then determined 5,000, 1,000, 500, and 100 isolated ESA+, CD44+, CD24−/low, Lin−, IL1R2−, and E-cadherin− cancer stem cells versus identical numbers of ESA+, CD44+, CD24−/low, and Lin− cancer stem cells or unsorted dissociated tumor cells are injected into the mammary fat pads of VP-16 and estrogen pretreated NOD/SCID mice. The number of injected cells required for consistent tumor formation in mice is used to determine the fold enrichment for tumorigenic versus non-tumorigenic cells based on isolating cancer stem cells with a signature 2 gene expression.

Also envisioned are cancer stem cells isolated and enriched based on cytoplasmic proteins, including alpha-catenin, identified by the alpha-catenin gene expression signature. Antibodies against alpha-catenin are generated, purified, and directly labeled with fluorochromes. Solid tumor cells are dissociated as described above, and the cells fixed in 4% paraformaldehyde and permeabilized with 0.5% Triton-X-100 detergent. Permeabilized tumor cells are incubated with labeled antibodies against ESA, CD44, CD24, Lineage markers, and alpha-catenin, and flow cytometry is then used to select for cells expressing high levels of ESA and CD44 and select against cells expressing alpha-catenin, CD24, and Lineage markers. Alternatively, ESA+, CD44+, CD24−/low, and Lin− cells are first isolated as described above and then fixed in 4% paraformaldehyde and permeabilized with 0.5% Triton-X-100 detergent. Permeabilized cells are then incubated with labeled antibodies against alpha-catenin, and flow cytometry is used to select against cells expressing high levels of alpha-catenin. Thus is obtained a tumor cell population enriched for ESA+CD44+CD24−/low, Lin−, and alpha-catenin−/low signature 1 type cancer stem cells.

To identify additional markers of cancer stem cells, isolated populations of cancer stem cells with an alpha-catenin or an E-cadherin gene expression signature are compared using microarray analysis to each other, to non-tumorigenic solid tumor cells, and to normal breast epithelium. Non-tumorigenic solid tumor cells and normal breast epithelium are isolated by flow cytometry as described in Example 4. Cancer stem cells with either signature 1 or 2 gene expression are isolated by flow cytometry as described above. Each population is independently isolated three times so that microarray analysis can be performed in triplicate.

Total RNA is isolated from the different cell populations using RNasy (Qiagen, Valencia, Calif.) according to the manufacturer's protocol. Probes for microarray analysis are then prepared according to Affymetrix protocols (Affymetrix, Santa Clara, Calif.). Affymetrix HG-U133 gene chips are hybridized with Cy3 versus Cy5 labeled probe sets representing the two isolated cell populations being compared and washed according to standard Affymetrix protocols. Arrays are scanned with an argon-ion laser confocal microscope and the intensity for each probe set on the array is assessed with Affymetrix Microarray Suite 4.0 software according to Affymetrix procedures.

EXAMPLE 6

Screening for Small Molecules that Affect the Behavior of Cancer Stem Cells

This example describes methods for screening agents to identify those that inhibit cancer stem cell proliferation. ESA+, CD44+, CD24−/low, Lin− cancer stem cells are isolated from patient tumor samples or from tumors passaged through immunocompromised mice as described herein. Isolated cancer stem cells are collected by centrifugation and resuspended in defined culture medium comprising a mixture of Ham's F12, 2% fetal calf serum, and B27 supplement and then cultured in suspension under conditions that allow the proliferation of cancer stem cells. Equal numbers of cells are plated per well in clear bottom microtiter plates. These plates are referred to as assay plates. Agents from a chemical library are diluted in culture medium in microtiter dilution plates and then added to assay plates in triplicate. Wells in which no agent is added and in which anisomyocin, a protein synthesis inhibitor, is added are included on each assay plate as controls for normal growth and no growth, respectively. Assay plates are incubated with test agents for 7, 14, and 21 days. On these days the number of colonies per well is determined by light microscopy.

EXAMPLE 7

Targeting the Signature 1 Cancer Stem Cell Marker c-Met to Inhibit Cancer Stem Cell Proliferation and Self-Renewal This example describes methods for targeting tumors based on the expression of cancer stem cell markers identified by the gene expression profiles of the present invention and for assaying the impact of this targeting. Gene expression signature 1 of the present invention identifies increased c-Met expression in signature 1 type cancer stem cells compared to normal breast epithelium (FIG. 11). c-Met is a receptor tyrosine kinase whose aberrant activation is linked to tumorigenesis and metastasis. Methods of inactivating c-Met expressed by cancer stem cells can reduce their proliferation and/or self-renewal properties and thus inhibit solid tumor growth. Alternatively eliminating cancer stem cells expressing high levels of c-Met can reduce tumor proliferation and reduce the risk of tumor regeneration and/or metastasis.

To target tumors, particularly those tumors comprising cancer stem cells expressing increased levels of c-Met, monoclonal antibodies against the extracellular domain of c-Met are produced. F1 hybrid mice are immunized using purified recombinant extracellular c-Met protein and the spleen from mice with circulating antibodies that specifically recognize the immunizing protein are used for hybridoma production. Hybridomas are again screened for antibodies that specifically recognize c-Met protein.

Antibodies generated against c-Met are assessed for antagonistic versus agonist activities against c-Met using an assay for cell proliferation. Human lung myofibroblast cell lines expressing c-Met (MRC5) are cultured in Dulbecco's modified Eagle medium (DMEM) containing 10% fetal calf serum (FCS), 100 U/ml penicillin, and 100 ug/ml streptomycin. Cells are plated at a density of $10^4$ cell per well in 96-well tissue culture microplates and allowed to spread for 24 hours. Subsequently cells are cultured for an additional 12 hours in fresh DMEM with 2% FCS at which point anti-c-Met versus control antibodies are added to the culture medium in the presence or absence of c-Met ligand, HGF/SF and 10 umol/L BrdU. Following BrdU labeling, the culture media is removed, and the cells fixed at room temperature for 30 min in ethanol and reacted for 90 min with peroxidase-conjugated monoclonal anti-BrdU antibody (clone BMG 6H8, Fab fragments). The substrate is developed in a solution containing tetramethylbenzidine and stopped after 15 min with 25 ul of 1 mol/L $H_2SO_4$. The color reaction is measured with an automatic ELISA plate reader using a 450 nm filter (UV Microplate Reader; Bio-Rad Laboratories, Richmond, Calif.). All experiments are performed in triplicate. Cells incubated with control antibody alone serve as a control for baseline levels of cell proliferation. Incubation of cells with HGF/SF serves as a positive control for cell proliferation following c-Met activation. Anti-c-Met antibodies that act as agonists to increase cell proliferation in the absence of HGF/SF are not investigated further. Antagonist anti-c-Met antibodies that block HGF/SF mediated stimulation of cell proliferation and antibodies that fail to activate c-Met are used to target cancer stem cells as described below.

In some embodiments, the effect of c-Met antibodies on cancer stem cell proliferation is determined in culture. Tumor cells from a patient tissue sample (a solid tumor biopsy, pleural effusion, etc.) or from a tumor passaged in a xenograft mouse model are removed under sterile conditions, dissociated, and signature 1 cancer stem cells that overexpress c-Met are isolated by flow cytometry as described in Example 5 above. Additionally, signature 2 cancer stem cells and non-sorted tumor cells can also be included for comparison. Sorted cancer stem cells are collected by centrifugation and resuspended in defined culture medium comprising a mixture of Ham's F12, 2% fetal calf serum, and B27 supplement under conditions that allow the proliferation of tumor cells. Tumor cells are cultured for 14 days in suspension to allow colony growth specifically from tumorigenic cells (U.S. Ser. No. 09/920,517) and then colonies are passaged by collecting tumor stem cell colonies by centrifugation followed by enzymatic digestion and mechanical disruption as described in Example 5 for 1 hour at 37° C. Dissociated cells are resuspended and equal numbers cultured in fresh medium containing either antagonist anti-c-Met antibodies, non-agonist anti-c-Met antibodies, antibodies pre-incubated with c-Met blocking peptide, or control antibodies. Passaged non-tumorigenic cells are capable only of forming small colonies consisting of 2-4 cells, while tumorigenic cancer stem cells continue to proliferate and the effect of different anti-c-Met antibodies is determined by assessing the number and size of colony growth by light microscopy.

In a second embodiment, the effect of antibodies against c-Met on a tumor and particularly on cancer stem cell proliferation is assessed in a xenograft model. Tumor cells from a patient tissue sample (a solid tumor biopsy, pleural effusion, etc.) or from a tumor passaged in a xenograft mouse model are removed under sterile conditions, dissociated, and signature 1 cancer stem cells that overexpress c-Met are isolated by flow cytometry as described in Example 5 above. Additionally, signature 2 cancer stem cells and non-sorted tumor cells can also be included for comparison. In triplicate sets 5,000, 2,500, 1,000, and 200 sorted cancer stem cells are incubated with antagonist anti-c-Met antibodies, non-agonist anti-c-Met antibodies, anti-c-Met antibodies pre-incubated with c-Met blocking peptide, or control antibodies at 37° C. for an hour to allow antibody binding and then injected into the mammary fat pads of NOD/SCID mice. Five days before cell injections, mice are prepared by treatment with 30 mg/kg VP-16 via intraperitoneal injection and the placement of estrogen pellets subcutaneously. Subsequent to injection, the ability of the injected tumor cells to form tumors, the length of time required for tumor formation, and the size of the tumors is assessed.

In other embodiments, the effect of anti-c-Met antibodies on cancer stem cell self renewal is examined Cancer stem cell colonies grown in suspension culture and treated with either antagonist anti-c-Met antibodies, non-agonist anti-c-Met antibodies, antibodies pre-incubated with blocking peptide, or control antibodies as described above are passaged a second time. Dissociated cells are then cultured in fresh medium in the absence of antibody and the number of colonies that grow representing the number of cancer stem cells present, and thus the self-renewal of cancer stem cells in the presence of c-Met antibody, is determined. Alternatively varying numbers of the dissociated tumor cells, ranging from 50,000 down to 5,000, are injected into the mammary fat pads of VP-16 and estrogen pre-treated NOD/SCID mice and the frequency rate of tumor formation for the number of injected cells is determined.

In another embodiment the effect of targeting cancer stem cells overexpressing c-Met on tumor growth in vivo is determined. Tumor cells from a patient tissue sample (a solid tumor biopsy, pleural effusion, etc.) or from a tumor passaged in a xenograft mouse model are removed under sterile conditions, and prepared as single cell suspensions, dissociated, and signature 1 cancer stem cells that overexpress c-Met are isolated by flow cytometry as described in Example 5 above. Additionally, signature 2 cancer stem cells and non-sorted tumor cells can also be included for comparison. In triplicate sets 5,000, 2,500, 1,000, and 200 sorted cancer stem cells are injected into the mammary fat pads of VP-16 and estrogen pre-treated NOD/SCID mice. On the day of tumor cell injection or alternatively once injected tumor cells have grown into palpable tumors, naked antagonist antibodies against c-Met or control antibodies are injected i.p. into tumor bearing mice.

In an alternative embodiment, the antibody is not a naked antagonistic antibody, but a non-agonist anti-c-Met antibody conjugated to therapeutic radionuclide iodine-131 to kill the targeted cancer stem cell. Injections are repeated twice a week for two to three weeks and the effect on tumor growth rate and size is assessed.

The embodiments of this example describe methods to investigate the role of c-Met in cancer stem cell tumorigenicity. If overexpression of c-Met by signature 1 type cancer stem cells contributes to their tumorigenicity, it is envisioned that antibodies against c-Met will inhibit tumor stem cell proliferation and/or self renewal. Targeting c-Met could inhibit cell proliferation so that cancer stem cells generate smaller colonies in culture or tumors in xenograft models. Targeting c-Met can also inhibit cancer stem self-renewal and thereby decrease the frequency of tumor formation compared to control. Yet independent of the role overexpression of c-Met plays in tumorigenicity, it is predicted that targeted killing of signature 1 type cancer stem cells will prove therapeutic against tumors in which cancer stem cells with an alpha catenin profile are detected.

EXAMPLE 8

Therapeutic Targeting of the Signature 1 Cancer Stem Cell Marker c-Met to Treat Cancer Patients This example describes methods for treating cancer using antibodies against c-Met to target tumors comprising cancer stem cells in which an alpha-catenin gene expression profile has been detected. The presence of cancer stem cells displaying an alpha-catenin profile based on the alpha-catenin signature is first determined from a tumor biopsy. Antibodies against c-Met are then administered to a cancer patient whose tumor is determined to have a signature 1 gene profile.

Tumor cells from a biopsy (solid tumor biopsy or pleural effusion) from a patient diagnosed with cancer are removed under sterile conditions. Tissue samples are cut up into small pieces and then minced completely using sterile blades. To obtain single cell suspensions, cells are subject to enzymatic digestion and mechanical disruption. Specifically, pleural effusion cells or the resulting tumor pieces are mixed with ultra-pure collangenase III in culture medium (200-250 units of collagenase per mL) and incubated at 37° C. for 3-4 hours with pipetting up and down through a 10-mL pipette every 15-20 min. Digested cells are filtered through a 45 ul nylon mesh, washed with RPMI/20% FBS, and washed twice with HBSS. Dissociated tumor cells are then incubated with antibodies to detect cancer stem cells expressing an alpha-catenin versus an E-cadherin gene profile, and the presence of tumor stem cells expressing either an alpha-catenin and/or an E-cadherin gene profile is determined by flow cytometry as described in Example 5 above.

Cancer patients whose tumors are diagnosed as containing cancer stem cells with an alpha-catenin gene expression profile are then treated with anti-c-Met antibodies. Monoclonal non-agonist anti-c-Met antibodies are generated as described above and humanized using standard techniques. The antibodies are purified and formulated with a suitable pharmaceutical carrier in PBS for injection. Patients are treated with humanized anti-c-Met antibodies, which can be chimeric, multimeric, heteromeric, single chain form, or fragments thereof (such as Fv, Fab, Fab$^1$, F(ab$^1$)$_2$, or other antigen-binding fragments), e.g., once a week for at least 10 weeks or once a week for at least about 14 weeks. Each administration of the antibody should be a pharmaceutically effective dose, e.g., about 2 to about 100 mg/ml or about 5 to about 40 mg/ml.

The antibody can be administered prior to, concurrently with, or after standard chemotherapy regimens using one or more chemotherapeutic agent, such as oxaliplatin, fluorouracil, leucovorin, streptozocin, etc. Treated patients will be monitored for tumor regression, reduction in the incidences of new tumors, etc.

EXAMPLE 9

Figure 12:
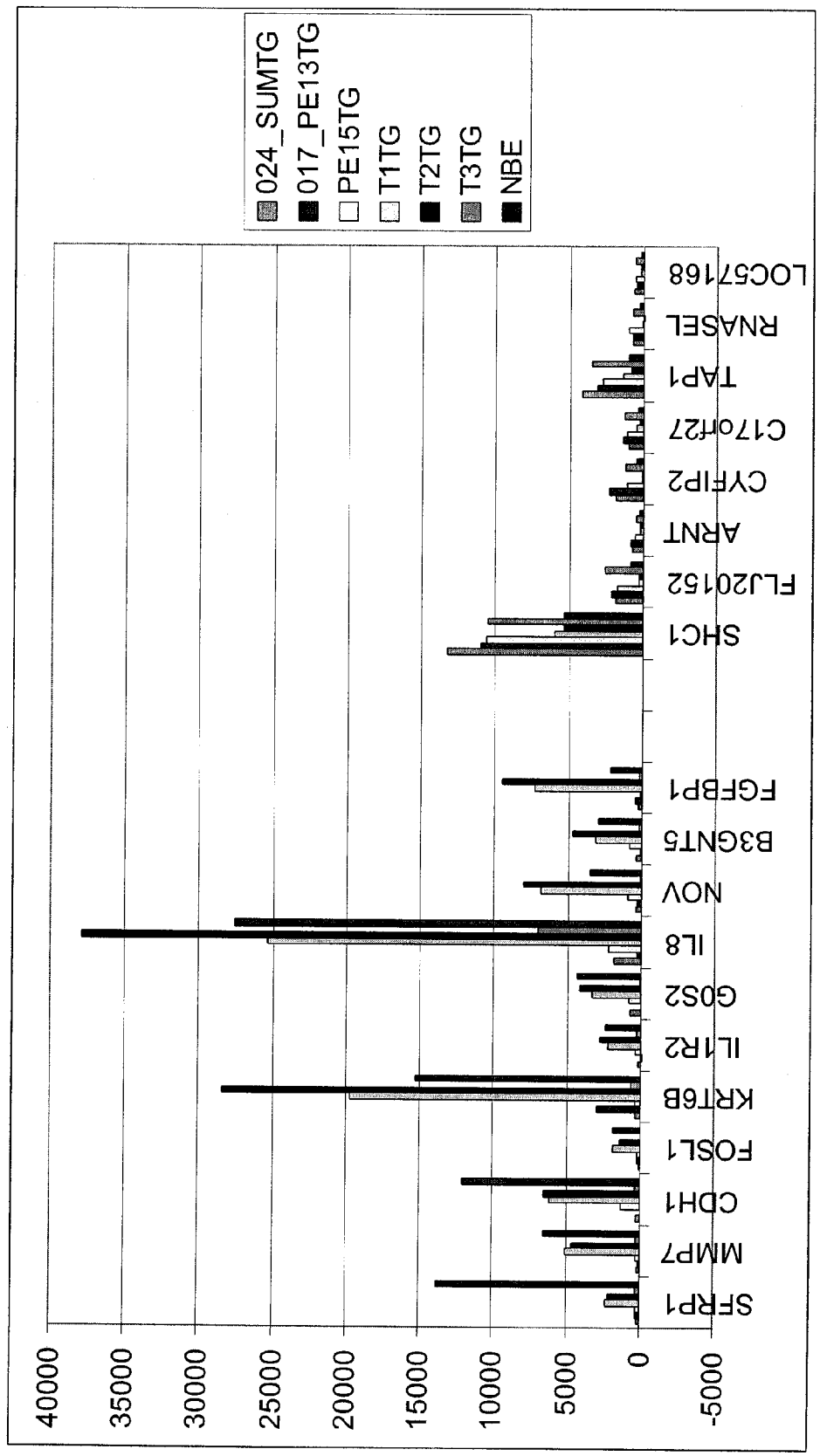
FIG. 12 shows gene expression levels as determined by microarray analysis for the E-cadherin gene signature in tumorigenic cells (TG) from three tumor samples: SUM, PE13, PE15, T1, T2, and T3 and in normal breast epithelium.

Restoring Expression of the Cancer Stem Cell Marker IL1R2 or Nov in Signature 2 Cancer Stem Cells This example describes methods for restoring expression of proteins down-regulated in cancer stem cells and for assaying the impact on the behavior of cancer stem cells when protein expression is restored. IL1R2 is a non-signaling decoy receptor for IL-1 that shows decreased expression in cancer stem cells with an E-cadherin gene expression signature compared to normal breast epithelium (Table 9; FIG. 12). IL-1 is a potent pro-inflammatory cytokine that can stimulate the production of pro-tumorigenic cytokines, and thus restoring IL1R2 expression in signature 2 type cancer stem cells can help to counteract tumor growth.

In some embodiments genetic modification of cancer stem cells is used to restore expression of IL1R2 and genetically modified cancer stem cells are tested for tumorigenicity.

Tumor cells from a patient sample (solid tumor biopsy, pleural effusion, etc) or from a biopsy passaged as a xenograft in an immunocompromised mouse are dissociated and flow cytometry used to isolate cancer stem cells expressing an E-cadher gene signature as described in Example 5 above. Additionally, signature 1 cancer stem cells and non-sorted tumor cells can also be included for comparison. The isolated cancer stem cells are collected after flow cytometry and resuspended in culture medium.

Cancer stem cells isolated based on an E-cadherin gene expression signature are then genetically modified using a replication incompetent lentivirus vector. Suitable expression systems include the ViraPower™ Lentiviral Expression System (Invitrogen, Carlsbad, Calif.), and viral particles are generated according to the manufacturer's protocol. Three different lentiviruses are constructed using standard methods of recombinant DNA technology: 1) a lentivirus encoding recombinant IL1R2, either transmembrane or soluble functional fragments of the IL1R2 protein capable of binding and inactivating IL-1 cytokine are envisioned, linked to an internal ribosomal entry site (IRES) GFP as a marker of cell infection (IL1R2-IRES-GFP); 2) a control virus encoding inactive IL1R2, in which the encoded IL1R2 does not contain a functional IL-1 binding domain because of deletions, mutations, etc. introduced into the coding domain, linked to an IRES GFP (inactive IL1R2-IRES-GFP); and 3) a control virus encoding GFP alone.

The proliferative and self-renewal properties of the genetically modified cancer stem cells are determined in a xenograft model. Triplicate set of 5,000, 1,000, and 200 isolated signature 2 cancer stem cells are infected with equal multiplicities of infection (MOI) of the IL1R2-IRES-GFP, inactive IL1R2-IRES-GFP, or GFP lentiviruses in culture medium in suspension. The infected cells are then washed in HBSS and injected into the mammary fat pads of VP-16 and estrogen pre-treated NOD/SCID mice. Tumor growth is monitored to assess the proliferative capacity of the different genetically modified cancer stem cells. After 28 days, xenografts from the mice are again isolated and 50,000, 25,000, and 5,000 dissociated tumor cells are repassaged into NOD/SCID mice. The frequency rate of tumor formation per number of injected cells is then determined to assess the self-renewal capacity of IL1R2-IRES-GFP versus inactive IL1R2-IRES-GFP or GFP expressing cancer stem cells.

In an alternative embodiment, cancer stem cell with an E-cadherin gene expression signature are genetically altered to restore expression of nephroblastoma overexpressed gene (Nov). Nov is a secreted protein associated with the extracellular matrix that plays various biological roles including cell proliferation, chemotaxis, and cellular adhesion. Nov has been implicated in cell cycle control and slowing cell growth as high levels of Nov expression are associated with less aggressive brain tumors and conversely decreasing levels of Nov are associated with progression of adrenocortical tumors to a malignant state. Thus restoring Nov protein in solid tumors can help limit their growth.

To restore Nov expression, plasmid vectors encoding recombinant Nov are introduced into signature 2 type cancer stem cells. A plasmid vector expressing Nov under the control of a CMV promoter is generated. A polynucleotide encoding full-length Nov is isolated by PCR from a human cDNA library and cloned into the multi-cloning site of the plasmid vector pcDNA3 (Invitrogen, Carlsbad, Calif.) upstream of an IRES GFP to mark transfected cells. The plasmid DNA is complexed with cationic lipids and used to transfect signature 2 cancer stem cells in culture medium. Plasmid DNA encoding GFP alone is used as a control. Transfected cancer stem cells are then washed in HBSS, FACs sorted for GFP expression, and triplicate sets of 5,000, 1,000, and 200 cells are injected into the mammary fat pads of VP-16 and estrogen pre-treated NOD/SCID mice. Tumor growth is monitored to assess the proliferative capacity of the different genetically modified cancer stem cells. After 28 days, xenografts from the mice are again isolated and 50,000, 25,000, and 5,000 dissociated tumor cells are repassaged into NOD/SCID mice. The frequency rate of tumor formation per number of injected cells is then determined to assess the self-renewal capacity of Nov expressing versus GFP only expressing cancer stem cells.

These methods address whether decreased expression of IL1R2 or Nov by signature 2 type cancer stem cells contributes to their tumorigenicity. It is envisioned that restoring IL1R2 or Nov expression will reduce signature 2 cancer stem cell proliferation and self-renewal and thus smaller tumors with reduced numbers of tumorigenic cells will grow in mice. However, as IL1R2 and Nov have anti-growth properties, it is further predicted that increasing their expression in all cancer stem cells regardless of their particular gene expression profile will inhibit or prevent tumor growth.

EXAMPLE 10

Therapeutic Restoration of the Signature 2 Cancer Stem Cell Marker Nov to Treat Cancer Patients This example describes methods for treating cancer using gene therapy to restore expression of Nov in solid tumors. The presence of cancer stem cells displaying a signature 2 profile is first determined from a tumor biopsy to identify patients that can best respond to such a therapy. Plasmid vectors expressing recombinant Nov are then administered to a cancer patient whose tumor contains cancer stem cells expressing a signature 2 gene profile.

Tumor cells from a patient sample (solid tumor biopsy or pleural effusion) from a patient diagnosed with cancer are removed under sterile conditions. Tissue samples are cut up into small pieces and then minced completely using sterile blades. To obtain single cell suspensions, cells are subject to enzymatic digestion and mechanical disruption. Either pleural effusion cells or the resulting tumor pieces are mixed with ultra-pure collangenase III in culture medium (200-250 units of collagenase per mL) and incubated at 37° C. for 3-4 hours with pipetting up and down through a 10-mL pipette every 15-20 min. Digested cells are filtered through a 45 ul nylon mesh, washed with RPMI/20% FBS, and washed twice with HBSS. Dissociated tumor cells are then incubated with antibodies to detect cancer stem cells expressing a signature 2 versus a signature 1 gene profile, and the presence of tumor stem cells expressing either a signature 2 and/or a signature 1 gene profile is determined by flow cytometry as described in Example 5 above.

Cancer patients whose tumors are diagnosed as containing cancer stem cells with a signature 2 gene expression profile are then treated with a therapeutically effective amount of plasmid vectors encoding Nov. In the some embodiment the plasmid vector is delivered by intratumor injection and is formulated in phosphate buffered saline with physiologic levels of calcium (0.9 mM). Alternatively the DNA is formulated in solutions containing higher quantities of Ca++, from 1 mM and 2M. The DNA can be formulated with other cations such as zinc, aluminum, and others. Therapeutically effective amounts of a plasmid vector are in the range of about 0.001 ug to about 1 g. A most some therapeutic amount is in the range of about 0.025 mg to about 5 mg. The plasmid vector is delivered monthly for 6-12 months, and then every 3-12 months as a maintenance dose. Alternative treatment regimens can be developed and can range from daily, to weekly, to every other month, to yearly, to a one-time administration depending upon the severity of the disease, the age of the patient, and such other factors. The DNA therapy can be administered prior to, concurrently with, or after standard chemotherapy regimens using one or more chemotherapeutic agent, such as oxaliplatin, fluorouracil, leucovorin, streptozocin, etc. Treated patients will be monitored for tumor regression, reduction in the incidences of new tumors, etc.

EXAMPLE 11

Combination Therapy to Treat Cancer Patients with Tumors that Contain Both Signature 1 and 2 Cancer Stem Cells This example describes methods for treating cancer using combination antibody and gene therapy to both target c-Met in cancer stem cells with a signature 1 gene expression profile and restore expression of Nov in solid tumors containing cancer stem cells with a signature 2 gene expression profile. The presence of cancer stem cells displaying both a signature 1 and 2 profile is first determined from a tumor biopsy as described above. Antibodies against c-Met and plasmid vectors expressing recombinant Nov are then administered to a cancer patient whose tumor contains cancer stem cells expressing a signature 1 and signature 2 gene profile as described above.

EXAMPLE 12

Lysophosphatidic Acid (LPA) and LPA Receptor EDG2 in Cancer Stem Cells

This example describes methods for assessing the effects of modulating LPA signaling and signaling by the LPA receptor EDG2 on the proliferation and self-renewal of cancer stem cells. Lysophosphatidic acid (LPA) is a bioactive phospholipid that stimulates cell proliferation over differentiation, morphological changes, and tumor cell invasion. LPA promotes growth of ovarian tumors and is found at high concentrations in patients with ovarian carcinomas, suggestive of an important role in ovarian cancers. Elevated levels of LPA have also been detected in patients with endometrial and cervical cancers (Mills and Moolenaar, 2003). Cancer stem cells that display an alpha gene expression signature comprise increased expression of Endothelial differentiation gene 2 (EDG2) a G-protein coupled receptor (GPCR) that belongs to a family of receptors activated by LPA (Table 9; FIG. 11). Increased expression of EDG2 in cancer stem cells can implicate responsiveness to LPA more broadly in tumorigenesis. Yet interestingly increased expression levels of EDG2 are associated with decreased cell growth rates via LPA-independent induction of apoptosis (Fang et al., 2000) suggesting that antagonizing LPA-dependent signaling but enhancing LPA-independent apoptosis must be balanced to counteract tumor cell growth.

In some embodiments the effect of LPA on cancer stem cell behavior is determined Cancer stem cells with both an alpha-catenin and an E-cadherin gene expression signature are isolated by flow cytometry based on differential protein expression as described in Example 5 above and the effect of the addition of exogenous LPA on cancer stem cell proliferation is determined. Sorted cancer stem cells are collected by centrifugation and resuspended in defined culture medium containing 0.1% (w/v) fatty acid-free BSA. Equal numbers of cells are grown in suspension culture in multi-well culture dishes for up to two weeks in the presence of 0.1 uM, 1 uM, and 10 uM 1-oleoyl LPA (Sigma) or vehicle control. Each condition is performed in triplicate, and the number and size of tumor colonies generated under each condition is assessed by light microscopy. Alternatively equal numbers of cancer stem cells are plated in suspension culture in multi-well culture dishes and allowed to grow for several days. Established tumor colonies are then treated overnight in the presence or absence of 0.1 uM, 1 uM, or 10 uM 1-oleoyl LPA and pulsed with [$^3$H]-thymidine for the last 8 hours. [$^3$H]-thymidine incorporation is quantitated to assess the effect of LPA on cell proliferation.

In another embodiment the presence and effect of endogenous LPA on cancer stem cell properties is determined. One potential source of endogenous LPA is the tumor cells themselves, which then act in a paracrine fashion to promote proliferation of cancer stem cells. To detect the presence of endogenously produced LPA, tumor cells are dissociated into single cell suspension by enzymatic digestion, resuspended in defined culture medium, and grown for several days to establish tumor colonies. LPA is butanol-extracted from conditioned medium and quantified using a radioenzymatic assay as previously described (Saulnier-Blache et al., 2000).

If LPA is produced by cultured tumor cells, the effect of reducing this endogenous LPA signaling can be assessed. The membrane-associated lysophosphatidic acid phosphatase (ACP6) degrades both extracellular and membrane-bound LPA, playing a prominent role in maintaining low LPA levels and limiting cellular responses to LPA (Fang et al., 2000). Increasing levels of ACP6 in tumor cells is thus used to decrease LPA levels and reveal the effect of endogenous LPA on cancer stem cell behavior. Tumor cells are isolated as above and transfected with a plasmid vector capable of expressing ACP6 linked to an IRES GFP to detect transfected cells. A plasmid vector expressing GFP alone is used as a control. Cells are transfected overnight using lipofectamine reagent (Invitrogen, Carlbad, Calif.) according to the manufacturer's protocol and flow cytometry is used to isolated transfected GFP positive tumor cells 24 hours later. Equal numbers of tumor cells are plated in suspension culture in multi-well culture dishes and allowed to grow. The number and size of tumor colonies is then assessed. LPA production is again quantified from ACP6 expressing versus control transfected tumor cells to determine the fold-reduction in LPA production. Alternatively cancer stem cells are isolated by flow cytometry as described in Example 5 above and resuspended in cultured medium from ACP6 expressing versus control transfected tumor cells and their ability to form tumor colonies in vitro examined.

In another embodiment the effect of targeting the LPA receptor EDG2 with an agonist antibody on cancer stem cell properties is determined. EDG2 is believed to act as a negative regulator of cell growth, suggesting that EDG2-selective agonists can limit tumor growth and survival (Fang et al., 2000). Overexpression of EDG2 in signature 1 cancer stem cells suggests that regulation of this GCPR can play a role in the tumorigenic properties of cancer stem cells. Antibodies against EDG2 are generated by standard immunization techniques using peptides from the extracellular domains of EDG2 that lack signals for glycosylation, and agonist antibodies that fail to activate LPA-dependent cytoplasmic Ca++ increases but activate LPA-independent apoptosis are identified.

The effect of EDG2 agonist antibodies on cancer stem cells expressing high (signature 1) and low (signature 2) levels of EDG2 can then be investigated. In some embodiments, the effect of agonist EDG2 antibodies on cancer stem cell proliferation is determined in culture. Signature 1 and signature 2 cancer stem cells are isolated from a patient tissue sample (a solid tumor biopsy, pleural effusion, etc.) or from a tumor passaged in a xenograft mouse model as described in Example 5 above. Isolate tumor stem cells are collected by centrifugation and equal numbers resuspended in defined culture medium containing either agonist anti-EDG2 antibodies, non-agonist anti-EDG2 antibodies, or control antibodies. The number and size of colonies generated by signature 1 versus signature 2 cancer stem cells in the presence of the different EDG2 or control antibodies is determined by light microscopy.

In a second embodiment, the effect of agonist antibodies against EDG2 on cancer stem cell proliferation is assessed in a xenograft model. In triplicate sets 5,000, 2,500, 1,000 and 200 isolated cancer stem cells are incubated with agonist anti-EDG2, non-agonist anti-EDG2, or control antibodies at 37° C. for an hour to allow antibody binding and then injected into the mammary fat pads of VP-16 and estrogen pretreated NOD/SCID mice. Following injection, the ability of the cancer stem cells to form tumors, the length of time required for tumor formation, and the size of the tumors is assessed.

In another embodiment the effect of agonist anti-EDG2 antibodies on tumor growth in vivo is determined. Cells from a primary tumor are cut up with scissors into small pieces that are then minced with a blade in sterile RPMI medium on ice to yield 2×2 mm pieces. The tumor pieces are washed in serum-free HBSS and implanted into the mammary fat pads of VP-16 and estrogen pre-treated NOD/SCID mice. Cells from pleural effusions are washed with serum-free HBSS, suspended in serum free-RPMI/Matrigel mixture (1:1 volume), and cell suspensions are injected in the mammary fat pads of NOD/SCID mice. Alternatively, tumor cells are dissociated and cancer stem cells are isolated by flow cytometry as described in Example 5 above and triplicate sets of 5,000, 2,500, 1,000, and 200 isolated cancer stem cells are injected into NOD/SCID mice. On the day of tumor cell injection or alternatively once injected tumor cells have grown into palpable tumors, naked agonist antibodies against EDG2 or control antibodies are injected i.p. into tumor bearing mice. Injections are repeated twice a week for two to three weeks and the effect on tumor growth rate is assessed.

The embodiments of this example describe methods to investigate the role of LPA and the LPA receptor EDG2 in cancer stem cell tumorigenicity. It is envisioned that targeting LPA production or EDG2 will inhibit cancer stem cell proliferation and thus act therapeutically against tumor growth.

EXAMPLE 13

Therapeutic Targeting of the Signature 1 Cancer Stem Cell Marker EDG2 to Treat Cancer Patients This example describes methods for treating cancer using agonist antibodies against the LPA receptor EDG2 to inhibit the proliferation of cancer stem cells in a cancer patient. Monoclonal agonist anti-EDG2 antibodies are generated as described above and humanized using standard techniques. The antibodies are purified and formulated with a suitable pharmaceutical carrier in PBS for injection. Patients are treated with humanized anti-EDG2 antibodies, which can be chimeric, multimeric, heteromeric, single chain form, or fragments thereof (such as Fv, Fab, $Fab^1$, $F(ab^1)_2$, or other antigen-binding fragments), such as once a week for at least 10 weeks or once a week for at least about 14 weeks. Each administration of the antibody should be a pharmaceutically effective dose, e.g., about 2 to about 100 mg/ml or about 5 to about 40 mg/ml. The antibody can be administered prior to, concurrently with, or after standard chemotherapy regimens using one or more chemotherapeutic agent, such as oxaliplatin, fluorouracil, leucovorin, streptozocin, etc. Treated patients will be monitored for tumor regression, reduction in the incidences of new tumors, etc.

EXAMPLE 14

Inhibiting Gamma-Secretase Activity in Cancer Stem Cells

This example describes methods for modulating gamma-secretase activity and thus inhibiting Notch signaling in cancer stem cells and assays for determining the effect of inhibiting gamma secretase on the behavior of cancer stem cells. Cancer stem cell gene expression signature 1 reveals decreased expression of Nicastrin (NCSTN) an essential component of the multimeric gamma-secretase complex that proteolytically cleaves the Notch receptor upon ligand binding. Notch cleavage results in release of an intracellular domain (NICD) that enters the nucleus and activates transcription. Notch signaling is involved in the process of lateral inhibition between adjacent cell fates and plays an important role in cell fate determination during asymmetric cell divisions. Furthermore, unregulated Notch signaling has been linked to the formation of a number of human cancers where it can alter the developmental fate of tumor cells to maintain them in an undifferentiated and proliferative state (Brennan and Brown, 2003).

Nicastrin is involved in stabilizing presenilin, the catalytic subunit of the gamma-secretase, and is required for gamma secretase activity and Notch signaling. However, Nicastrin can also play an inhibitory role in gamma-secretase activity as fibroblasts from heterozygotes nicastrin mice unexpectedly display increased gamma-secretase activity compared to the complete absence of activity in the knock out mice (Li et al., 2003) suggesting that decreased Nicastrin expression in signature 1 cancer stem cells can actually increase gamma-secretase activity and Notch signaling in these cancer stem cells. Thus whereas methods for eliminating Nicastrin expression can be therapeutic in shifting cancer stem cells from an undifferentiated and proliferative state to a differentiated state, tumors derived from signature 1 cancer stem cells can be particularly suitable for this type of therapy.

In some embodiments of the present invention, small interfering RNAs (siRNAs) are used to decrease expression of Nicastrin in cancer stem cells. siRNAs designed to target human Nicastrin (5'-GGGCAAGTTTCCCGTGCAGTT-3', SEQ ID NO:1, for example) and a mutated control are chemically synthesized, annealed, and transfected into tumor stem cells using standard techniques (Elbashir et al., 2001). Alternatively plasmid vectors such as pSilencer (Ambion, Austin, Tex.) are used to transcribe siRNAs using a RNA polymerase III promoter. Knock down of Nicastrin is first tested by analyzing protein expression in human fibroblast cell lines transfected with Nicastrin siRNAs versus Nicastrin mismatched control siRNAs using Western blot. Only siRNAs that decrease Nicastrin expression most strongly are used for further experimentation.

To determine if siRNA knock down of Nicastrin affects Notch signaling in cancer stem cells, the nuclear localization of the NICD is determined following transfection with Nicastrin versus control siRNAs. Cancer stem cells are isolated from solid tumors as described in Example 5 and equal numbers of cells are transfected with Nicastrin siRNA versus control siRNA in suspension culture. After 24 hours the subcellular localization of endogenous Notch 1 is determined by biochemical cell fractionation. Cancer stem cells are extracted and separated into cytoplasmic and nuclear components on a sucrose-density gradient. Equal protein from each component is separated by SDS-PAGE, blotted onto nitrocellulose, and probed with anti-Notch1.IC (Ledmond et al., 2000). The relative amount of Notch.IC in the nuclear fraction serves as an indication of the level of Notch signaling.

To determine if decreased gamma secretase activity by reductions in Nicastrin expression affects cancer stem cell behavior, the proliferation and self-renewal of cancer stem cells is determined in a xenograft model. Triplicate set of 5,000, 1,000, and 200 cancer stem cells with either an alpha-catenin or an E-cadherin gene expression signature are isolated according to Example 5 and are transfected with Nicastrin or control siRNAs in culture medium in suspension. After 24 hours the transfected cells are washed in HBSS and injected into the mammary fat pads of VP-16 and estrogen pre-treated NOD/SCID mice. Tumor growth is monitored to assess the proliferative capacity. After 28 days, xenografts from the mice are isolated and dissociated tumor cells are analyzed by flow cytometry as described in Example 5 to determine the number of ESA+, CD44+, CD24−/low, and Lin−; ESA+, CD44+, CD24−/low, Lin−, c-Met+, EDG2+, and DCBLD2+; and ESA+, CD44+, CD24−/low, Lin−, E-cadherin−, and IL1R2− cancer stem cells present per 1000 tumor cells.

Figure 13:
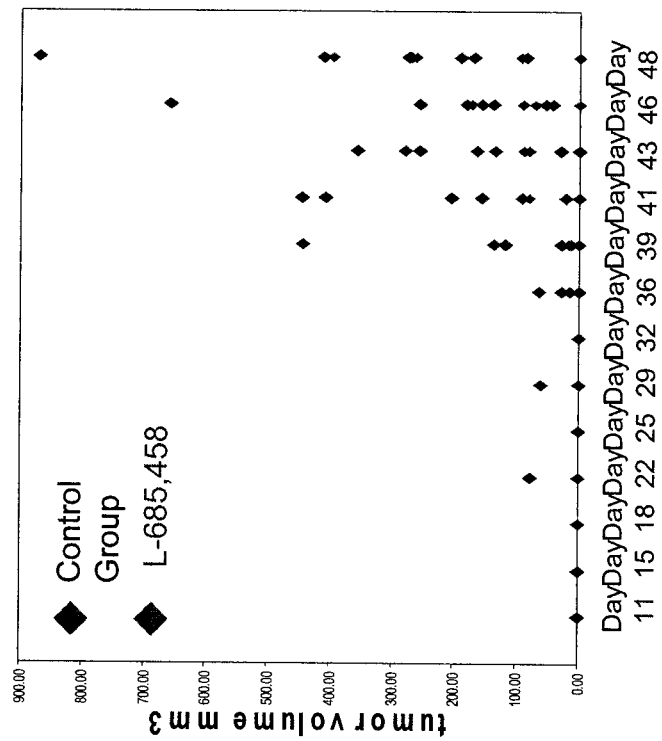
FIG. 13 shows the effect of a small molecule inhibitor of gamma secretase, L-685,458, on the volume of tumors arising from cancer stem cells in a xenograft model. A) The average tumor volume from L-685-458 treated (n=5) versus control (n=7) animals is plotted for each day measured over 37 days. B) The tumor volume of individual L-685-458 treated and control mice is plotted for each day measured.
Figure 13:
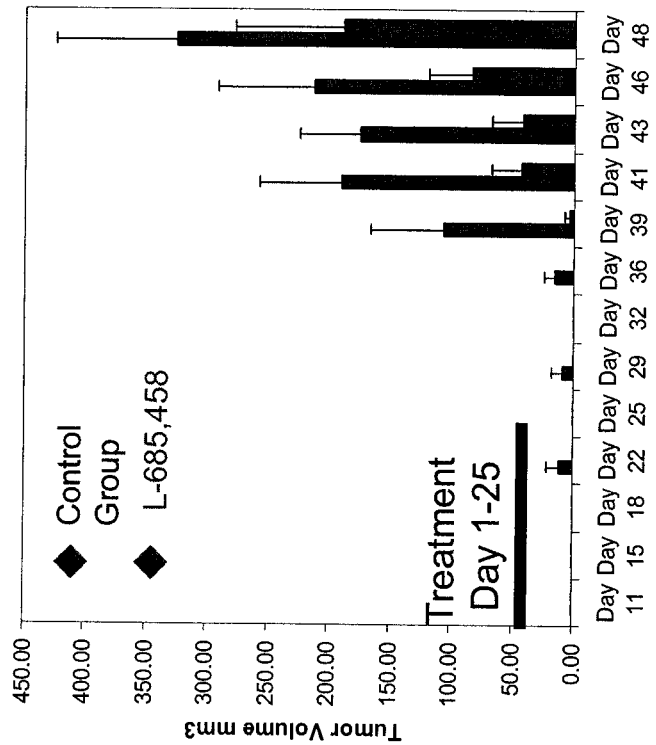

In alternative embodiments, gamma secretase activity was decreased using the small-molecule inhibitor L-685,458 (Yan et al., 2004, J. Neurosci. 24:2942) and the effect on tumor growth was assessed in a xenograft model. 20,000 PE13 passaged human breast tumor cells were injected into the mammary fat pads of NOD/SCID mice. The mice were then injected subcutaneously daily with 9 mg/kg L-685,458 (n=5) or vehicle control (n=7) for 25 days. Starting on day 11, the tumor volume was measured three times a week for a total of 48 days. Treatment with L-685,458 significantly inhibited the growth of injected tumor cells with the average tumor volume reduced compared to control animals throughout the study (FIG. 13A). The tumor volumes for individual mice are plotted in FIG. 13B. Thus inhibiting gamma secretase activity by using a small molecule gamma secretase inhibitor predicted to reduce Notch signaling reduced tumor growth.

EXAMPLE 15

Figure 14:
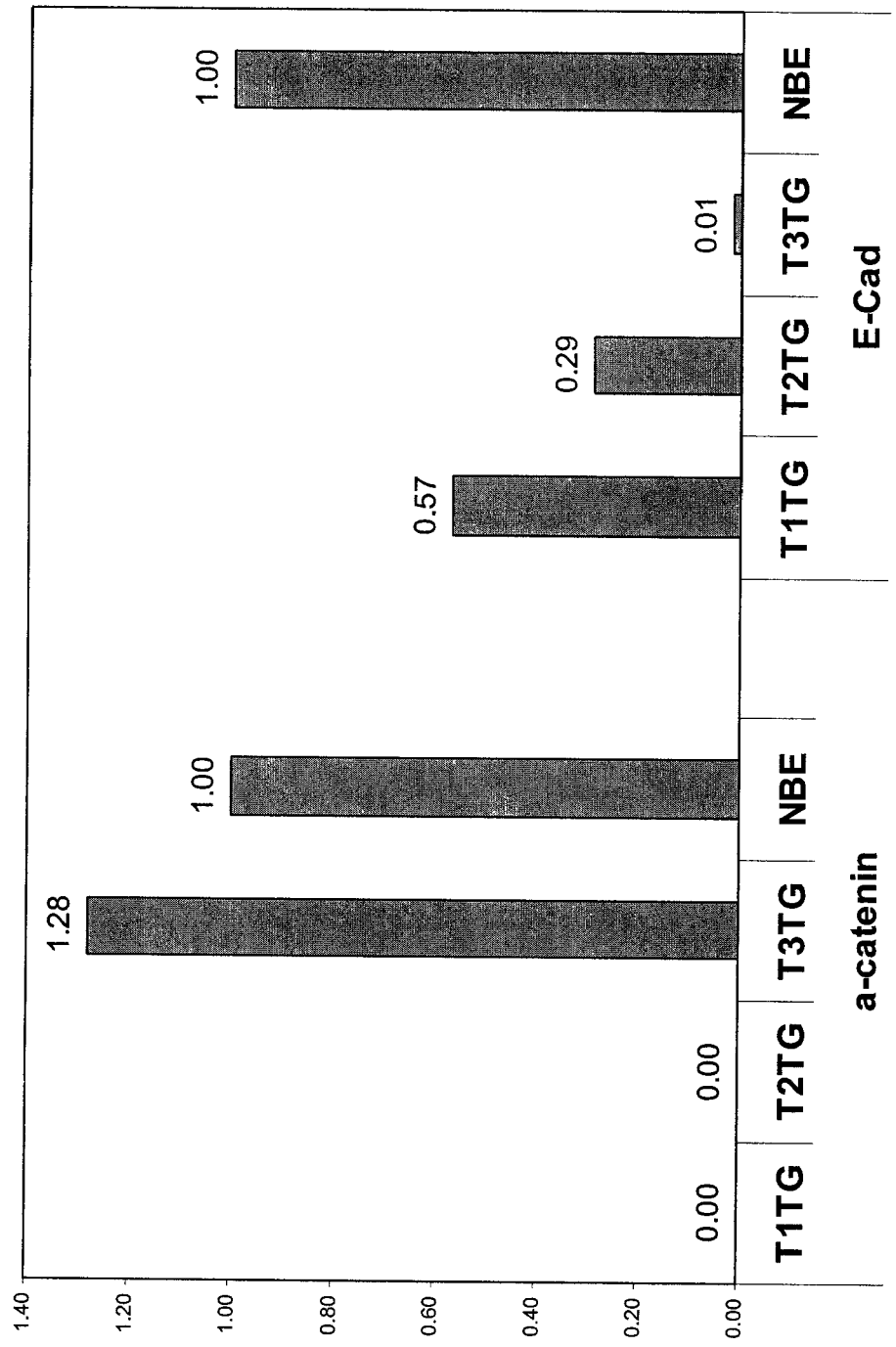
FIG. 14 shows expression levels of alpha-catenin and e-cadherin using real-time PCR in tumorigenic cells (TG) from three breast tumors: T1, T2, and T3
Figure 15:
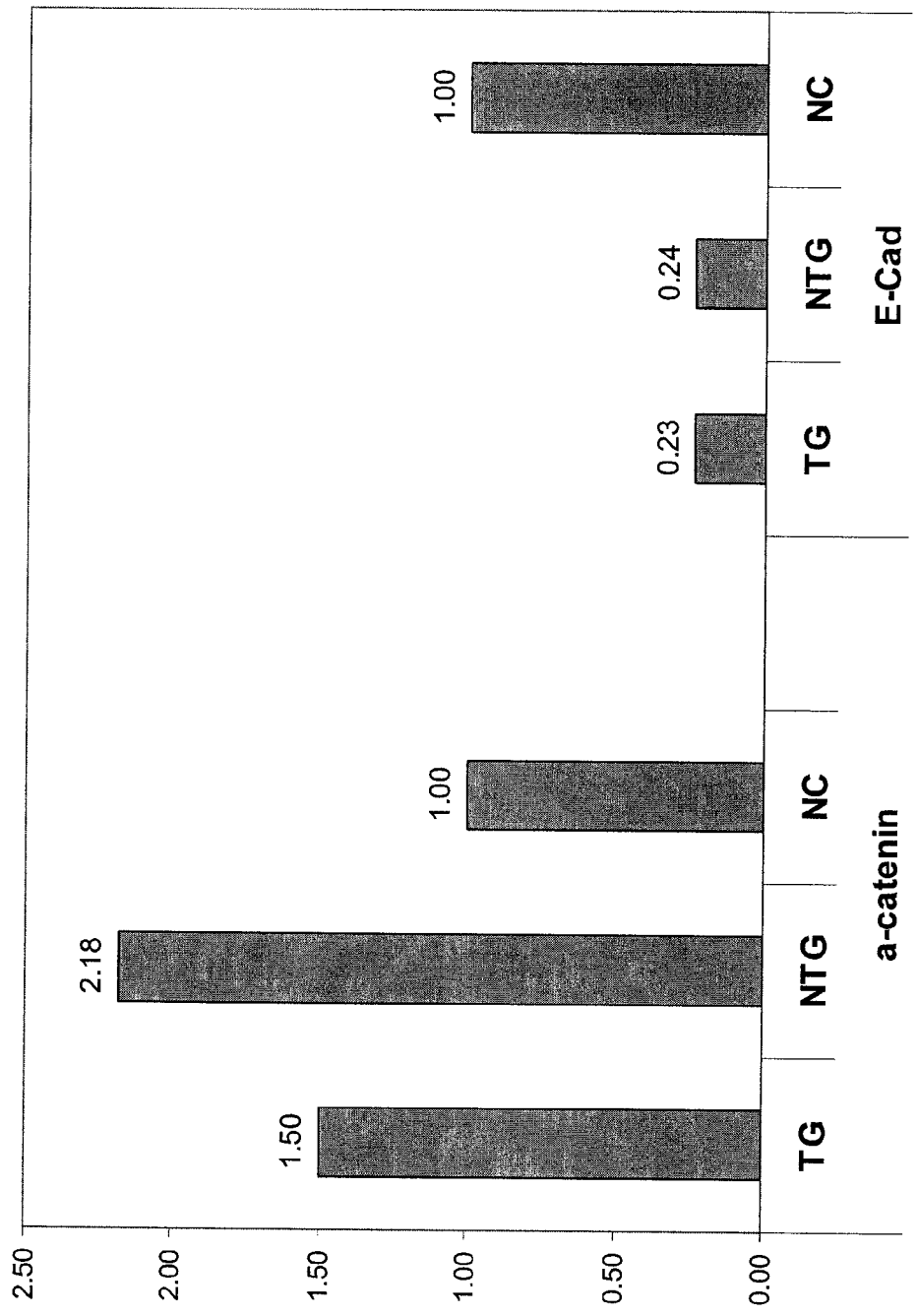
FIG. 15 shows expression levels of alpha-catenin and e-cadherin using real-time PCR in tumorigenic (TG) and nontumorigenic (NTG) cells from a colon tumor sample compared to normal colon epithelium (NC).

Isolated Cancer Stem Cells from Colon Cancer Display Differential Expression of Alpha-Catenin and E-Cadherin This study extended the differential expression of alpha-catenin and E-cadherin in the gene expression signatures of the present invention to colon cancers. Real-time PCR again showed the differential expression of alpha-catenin and E-cadherin in three breast cancer tumors (FIG. 14). To investigate the expression of alpha-catenin and E-cadherin in colon cancer, tumorigenic and nontumorigenic cells from colon tumor biopsies were isolated by flow cytometry based on their differential expression of ESA, CD44, CD24, and Lineage markers as described above and in Al-Hajj et al., 2003. Total RNA was extracted from isolated tumorigenic cancer stem cells, non-tumorigenic tumor cells, and normal colon epithelium and the relative levels of RNA encoding alpha-catenin and E-cadherin were determined by real-time RT-PCR. As shown in FIG. 15 tumorigenic cancer cells show differential expression of alpha-catenin and E-cadherin similar to the E-cadherin gene expression signature with unchanged to increased levels of alpha-catenin and decreased levels of E-cadherin. This differential expression can be used to diagnose and treat metastatic colon cancer stem cells as described in detail below.

EXAMPLE 16

Using the Alpha-catenin and E-cadherin Gene Expression Signatures to Assess the Presence of and Metastatic Potential of Cancer Stem Cells This example describes methods for monitoring the presence of and metastatic potential of cancer stem cells using the gene expression signatures of the present invention. In some embodiments the presence of and metastatic potential of cancer stem cells is monitored by assessing E-cadherin and alpha-catenin expression and E-cadherin, alpha-catenin, and beta-catenin protein localization. E-cadherin, alpha-catenin, and/or beta-catenin are essential components of adherens junctions, sites of cell-cell adhesion between epithelial cells. Assembly of adherens junctions is regulated by gamma secretase proteolytic cleavage of E-cadherin. E-cadherin cleavage results in the disassembly of the adherens junction complex and increased levels of E-cadherin, alpha-catenin, and beta-catenin proteins in the cytoplasm that in turn can contribute to nuclear accumulation of beta-catenin and activation of the Wnt signaling pathway (Marambaud et al., 2002, EMBO 21:1948). Consistent with this, cytoplasmic E-cadherin and nuclear localized beta-catenin are associated with mesenchyme-like cell that have lost normal epithelial adhesive contacts at the invasive front of a tumor (Brabletz et al., 2001, PNAS 98:10356). Furthermore, these mesenchyme-like cells show proliferative activity and can generate metastases containing well-differentiated cell populations that characterize the original tumor consistent with these cells representing tumor stem cells.

The identification of reduced expression of either alpha-catenin or E-cadherin in signature 1 and signature 2 cancer stem cells respectively further indicates that cancer stem cells are both tumorigenic and metastatic. Downregulation of Nicastrin in signature 1 cancer stem cells and the potential increased activation of gamma secretase as discussed in detail in above can further facilitate loss of cell-cell contact and contribute to metastasis in signature 1 type cancer stem cells. Thus the present invention enables the use of the differential expression of E-cadherin and alpha-catenin and localization of E-cadherin, alpha-catenin, and beta-catenin to monitor the metastatic potential of tumor stem cells.

In some embodiments of this invention, the activity of gamma secretase is inhibited and the effect on alpha-catenin, beta-catenin, and E-cadherin expression in cancer stem cells is determined. To inhibit gamma-secretase activity a small-molecule inhibitors L-685,458 was used (Yan et al., 2004, J. Neurosci. 42:2942). 20,000 PE13 tumor cells were injected into the mammary fat pads of VP-16 and estrogen pre-treated NOD/SCID mice. The mice were then injected subcutaneously daily with 9 mg/kg L-685,458 or vehicle control for 25 days. After the 25 days and one week after the last injection, biopsies are taken from L-685,458 treated and control treated mice. Biopsies are fresh frozen in liquid nitrogen, embedded in O.C.T., and cut on a cryostat as 10 um sections onto glass slides. Alternatively biopsies are formalin-fixed, paraffin-embedded, and cut on a microtome as 10 um section onto glass slides.

In some embodiments indirect double immunohistochemistry is combined with laser capture microdissection to determine if the cytoplasmic localization of E-cadherin and/or nuclear localization of beta-catenin in potentially metastatic tumor cells (Brabletz et al., 2001) is indicative of cancer stem cells and to monitor changes induced by treatment with the gamma secretase inhibitor L-685,458. Frozen sections of tumor biopsies are fixed with 4% paraformaldehyde, blocked in 3% normal goat serum, and incubated with biotin-conjugated anti-beta-catenin antibodies. Biotin is detected by the enzymatic activity of horseradish peroxidase (HRP)-conjugated avidin using a colored substrate. Next sections are incubated with alkaline phosphatase (AP)-conjugated anti-E-cadherin or alpha-catenin antibodies, and AP enzymatic activity is detected using a different colored substrate. Cells on the leading edge of the tumor with a mesenchymal morphology, cytoplasmic localization of either E-cadherin or alpha-catenin and/or nuclear localization of beta-catenin are identified as potential tumorigenic and metastatic cancer stem cells. To confirm these cells are cancer stem cells laser-capture microdissection is performed using a Leica AS LMD instrument. Total RNA is extracted from the microdissected sample using RNeasy Micro Kit (Qiagen) according to the manufacture's protocol. The isolated RNA is used for Taqman quantitative RT-PCR analysis using standard techniques. Primer and probe sets for genes that comprise signature 1, signature 2, CD44, CD24, and Lineage markers are designed over exon-intron borders. Each primer/probe set is used to quantify the level of gene expression from laser captured metastatic cells compared to cancer stem cell populations isolated according to Example 5 or normal breast epithelium isolated according to Example 4 to determine if metastatic cells are also tumorigenic and if treatment with L-685,458 changes the metastatic or tumorigenic markers compared to control.

In another embodiment multi-color quantitative immunofluorescence is used to determine the subcellular localization and expression levels of alpha-catenin and E-cadherin or the nuclear localization of beta-catenin in cancer stem cells to assess their metastatic potential and changes associated with L-685,458 treatment. Frozen sections of tumor biopsies are fixed with 4% paraformaldehyde, blocked in 3% normal goat serum, and incubated with fluorescently labeled antibodies against CD44, CD24, and on alternating adjacent sections either alpha-catenin, beta-catenin, or E-cadherin. In alternative embodiments antibodies to other cancer stem cell markers of either the alpha-catenin and/or E-cadherin gene expression signatures can be used. For example antibodies to NCSTN and MET can be used on alternating adjacent sections to assess the presence of type 1 cancer stem cells by decreased expression of NCSTN and increased expression of MET. Similarly, antibodies to IL1R2 and SHC1 can be used to assess the presence of type 2 cancer stem cells by decreased expression of IL1R2 and increased expression of SHC1.

Cancer stem cells are identified as lineage– cells based on their neoplastic morphology (Al-Hajj et al., 2003) and as CD44+ and CD24– by the presence and absence, respectively, of a fluorescent signal. Total expression levels as well as the ratio of membrane to cytoplasmic localized of alpha-catenin and E-cadherin, or any combination of type 1 or type 2 cancer stem cell markers of the present invention, is determined by quantitative immunofluorescence (Dunn et al., 1994; Kirchner et al., 2003) using a Quantics CCD camera equipped with an EEV 57-10 G1 Chip (Photometrics, Tucson, Ariz.) generating 12-bit digital data. Nuclear localization of beta-catenin is also assessed.

It is expected that proliferating mesenchymal cells at the leading edge of a tumor with cytoplasmic E-cadherin and nuclear beta-catenin will also prove to be tumorigenic cancer stem cells. If gamma secretase activity contributes to the metastatic potential of cancer stem cells through cleavage of E-cadherin, it is predicted that gamma secretase inhibitors should reduce both the number of these cells and the cytoplasmic expression of E-cadherin and alpha-catenin.

EXAMPLE 17

Targeting the Signature 1 Cancer Stem Cell Marker DCBLD2 to Inhibit Metastasis

This example describes methods for targeting cancer stem cells based on the expression of cancer stem cell markers identified by the gene expression signatures of the present invention and for assaying the impact of this targeting on tumor metastasis potential. Specifically, metastasis is monitored by alpha-catenin and E-cadherin expression levels and E-cadherin, alpha-catenin, and beta-catenin subcellular localization in cancer stem cells after targeting a transmembrane protein that can contribute to tumor metastasis and that is overexpressed in cancer stem cells. Gene expression signature 1 of the present invention identifies increased DCBLD2 expression in signature 1 cancer stem cells compared to normal breast epithelium (FIG. 11). DCBLD2 is a type-I transmembrane protein structurally similar to the neurophilins, cell surface receptors for semaphorins that mediate axon repulsion and attraction in the nervous system. CUB and discoidin domains present in DCBLD2 have been linked to the regulation of cell aggregation and migration. Furthermore, DCBLD2 is overexpressed in highly metastatic cancers, and thus targeting cells expressing high levels of DCBLD2 could eliminate cancer stem cells with high metastatic potential.

To target cancer stem cells with increased expression of DCBLD2, monoclonal antibodies against the extracellular domain of DCBLD2 are produced. F1 hybrid mice are immunized using purified recombinant extracellular DCBLD2 protein and the spleen from mice with circulating antibodies that specifically recognize the immunizing protein are used for hybridoma production.

Antibodies against the different domains of DCBLD2 are then used as therapeutic agents in a mouse xenograft model. Cells from a primary tumor are cut up with scissors into small pieces that are then minced with a blade in sterile RPMI medium on ice to yield 2×2 mm pieces. The tumor pieces are washed in serum-free HBSS and implanted into the mammary fat pads of VP-16 and estrogen pre-treated NOD/SCID mice. Alternatively, cancer stem cells with an alpha-catenin gene expression signature are isolated as described in Example 5 above and 5,000 down to 200 isolated cells are injected into NOD/SCID mice. Once palpable tumors are formed, mice are injected i.p. with antibodies against DCBLD2 or control antibodies every third day for two weeks. Mice are sacrificed at various times during the treatment and the tumor assessed for the presence and number of metastatic tumor stem cells at the leading edge of the tumors using qualitative immunofluorescence as described in detail above.

EXAMPLE 18

Using E-cadherin, Alpha-Catenin, Table 4 and Table 6 Genes Differentially Expressed by Cancer Stem Cells, and/or Beta-catenin Expression and Protein Localization to Determine the Metastatic Potential of Cancer Stem Cells in a Patient Biopsy This example describes methods for monitoring the presence of metastatic cancer stem cells in a patient biopsy by E-cadherin and/or alpha-catenin expression and E-cadherin, alpha-catenin, one or more of the genes listed in tables 4 and 6 that are differentially expressed by cancer stem cells and non-tumorigenic cancer cells, and/or beta-catenin protein localization. A patient tumor biopsy is taken and embedded in O.C.T., and cut on a cryostat as 10 um sections onto glass slides. Alternatively biopsies are formalin-fixed, paraffin-embedded, and cut on a microtome as 10 um section onto glass slides. Slides are then processed for quantitative immunofluorescence for alpha-catenin, E-cadherin protein, and/or beta-catenin expression and localization as described in Example 14 above. Patients with cancer stem cells with low expression of either alpha-catenin or E-cadherin combined with increase protein in the cytoplasm relative to associated with adherens junctions are assessed as at high risk for metastasis and therapy adjusted accordingly.

Example 19

Using Cancer Stem Cells Markers to Determine the Tumorigenic Potential of Circulating Metastatic Tumor Cells in a Cancer Patient This example describes methods for determining the tumorigenicity of tumor cells circulating in the peripheral blood of a cancer patient. Tumor burden is a critical factor in the clinical outcome of cancer patients, and the frequency of metastasis, relapse, and death appears to correlate with levels of circulating tumor cells (Wong, 2003, Oncol. Reports 10:229). Currently quantitative RT-PCR is used against a wide range of tumor markers to determine the presence of tumor cells with varying success (Wong, 2003, Oncol. Reports 10:229). There is thus a need for sensitive, specific, and non-invasive blood tests to assess tumor burden to determine the need for more intensive therapeutic intervention. The cancer stem cell gene signatures of the present invention further enables one to identify circulating cells as not only metastatic but also tumorigenic. Blood from patients is collected and the presence of cancer stem cells is determined using flow cytometry as described in Example 5. Furthermore, the isolated tumor stem cells can be injected in the mammary fat pads of VP-16 and estrogen pretreated NOD/SCID mice to assess tumorigenicity. The presence and tumorigenicity of tumor cells in the blood of a patient can be monitored over time to determine the effect of a cancer therapy.

EXAMPLE 20

The Alpha-catenin Signature Predicts Poor Clinical Outcome

This example describes the identification of the alpha-catenin signature as predictive of clinical outcome of early breast cancer including metastasis and overall survival. Furthermore, use of the alpha-catenin gene signature to classify tumor samples into low and high risk for the purpose of prognosis and therapy selection is provided.

The genome-wide analysis of solid tumor stem cell gene expression of the present invention identified gene profiles that subclassify tumors and thus can be useful in predicting clinical outcome. The genes differentially expressed in tumor stem cells were divided into solid tumor stem cell gene signatures based on the correlation of their expression with alpha-catenin and then further selected based on their fold or percentage expression change in tumor stem cells with undetectable or low levels of alpha-catenin compared to normal breast tissue and alpha-catenin non-deficient tumor stem cells. Genes with undetectable to low expression in tumor stem cells comprising low to undetectable alpha-catenin expression were identified as having a positive correlation, from 0.9 to 1, with alpha-catenin expression in all tumor stem cells as well as expression levels lower by 90% or more in tumor stem cells comprising low to undectable alpha-catenin compared to normal breast tissue and alpha-catenin non-deficient tumor stem cells. Genes with elevated expression in tumor stem cells comprising low to undetectable alpha-catenin expression were identified as having a negative correlation, from −0.9 to −1, with alpha-catenin expression in all tumor stem cells as well as expression levels in tumor stem cells comprising low to undectable alpha-catenin expression that are 9 fold or more than in normal breast tissue and alpha-catenin non-deficient tumor stem cells. Together these genes comprise the alpha-catenin signature 1 (Table 9). A second alpha-catenin signature (alpha-catenin signature 2) was then generated by further including genes that slightly violated the fold or expression change criteria described above but were subjectively determined to be therapeutically and/or biologically interesting genes: one gene with undetectable to low expression and three genes with elevated expression (underlined in Table 9). A third alpha-catenin signature (alpha-catenin signature 3) was then generated by excluding genes from alpha-catenin signature 2: nine genes with undetectable to low expression and fifteen genes with elevated expression (Table 9).

The genes differentially expressed in tumor stem cells were also divided into solid tumor stem cell gene signatures based on the correlation of their expression with E-cadherin and then further selected based on their fold or percentage expression change in tumor stem cells with undetectable or low levels of E-cadherin compared to normal breast tissue and E-cadherin non-deficient tumor stem cells. Genes with undetectable to low expression in tumor stem cells comprising low to undetectable E-cadherin expression were identified as having a positive correlation, from 0.9 to 1, with E-cadherin expression in all tumor stem cells as well as expression levels lower by 85% or more in tumor stem cells comprising low to undectable E-cadherin compared to normal breast tissue and E-cadherin non-deficient tumor stem cells. Genes with elevated expression in tumor stem cells comprising low to undetectable E-cadherin expression were identified as having a negative correlation, from −0.9 to −1, with E-cadherin expression in all tumor stem cells as well as expression levels in tumor stem cells comprising low to undectable E-cadherin expression that are 2.5 fold or more than in normal breast tissue and E-cadherin non-deficient tumor stem cells. Together these genes comprise the E-cadherin signature 1. A second E-cadherin signature (E-cadherin signature 2) was then generated by further including genes that slightly violated the fold or expression change criteria described above but were subjectively determined to be therapeutically and/or biologically interesting genes: one gene with elevated expression (underlined in Table 9). A third E-cadherin signature (E-cadherin signature 3) was then generated by excluding genes from E-cadherin signature 2 that were subjectively determined not to be therapeutically and/or biologically interesting genes: six genes with undetectable to low expression and six genes with elevated expression (Table 9).

To assess the ability of cancer stem cell gene signatures to predict metastasis and death two independent cancer patient populations were used: 295 consecutive early breast cancer patients from the Netherlands Cancer Institute (van de Vijver et al., 2002, N. Eng. J. Med. 347:1999) and 286 lymph node negative breast cancer patients from the Erasmus Medical Center (Wang et al., 2005, Lancet 365:671). The gene expression from both patient populations had been analyzed by microarray analysis. The alpha-catenin signature 2 was compared against gene expression analysis from these two independent cancer patient populations resulting in alpha-catenin profile 4 and alpha-catenin profile 5, respectively (Table 9). Similarly, the E-cadherin signature 2 was compared against gene expression analysis from these two patient populations resulting in E-cadherin profile 4 and E-cadherin profile 5, respectively (Table 9).

Correlation and Cox proportional hazard survival analysis of microarray data from 295 consecutive early breast cancer patients from the Netherlands Cancer Institute (van de Vijver et al., 2002, N. Eng. J. Med. 347:1999) identified 125 patient tumors with a gene expression profile (alpha-catenin profile 4) that positively correlated with the alpha-catenin signature 2, and showed alpha-catenin signature 2 as significantly predictive of metastasis with a univariate hazard ratio of 1.15 per 0.1 correlation ($P=5.9 \times 10^{-4}$) and significantly predictive of death with a univariate hazard ratio of 1.24 per 0.1 correlation ($P=3.7 \times 10^{-7}$). Furthermore, correlation and chi-square analysis of the microarray data from 286 lymph-node negative breast cancer patients from the Erasmus Medical Center (Wang et al., 2005, Lancet 365:671) revealed that patient tumors with a gene expression profile (alpha-catenin profile 5) that correlated with the alpha-catenin signature 2 (n=77) had an increased risk of metastasis (P=0.67). Thus a tumor stem cell gene signature, such as the alpha-catenin expression signature 2 provides a gene signature for tumors with high risk of metastasis and death, and is thus a gene signature that predicts a poor prognosis. Although any particular gene of the alpha-catenin expression signature can or can not have either reduced expression or elevated expression in a tumor sample, the expression level and its relationship with the other genes in the signature creates a unique solid tumor stem cell signature that can be used to classify a tumor sample.

A similar comparison using the E-cadherin gene expression signature described above was again used to assess clinical outcome as summarized in Table 10. Correlation and Cox proportional hazard survival analysis of microarray data from 295 consecutive early breast cancer patients from the Netherlands Cancer Institute identified 240 patient tumors with a gene expression profile (E-cadherin profile 4) that positively correlated with the E-cadherin signature 2, and showed E-cadherin signature 2 as predictive of metastasis with a univariate hazard ratio for metastasis of 0.981 per 0.1 correlation (P=0.59) and predictive of death with a univariate hazard ratio of 0.938 per 0.1 correlation (P=0.1). Combining the alpha-catenin and E-cadherin gene expression signatures was also predictive of metastasis in patients (univariate hazard ratio for metastasis of 1.28 per 0.1 correlation ($P=4.2 \times 10^{-4}$)). In addition, correlation and chi-square analysis of microarray data from 286 lymph-node negative breast cancer patients from the Erasmus Medical Center (Wang et al., 2005, Lancet 365:671) showed that patient tumors with a gene expression profile (E-cadherin gene profile 5) that correlated with the E-cadherin gene signature (n=198) had an increased risk of metastasis (P=0.57).

Figure 16:
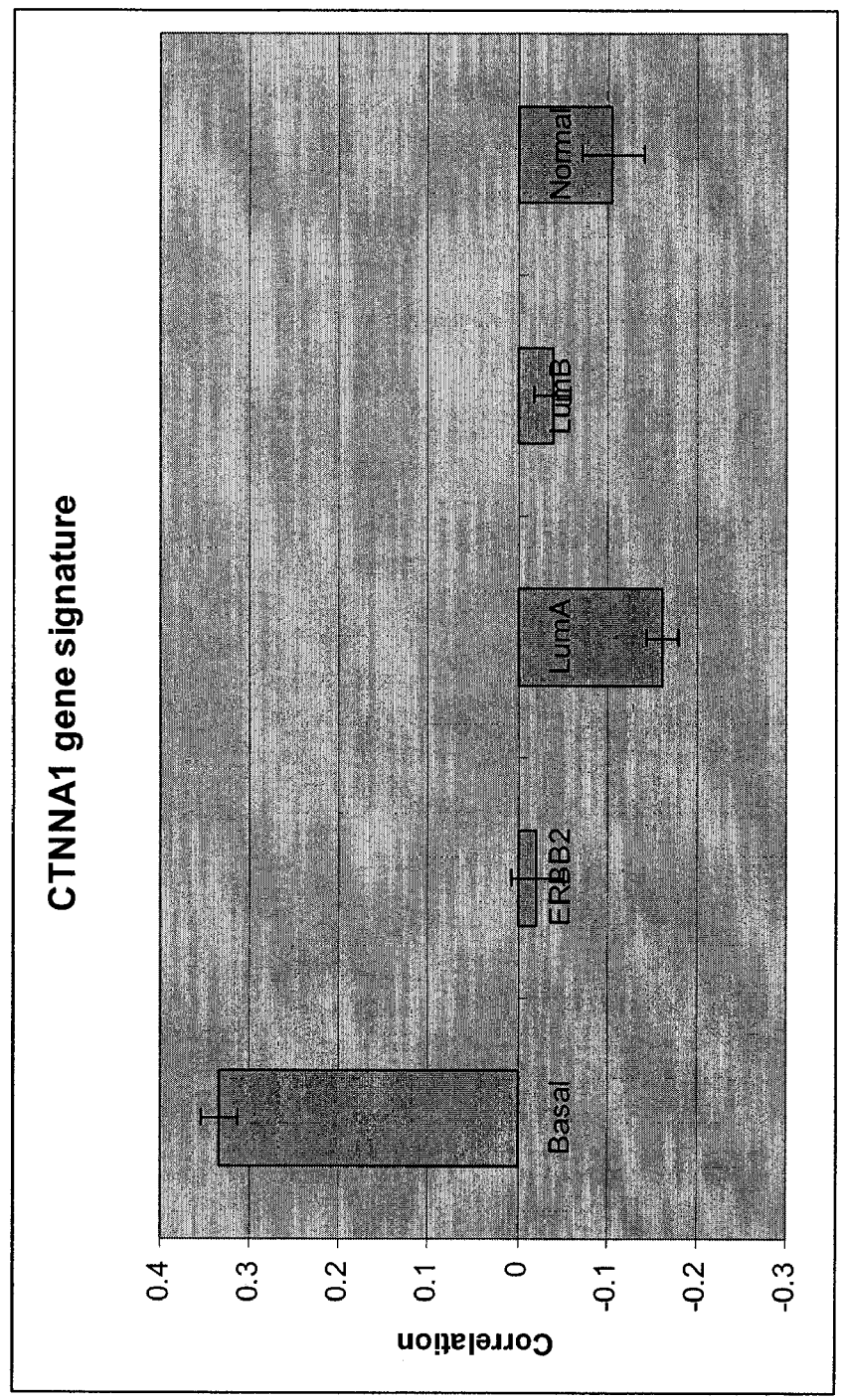
FIG. 16 shows the correlation of A) the alpha-catenin tumor stem cell signature.
Figure 17:
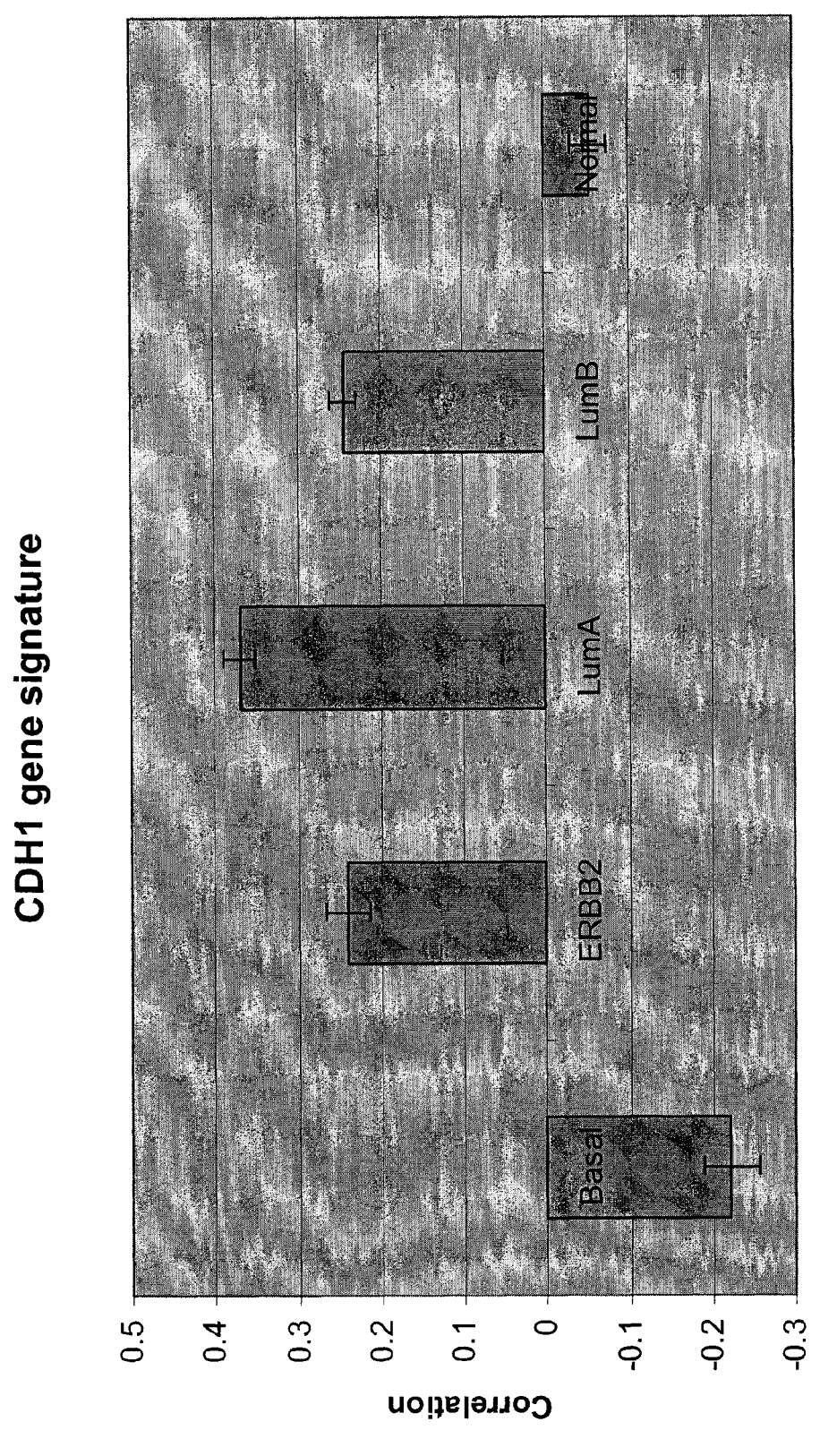

Because of their different abilities in the prediction of clinical outcome, the alpha catenin signature 2 and E-cadherin signature 2 were further correlated against gene expression patterns of different tumor subclasses. Microarray analysis has been used to segregate breast carcinomas based on gene expression into five distinct subclasses: Luminal A, Luminal B, ERBB2, Basal, and Normal-like of which the Luminal A subclass has the best prognosis and the Basal subclass has the poorest prognosis (Sorlie et al., 2001, PNAS 98:10869). The correlation of the alpha-catenin signature 2 with these different tumor subclasses is strongest to the Basal subclass and is negative with the Luminal A subclass (FIG. 16) again highlighting the alpha-catenin signature as a good predictor of poor prognosis. In contrast the E-cadherin signature correlates negatively with the Basal subtype while correlating most positively with the Luminal A subtype (FIG. 17) suggesting that these two tumor stem cell signatures identify two different tumor types with different clinical outcomes.

In addition to the solid tumor stem cell gene signature, one or more individual genes that comprise the solid tumor stem cell gene signatures are significantly predictive of metastasis and death in the 295 patients from the Netherlands Cancer Institute suggesting that one or more of these genes can be used in place of the entire solid tumor stem cell gene signature as described above. In the case of the alpha-catenin gene signature it was discovered that the following genes GALC, CTSL2, FOXQ1, MYEOV, RB1, and SLC7A5 were significantly predictive of metastases and death. Expression of low to undetectable levels of GALC compared to a reference set of expression across all tumor samples (described in van't Veer et al., 2002, Nature 415:530 and van de Vijver et al., 2002, N. Eng. J. Med. 347:1999) was significantly predictive of metastasis with a univariate hazard ratio of 0.632 per 0.1 correlation (P=8.1×10$^{-3}$) and significantly predictive of death with a univariate hazard ratio of 0.583 per 0.1 correlation (P=5.4×10$^{-3}$). Expression of elevated levels of CTSL2 compared to the reference set was significantly predictive of metastasis with a univariate hazard ratio of 1.52 per 0.1 correlation (P=1.7×10$^{-6}$) and significantly predictive of death with a univariate hazard ratio of 1.86 per 0.1 correlation (P=4.0×10$^{-11}$). Expression of elevated levels of FOXQ1 compared to the reference set was significantly predictive of metastasis with a univariate hazard ratio of 1.44 per 0.1 correlation (P=1.7×10$^{-3}$) and significantly predictive of death with a univariate hazard ratio of 1.73 per 0.1 correlation (P=1.6×10$^{-5}$). Expression of elevated levels of MYEOV compared to the reference set was significantly predictive of metastasis with a univariate hazard ratio of 1.76 per 0.1 correlation (P=2.2×10$^{-2}$) and significantly predictive of death with a univariate hazard ratio of 2.09 per 0.1 correlation (P=5.9×10$^{-3}$). Expression of elevated levels of RB1 compared to the reference set was significantly predictive of metastasis with a univariate hazard ratio of 0.72 per 0.1 correlation (P=1.6×10$^{-2}$) and significantly predictive of death with a univariate hazard ratio of 0.664 per 0.1 correlation (P=6.8×10$^{-3}$). Expression of elevated levels of SCL7A5 compared to the reference set was significantly predictive of metastasis with a univariate hazard ratio of 3 per 0.1 correlation (P=2.6×10$^{-4}$) and significantly predictive of death with a univariate hazard ratio of 3.52 per 0.1 correlation (P=1.1×10$^{-4}$).

In addition, several of the genes comprising the E-cadherin gene expression signature were predictive alone including some with low to undetectable expression: IL8 and KRT6B and some with elevated expression: RNASEL and C17orf27. Expression of low to undetectable levels of IL8 compared to the reference set was significantly predictive of metastasis with a univariate hazard ratio of 1.17 per 0.1 correlation (P=5.2×10$^{-2}$) and significantly predictive of death with a univariate hazard ratio of 1.3 per 0.1 correlation (P=3.0×10$^{-3}$). Expression of low to undetectable levels of KRT6B compared to the reference set was significantly predictive of metastasis univariate hazard ratio of 1.35 per 0.1 correlation (P=3.9×10$^{-2}$) and significant predictive of death with aunivariate hazard ratio of 1.54 per 0.1 correlation (P=4.7×10$^{-3}$). Expression of elevated levels of RNASEL compared to the reference set was significantly predictive of metastasis with a univariate hazard ratio of 0.655 per 0.1 correlation (P=3.7×10$^{-2}$) and significantly predictive of death with a univariate hazard ratio of 0.498 per 0.1 correlation (P=1.4×10$^{-3}$). Elevated expression levels of C17orf27 compared to the reference set was significantly predictive of metastasis with a univariate hazard ratio of 2.35 per 0.1 correlation (P=1.5×10$^{-2}$) and significantly predictive of death with a univariate hazard ratio of 3.19 per 0.1 correlation (P=3.1×10$^{-3}$).

The identification of the alpha-catenin gene signature as predictive of poor prognosis suggests its use clinically in providing a prognosis and selecting a therapy for patients. The alpha-catenin gene expression signature was discovered from a comparison of cancer stem cells against normal breast tissue, its prognostic ability was identified from microarray analysis of unfractionated, and thus heterogenous, breast tumor samples normalized against a reference set of tumor samples (van't Veer et al., 2002, Nature 415:530; van de Vijver et al., 2002, N. Eng. J. Med. 347:1999) or scaled to a target intensity (Wang et al., 2005, Lancet 365:671). Thus unfractioned tumor samples including but not limited to solid tissue biopsies, fine needle aspirations, or pleural effusions can be used for detecting the alpha-catenin signature in cancer patients.

To test additional patients, a tumor sample is obtained and is fresh-frozen for storage in liquid nitrogen at −180° C. before analysis. RNA is extracted from the tumor sample and fluorescently labeled cDNA probes are generated for microarray analysis using standard techniques in the art. cDNA probes from the patient sample are hybridized on DNA microarrays containing genes, or fragments thereof, which comprise an alpha-catenin signature. The hybridization is performed in combination with a reference sample composed of a pool of cDNAs from a number of tumor samples that are labeled with a complementary fluorophore. The hybridized array is scanned and the fluorescence intensities quantified, normalized, and corrected to yield the transcript abundance of each gene as an intensity ratio with respect to that of the signal of the reference sample. Alternatively the isolated RNA is used for quantitative RT-PCR using primer sets that specifically amplify the gene that comprise the alpha-catenin signature. The gene expression profile in the patient sample is then correlated with the alpha-catenin signature. The detection of a positive correlation with the alpha-catenin signature is used to categorize a tumor as high risk and an appropriate therapy is thus administered and the signature can further be used over time to monitor the chosen therapy. Alternatively, if no correlation or a negative correlation with the alpha-catenin signature is detected in the sample, a patient can be monitored over time for the appearance of the signature.

All publications and patents mentioned in the above specification are herein incorporated by reference. Various modifications and variations of the described method and system of the invention will be apparent to those skilled in the art without departing from the scope and spirit of the invention. Although the invention has been described in connection with specific some embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A method of classifying a solid tumor breast cancer comprising:
   (a) determining mRNA expression levels for genes: CTNNA1, ARMCX3, GLUL, RB1, CAV1, CAV2, IGFBP3, S100A2, MET, CDKN2A, and MFHAS1 from a solid tumor breast cancer sample;
   (b) comparing the determined mRNA expression levels of the genes in (a) to a pre-determined high risk expression profile, wherein the expression levels of CTNNA1, ARMCX3, GLUL, and RB1 are low or undetectable in the pre-determined high risk expression profile compared to expression in normal breast tissue and the expression levels of CAV1, CAV2, IGFBP3, S100A2, MET, CDKN2A, and MFHAS1 are elevated in the pre-determined high risk expression profile compared to expression in normal breast tissue; and,
   (c) classifying the cancer sample as high risk for a poor prognosis if the comparison in (b) is positively correlated or low risk for a poor prognosis if the comparison in (b) is negatively correlated.

2. The method of claim 1, wherein the mRNA is detected using a DNA array comprising a polynucleotide that hybridizes to the mRNA.

3. The method of claim 1, wherein the mRNA is detected using polymerase chain reaction comprising polynucleotide primers that specifically amplify the mRNA.

4. The method of claim 1, wherein said determining further comprises determining the mRNA expression levels for one or more of NCSTN, LNX, D2S448, TUSC1, BEX2, SLC12A2, GALC, NGFRAP1, FGF13, KIAA1102, SLC1A4, DNAJD1, EDG2, DCBLD2, CXCL5, FOXQ1, IL27RA, KLRF1, PKCA, UPP1, CTSL2, SLC7A5, ARNTL2, PRSS1, PRSS2, PRSS3, VNN1, RAB38, ZBED2, MYEOV, MAL, IMP-3, and DHRS9.

5. The method of claim 1, wherein said determining further comprises determining the mRNA expression levels for: NCSTN, LNX, D2S448, EDG2, DCBLD2, CXCL5, FOXQ1, and CTSL2.

6. The method of claim 1, wherein said determining further comprises determining the mRNA expression levels for: NCSTN, LNX, D2S448, TUSC1, BEX2, SLC12A2, GALC, NGFRAP1, FGF13, KIAA1102, SLC1A4, DNAJD1, EDG2, DCBLD2, CXCL5, FOXQ1, IL27RA, KLRF1, PKCA, UPP1, CTSL2, SLC7A5, ARNTL2, PRSS1, PRSS2, PRSS3, VNN1, RAB38, ZBED2, MYEOV, MAL, IMP-3, and DHRS9.

7. The method of claim 1, wherein said determining further comprises determining the mRNA expression levels for: LNX, D2S448, TUSC1, BEX2, SLC12A2, GALC, NGFRAP1, FGF13, KIAA1102, SLC1A4, DNAJD1, DCBLD2, CXCL5, FOXQ1, CTSL2, IL27RA, KLRF1, PKCA, UPP1, SLC7A5, ARNTL2, PRSS1, PRSS2, PRSS3, VNN1, RAB38, ZBED2, MYEOV, MAL, IMP-3, and DHRS9.

* * * * *